United States Patent [19]
Gallatin et al.

[11] Patent Number: 5,766,850
[45] Date of Patent: Jun. 16, 1998

[54] HUMAN β2 INTEGRIN α SUBUNIT

[75] Inventors: W. Michael Gallatin; Monica Van der Vieren, both of Seattle, Wash.

[73] Assignee: ICOS Corporation, Bothell, Wash.

[21] Appl. No.: 362,652

[22] Filed: Dec. 21, 1994

Related U.S. Application Data

[63] Continuation-in-part of Ser. No. 286,889, Aug. 5, 1994, Pat. No. 5,470,953, which is a continuation-in-part of Ser. No. 173,497, Dec. 23, 1993, Pat. No. 5,437,958.

[51] Int. Cl.$^6$ .......................... C12N 15/00; C12N 15/02; C12N 15/10; C12N 15/12
[52] U.S. Cl. .................. 435/6; 435/7.2; 435/7.8; 536/25.4; 935/19
[58] Field of Search .................. 435/6, 7.2, 7.8; 536/25.4; 935/19

[56] References Cited

U.S. PATENT DOCUMENTS

| | | | |
|---|---|---|---|
| 4,271,139 | 6/1981 | Hart | 436/531 |
| 4,568,649 | 2/1986 | Bertoglio-Matte | 436/534 |

OTHER PUBLICATIONS

DIALOG Medline file 155 abstract 96111956 of Van der Vieren et al. Dec. 1995. Immunity 3(6):683–690.

Adams, et al., "Experimental graft arteriosclerosis: I. The Lewis-toF-44 Allograft Model," *Transplantation*, 53:30–39 (1993).

Adams, et al., "Experimental graft arteriosclerosis: II. Immunocytochemical analysis of lesion development," *Transplantation*, 56:794–799 (1993).

Arfors, et al., "A monoclonal antibody to the membrane glycoprotein complex CD18 inhibits polymorphonuclear leukocyte accumulation and plasma leakage in vivo," *Blood* 69:338–340 (1987).

Arnaout, "Structure and function of the leukocyte adhesion molecules CD11/CD18," *Blood* 75:1037–1050 (1990).

Berman, et al., "Biosynthesis and function of membrane bound and secreted forms of recombinant CD11b/CD18 (Mac-1)," *J. Cell, Biochem* 52:183–195 (1993).

Burnett, et al., "The IgA heavy-chain gene family in rabbits: cloning and sequence analysis of 13 Cα genes," *EMBO J.* 8:4041–4047 (1989).

Corbi, et al., "cDNA cloning and complete primary structure of the α subunit of a leukocyte adhesion glycoprotein, p150,95," *EMBO J.* 6:4023–4028 (1987).

Corbi, et al., "The human leukocyte adhesion glycoprotein Mac-1 (complement respector type 3, CD11b α subunit," *J.Biol.Chem.* 263:12403–12411 (1988).

Cromartie, et al., "Arthritis in rats after sytemic injection of Streptococcal cells or cell walls," *J.Exp.Med.* 146:1585–1602 (1977).

Chisaka, et al., "Developmental defects of the ear, cranial nerves and hindbrain resulting from targeted disruption of the mouse homeobox gene Hox-1.6," *Nature* 355:516–520 (1992).

Dana, et al., "Deficiency of a surface membrane glycoprotein (Mo1) in man," *J.Clin.Invest.* 73:153–159 (1984).

Diamond, et al., "The I domain is a major recognition site on the leukocyte integrin Mac-1 (CD11b/CD18) for four distince adhesion ligands," *J.Cell, Biol.* 120:1031–1043 (1993).

(List continued on next page.)

*Primary Examiner*—Keith C. Furman
*Attorney, Agent, or Firm*—Marshall, O'Toole, Gerstein, Murray & Borun

[57] ABSTRACT

DNA encoding a novel human β$_2$ integrin α subunit polypeptide, designated α$_d$, is disclosed along with methods and materials for production of the same by recombinant procedures. Fusion proteins are also disclosed which include extracellular α$_d$ protein fragments, α$_d$ I domain fragments or full length α$_d$ polypeptides and human immunoglobulin constant regions. Binding molecules specific for α$_d$ are also disclosed as useful for modulating the biological activities of α$_d$. DNA from other species which show homology to human α$_d$ encoding sequences are also disclosed.

1 Claim, 4 Drawing Sheets

```
αD     TF-GT--VLL LSVLASYHGF NLDVEEPTIF QEDAGGFGQS VVQFGGSRLV    47
CD11B  MA-LR--VLL LTALTLCHGF NLDTENAMTF QENARGFGQS VVQLQGSRVV    47
CD11c  MTRTRAALLL FTALATSLGF NLDTEELTAF RVDSAGFGDS VVQYANSWVY    50

αD     VGAPLEVVAA NQTGRLYDCA AATGMCQPIP LHIRPEAVNM SLGLTLAAST    97
CD11B  VGAPQEIVAA NQRGSLYQCD YSTGSCEPIR LQVPVEAVNM SLGLSLAATT    97
CD11c  VGAPQKIIAA NQIGGLYQCG YSTGACEPIG LQVPPEAVNM SLGLSLASTT    100

αD     NGSRLLACGP TLHRVCGENS YSKGSCLLLG SR-WEIIQTV PDATPECPHQ   146
CD11B  SPPQLLACGP TVHQTCSENT YVKGLCFLFG SNLRQOPQKF PEALRGCPQE   147
CD11c  SPSQLLACGP TVHHECGRNM YLTGLCFLLG PT--QLTQRL PVSRQECPRQ   148

αD     EMDIVFLIDG SGSIDQNDFN QMKGFVQAVM GQFEGTDTLF ALMQYSNLLK    196
CD11B  DSDIAFLIDG SGSIIPHDFR RMKEFVSTVM EQLKKSKTLF SLMQYSEEFR    197
CD11c  EQDIVFLIDG SGSISSRNFA TMMNFVRAVI SQFQRPSTQF SLMQFSNKFQ    198

αD     IHFTFTQFRT SPSQQSLVDP IVQLKGLTFT ATGILTVVTQ LFHHKNGARK   246
CD11B  IHFTFKEFQN NPNPRSLVKP ITQLLGRTHT ATGIRKVVRE LFNITNGARK   247
CD11c  THFTFEEFRR TSNPLSLLAS VHQLQGFTYT ATAIQNVVHR LFHASYGARR   248

αD     SAKKILIVIT DGQKYKDPLE YSDVIPQAEK AGIIRYAIGV GHAFQGPTAR   296
CD11B  NAFKILVVIT DGEKFGDPLG YEDVIPEADR EGVIRYVIGV GDAFRSEKSR   297
CD11c  DAIKILIVIT DGKKEGDSLD YKDVIPMADA AGIIRYAIGV GLAFQNRNSW   298
```

OTHER PUBLICATIONS

Danilenko, et al., "Canine leukocyte cell adhesion molecules (LeuCAMS): characterization of the CD11/CD18 family," *Tissue Antigens* 40:13–21 (1992).

Deng, et al., "Location of crossovers during gene targeting with insertion and replacement vectors," *Mol.Cell.Biol.* 13:2134–2140 (1993).

Frohman, "RACE: Rapid amplication of cDNA ends" in *PCR Protocols: A Guide to Methods and Applications*, Innis, et al. (eds.) Academic press:New York (1990) pp. 28–38.

Greve, et al., "The major human rhinovirus receptor is ICAM–1," *Cell* 56:839 (1989).

Hanenberg et al., "Macrophage infiltration precedes and is a prerequisite for lymphocytic insulitis in pancreatic islets of prediabetic BB rats," *Diatetologia* 32:126–134 (1989).

Hart and Greenwald, "Scintillation proximity assay of antigen–antibody binding kinetics: concise communication," *J.Nuc.Med* 20:1062–1065 (1979).

Hildreth & Orentas, "Involvement of a leukocyte adhesion receptor (LFA–1) in HIV–induced synscytium formation," *Science* 244:1075–1078 (1989).

Huitinga, et al., "Treatment with anti–CR3 antibodies ED7 and ED8 supresses experimental allergic encephalomyelitis in Lewis rats," *Eur.J.Immunol* 23:709–715 (1993).

Jutila, et al., "In vivo distribution and characterization of two novel mononuclear phagocyte differentiation antigens in mice," *J.Leukocyte Biol.* 54:30–39 (1993).

Capecchi, "Altering the genome by homologous recombination," *Science* 244:1288–1292 (1989).

Karin and Richards, "Human metalothionein genes—primary structure of the metalothionein–II gene and a related processed protein," *Nature* 299:797–802 (1982).

Kishimoto, et al., "Heterologous mutations of the β subunit common to the LFA–1, Mac–1 and p1150,95 glycoproteins cause leukocyte adhesion deficiency," *Cell* 50:193–202 (1987).

Kishimoto, et al., "Cloning of the β subunit of the leukocyte adhesion proteins: homology to an extracellular matrix receptor defines a novel supergene family," *Cell* 48:681–690 (1987).

Landis, et al., "A novel LFA–1 activation epitope maps to the I domain," *J.Cell.Biol.* 120:1519–1527 (1993).

Larson, et al., "Primary structure of the leukocyte function–associated molecule–1 α subunit: an integrin with an embedded domain defining a protein superfamily," *J.Cell.Biol.* 108:703–712 (1989).

Larson and Springer, "Structure and function of leukocyte integrins," *Immunol.Rev.* 114:181–217 (1990).

Letvin, et al., "Conservation of myeloid surface antigens on primary granulocytes," *Blood* 61:408–410 (1983).

McCabe, "Production of single–stranded DNa by assymetric PCR," in *PCR Protocols: A Guide to Methods and Applications*, Innis et al. (ed) Academic Press: New York (1990) pp.76–83.

Metlay, et al., "The distinct leukocyte integrins of mouse spleen dendritic cells as identified with new hamster monoclonal antibodies," *J.Exp.Med.* 171:1753–1771 (1990).

Michishita, et al., "A novel divalent cation–binding site in the A domain of the β2 integrin CR3 (CD11b/CD18) is essential for lignad binding," *Cell* 72:857–867 (1993).

Moore, et al., "Canine leukocyte integrins: characterization of a CD18 homologue," *Tissue Antigens* 36:211–220 (1990).

Nourshargh, et al., "Accumulation of $^{111}$In–neutrophils in rabbit skin allergic and non–allergic inflammatory reactions in vivo," *J.Immunol.* 142:3193–3198 (1989).

Patarroyo, et al., "Leukocyte–cell adhesion: a molecular process fundamental in leukocyte physiology," *Immunol. Rev.* 114:67–108 (1990).

Price, et al., "In vivo inhibition of neutrophil function in the rabbis using monoclonal antibody to CD18," *J.Immunol.* 139:4174–4177 (1987).

Randi and Hogg, "I domain of $\beta_2$ integrin lymphocyte function–associated antigen–1 contains a binding site for ligand intecellular adhesion molecule–1," *J.Biol.Chem.* 269:12395–12398 (1994).

Rojiani et al., "In vitro interaction of a polypeptide homologous to human Ro/SS–A antigen (calreticulin) 3with a highly conserved amino acid sequence in the cytoplasmic domain of integrin α subunits," *Biochemistry* 30:9859–9866 (1991).

Rosenfeld, et al., "Fatty streak initiation in Watanabe heritable hyperlipemic and comparably hypercholesterolemic fat–fed rabbits" *Arteriosclerosis* 7:9–23 (1987).

Rosenfeld, et al., "Fatty streak expansion and maturation in Watanabe heritable hyperlipemic and hypercholesterolemic fat–fed rabbits" *Arteriosclerosis* 7:24–43 (1987).

Sambrook, et al.,(eds), "Immobilization of Bacteriphage λ plaques on nitrocellulose filters or nylon membranes" in *Molecular Cloning: a laboratory manual*, Cold Spring Harbor Press:ColdSring Harbor, NY (1989) p. 2.110.

Sanchez–Madrid, et al., "A human leukocyte differentiation antigen family with distinct α–subunits and a common β–subunit," *J.Exp.Med.* 154:1517 (1981).

Schneiderman, et al., "Expression of 12 rabbit IgA Cα genes as chimeric rabbit–mouse IgA antibodies," *Proc.Natl.Acad. Sci. (USA)* 86:7562–7565 (1989).

Schwab, et al., "Pro–and anti–inflammatory roles of interleukin–1 in recurrence of bacterail cell wall–induced arthritis in rats," *Infection and Immunity* 59:4436–4442 (1991).

Searle, et al., "Regulation, linkage, and sequence of mouse metalothionein I and II genes," *Mol.Cell.Biol.* 4:1221–1230 (1984).

Shaw, et al., "Molecular cloning of the human mucosal lymphocyte integrin $\alpha_E$ subunit," *J.Biol.Chem.* 269:6016–6025 (1994).

Smith, et al., "Cooperative interactions of LFA–1 and Mac–1 with intercellular adhesion molecule–1 in facilitating adherence and transendothelial migration of human neutrophils in vitro," *J.Clin.Invest.* 83:2008–2017 (1989).

Springer, "Adhesion molecules of the immune system," *Nature* 346:425–434 (1990).

Tamura, et al., "Epithelial integrin$\alpha_6\beta^4$: complete primary structure of $\alpha^6$ and variant forms of $\beta^4$," *J.Cell.Biol.* 111:1593–1604 (1990).

Ueda, et al., "Identification of the complement iC3b binding site in the β2 integrin CR3 (CD11b/CD18)," *Proc.Natl.Acad.Sci. (USA)* 91:10680–10684 (1994).

Varshney, et al., "Structure, organization, and regulation of human metalothionein $I^F$ gene: differential and cell–type–specific expression in response to heavy metals and glucocorticoids," *Mol.Cell.Biol.* 6:26–36 (1986).

Yamada, et al., "Mucosal injury and inflammation in a model of chronic granulomatous colitis in rats," *Gastroenterology* 104:759–771 (1993).

Zhou, et al., "Differential ligand binding specificities of recombinant CD11b/CD8 integrin I–domain" *J.Biol.Chem.* 269: 17076–17079 (1994).

```
αD    TF-GT--VLL LSVLASYHGF NLDVEEPTIF QEDAGGFGQS VVQFGGSRLV   47
CD11B MA-LR--VLL LTALTLCHGF NLDTENAMTF QENARGFGQS VVQLQGSRVV   47
CD11C MTRTRAALLL FTALATSLGF NLDTEELTAF RVDSAGFGDS VVQYANSWVV   50

αD    VGAPLEVVAA NQTGRLYDCA AATGMCQPIP LHIRPEAVNM SLGLTLAAST   97
CD11B VGAPQEIVAA NQRGSLYQCD YSTGSCEPIR LQVPVEAVNM SLGLSLAATT   97
CD11C VGAPQKIIAA NQIGGLYQCG YSTGACEPIG LQVPPEAVNM SLGLSLASTT  100

αD    NGSRLLACGP TLHRVCGENS YSKGSCLLLG SR-WEIIQTV PDATPECPHQ  146
CD11B SPPQLLACGP TVHQTCSENT YVKGLCFLFG SNLRQQPQKF PEALRGCPQE  147
CD11C SPSQLLACGP TVHHECGRNM YLTGLCFLLG PT--QLTQRL PVSRQECPRQ  148

αD    EMDIVFLIDG SGSIDQNDFN QMKGFVQAVM GQFEGTDTLF ALMQYSNLLK  196
CD11B DSDIAFLIDG SGSIIPHDFR RMKEFVSTVM EQLKKSKTLF SLMQYSEEFR  197
CD11C EQDIVFLIDG SGSISSRNFA TMMNFVRAVI SQFQRPSTQF SLMQFSNKFQ  198

αD    IHFTFTQFRT SPSQQSLVDP IVQLKGLTFT ATGILTVTQ  LFHHKNGARK  246
CD11B IHFTFKEFQN NPNPRSLVKP ITQLLGRTHT ATGIRKVVRE LFNITNGARK  247
CD11C THFTFEEFRR TSNPLSLLAS VHQLQGFTYT ATAIQNVVHR LFHASYGARR  248

αD    SAKKILIVIT DGQKYKDPLE YSDVIPQAEK AGIIRYAIGV GHAFQGPTAR  296
CD11B NAFKILVVIT DGEKFGDPLG YEDVIPEADR EGVIRYVIGV GDAFRSEKSR  297
CD11C DAIKILIVIT DGKKEGDSLD YKDVIPMADA AGIIRYAIGV GLAFQNRNSW  298
```

FIGURE 1A

| | | | | | |
|---|---|---|---|---|---|
| αD    | QELNTISSAP | PQDHVFKVDN | FAALGSIQKQ | LQEKIYAVEG | TQSRASSSFQ | 346 |
| CD11b | QELNTIASKP | PRDHVFQVNN | FEALKTIQNQ | LREKIFAIEG | TQTGSSSSFE | 347 |
| CD11c | KELNDIASKP | SQEHIFKVED | FDALKDIQNQ | LKEKIFAIEG | TETISSSSFE | 348 |
| αD    | HEMSQEGFST | ALTMDGLFLG | AVGSFSWSGG | AFLYPPNMSP | TFINMSQENV | 396 |
| CD11b | HEMSQEGFSA | AITSNGPLLS | TVGSYDWAGG | VFLYTSKEKS | TFINMTRVDS | 397 |
| CD11c | LEMAQEGFSA | VFTPDGPVLG | AVGSFTWSGG | AFLYPPNMSP | TFINMSQENV | 398 |
| αD    | DMRDSYLGYS | TELALWKGVQ | NLVLGAPRYQ | HTGKAVIFTQ | VSRQWRKKAE | 446 |
| CD11b | DMNDAYLGYA | AAILRNRVQ  | SLVLGAPRYQ | HIGLVAMFRQ | NTGMWESNAN | 447 |
| CD11c | DMRDSYLGYS | TELALWKGVQ | SLVLGAPRYQ | HIGKAVIFIQ | VSRQWRKKAE | 448 |
| αD    | VTGTQIGSYF | GASLCSVDVD | SDGSTDLILI | GAPHYYEQTR | GGQVSVCPLP | 496 |
| CD11b | VKGTQIGAYF | GASLCSVDVD | SNGSTDLVLI | GAPHYYEQTR | GGQVSVCPLP | 497 |
| CD11c | VIGTQIGSYF | GASLCSVDVD | TDGSTDLVLI | GAPHYYEQTR | GGQVSVCPLP | 498 |
| αD    | RGQRVQWQCD | AVLRGEQGHP | WGRFGAALTV | LGDVNEDKLI | DVAIGAPGEQ | 546 |
| CD11b | RGQRARWQCD | AVLYGEQGQP | WGRFGAALTV | LGDVNGDKLT | DVAIGAPGEE | 547 |
| CD11c | RGWRRWW-CD | AVLYGEQGHP | WGRFGAALTV | LGDVNGDKLT | DVVIGAPGEE | 547 |
| αD    | ENRGAVYLFH | GASESGISPS | HSQRIASSQL | SPRLQYFGQA | LSGGQDLTQD | 596 |
| CD11b | DNRGAVYLFH | GTSGSGISPS | HSQRIAGSKL | SPRLQYFGQS | LSGGQDLTMD | 597 |
| CD11c | ENRGAVYLFH | GVLGPSISPS | HSQRIAGSQL | SSRLQYFGQA | LSGGQDLTQD | 597 |

FIGURE 1B

|      |            |            |            |            |            |     |
|------|------------|------------|------------|------------|------------|-----|
| αD   | GLMDLAVGAR | GQVLLLRSLP | VLKVGVAMRF | SPVEVAKAVY | RCWEEKPSAL | 646 |
| CD11B | GLVDLTVGAQ | GHVLLLRSQP | VLRVKAIMEF | NPREVARNVF | ECNDQVVKGK | 647 |
| CD11C | GLVDLAVGAR | GQVLLLRTRP | VLWVGVSMQF | IPAEIPRSAF | ECREQVVSEQ | 647 |

|      |            |            |            |            |            |     |
|------|------------|------------|------------|------------|------------|-----|
| αD   | EAGDATVCLT | IQKSSLDQL- | -GDIQSSVRF | DLALDPGRLT | SRAIFNETKN | 694 |
| CD11B | EAGEVRVCLH | VQKSTRDRLR | EGQIQSVVTY | DLALDSGRPH | SRAVFNETKN | 697 |
| CD11C | TLVQSNICLY | IDKRSKNLLG | SRDLQSSVTL | DLALAPGRLS | PRAIFQETKN | 697 |

|      |            |            |            |            |            |     |
|------|------------|------------|------------|------------|------------|-----|
| αD   | PTLTTRKTLG | LGIHCETLKL | LLPDCVEDVV | SPIILHLNFS | LVREPIPSPQ | 744 |
| CD11B | STRRQTQVLG | LTQTCETLKL | QLPNCIEDPV | SPIVLRLNFS | LVGTPLSAFG | 747 |
| CD11C | RSLSRVRVLG | LKAHCENFNL | LLPSCVEDSV | IPIILRLNFT | LVGKPLLAFR | 747 |

|      |            |            |            |            |            |     |
|------|------------|------------|------------|------------|------------|-----|
| αD   | NLRPVLAVGS | QDLFTASLPF | EKNCGQDGLC | EGDLGVTLSF | SGLQTLTVGS | 794 |
| CD11B | NLRPVLAEDA | QRLFTALFPF | EKNCGNDNIC | QDDLSITFSF | MSLDCLVVGG | 797 |
| CD11C | NLRPHLAALA | QRYFTASLPF | EKNCGADHIC | QDNLGISFSF | PGLKSLLVGS | 797 |

|      |            |            |            |            |            |     |
|------|------------|------------|------------|------------|------------|-----|
| αD   | SLELNVIVTV | WNAGEDSYGT | VVSLYYPAGL | SHRRVSGAQK | QPHQSALRLA | 844 |
| CD11B | PREFNVTVTV | RNDGEDSYRT | QVTFFFPLDL | SYRKVSTLQN | QRSQRSWRLA | 847 |
| CD11C | NLELNAEVMV | WNDGEDSYGT | TITFSHPAGL | SYRYVAEGQK | QGQLRSLHLT | 847 |

|      |            |            |            |            |            |     |
|------|------------|------------|------------|------------|------------|-----|
| αD   | CETVPTED-- | EGLRSSRCSV | NHPIFHEGSN | GTFIVTFDVS | Y---KATLG  | 888 |
| CD11B | CESASSTEVS | GALKSTSCSI | NHPIFPENSE | ----VTFNIT | FDVDSKASLG | 893 |
| CD11C | CCSA-PVGSQ | GTW-STSCRI | NHLIFRGGAQ | ----ITFLAT | FDVSPKAVGL | 891 |

FIGURE 1C

|  |  |  |  |  |  |  |
|---|---|---|---|---|---|---|
| αD    | DRMLMRASAS | SENNKASSSK | ATFQLELPVK | YAVYTMISRQ | EESTKYFNFA | 938 |
| CD11b | NKLLLKANVT | SENNMPRTNK | TEFQLELPVK | YAVYMVVTSH | GVSTKYLNFT | 943 |
| CD11c | DRLLIANVS  | SENNIPRTSK | TIFQLELPVK | YAVYIVVSSH | EQFTKYLNFS | 941 |

|  |  |  |  |  |  |  |
|---|---|---|---|---|---|---|
| αD    | TS-DEKMKE  | AEHRYRVNNL | SQRDLAISIN | FWVPVLLNGV | AVWDVVMEAP | 987 |
| CD11b | AS-ENTS-RV | MQHQYQVSNL | GQRSLPISLV | FLVPVRLNQT | VIWDRPQVTF | 991 |
| CD11c | ESEEKES-HV | AMHRYQVNNL | GQRDLPVSIN | FWVPVELNQE | AVWMDVEVSH | 990 |

|  |  |  |  |  |  |  |
|---|---|---|---|---|---|---|
| αD    | SQSLP--CVS | ERKPPQHSDF | LTQISRSPML | DCSIADCLQF | RCDVPSFSVQ | 1035 |
| CD11b | SENLSSTCHT | KERLPSHSDF | LAELRKAPVV | NCSIAVCQRI | QCDIPFFGIQ | 1041 |
| CD11c | PQNPSLRCSS | EKIAPPASDF | LAHIQKNPVL | DCSIAGCLRF | RCDVPSFSVQ | 1040 |

|  |  |  |  |  |  |  |
|---|---|---|---|---|---|---|
| αD    | EELDFTLKGN | LSFGWVRETL | QKKVLVVSVA | EITFDTSVYS | QLPGQEAFMR | 1085 |
| CD11b | EEFNATLKGN | LSFDWYIKTS | HNHLLIVSTA | EILFNDSVFT | LLPGQGAFVR | 1091 |
| CD11c | EELDFTLKGN | LSFGWVRQIL | QKKVSVSVA  | EIIFDTSVYS | QLPGQEAFMR | 1090 |

|  |  |  |  |  |  |  |
|---|---|---|---|---|---|---|
| αD    | AQMEMVLEED | EVYNAIPIIM | GSSVGALLLL | ALITATLYKL | GFFKRHYKEM | 1135 |
| CD11b | SQTETKVEPF | EVPNPLPLIV | GSSVGGLLLL | ALITAALYKL | GFFKRQYKDM | 1141 |
| CD11c | AQTITVLEKY | KVHNPIPLIV | GSSIGGLLLL | ALITAVLYKV | GFFKRQYKEM | 1140 |

|  |  |  |  |  |
|---|---|---|---|---|
| αD    | LEDKPED---   | ----TATFS  | GDDFSCVAPN | VPLS | 1161 |
| CD11b | M---SEG---   | -----GP--P | GAE-----PQ | ---  | 1153 |
| CD11c | M---EEANGQ   | IAPENGT--Q | TPS-----PP | SEK  | 1163 |

FIGURE 1D

HUMAN β2 INTEGRIN α SUBUNIT

This application is a continuation-in-part of U.S. application Ser. No. 08/286,889, filed Aug. 5, 1994, U.S. Pat. No. 5,470,953, which in turn is a continuation-in-part of U.S. application Ser. No. 08/173,497, filed Dec. 23, 1993, U.S. Pat. No. 5,437,958.

FIELD OF THE INVENTION

The present invention relates to the cloning and expression of polynucleotides encoding a novel human $\beta_2$ integrin a subunit, designated $\alpha_d$, which is structurally related to the known human $\beta_2$ integrin α subunits, CD11a, CD11b and CD11c. The present invention also relates to polynucleotides isolated from other species which show homology to human $\alpha_d$ encoding sequences.

BACKGROUND OF THE INVENTION

The integrins are a class of membrane-associated molecules which actively participate in cellular adhesion. Integrins are transmembrane heterodimers comprising an α subunit in noncovalent association with a β subunit. To date, at least fourteen α subunits and eight β subunits have been identified [reviewed in Springer, *Nature* 346:425–434 (1990)]. The β subunits are generally capable of association with more than one α subunit and the heterodimers sharing a common β subunit have been classified as subfamilies within the integrin population.

One class of human integrins, restricted to expression in white blood cells, is characterized by a common $\beta_2$ subunit. As a result of this cell-specific expression, these integrins are commonly referred to as the leukocyte integrins, Leu-CAMs or leukointegrins. Because of the common $\beta_2$ subunit, an alternative designation of this class is the $\beta_2$ integrins. The $\beta_2$ subunit (CD18) has previously been isolated in association with one of three distinct α subunits, CD11a, CD11b or CD11c. The isolation of a cDNA encoding human CD18 is described in Kishimoto, et al., *Cell* 48:681–690 (1987). In official WHO nomenclature, the heterodimeric proteins are referred to as CD11a/CD18, CD11b/CD18, and CD11c/CD18; in common nomenclature they are referred to as LFA-1, Mac-1 or Mo1 and p150,95 or LeuM5, respectively [Cobbold, et al., in *Leukocyte Typing III*, McMichael (ed), Oxford Press, p.788 (1987)]. The human $\beta_2$ integrin α subunits CD11a, CD11b and CD11c have been demonstrated to migrate under reducing condition in electrophoresis with apparent molecular weights of approximately 180 kD, 155 kD and 150 kD, respectively, and DNAs encoding these subunits have been cloned [CD11a, Larson, et al., *J.Cell Biol.* 108:703–712 (1989); CD11b, Corbi, et al., *J.Biol.Chem.* 263:12403–12411(1988) and CD11c, Corbi, et al. *EMBO J.* 6:4023–4028 (1987)]. Putative homologs of the human $\beta_2$ integrin α and β chains, defined by approximate similarity in molecular weight, have been variously identified in other species including monkeys and other primates [Letvin, et al., *Blood* 61:408–410 (1983)], mice [Sanchez-Madrid, et al., *J.Exp.Med.* 154:1517 (1981)], and dogs [Moore, et al., *Tissue Antigens* 36:211–220 (1990)].

The absolute molecular weights of presumed homologs from other species have been shown to vary significantly [see, e.g., Danilenko et al., *Tissue Antigens* 40:13–21 (1992) ], and in the absence of sequence information, a definitive correlation between human integrin subunits and those identified in other species has not been possible. Moreover, variation in the number of members in a protein family has been observed between different species. Consider, for example, that more IgA isotypes have been isolated in rabbits than in humans [Burnett, et al., *EMBO J.* 8:4041–4047 (1989) and Schneiderman, et al., *Proc.Natl.Acad.Sci.(USA)* 86:7561–7565 (1989)]. Similarly, in humans, at least six variants of the metallothionine protein have been previously identified [Karin and Richards, *Nature* 299:797–802 (1982) and Varshney, et al., *Mol.Cell.Biol.* 6:26–37, (1986)], whereas in the mouse, only two such variants are in evidence [Searle, et al., *Mol.Cell.Biol.* 4:1221–1230 (1984)]. Therefore, existence of multiple members of a protein family in one species does not necessarily imply that corresponding family members exist in another species.

In the specific context of $\beta_2$ integrins, in dogs it has been observed that the presumed canine $\beta_2$ counterpart to the human CD18 is capable of dimer formation with as many as four potentially distinct α subunits [Danilenko, et al., supra]. Antibodies generated by immunizing mice with canine splenocytes resulted in monoclonal antibodies which immunoprecipitated proteins tentatively designated as canine homologs to human CD18, CD11a, CD11b and CD11c based mainly on similar, but not identical, molecular weights. Another anti-canine splenocyte antibody, Ca11.8H2, recognized and immunoprecipitated a fourth α-like canine subunit also capable of association with the $\beta_2$ subunit, but having a unique molecular weight and restricted in expression to a subset of differentiated tissue macrophages. Antibodies generated by immunization of hamsters with murine dendritic cells resulted in two anti-integrin antibodies [Metlay, et al., *J.Exp.Med.* 171:1753–1771 (1990)]. One antibody, 2E6, immunoprecipitated a predominant heterodimer with subunits having approximate molecular weights of 180 kD and 90 kD in addition to minor bands in the molecular weight range of 150–160 kD. The second antibody, N418, precipitated another apparent heterodimer with subunits having approximate molecular weights of 150 kD and 90 Kd. Based on cellular adhesion blocking studies, it was hypothesized that antibody 2E6 recognized a murine counterpart to human CD18. While the molecular weight of the N418 antigen suggested recognition of a murine homolog to human CD11c/CD18, further analysis indicated that the murine antigen exhibited a tissue distribution pattern which was inconsistent with that observed for human CD11c/CD18.

The antigens recognized by the canine Ca11. 8H2 antibody and the murine N418 antibody could represent a variant species (e.g., a glycosylation or splice variant) of a previously identified canine or murine α subunit. Alternatively, these antigens may represent unique canine and murine integrin α subunits. In the absence of specific information regarding primary structure, these alternatives cannot be distinguished.

In humans, CD11a/CD18 is expressed on all leukocytes. CD11b/CD18 and CD11c/CD18 are essentially restricted to expression on monocytes, granulocytes, macrophages and natural killer (NK) cells, but CD11c/CD18 is also detected on some B-cell types. In general, CD11a/CD18 predominates on lymphocytes, CD11b/CD18 on granulocytes and CD11c/CD18 on macrophages [see review, Arnaout, *Blood* 75:1037–1050 (1990)]. Expression of the α chains, however, is variable with regard to the state of activation and differentiation of the individual cell types [See review, Larson and Springer, *Immunol.Rev.* 114:181–217 (1990).]

The involvement of the $\beta_2$ integrins in human immune and inflammatory responses has been demonstrated using monoclonal antibodies which are capable of blocking $\beta_2$ integrin-associated cell adhesion. For example, CD11a/

CD18, CD11b/CD18 and CD11c/CD18 actively participate in natural killer (NK) cell binding to lymphoma and adenocarcinoma cells [Patarroyo, et al., *Immunol.Rev.* 114:67–108 (1990)], granulocyte accumulation [Nourshargh, et al., *J.Immunol.* 142:3193–3198 (1989)], granulocyte-independent plasma leakage [Arfors, et al., *Blood* 69:338–340 (1987)], chemotactic response of stimulated leukocytes [Arfors, et al., supra] and leukocyte adhesion to vascular endothelium [Price, et al., *J.Immunol.* 139:4174–4177 (1987) and Smith, et al., *J.Clin.Invest.* 83:2008–2017 (1989)]. The fundamental role of $\beta_2$ integrins in immune and inflammatory responses is made apparent in the clinical syndrome referred to as leukocyte adhesion deficiency (LAD), wherein clinical manifestations include recurrent and often life threatening bacterial infections. LAD results from heterogeneous mutations in the $\beta_2$ subunit [Kishimoto, et al., *Cell* 50:193–202 (1987)] and the severity of the disease state is proportional to the degree of the deficiency in $\beta_2$ subunit expression. Formation of the complete integrin heterodimer is impaired by the $\beta_2$ mutation [Kishimoto, et al., supra].

Interestingly, at least one antibody specific for CD18 has been shown to inhibit human immunodeficiency virus type-1 (HIV-1) syncytia formation in vitro, albeit the exact mechanism of this inhibition is unclear [Hildreth and Orentas, *Science* 244:1075–1078 (1989)]. This observation is consistent with the discovery that a principal counterreceptor of CD11a/CD18, ICAM-1, is also a surface receptor for the major group of rhinovirus serotypes [Greve, et al., *Cell* 56:839 (1989)].

The significance of $\beta_2$ integrin binding activity in human immune and inflammatory responses underscores the necessity to develop a more complete understanding of this class of surface proteins. Identification of yet unknown members of this subfamily, as well as their counterreceptors, and the generation of monoclonal antibodies or other soluble factors which can alter biological activity of the $\beta_2$ integrins will provide practical means for therapeutic intervention in $\beta_2$ integrin-related immune and inflammatory responses.

BRIEF DESCRIPTION OF THE INVENTION

In one aspect, the present invention provides novel purified and isolated polynucleotides (e.g., DNA and RNA transcripts, both sense and anti-sense strands) encoding a novel human $\beta_2$ integrin $\alpha$ subunit, $\alpha_d$, and variants thereof (i.e., deletion, addition or substitution analogs) which possess binding and/or immunological properties inherent to $\alpha_d$. Preferred DNA molecules of the invention include cDNA, genomic DNA and wholly or partially chemically synthesized DNA molecules. A presently preferred polynucleotide is the DNA as set forth in SEQ ID NO: 1, encoding the polypeptide of SEQ ID NO: 2. Also provided are recombinant plasmid and viral DNA constructions (expression constructs) which include $\alpha_d$ encoding sequences, wherein the $\alpha_d$ encoding sequence is operatively linked to a homologous or heterologous transcriptional regulatory element or elements.

Also provided by the present invention are isolated and purified mouse and rat polynucleotides which exhibit homology to polynucleotides encoding human $\alpha_d$. A preferred mouse polynucleotide is set forth in SEQ ID NO: 52; a preferred rat polynucleotide is set forth in SEQ ID NO: 54.

As another aspect of the invention, prokaryotic or eukaryotic host cells transformed or transfected with DNA sequences of the invention are provided which express $\alpha_d$ polypeptide or variants thereof. Host cells of the invention are particularly useful for large scale production of $\alpha_d$ polypeptide, which can be isolated from either the host cell itself or from the medium in which the host cell is grown. Host cells which express $\alpha_d$ polypeptide on their extracellular membrane surface are also useful as immunogens in the production of $\alpha_d$-specific antibodies. Preferably, host cells transfected with $\alpha_d$ will be co-transfected to express a $\beta_2$ integrin subunit in order to allow surface expression of the heterodimer.

Also provided by the present invention are purified and isolated $\alpha_d$ polypeptides, fragments and variants thereof. Preferred $\alpha_d$ polypeptides are as set forth in SEQ ID NO: 2. Novel $\alpha_d$ products of the invention may be obtained as isolates from natural sources, but, along with $\alpha_d$ variant products, are preferably produced by recombinant procedures involving host cells of the invention. Completely glycosylated, partially glycosylated and wholly deglycosylated forms of the $\alpha_d$ polypeptide may be generated by varying the host cell selected for recombinant production and/or post-isolation processing. Variant $\alpha_d$ polypeptides of the invention may comprise water soluble and insoluble $\alpha_d$ polypeptides including analogs wherein one or more of the amino acids are deleted or replaced: (1) without loss, and preferably with enhancement, of one or more biological activities or immunological characteristics specific for $\alpha_d$; or (2) with specific disablement of a particular ligand/receptor binding or signalling function. Fusion polypeptides are also provided, wherein $\alpha_d$ amino acid sequences are expressed contiguously with amino acid sequences from other polypeptides. Such fusion polypeptides may possess modified biological, biochemical, and/or immunological properties in comparison to wild-type $\alpha_d$. Analog polypeptides including additional amino acid (e.g., lysine or cysteine) residues that facilitate multimer formation are contemplated.

Also comprehended by the present invention are polypeptides and other non-peptide molecules which specifically bind to $\alpha_d$. Preferred binding molecules include antibodies (e.g., monoclonal and polyclonal antibodies), counterreceptors (e.g., membrane-associated and soluble forms) and other ligands (e.g., naturally occurring or synthetic molecules), including those which competitively bind $\alpha_d$ in the presence of $\alpha_d$ monoclonal antibodies and/or specific counterreceptors. Binding molecules are useful for purification of $\alpha_d$ polypeptides and identifying cell types which express $\alpha_d$. Binding molecules are also useful for modulating (i.e., inhibiting, blocking or stimulating) of in vivo binding and/or signal transduction activities of $\alpha_d$.

Assays to identify $\alpha_d$ binding molecules are also provided, including immobilized ligand binding assays, solution binding assays, scintillation proximity assays, di-hybrid screening assays, and the like.

In vitro assays for identifying antibodies or other compounds that modulate the activity of $\alpha_d$ may involve, for example, immobilizing $\alpha_d$ or a natural ligand to which $\alpha_d$ binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of $\alpha_d$ binding.

Another type of assay for identifying compounds that modulate the interaction between $\alpha_d$ and a ligand involves immobilizing $\alpha_d$ or a fragment thereof on a solid support coated (or impregnated with) a fluorescent agent, labelling the ligand with a compound capable of exciting the fluorescent agent, contacting the immobilized $\alpha_d$ with the labelled ligand in the presence and absence of a putative modulator compound, detecting light emission by the fluorescent agent, and identifying modulating compounds as those compounds that affect the emission of light by the fluorescent agent in comparison to the emission of light by the fluorescent agent in the absence of a modulating compound. Alternatively, the $\alpha_d$ ligand may be immobilized and $\alpha_d$ may be labelled in the assay.

Yet another method contemplated by the invention for identifying compounds that modulate the interaction between $\alpha_d$ and a ligand involves transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a second hybrid DNA sequence encoding part or all of the ligand and the DNA binding domain or activating domain of the transcription factor which is not incorporated in the first fusion, evaluating the effect of a putative modulating compound on the interaction between $\alpha_d$ and the ligand by detecting binding of the ligand to $\alpha_d$ in a particular host cell by measuring the production of reporter gene product in the host cell in the presence or absence of the putative modulator, and identifying modulating compounds as those compounds altering production of the reported gene product in comparison to production of the reporter gene product in the absence of the modulating compound. Presently preferred for use in the assay are the lexA promoter, the lexA DNA binding domain, the GAL4 transactivation domain, the lacZ reporter gene, and a yeast host cell.

A modified version of the foregoing assay may be used in isolating a polynucleotide encoding a protein that binds to $\alpha_d$ by transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a library of second hybrid DNA sequences encoding second fusions of part or all of putative $\alpha_d$ binding proteins and the DNA binding domain or activating domain of the transcription factor which is not incorporated in the first fusion, detecting binding of an $\alpha_d$ binding protein to $\alpha_d$ in a particular host cell by detecting the production of reporter gene product in the host cell, and isolating second hybrid DNA sequences encoding $\alpha_d$ binding protein from the particular host cell.

Hybridoma cell lines which produce antibodies specific for $\alpha_d$ are also comprehended by the invention. Techniques for producing hybridomas which secrete monoclonal antibodies are well known in the art. Hybridoma cell lines may be generated after immunizing an animal with purified $\alpha_d$, variants of $\alpha_d$ or cells which express $\alpha_d$ or a variant thereof on the extracellular membrane surface. Immunogen cell types include cells which express $\alpha_d$ in vivo, or transfected prokaryotic or eukaryotic cell lines which normally do not normally express $\alpha_d$ in vivo.

The value of the information contributed through the disclosure of the DNA and amino acid sequences of $\alpha_d$ is manifest. In one series of examples, the disclosed $\alpha_d$ CDNA sequence makes possible the isolation of the human $\alpha_d$ genomic DNA sequence, including transcriptional control elements for the genomic sequence. Identification of $\alpha_d$ allelic variants and heterologous species (e.g., rat or mouse) DNAs is also comprehended. Isolation of the human $\alpha_d$ genomic DNA and heterologous species DNAs can be accomplished by standard DNA/DNA hybridization techniques, under appropriately stringent conditions, using all or part of the $\alpha_d$ cDNA sequence as a probe to screen an appropriate library. Alternatively, polymerase chain reaction (PCR) using oligonucleotide primers that are designed based on the known cDNA sequence can be used to amplify and identify genomic $\alpha_d$ DNA sequences. Synthetic DNAs encoding the $\alpha_d$ polypeptide, including fragments and other variants thereof, may be produced by conventional synthesis methods.

DNA sequence information of the invention also makes possible the development, by homologous recombination or "knockout" strategies [see, e.g., Kapecchi, *Science* 244:1288–1292 (1989)], to produce rodents that fail to express a functional $\alpha_d$ polypeptide or that express a variant $\alpha_d$ polypeptide. Such rodents are useful as models for studying the activities of $\alpha_d$ and $\alpha_d$ modulators in vivo.

DNA and amino acid sequences of the invention also make possible the analysis of $\alpha_d$ epitopes which actively participate in counterreceptor binding as well as epitopes which may regulate, rather than actively participate in, binding. Identification of epitopes which may participate in transmembrane signal transduction is also comprehended by the invention.

DNA of the invention is also useful for the detection of cell types which express $\alpha_d$ polypeptide. Standard DNA/RNA hybridization techniques which utilize $\alpha_d$ DNA to detect $\alpha_d$ RNA may be used to determine the constitutive level of $\alpha_d$ transcription within a cell, as well as changes in the level of transcription in response to internal or external agents. Identification of agents which modify transcription and/or translation of $\alpha_d$ can, in turn, be assessed for potential therapeutic or prophylactic value. DNA of the invention also makes possible in situ hybridization of $\alpha_d$ DNA to cellular RNA to determine the cellular localization of $\alpha_d$ specific messages within complex cell populations and tissues.

DNA of the invention is also useful for identification of non-human polynucleotide sequences which display homology to human $\alpha_d$ sequences. Possession of non-human $\alpha_d$ DNA sequences permits development of animal models (including, for example, transgenic models) of the human system.

As another aspect of the invention, monoclonal or polyclonal antibodies specific for $\alpha_d$ may be employed in immunohistochemical analysis to localize $\alpha_d$ to subcellular compartments or individual cells within tissues. Immunohistochemical analyses of this type are particularly useful when used in combination with in situ hybridization to localize both $\alpha_d$ mRNA and polypeptide products of the $\alpha_d$ gene.

Identification of cell types which express $\alpha_d$ may have significant ramifications for development of therapeutic and prophylactic agents. It is anticipated that the products of the invention related to $\alpha_d$ can be employed in the treatment of diseases wherein macrophages are an essential element of the disease process. Animal models for many pathological conditions associated with macrophage activity have been described in the art. For example, in mice, macrophage recruitment to sites of both chronic and acute inflammation is reported by Jutila, et al., *J.Leukocyte Biol.* 54:30–39 (1993). In rats, Adams, et al., [*Transplantation* 53:1115–1119(1992) and *Transplantation* 56:794–799 (1993)] describe a model for graft arteriosclerosis following heterotropic abdominal cardiac allograft transplantation. Rosenfeld, et al., [*Arteriosclerosis* 7:9–23 (1987) and *Arteriosclerosis* 7:24–34 (1987)] describe induced atherosclerosis in rabbits fed a cholesterol supplemented diet. Hanenberg, et al., [*Diabetologia* 32:126–134 (1989)] report the spontaneous development of insulin-dependent diabetes in BB rats. Yamada et al., [*Gastroenterolgy* 104:759–771 (1993)] describe an induced inflammatory bowel disease, chronic granulomatous colitis, in rats following injections of streptococcal peptidoglycan-polysaccharide polymers. Cromartie, et al., [*J.Exp.Med.* 146:1585–1602 (1977)] and Schwab, et al., [*Infection and Immunity* 59:4436–4442 (1991)] report that injection of streptococcal cell wall protein into rats results in an arthritic condition characterized by inflammation of peripheral joints and subsequent joint destruction. Finally, Huitinga, et al., [*Eur.J.Immunol* 23:709–715 (1993) describe experimental allergic encephalomyelitis, a model for multiple sclerosis, in Lewis rats. In each of these models, $\alpha_d$ antibodies, other $\alpha_d$ binding proteins, or soluble forms of $\alpha_d$ are utilized to attenuate the disease state, presumably through inactivation of macrophage activity.

Pharmaceutical compositions for treatment of these and other disease states are provided by the invention. Pharmaceutical compositions are designed for the purpose of inhibiting interaction between $\alpha_d$ and its ligand(s) and include various soluble and membrane-associated forms of $\alpha_d$ (comprising the entire $\alpha_d$ polypeptide, or fragments thereof which actively participate in $\alpha_d$ binding), soluble and membrane-associated forms of $\alpha_d$ binding proteins (including antibodies, ligands, and the like), intracellular or extracellular modulators of $\alpha_d$ binding activity, and/or modulators of $\alpha_d$ and/or $\alpha_d$-ligand polypeptide expression, including modulators of transcription, translation, post-translational processing and/or intracellular transport. The invention also comprehends methods for treatment of disease states in which $\alpha_d$ binding is implicated, wherein a patient suffering from said disease state is provided an amount of a pharmaceutical composition of the invention sufficient to modulate levels of $\alpha_d$ binding. The method of treatment of the invention is applicable to disease states such as, but not limited to, Type I diabetes, atherosclerosis, multiple sclerosis, asthma, psoriasis, and rheumatoid arthritis.

BRIEF DESCRIPTION OF THE DRAWING

Numerous other aspects and advantages of the present invention will be apparent upon consideration of the following description thereof, reference being made to the drawing wherein:

FIG. 1A through 1D comprises an alignment of the human amino acid sequences of CD11b (SEQ ID NO: 3), CD11c (SEQ ID NO: 4) and $\alpha_d$ (SEQ ID NO: 2).

DETAILED DESCRIPTION OF THE INVENTION

The present invention is illustrated by the following examples relating to the isolation of a cDNA clone encoding $\alpha_d$ from a human spleen cDNA library. More particularly, Example 1 illustrates the use of anti-canine $\alpha_{TM1}$ antibody in an attempt to detect a homologous human protein. Example 2 details purification of canine $\alpha_{TM1}$ and N-terminal sequencing of the polypeptide to design oligonucleotide primers for PCR amplification of the canine $\alpha_{TM1}$ gene. Example 3 addresses large scale purification of canine $\alpha_{TM1}$ for internal sequencing in order to design additional PCR primers. Example 4 describes use of the PCR and internal sequence primers to amplify a fragment of the canine $\alpha_{TM1}$ gene. Example 5 addresses cloning of the human $\alpha_d$-encoding cDNA sequence. Example 6 describes Northern blot hybridization analysis of human tissues and cells for expression of $\alpha_d$ mRNA. Example 7 details the construction of human $\alpha_d$ expression plasmids and transfection of COS cells with the resulting plasmids. Example 8 addresses ELISA analysis of $\alpha_d$ expression in transfected COS cells. Example 9 describes FACS analysis of COS cells transfected with human $\alpha_d$ expression plasmids. Example 10 addresses immunoprecipitation of CD18 in association with $\alpha_d$ in co-transfected COS cells. Example 11 relates to stable transfection of $\alpha_d$ expression constructs in Chinese hamster ovary cells. Example 12 addresses CD18-dependent binding of $\alpha_d$ to the intercellular adhesion molecule, ICAM-R. Example 13 describes scintillation proximity screening assays to identify inhibitors of $\alpha_d$ ligand/anti-ligand binding interactions. Example 14 addresses construction of expression plasmids which encode soluble forms of $\alpha_d$. Example 15 relates to production of $\alpha_d$-specific monoclonal antibodies. Example 16 describes analysis of $\alpha_d$ tissue distribution using polyclonal antiserum. Example 17 describes isolation of rat cDNA sequences which show homology to human $\alpha_d$ gene sequences. Example 18 relates to construction of rat $\alpha_d$ I domain expression plasmids, including I domain/IgG fusion proteins, and production of monoclonal antibodies to I domain fusion proteins. Example 19 addresses isolation of mouse cDNA sequences which show homology to human $\alpha_d$ gene sequences. Example 20 describes isolation of additional mouse $\alpha_d$ cDNA clones used for conformational sequence analysis. Example 21 relates to in situ hybridization analysis of various mouse tissues to determine tissue and cell specific expression of the putative mouse homolog to human $\alpha_d$. Example 22 describes generation of expression constructs which encode the putative mouse homolog of human $\alpha_d$. Example 23 addresses design of a "knock-out" mouse wherein the gene encoding the putative mouse homolog of human $\alpha_d$ is disrupted. Example 24 describes isolation of rabbit cDNA clones which show homology to human $\alpha_d$ encoding sequences. Example 25 describes animal models which resemble human disease states wherein modulation of $\alpha_d$ is assayed for therapeutic capabilities.

EXAMPLE 1

Attempt to Detect a Human Homolog of Canine $\alpha_{TM1}$

The monoclonal antibody Ca11.8H2 [Moore, et al., supra] specific for canine $\alpha_{TM1}$ was tested for cross-reactivity on human peripheral blood leukocytes in an attempt to identify a human homolog of canine $\alpha_{TM1}$. Cell preparations (typically 1×10⁶ cells) were incubated with undiluted hybridoma supernatant or a purified mouse IgG-negative control antibody (10 µg/ml) on ice in the presence of 0.1% sodium azide. Monoclonal antibody binding was detected by subsequent incubation with FITC-conjugated horse anti-mouse IgG (Vector Laboratories, Burlingame, Calif.) at 6 µg/ml. Stained cells were fixed with 2% w/v paraformaldehyde in phosphate buffered saline (PBS) and were analyzed with a Facstar Plus fluorescence-activated cell sorter (Becton Dickinson, Mountain View, Calif.). Typically, 10,000 cells were analyzed using logarithmic amplification for fluorescence intensity.

The results indicated that Ca11.8H2 did not cross-react with surface proteins expressed on human peripheral blood leukocytes, while the control cells, neoplastic canine peripheral blood lymphocytes, were essentially all positive for $\alpha_{TM1}$.

Because the monoclonal antibody Ca11.8H2 specific for the canine $\alpha$ subunit did not cross react with a human homolog, isolation of canine $\alpha_{TM1}$ DNA was deemed a necessary prerequisite to isolate a counterpart human gene if one existed.

EXAMPLE 2
Affinity Purification Of Canine $\alpha_{TM1}$ For N-Terminal Sequencing Canine $\alpha_{TM1}$ was affinity purified in order to determine N-terminal amino acid sequences for oligonucleotide probe/primer design. Briefly, anti-$\alpha_{TM1}$ monoclonal antibody Ca11.8H2 was coupled to Affigel 10 chromatographic resin (BioRad, Hercules, Calif.) and protein was isolated by specific antibody-protein interaction. Antibody was conjugated to the resin, according to the BioRad suggested protocol, at a concentration of approximately 5 mg antibody per ml of resin. Following the conjugation reaction, excess antibody was removed and the resin blocked with three volumes of 0.1M ethanolamine. The resin was then washed with thirty column volumes of phosphate buffered saline (PBS).

Twenty-five grams of a single dog spleen were homogenized in 250 ml of buffer containing 0.32M sucrose in 25 mM Tris-HCl, Ph 8.0, with protease inhibitors. Nuclei and cellular debris were pelleted with centrifugation at 1000 g for 15 minutes. Membranes were pelleted from the supernatant with centrifugation at 100,000 g for 30 minutes. The membrane pellet was resuspended in 200 ml lysis buffer (50 mM NaCl, 50 mM borate, pH 8.0, with 2% NP-40) and incubated for 1 hour on ice. Insoluble material was then pelleted by centrifugation at 100,000 g for 60 minutes. Ten milliliters of the cleared lysate were transferred to a 15 ml polypropylene tube with 0.5 ml Ca11.8H2-conjugated Affigel 10 resin described above. The tube was incubated overnight at 4° C. with rotation and the resin subsequently washed with 50 column volumes D-PBS. The resin was then transferred to a microfuge tube and boiled for ten minutes in 1 ml Laemmli (non-reducing) sample buffer containing 0.1M Tris-HCl, pH 6.8, 2% SDS, 20% glycerol and 0.002% bromophenol blue. The resin was pelleted by centrifugation and discarded; the supernatant was treated with 1/15 volume β-mercaptoethanol (Sigma, St. Louis, Mo.) and run on a 7% polyacrylamide gel. The separated proteins were transferred to Immobilon PVDF membrane (Millipore, Bedford, Mass.) as follows.

The gels were washed once in deionized, Millipore-filtered water and equilibrated for 15-45 minutes in 10 mM 3-[cyclohexylamino]-1-propanesulfonic acid (CAPS) transfer buffer, pH 10.5, with 10% methanol. Immobilon membranes were moistened with methanol, rinsed with filtered water, and equilibrated for 15-30 minutes in CAPS transfer buffer. The initial transfer was carried out using a Biorad transfer apparatus at 70 volts for 3 hours. The Immobilon membrane was removed after transfer and stained in filtered 0.1% R250 Coomassie stain for 10 minutes. Membranes were destained in 50% methanol/10% acetic acid three times, ten minutes each time. After destaining, the membranes were washed in filtered water and air-dried.

Protein bands of approximately 150 kD, 95 kD, 50 kD and 30 kD were detected. Presumably the 50 kD and 30 kD bands resulted from antibody contamination. N-terminal sequencing was then attempted on both the 150 kD and 95 kD bands, but the 95 kD protein was blocked, preventing sequencing. The protein band of 150 kD was excised from the membrane and directly sequenced with an Applied Biosystems (Foster City, Calif.) Model 473A protein sequencer according to the manufacturer's instructions. The resulting amino acid sequence is set in SEQ ID NO: 5 using single letter amino acid designations.

| FNLDVEEPMVFQ | (SEQ ID NO: 5) |

The identified sequence included the FNLD sequence characteristic of α subunits of the integrin family [Tamura, et al., *J.Cell.Biol.* 111:1593–1604 (1990)].

Primer Design and Attempt to Amplify Canine $\alpha_{TM1}$ Sequences

From the N-terminal sequence information, three oligonucleotide probes were designed for hybridization: a) "Tommer," a fully degenerate oligonucleotide; b) "Patmer," a partially degenerate oligonucleotide; and c) "Guessmer," a nondegenerate oligonucleotide based on mammalian codon usage. These probes are set out below as SEQ ID NOS: 6, 7 and 8, respectively. Nucleic acid symbols are in accordance with 37 C.F.R. §1.882 for these and all other nucleotide sequences herein.

| 5'-TTYAAYYTGGAYGTNGARGARCCNATGGTNTTYCA-3' | (SEQ ID NO: 6) |
| 5'-TTCAACCTGGACGTGGAGGAGCCCATGGTGTTCCAA-3' | (SEQ ID NO: 7) |
| 5'-TTCAACCTGGACGTNGAASANCCCATGGTCTTCCAA-3' | (SEQ ID NO: 8) |

Based on sequencing data, no relevant clones were detected using these oligonucleotides in several low stringency hybridizations to a canine spleen/peripheral blood macrophage cDNA library cloned into λZAP (Stratagene, La Jolla, Calif.).

Four other oligonucleotide primers, designated 5'Deg, 5'Spec, 3'Deg and 3'Spec (as set out in SEQ ID NOS: 9, 10, 11 and 12, respectively, wherein Deg indicates degenerate and Spec indicates non-degenerate) were subsequently designed based on the deduced N-terminal sequence for attempts to amplify canine $\alpha_{TM1}$ sequences by PCR from phage library DNA purified from plate lysates of the Stratagene library described above.

| 5'-TTYAAYYTNGAYGTNGARGARCC-3' | (SEQ ID NO: 9) |
| 5'-TTYAAYYTGGACGTNGAAGA-3' | (SEQ ID NO: 10) |
| 5'-TGRAANACCATNGGYTC-3' | (SEQ ID NO: 11) |
| 5'-TTGGAAGACCATNGGYTC-3' | (SEQ ID NO: 12) |

The $\alpha_{TM1}$ oligonucleotide primers were paired with T3 or T7 vector primers, as set out in SEQ ID NOS: 13 and 14, respectively, which hybridize to sequences flanking the polylinker region in the Bluescript phagemid found in λZAP.

| 5'-ATTAACCCTCACTAAAG-3' | (SEQ ID NO: 13) |
| 5'-AATACGACTCACTATAG-3' | (SEQ ID NO: 14) |

The PCR amplification was carried out in Taq buffer (Boehringer Mannheim, Indianapolis, Ind.) containing magnesium with 150 ng of library DNA, 1 μg of each primer, 200 μM dNTPs and 2.5 units Taq polymerase (Boehringer Mannheim) and the products were separated by electrophoresis on a 1% agarose gel in Tris-Acetate-EDTA (TAE)

buffer with 0.25 µg/ml ethidium bromide. DNA was transferred to a Hybond (Amersham, Arlington Heights, Ill.) membrane by wicking overnight in 10X SSPE. After transfer, the immobilized DNA was denatured with 0.5M NaOH with 0.6M NaCl, neutralized with 1.0M Tris-HCl, pH 8.0, in 1.5M NaCl, and washed with 2X SSPE before UV crosslinking with a Stratalinker (Stratagene) crosslinking apparatus. The membrane was incubated in prehybridization buffer (5X SSPE, 4X Denhardts, 0.8% SDS, 30% formamide) for 2 hr at 50° C. with agitation.

Oligonucleotide probes 5'Deg, 5'Spec, 3'Deg and 3'Spec (SEQ ID NOS: 9, 10, 11 and 12, respectively) were labeled using a Boehringer Mannheim kinase buffer with 100–300 µCi γP$^{32}$-dATP and 1–3 units of polynucleotide kinase for 1–3 hr at 37° C. Unincorporated label was removed with Sephadex G-25 fine (Pharmacia, Piscataway, N.J.) chromatography using 10 mM Tris-HCl, pH 8.0, 1 mM EDTA (TE) buffer and the flow-through added directly to the prehybridization solution. Membranes were probed for 16 hr at 42° C. with agitation and washed repeatedly, with a final stringency wash of 1X SSPE/0.1% SDS at 50° for 15 min. The blot was then exposed to Kodak X-Omat AR film for 1–4 hours at −80° C.

The oligonucleotides 5'Deg, 5'Spec, 3'Deg and 3'Spec only hybridized to PCR products from the reactions in which they were used as primers and failed to hybridize as expected to PCR products from the reactions in which they were not used as primers. Thus, it was concluded that none of the PCR products were specific for $\alpha_{TM1}$ because no product hybridized with all of the appropriate probes.

EXAMPLE 3
Large Scale Affinity Purification Of Canine $\alpha_{TM1}$ For Internal Sequencing In order to provide additional amino acid sequence for primer design, canine $\alpha_{TM1}$ was purified for internal sequencing. Three sections of frozen spleen (approximately 50 g each) and frozen cells from two partial spleens from adult dogs were used to generate protein for internal sequencing. Fifty grams of spleen were homogenized in 200–300 ml borate buffer with a Waring blender. The homogenized material was diluted with 1 volume of buffer containing 4% NP-40, and the mixture then gently agitated for at least one hour. The resulting lysate was cleared of large debris by centrifugation at 2000 g for 20 min, and then filtered through either a Corning (Corning, N.Y.) prefilter or a Corning 0.8 micron filter. The lysate was further clarified by filtration through the Corning 0.4 micron filter system.

Splenic lysate and the antibody-conjugated Affigel 10 resin described in Example 2 were combined at a 150:1 volume ratio in 100 ml aliquots and incubated overnight at 4° C. with rocking. The lysate was removed after centrifugation at 1000 g for 5 minutes, combined with more antibody-conjugated Affigel 10 resin and incubated overnight as above. The absorbed resin aliquots were then combined and washed with 50 volumes D-PBS/0.1% Tween 20 and the resin transferred to a 50 ml Biorad column. Adsorbed protein was eluted from the resin with 3–5 volumes of 0.1M glycine (pH 2.5); fractions of approximately 900 µl were collected and neutralized with 100 µl 1M Tris buffer, pH 8.0. Aliquots of 15 µl were removed from each fraction and boiled in an equal volume of 2X Laemmli sample buffer with ⅕ volume 1M dithiothreitol (DTT). These samples were electrophoresed on 8% Novex (San Diego, Calif.) polyacrylamide gels and visualized either by Coomassie stain or by silver stain using a Daiichi kit (Enprotech, Natick, Mass.) according to the manufacturer's suggested protocol. Fractions which contained the largest amounts of protein were combined and concentrated by vacuum. The remaining solution was diluted by 50% with reducing Laemmli sample buffer and run on 1.5 mm 7% polyacrylamide gels in Tris-glycine/SDS buffer. Protein was transferred from the gels to Immobilon membrane by the procedure described in Example 2 using the Hoefer transfer apparatus.

The protein bands corresponding to canine $\alpha_{TM1}$ were excised from 10 PVDF membranes and resulted in approximately 47 µg total protein. The bands were destained in 4 ml 50% methanol for 5 minutes, air dried and cut into 1×2 mm pieces. The membrane pieces were submerged in 2 ml 95% acetone at 4° C. for 30 minutes with occasional vortexing and then air dried.

Prior to proteolytic cleavage of the membrane bound protein, 3 mg of cyanogen bromide (CNBr) (Pierce, Rockford, Ill.) were dissolved in 1.25 ml 70% formic acid. This solution was then added to a tube containing the PVDF membrane pieces and the tube incubated in the dark at room temperature for 24 hours. The supernatant (S1) was then removed to another tube and the membrane pieces washed with 0.25 ml 70% formic acid. This supernatant (S2) was removed and added to the previous supernatant (S1). Two milliliters of Milli Q water were added to the combined supernatants (S1 and S2) and the solution lyophilized. The PVDF membrane pieces were dried under nitrogen and extracted again with 1.25 ml 60% acetonitrile, 0.1% tetrafluoroacetic acid (TFA) at 42° C. for 17 hours. This supernatant (S3) was removed and the membrane pieces extracted again with 1.0 ml 80% acetonitrile with 0.08% TFA at 42° C. for 1 hour. This supernatant (S4) was combined with the previous supernatants (S1, S2 and S3) and vacuum dried.

The dried CNBr fragments were then dissolved in 63 µl 8M urea, 0.4M NH$_4$HCO$_3$. The fragments were reduced in 5 µl 45 mM dithiothreitol (DTT) and subsequently incubated at 50° C. for 15 minutes. The solution was then cooled to room temperature and the fragments alkylated by adding 5 µl 100 mM iodoacetamide (Sigma, St. Louis, Mo.). Following a 15 minute incubation at room temperature, the sample was diluted with 187 µl Milli Q water to a final urea concentration of 2.0M. Trypsin (Worthington, Freehold, N.J.) was then added at a ratio of 1:25 (w:w) of enzyme to protein and the protein digested for 24 hours at 37° C. Digestion was terminated with addition of 30 µl TFA.

The protein fragments were then separated with high performance liquid chromatography (HPLC) on a Waters 625 LC system (Millipore, Milford, Mass.) using a 2.1×250 mm, 5 micron Vydac C-18 column (Vydac, Hesperia, Calif.) equilibrated in 0.05% TFA and HPLC water (buffer A). The peptides were eluted with increasing concentration of 80% acetonitrile in 0.04% TFA (buffer B) with a gradient of 38–75% buffer B for 65–95 minutes and 75–98% buffer B for 95–105 minutes. Peptides were fractionated at a flow rate of 0.2 ml/minute and detected at 210 nm.

Following fractionation, the amino acid sequence of the peptides was analyzed by automated Edman degradation performed on an Applied Biosystems Model 437A protein sequencer using the manufacturer's standard cycles and the Model 610A Data Analysis software program. Version 1.2.1. All sequencing reagents were supplied by Applied Biosystems. The amino acid sequences of seven of the eight internal fragments are set out below wherein "X" indicates the identity of the amino acid was not certain.

| | |
|---|---|
| VFQEXGAGFGQ | (SEQ ID NO: 15) |
| LYDXVAATGLXQPI | (SEQ ID NO: 16) |
| PLEYXDVIPQAE | (SEQ ID NO: 17) |
| FQEGFSXVLX | (SEQ ID NO: 18) |
| TSPTFIXMSQENVD | (SEQ ID NO: 19) |
| LVVGAPLEVVAVXQTGR | (SEQ ID NO: 20) |
| LDXKPXDTA | (SEQ ID NO: 21) |

Primer Design

One internal amino acid sequence (set out in SEQ ID NO: 22) obtained was then used to design a fully degenerate oligonucleotide primer, designated p4(R) as set out in SEQ ID NO: 23.

| | |
|---|---|
| FGEQFSE | (SEQ ID NO: 22) |
| 5'-RAANCCYTCYTGRAAACTYTC-3' | (SEQ ID NO: 23) |

EXAMPLE 4
PCR Cloning Of A Canine $\alpha_{TM1}$ Fragment

The 5' portion of the canine $\alpha_{TM1}$ gene was amplified from double-stranded canine splenic cDNA by PCR.

A. Generation of Double Stranded Canine Spleen cDNA

One gram of frozen material from ajuvenile dog spleen was ground in liquid nitrogen on dry ice and homogenized in 20 ml RNA-Stat 60 buffer (TelTest B, Inc, Friendswood, Tex.). Four ml chloroform were added, and the solution extracted by centrifugation at 12,000 g for 15 minutes. RNA was precipitated from the aqueous layer with 10 ml ethanol. Poly A$^+$RNA was then selected on Dynal Oligo dT Dynabeads (Dynal, Oslo, Norway). Five aliquots of 100 µg total RNA were combined and diluted with an equal volume of 2X binding buffer (20 mM Tris-HCl, pH 7.5, 1.0M LiCl, 1 mM EDTA, 0. 1% SDS). RNA was then incubated 5 minutes with the Oligo dT Dynabeads (1.0 ml or 5 mg beads for all the samples). Beads were washed with buffer containing 10 mM Tris-HCl, pH 7.5, 0.15M LiCl, 1 mM EDTA and 0.1% SDS, according to the manufacturer's suggested protocol prior to elution of poly A$^+$mRNA with 2 mM EDTA, pH 7.5. Double-stranded cDNA was then generated using the eluted poly A$^+$mRNA and the Boehringer Mannheim cDNA Synthesis Kit according to the manufacturer's suggested protocol.

B. Isolation of a Partial Canine $\alpha_{TM1}$ cDNA

Oligonucleotide primers 5'Deg (SEQ ID NO: 9) and p4(R) (SEQ ID NO: 23) were employed in a standard PCR reaction using 150 ng double-stranded cDNA, 500 ng of each primer, 200 µM dNTPs and 1.5 units Taq polymerase (Boehringer Mannheim) in Taq buffer (Boehringer Mannheim) with magnesium. The resulting products (1 µl of the original reaction) were subjected to a second round of PCR with the same primers to increase product yield. This band was eluted from a 1% agarose gel onto Schleicher & Schuell (Keene, N.H.) NA45 paper in a buffer containing 10 mM Tris-HCl, pH 8, 1 mM EDTA, 1.5M NaCl at 65° C., precipitated, and ligated into the pCR$^{TM}$II vector (Invitrogen, San Diego, Calif.) using the TA cloning kit (Invitrogen) and the manufacturer's suggested protocol. The ligation mixture was transformed by electroporation into XL-1 Blue bacteria (Stratagene). One clone, 2.7, was determined to contain sequences corresponding to $\alpha_{TM1}$ peptide sequences which were not utilized in design of the primers.

Sequencing was performed with an Applied Biosystems 373A DNA sequencer (Foster City, Calif.) with a Dye-deoxy terminator cycle sequence kit (ABI) in which fluorescent-labeled dNTPs were incorporated in an asymmetric PCR reaction [McCabe, "Production of Single Stranded DNA by Asymmetric PCR," in *PCR Protocols: A Guide to Methods and Applications*, Innis, et al. (eds.) pp. 76–83 Academic Press: New York (1990)] as follows. Samples were held at 96° C. for 4 minutes and subjected to 25 cycles of the step sequence: 96° C., for 15 seconds; 50° C. for 1 second; 60° C. for 4 minutes. Sequence data was automatically downloaded into sample files on the computer that included chromatogram and text files. The sequence of the entire insert of clone 2.7 is set out in SEQ ID NO: 24.

Attempts to isolate the full length canine $\alpha_{TM1}$ cDNA from the Stratagene library (as described in Example 2) were unsuccessful. Approximately $1 \times 10^6$ phage plaques were screened by hybridization under low stringency conditions using 30% formamide with clone 2.7 as a probe, but no positive clones resulted. Attempts to amplify relevant sequences downstream from those represented in clone 2.7 using specific oligonucleotides derived from clone 2.7 or degenerate primers based on amino acid sequence from other peptide fragments paired with a degenerate oligonucleotide based on the conserved $\alpha$ subunit amino acid motif GFFKR [Tamura, et al., supra] were also unsuccessful.

EXAMPLE 5
Cloning Of A Putative Human Homolog Of Canine $\alpha_{TM1}$

To attempt the isolation of a human sequence homologous to canine $\alpha_{TM1}$ the approximately 1 kb canine $\alpha_{TM1}$ fragment from clone 2.7 was used as a probe. The probe was generated by PCR under conditions described in Example 2 using NT2 (as set out in SEQ ID NO: 25) and p4(R) (SEQ ID NO: 23) primers.

| | |
|---|---|
| 5'-GTNTTYCARGARGAYGG-3' | (SEQ ID NO: 25) |

The PCR product was purified using the Qiagen (Chatsworth, Ga.) Quick Spin kit and the manufacturer's suggested protocol. The purified DNA (200 ng) was labeled with 200 µCi $\alpha^{32}$PdCTP using the Boehringer Mannheim Random Prime Labelling kit and the manufacturer's suggested protocol. Unincorporated isotope was removed with Sephadex G25 (fine) gravity chromatography. The probe was denatured with 0.2N NaOH and neutralized with 0.4M Tris-HCl, pH 8.0, before use.

Colony lifts on Hybond filters (Amersham) of a human spleen cDNA library in pCDNA/Amp (Invitrogen, San Diego, Calif.) were prepared. The filters were initially denatured and neutralized as described in Example 2 and subsequently incubated in a prehybridization solution (8 ml/filter) with 30% formamide at 50° C. with gentle agitation for 2 hours. Labeled probe as described above was added to this solution and incubated with the filters for 14 hours at 42° C. The filters were washed twice in 2X SSC/0.1% SDS at 37° C. and twice in 2X SSC/0.1% SDS at 50° C. Final stringency washes were 1X SSC/0.1% SDS, twice at 65° C. (1X SSC is 150 mM NaCl, 15 mM sodium citrate, pH 7.0). Filters were exposed to Kodak X-Omat AR film for six hours with an intensifying screen. Colonies giving signals on duplicate lifts were streaked on LB medium with magnesium (LBM)/carbenicillin plates and incubated overnight at 37° C. Resulting streaked colonies were lifted with Hybond filters and these filters were treated as above. The filters were hybridized under more stringent conditions with the 1 kb probe from clone 2.7, labeled as previously described, in a 50% formamide hybridization solution at 50° C. for 3 hours. Probed filters were washed with a final stringency of 0.1X SSC/0.1% SDS at 65° C. and exposed to Kodak X-Omat AR film for 2.5 hours at −80° C. with an intensifying screen. Positive colonies were identified and cultured in LBM/carbenicillin medium overnight. DNA from the cultures was prepared using the Promega Wizard miniprep kit according to the manufacturer's suggested protocol and the resulting DNA was sequenced.

The initial screening resulted in 18 positive clones, while the secondary screening under more stringent hybridization conditions produced one positive clone which was designated 19A2. The DNA and deduced amino acid sequences of the human $\alpha_d$ clone 19A2 are set out in SEQ ID NOS: 1 and 2, respectively.

Characteristics Of The Human $\alpha_d$ cDNA and Predicted Polypeptide

Clone 19A2 encompasses the entire coding region for the mature protein, plus 48 bases (16 amino acid residues) of the 5' upstream signal sequence and 241 bases of 3' untranslated sequence which do not terminate in a polyadenylation sequence. The core molecular weight of the mature protein is predicted to be around 125 kD. The extracellular domain is predicted to encompass approximately amino acid residues 17 through 1108 of SEQ ID NO: 2. This extracellular region is contiguous with about a 20 amino acid region homologous to the human CD11c transmembrane region (residues 1109 through 1128 of SEQ ID NO: 2). The cytoplasmic domain comprises approximately 30 amino acids (about residues 1129 through 1161 of SEQ ID NO: 2). The protein also contains a region (around residues 150 through 352) of approximately 202 amino acids homologous to the I (insertion) domain common to CD11a, CD11b and CD11c [Larson and Springer, supra], $\alpha_E$ [Shaw, et al., *J.Biol.Chem.* 269:6016–6025 (1994)] and in VLA-1 and VLA-2, [Tamura, et al., supra]. The I domain in other integrins has been shown to participate in ICAM binding [Landis, et al., *J. Cell.Biol.* 120:1519–1527 (1993); Diamond, et al., *J.Cell.Biol.* 120:1031–1043 (1993)], suggesting that $\alpha_d$ may also bind members of the ICAM family of surface molecules. This region has not been demonstrated to exist in any other integrin subunits.

The deduced amino acid sequence of $\alpha_d$ shows approximately 36% identity to that of CD11a, approximately 60% identity to CD11b and approximately 66% identity to CD11c. An alignment of amino acid sequences for (CD11b SEQ ID NO: 3), CD11c (SEQ ID NO: 4) and $\alpha_d$ (SEQ ID NO: 2) is presented in FIG. 1.

The cytoplasmic domains of α subunits in $\beta_2$ integrins are typically distinct from one another within the same species, while individual α subunits show high degrees of homology across species boundaries. Consistent with these observations, the cytoplasmic region of $\alpha_d$ differs markedly from CD11a, CD11b, and CD11c except for a membrane proximal GFFKR amino acid sequence which has been shown to be conserved among all α integrins [Rojiani, et al., *Biochemistry* 30:9859–9866 (1991)]. Since the cytoplasmic tail region of integrins has been implicated in "inside out" signaling and in avidity regulation [Landis et al., supra], it is possible that $\alpha_d$ interacts with cytosolic molecules distinct from those interacting with CD11a, CD11b, and CD11c, and, as a result, participates in signaling pathways distinct from those involving other $\beta_2$ integrins.

The extracellular domain of $\alpha_d$ contains a conserved DGSGS amino acid sequence adjacent the I-domain; in CD11b, the DGSGS sequence is a metal-binding region required for ligand interaction [Michishita, et al. *Cell* 72:857–867 (1993)]. Three additional putative cation binding sites in CD11b and CD11c are conserved in the $\alpha_d$ sequence at amino acids 465–474, 518–527, and 592–600 in clone 19A2 (SEQ ID NO: 1). The $\alpha_d$ I-domain is 36%, 62%, and 57% identical to the corresponding regions in CD11a, CD11b, and CD11c, respectively, and the relatively low sequence homology in this region suggests that $\alpha_d$ may interact with a set of extracellular proteins distinct from proteins with which other known $\beta_2$ integrins interact. Alternatively, the affinity of $\alpha_d$ for known $\beta_2$ integrin ligands, for example, ICAM-1, ICAM-2 and/or ICAM-R, may be distinct from that demonstrated for the other $\beta_2$ integrin/ICAM interactions. [See Example 12.]

EXAMPLE 6
Northern Analysis of Human $\alpha_d$ Expression in Tissues

In order to determine the relative level of expression and tissue specificity of $\alpha_d$, Northern analysis was performed using fragments from clone 19A2 as probes. Approximately 10 μg of total RNA from each of several human tissues or cultured cell lines were loaded on a formaldehyde agarose gel in the presence of 1 μg of ethidium bromide. After electrophoresis at 100 V for 4 hr, the RNA was transferred to a nitrocellulose membrane (Schleicher & Schuell) by wicking in 10X SSC overnight. The membrane was baked 1.5 hr at 80° C. under vacuum. Prehybridization solution containing 50% formamide in 3-(N-morpholino)propane sulfonic acid (MOPS) buffer was used to block the membrane for 3 hr at 42° C. Fragments of clone 19A2 were labeled with the Boehringer Mannheim Random Prime kit according to the manufacturer's instructions including both $\alpha P^{32}dCTP$ and $\alpha P^{32}dTTP$. Unincorporated label was removed on a Sephadex G25 column in TE buffer. The membrane was probed with $1.5 \times 10^6$ counts per ml of prehybridization buffer. The blot was then washed successively with 2X SSC/0.1% SDS at room temperature, 2X SSC/0.1% SDS at 42° C., 2X SSC/0.1% SDS at 50° C., 1X SSC/0.1% SDS at 50° C., 0.5X SSC/0.1% SDS at 50° C. and 0.1X SSC/0.1% SDS at 50° C. The blot was then exposed to film for 19 hr.

Hybridization using a BstXI fragment from clone 19A2 (corresponding to nucleotides 2011 to 3388 in SEQ ID NO: 1) revealed a weak signal in the approximately 5 kb range in liver, placenta, thymus, and tonsil total RNA. No signal was detected in kidney, brain or heart samples. The amount of RNA present in the kidney lane was minimal, as determined with ethidium bromide staining.

When using a second fragment of clone 19A2 (encompassing the region from bases 500 to 2100 in SEQ ID NO: 1), RNA transcripts of two different sizes were detected in a human multi-tissue Northern (MTN) blot using polyA+ RNA (Clontech). An approximately 6.5 kb band was observed in spleen and skeletal muscle, while a 4.5 kb band was detected in lung and peripheral blood leukocytes. The variation in sizes observed could be caused by tissue specific polyadenylation, cross reactivity of the probe with other integrin family members, or hybridization with alternatively spliced mRNAs.

Northern analysis using a third fragment from clone 19A2, spanning nucleotides 2000 to 3100 in SEQ ID NO: 1, gave results consistent with those using the other clone 19A2 fragments.

RNA from three myeloid lineage cell lines was also probed using the fragments corresponding to nucleotides 500 to 2100 and 2000 to 3100 in SEQ ID NO: 1. A THP-1 cell line, previously stimulated with PMA, gave a diffuse signal in the same size range (approximately 5.0 kb), with a slightly stronger intensity than the tissue signals. RNA from unstimulated and DMSO-stimulated HL-60 cells hybridized with the $\alpha_d$ probe at the same intensity as the tissue samples, however, PMA treatment seemed to increase the signal intensity. Since PMA and DMSO drive HL-60 cell differentiation toward monocyte/macrophage and granulocyte pathways, respectively, this result suggests enhanced $\alpha_d$ expression in monocyte/macrophage cell types. U937 cells expressed the $\alpha_d$ message and this signal did not increase with PMA stimulation. No band was detected in Molt, Daudi, H9, JY, or Jurkat cells.

EXAMPLE 7
Transient Expression of Human $\alpha_d$ Constructs
A. Generation of expression constructs The human clone 19A2 lacks an initiating methionine codon and possibly some of the 5' signal sequence. Therefore, in order to generate a human expression plasmid containing 19A2 sequences, two different strategies were used. In the first, two plasmids were constructed in which signal peptide sequences derived from genes encoding either CD11b or CD11c were spliced into clone 19A2 to generate a chimeric $\alpha_d$ sequence. In the second approach, a third plasmid was constructed in which an adenosine base was added at position 0 in clone 19A2 to encode an initiating methionine.

The three plasmids contained different regions which encoded the 5' portion of the $\alpha_d$ sequence or the chimeric $\alpha_d$ sequence. The $\alpha_d$ region was PCR amplified (see conditions in Example 2) with a specific 3' primer BamRev (set out below in SEQ ID NO: 26) and one of three 5' primers. The three 5' primers contained in sequence: (1) identical non-specific bases at positions 1–6 allowing for digestion, an EcoRI site from positions 7–12 and a consensus Kozak sequence from positions 13–18; (2) a portion of the CD11b (primer ER1B) or CD11c (primer ER1C) signal sequence, or an adenosine (primer ER1D); and (3) an additional 15–17 bases specifically overlapping 5' sequences from clone 19A2 to allow primer annealing. Primers ER1B, ER1C or ER1D are set out in SEQ ID NOS: 27, 28 or 29, respectively, where the initiating methionine codon is underlined and the EcoRI site is double underlined.

sequences. The clones were designated pATM.B1 (CD11b/$\alpha_d$, from primer ER1B), pATM.C10 (CD11c/$\alpha_d$, from primer ER1C) and pATM.D12 (adenosine/$\alpha_d$ from primer ER1d). The presence of the appropriate signal sequences in each clone was verified by nucleic acid sequencing.

B. Transfection of COS Cells

Expression from the $\alpha_d$ plasmids discussed above was effected by cotransfection of COS cells with the individual plasmids and a CD18 expression plasmid, pRC.CD18. As a positive control, COS cells were also co-transfected with the plasmid pRC.CD18 and a CD11a expression plasmid, pDC.CD11A.

Cells were passaged in culture medium (DMEM/ 10%FBS/penstrep) into 10 cm Corning tissue culture-treated petri dishes at 50% confluency 16 hours prior to transfection. Cells were removed from the plates with Versene buffer (0.5 mM NaEDTA in PBS) without trypsin for all procedures. Before transfection, the plates were washed once with serum-free DMEM. Fifteen micrograms of each plasmid were added to 5 ml transfection buffer (DMEM with 20 µg/ml DEAE-Dextran and 0.5 mM chloroquine) on each plate. After 1.5 hours incubation at 37° C., the cells were shocked for 1 minute with 5 ml DMEM/10% DMSO. This DMSO solution was then replaced with 10 ml/plate culture medium.

Resulting transfectants were analyzed by ELISA, FACS, and immunoprecipitation as described in Examples 8, 9, and 10.

EXAMPLE 8
ELISA Analysis of COS Transfectants

In order to determine if the COS cells co-transfected with CD18 expression plasmid pRC. CD18 and an $\alpha_d$ plasmid expressed $\alpha_d$ on the cell surface in association with CD18, ELISAs were performed using primary antibodies raised against CD18 (e.g., TS1/18 purified from ATCC HB203). As a positive control, ELISAs were also performed on cells co-transfected with the CD18 expression plasmid and a

| | |
|---|---|
| 5'-CCACTGTCAGGATGCCCGTG-3' | (SEQ ID NO: 26) |
| 5'-AGTTAC<u>GAATTC</u>GCCACC<u>ATG</u>GCTCTACGGGTGCTT | (SEQ ID NO: 27) |
| 5'-AGTTAC<u>GAATTC</u>GCCACC<u>ATG</u>ACTCGGACTGTGCTT | (SEQ ID NO: 28) |
| 5'-AGTTAC<u>GAATTC</u>GCCACC<u>ATG</u>ACCTTCGGCACTGTG | (SEQ ID NO: 29) |

The resulting PCR product was digested with EcoRI and BamHI.

All three plasmids contained a common second $\alpha_d$ region (to be inserted immediately downstream from the 5' region described in the previous paragraph) including the 3' end of the $\alpha_d$ clone. The second $\alpha_d$ region, which extended from nucleotide 625 into the XbaI site in the vector 3' polylinker region of clone 19A2, was isolated by digestion of clone 19A2 with BamHI and XbaI.

Three ligation reactions were prepared in which the 3' $\alpha_d$ BamHI/XbaI fragment was ligated to one of the three 5' $\alpha_d$ EcoRI/BamHI fragments using Boehringer Mannheim ligase buffer and T4 ligase (1 unit per reaction). After a 4 hour incubation at 14° C., an appropriate amount of vector pcDNA.3 (Invitrogen) digested with EcoRI and XbaI was added to each reaction with an additional unit of ligase. Reactions were allowed to continue for another 14 hours. One tenth of the reaction mixture was then transformed into competent XL-1 Blue cells. The resulting colonies were cultured and the DNA isolated as in Example 5. Digestion with EcoRI identified three clones which were positive for that restriction site, and thus, the engineered signal CD11a expression plasmid, pDC.CD11A. The primary antibodies in this control included CD18 antibodies and anti-CD11a antibodies (e.g., TS1/22 purified from ATCC HB202).

For ELISA, cells from each plate were removed with Versene buffer and transferred to a single 96-well flat-bottomed Corning tissue culture plate. Cells were allowed to incubate in culture media 2 days prior to assay. The plates were then washed twice with 150 µl/well D-PBS/0.5% teleost skin gelatin (Sigma) solution. This buffer was used in all steps except during the development. All washes and incubations were performed at room temperature. The wells were blocked with gelatin solution for 1 hour. Primary antibodies were diluted to 10 µg/ml in gelatin solution and 50 µl were then added to each well. Triplicate wells were set up for each primary antibody. After 1 hour incubation, plates were washed 3× with 150 µl/well gelatin solution. Secondary antibody (goat anti-mouse Ig/HRP-Fc specific [Jackson, West Grove, Pa.]) at a 1:3500 dilution was added at 50 µl/well and plates were incubated for 1 hour. After three washes, plates were developed for 20 minutes with 100

μl/well o-phenyldiamine (OPD) (Sigma) solution (1 mg/ml OPD in citrate buffer) before addition of 50 μl/well 15% sulfuric acid.

Analysis of transfectants in the ELISA format with anti-CD18 specific antibodies revealed no significant expression above background in cells transfected only with the plasmid encoding CD18. Cells co-transfected with plasmid containing CD11a and CD18 showed an increase in expression over background when analyzed with CD18 specific antibodies or with reagents specific for CD11a. Further analysis of cells co-transfected with plasmids encoding CD18 and one of the $\alpha_d$ expression constructs (pATM.C10 or pATM.D12) revealed that cell surface expression of CD18 was rescued by concomitant expression of $\alpha_d$. The increase in detectable CD18 expression in COS cells transfected with pATM.C10 or pATM.D12 was comparable to that observed in co-transfected CD11a/CD18 positive control cells.

EXAMPLE 9
FACS Analysis of COS Transfectants

For FACS analysis, cells in petri dishes were fed with fresh culture medium the day after transfection and allowed to incubate 2 days prior to the assay. Transfectant cells were removed from the plates with 3 ml Versene, washed once with 5 ml FACS buffer (DMEM/2% FBS/0.2% sodium azide) and diluted to 500,000 cells/sample in 0.1 ml FACS buffer. Ten microliters of either 1 mg/ml FITC-conjugated CD18, CD11a, or CD11b specific antibodies (Becton Dickinson) or 800 μg/ml CFSE-conjugated murine 23F2G (anti-CD18) (ATCC HB11081) were added to each sample. Samples were then incubated on ice for 45 minutes, washed 3× with 5 ml/wash FACS buffer and resuspended in 0.2 ml FACS buffer. Samples were processed on a Becton Dickinson FACscan and the data analyzed using Lysys II software (Becton Dickinson).

COS cells transfected with CD18 sequences only did not stain for CD18, CD11a or CD11b. When co-transfected with CD11a/CD18, about 15% of the cells stained with antibodies to CD11a or CD18. All cells transfected with CD18 and any $\alpha_d$ construct resulted in no detectable staining for CD11a and CD11b. The pATM.B1, pATM.C10 and pATM.D12 groups stained 4%, 13% and 8% positive for CD18, respectively. Fluorescence of the positive population in the CD11a/CD18 group was 4-fold higher than background. In comparison, the co-transfection of $\alpha_d$ constructs with the CD18 construct produced a positive population that showed a 4– to 7-fold increase in fluorescence intensity over background.

EXAMPLE 10
Biotin-Labeled Immunoprecipitation of Human $\alpha_d$/CD18 Complexes from Co-transfected COS Cells Immunoprecipitation was attempted on cells co-transfected with CD18 and each of the $\alpha_d$ expression plasmids separately described in Example 7 in order to determine if $\alpha_d$ could be isolated as part of the αβ heterodimer complex characteristic of integrins.

Transfected cells (1–3×10$^8$ cells/group) were removed from petri dishes with Versene buffer and washed 3 times in 50 ml/group D-PBS. Each sample was labeled with 2 mg Sulpho-NHS Biotin (Pierce, Rockford, Ill.) for 15 minutes at room temperature. The reaction was quenched by washing 3 times in 50 ml/sample cold D-PBS. Washed cells were resuspended in 1 ml lysis buffer (1% NP40, 50 mM Tris-HCl, pH 8.0, 0.2M NaCl, 2 mM Ca$^{++}$, 2 mM Mg$^{++}$, and protease inhibitors) and incubated 15 minutes on ice. Insoluble material was pelleted by centrifugation at 10,000 g for 5 minutes, and the supernatant removed to fresh tubes.

In order to remove material non-specifically reactive with mouse immunoglobulin, a pre-clearance step was initially performed. Twenty-five micrograms of mouse immunoglobulin (Cappel, West Chester, Pa.) was incubated with supernatants at 4° C. After 2.5 hr, 100 μl (25 μg) rabbit anti-mouse Ig conjugated Sepharose (prepared from Protein A Sepharose 4B and rabbit anti-mouse IgG, both from Zymed, San Francisco, Calif.) was added to each sample; incubation was continued at 4° C. with rocking for 16 hours. Sepharose beads were removed from the supernatants by centrifugation. After pre-clearance, the supernatants were then treated with 20 μg anti-CD18 antibody (TS1.18) for 2 hours at 4° C. Antibody/antigen complexes were isolated from supernatants by incubation with 100 μl/sample rabbit anti-mouse/Protein A-sepharose preparation described above. Beads were washed 4 times with 10 mM HEPES, 0.2M NaCl, and 1% Triton-X 100. Washed beads were pelleted and boiled for 10 minutes in 20 μl 2X Laemmli sample buffer with 2% β-mercaptoethanol. Samples were centrifuged and run on an 8% prepoured Novex polyacrylamide gel (Novex) at 100 V for 30 minutes. Protein was transferred to nitrocellulose membranes (Schleicher & Schuell) in TBS-T buffer at 200 mAmps for 1 hour. Membranes were blocked for 2 hr with 3% BSA in TBS-T. Membranes were treated with 1:6000 dilution of Strep-avidin horse radish peroxidase (POD) (Boehringer Mannheim) for 1 hour, followed by 3 washes in TBS-T. The Amersham Enhanced Chemiluminescence kit was then used according to the manufacturer's instructions to develop the blot. The membrane was exposed to Hyperfilm MP (Amersham) for 0.5 to 2 minutes.

Immunoprecipitation of CD18 complexes from cells transfected with pRC.CD18 and either pATM.B1, pATM.C10 or pATM.D12 revealed surface expression of a heterodimeric species consisting of approximately 100 kD β chain, consistent with the predicted size of CD18, and an α chain of approximately 150 kD, corresponding to $\alpha_d$.

EXAMPLE 11
Stable Transfection of Human $\alpha_d$ in Chinese Hamster Ovary Cells To determine whether $\alpha_d$ is expressed on the cell surface as a heterodimer in association with CD18, cDNAs encoding each chain were both transiently and stably transfected into a cell line lacking both $\alpha_d$ and CD18.

For these experiments, $\alpha_d$ cDNA was augmented with additional leader sequences and a Kozak consensus sequence, as described in Example 7, and subcloned into expression vector pcDNA3. The final construct, designated pATM.D12, was co-transfected with a modified commercial vector, pDC1.CD18 encoding human CD18 into dihydrofolate reductase (DHFR)$^-$ Chinese hamster ovary (CHO) cells. The plasmid pDC1.CD18 encodes a DHFR$^+$ marker and transfectants can be selected using an appropriate nucleoside-deficient medium. The modifications which resulted in pDC1.CD18 are as follows.

The plasmid pRC/CMV (Invitrogen) is a mammalian expression vector with a cytomegalovirus promoter and ampicillin resistance marker gene. A DHFR gene from the plasmid pSC1190-DHFR was inserted into pRC/CMV 5' of the SV40 origin of replication. In addition, a polylinker from the 5' region of the plasmid pHF2G-DHF was ligated into the pRC/CMV/DHFR construct, 3' to the DHFR gene. CD18 encoding sequences are subsequently cloned into the resulting plasmid between the 5' flanking polylinker region and the bovine growth hormone poly A encoding region.

Surface expression of CD18 was analyzed by flow cytometry using the monoclonal antibody TS1/18. Heterodimer formation detected between $\alpha_d$ and CD18 in this cell line was consistent with the immunoprecipitation described in Example 10 with transient expression in COS cells.

EXAMPLE 12
Human $\alpha_d$ binds to ICAM-R in a CD18-dependent fashion

In view of reports that demonstrate interactions between the leukocyte integrins and intercellular adhesion molecules (ICAMs) which mediate cell—cell contact [Hynes, Cell 69:11–25 (1992)], the ability of CHO cells expressing $\alpha_d$/CD18 to bind ICAM-1, ICAM-R, or VCAM-1 was assessed by two methods.

In replicate assays, soluble ICAM-1, ICAM-R, or VCAM-1 IgG1 fusion proteins were immobilized on plastic and the ability of $\alpha_d$/CD18 CHO transfected cells to bind the immobilized ligand was determined. Transfected cells were labeled internally with calcein, washed in binding buffer (RPMI with 1% BSA), and incubated in either buffer only (with or without 10 ng/ml PMA) or buffer with anti-CD18 monoclonal antibodies at 10 µg/ml. Transfected cells were added to 96-well Immulon 4 microtiter plates previously coated with soluble ICAM-1/IgG1, ICAM-R/IgG1 or VCAM-1/IgG1 fusion protein, or bovine serum albumin (BSA) as a negative control. Design of the soluble forms of these adhesion molecules is described and fully disclosed in co-pending and co-owned U.S. patent application Ser. No. 08/102,852, filed Aug. 5, 1993. Wells were blocked with 1% BSA in PBS prior to addition of labeled cells. After washing the plates by immersion in PBS with 0.1% BSA for 20 minutes, total fluorescence remaining in each well was measured using a Cytofluor 2300 (Millipore, Milford, Mass.).

In experiments with immobilized ICAMs, $\alpha_d$/CD 18 co-transfectants consistently showed a 3–5 fold increase in binding to ICAM-R/IgG1 wells over BSA coated wells. The specificity and CD18-dependence of this binding was demonstrated by the inhibitory effects of anti-CD18 antibody TS1/18. The binding of cells transfected with CD11a/CD18 to ICAM-1/IgG1 wells was comparable to the binding observed with BSA coated wells. CD11a/CD18 transfected cells showed a 2–3 fold increase in binding to ICAM-1/IgG1 wells only following pretreatment with PMA. PMA treatment of $\alpha_d$/CD18 transfectants did not affect binding to ICAM-1/IgG1 or ICAM-R/IgG1 wells. No detectable binding of $\alpha_d$/CD18 transfectants to VCAM-1/IgG1 wells was observed.

Binding of $\alpha_d$/CD18-transfected cells to soluble ICAM-1/IgG1, ICAM-R/IgG1, or VCAM-1/IgG1 fusion proteins was determined by flow cytometry. Approximately one million $\alpha_d$/CD18-transfected CHO cells (grown in spinner flasks for higher expression) per measurement were suspended in 100 µl binding buffer (RPMI and 1% BSA) with or without 10µg/ml anti-CD18 antibody. After a 20 minute incubation at room temperature, the cells were washed in binding buffer and soluble ICAM-1/IgG1 or ICAM-R/IgG1 fusion protein was added to a final concentration of 5 µg/ml. Binding was allowed to proceed for 30 minute at 37° C., after which the cells were washed three times and resuspended in 100 µl binding buffer containing FITC-conjugated sheep anti-human IgG1 at a 1:100 dilution. After a 30 minute incubation, samples were washed three times and suspended in 200 µl binding buffer for analysis with a Becton Dickinson FACScan.

Approximately 40–50% of the $\alpha_d$/CD18 transfectants indicated binding to ICAM-R/IgG1, but no binding to ICAM-1/IgG1 or VCAM-1/IgG1 proteins. Pretreatment of transfected cells with PMA has no effect on $\alpha_d$/CD18 binding to either ICAM-1/IgG1, ICAM-R/IgG1 or VCAM-1/IgG1, which was consistent with the immobilized adhesion assay. Binding by ICAM-R was reduced to background levels after treatment of $\alpha_d$/CD18 transfectants with anti-CD18 antibody TS1/18.

The collective data from these two binding assays illustrate that $\alpha_d$/CD18 binds to ICAM-R and does so preferentially as compared to ICAM-1 and VCAM-1. The $\alpha_d$/CD18 binding preference for ICAM-R over ICAM-1 is opposite that observed with CD11a/CD18 and CD11b/CD18. Thus modulation of $\alpha_d$/CD18 binding may be expected to selectively affect normal and pathologic immune function where ICAM-R plays a prominent role. Moreover, results of similar assays, in which antibodies immunospecific for various extracellular domains of ICAM-R were tested for their ability to inhibit binding of ICAM-R to $\alpha_d$/CD18 transfectants, indicated that $\alpha_d$/CD18 and CD11a/CD18 interact with different domains of ICAM-R.

The failure of CD11a/CD18 to bind ICAM-1/IgG1 or ICAM-R/IgG1 in solution suggests that the affinity of binding between CD11a/CD18 and ICAM-1 or ICAM-R is too low to permit binding in solution. Detection of $\alpha_d$/CD18 binding to ICAM-R/IgG1, however, suggests an unusually high binding affinity.

$\alpha_d$ Binding to iC3b

Complement component C3 can be proteolytically cleaved to form the complex iC3b, which initiates the alternative pathway of complement activation and leads ultimately to cell-mediated destruction of a target. Both CD11b and CD11c have been implicated in iC3b binding and subsequent phagocytosis of iC3b-coated particles. A peptide fragment in the CD11b I domain has recently been identified as the site of iC3b interaction [Ueda, et al., Proc.Natl.Acad.Sci.(USA) 91:10680–10684 (1994)]. The region of iC3b binding is highly conserved in CD11b, CD11c, and $\alpha_d$, suggesting an $\alpha_d$/iC3b binding interaction.

Binding of $\alpha_d$ to iC3b is performed using transfectants or cell lines naturally expressing $\alpha_d$ (for example, PMA-stimulated HL60 cells) and iC3b-coated sheep red blood cells (sRBC) in a rosette assay [Dana, et al., J.Clin.Invest. 73:153–159 (1984)]. The abilities of $\alpha_d$/CD18 CHO transfectants, VLA4-CHO transfectants (negative control) and PMA-stimulated HL60 cells (positive control) to form rosettes are compared in the presence and absence of an anti-CD18 monoclonal antibody (for example TS1/18.1).

EXAMPLE 13
Screening by Scintillation Proximity Assay

Specific inhibitors of binding between the $\alpha_d$ ligands of the present invention and their binding partners ($\alpha_d$ ligand/anti-ligand pair) may be determined by a variety of means, such as scintillation proximity assay techniques as generally described in U.S. Pat. No. 4,271,139, Hart and Greenwald, Mol.Immunol. 12:265–267 (1979), and Hart and Greenwald, J.Nuc.Med. 20:1062–1065 (1979), each of which is incorporated herein by reference.

Briefly, one member of the $\alpha_d$ ligand/anti-ligand pair is bound to a solid support. A fluorescent agent is also bound to the support. Alternatively, the fluorescent agent may be integrated into the solid support as described in U.S. Pat. No. 4,568,649, incorporated herein by reference. The non-support bound member of the $\alpha_d$ ligand/anti-ligand pair is labeled with a radioactive compound that emits radiation capable of exciting the fluorescent agent. When the ligand binds the radiolabeled anti-ligand, the label is brought sufficiently close to the support-bound fluorescer to excite the fluorescer and cause emission of light. When not bound, the label is generally too distant from the solid support to excite the fluorescent agent, and light emissions are low. The emitted light is measured and correlated with binding between the ligand and the anti-ligand. Addition of a binding inhibitor to the sample will decrease the fluorescent emission by keeping the radioactive label from being captured in the proximity of the solid support. Therefore, binding inhibitors may be identified by their effect on fluorescent emissions from the samples. Potential anti-ligands to $\alpha_d$ may also be identified by similar means.

EXAMPLE 14

Soluble Human $\alpha_d$ Expression Constructs

The expression of full-length, soluble human $\alpha_d$/CD18 heterodimeric protein provides easily purified material for immunization and binding assays. The advantage of generating soluble protein is that it can be purified from supernatants rather than from cell lysates (as with full-length membrane-bound $\alpha_d$/CD18); recovery in therefore improved and impurities reduced.

The soluble $\alpha_d$ expression plasmid was constructed as follows. A nucleotide fragment corresponding to the region from bases 0 to 3161 in SEQ ID NO: 1, cloned into plasmid pATM.D12, was isolated by digestion with HindIII and AatII. A PCR fragment corresponding to bases 3130 to 3390 in SEQ ID NO: 1, overlapping the HindIII/AatII fragment and containing an addition MluI restriction site at the 3' terminus, was amplified from pATM.D12 with primers sHAD.5 and sHAD.3 set out in SEQ ID NOS: 30 and 31, respectively.

| | |
|---|---|
| 5'-TTGCTGACTGCCTGCAGTTC-3' | (SEQ ID NO: 30) |
| 5'-GTTCTGACGCGTAATGGCATTGTAGACCTCGTCTTC-3' | (SEQ ID NO: 31) |

The PCR amplification product was digested with AatII and MluI and ligated to the HindIII/AatII fragment. The resulting product was ligated into HindIII/MluI-digested plasmid pDC1.s.

This construct is co-expressed with soluble CD18 in stably transfected CHO cells, and expression is detected by autoradiographic visualization of immunoprecipitated CD18 complexes derived from $^{35}$S-methionine labeled cells. The construct is also co-expressed with CD18 in 293 cells [Berman, et al., *J.Cell.Biochem.* 52:183–195 (1993)].

Soluble Human $\alpha_d$ Domain Expression Constructs

It has previously been reported that the I domain in CD11a can be expressed as an independent structural unit that maintains ligand binding capabilities and antibody recognition [Randi and Hogg, *J.Biol.Chem.* 269:12395–12398 (1994); Zhout, et al., *J.Biol.Chem.* 269:17075–17079 (1994); Michishita, et al., *Cell* 72:857–867 (1993)]. To generate a soluble fusion protein comprising the $\alpha_d$ I domain and human IgG4, the $\alpha_d$ I domain is amplified by PCR using primers designed to add flanking BamHI and XhoI restriction sites to facilitate subcloning. These primers are set out in SEQ ID NOS: 32 and 33 with restriction sites underlined.

amplified I domain is digested with the appropriate enzymes, the purified fragment ligated into the mammalian expression vector pDCs and the prokaryotic expression vector pGEX-4T-3 (Pharmacia) and the I domain fragment sequenced. The fusion protein is then expressed in COS, CHO or *E.coli* cells transfected or transformed with an appropriate expression construct.

Given the affinity of $\alpha_d$ for ICAM-R, expression of the $\alpha_d$ I domain may be of sufficient affinity to be a useful inhibitor of cell adhesion in which $\alpha_d$ participates.

Analysis of Human $\alpha_d$ I Domain/IgG4 Fusion Proteins

Protein was resolved by SDS-PAGE under reducing and non-reducing reducing conditions and visualized by either silver staining or Coomassie staining. Protein was then transferred to Immobilon PVDF membranes and subjected to Western blot analysis using anti-human IgG monoclonal antibodies or anti-bovine Ig monoclonal antibodies.

Protein detected was determined to migrate at about 120 kD under non-reducing conditions and at about 45 kD under reducing conditions. Minor bands were also detected on non-reducing gels at approximately 40–50 kD which were reactive with the anti-human, but not anti-bovine, antibodies. A 200 kD minor band was determined to be bovine Ig by Western blot.

Binding Assays Using I Domain Expression Products

The ability of the I domain to specifically recognize ICAM-R/IgG chimeric protein was tested in an ELISA format. Serial dilutions of $\alpha_d$ I domain IgG4 fusion protein (I$\alpha_d$/IgG4) in TBS were incubated with ICAM-1/IgG, ICAM-R/IgG, VCAM-1/IgG, or an irrelevant IgG1 myeloma protein immobilized on Immulon IV RIA/EIA plates. CD11a I domain/IgG chimeric protein and human IgG4/kappa myeloma protein were used as negative controls. Bound IgG4 was detected with the biotinylated anti-IgG4 monoclonal antibody HP6023 followed by addition of strepavidin-peroxidase conjugate and development with substrate o-phenyldiamine.

In repeated assays, no binding of the CD11a/IgG4 protein or the IgG4 myeloma protein was detected with any of the immobilized proteins. The I$\alpha_d$/IgG$^4$ protein did not bind to fish skin gelatin or bovine serum albumin blocking agents, human IgG1, or ICAM-1/IgG. A two to three fold increase in binding signal over background was detected in ICAM-R/IgG protein coated wells using 1–5 µg/ml concentrations of I$\alpha_d$/IgG$^4$ protein. The signal in VCAM-1/IgG protein coated wells was 7–10 fold higher than background. In previous assays, $\alpha_d$/CD18 transfected CHO cells did not bind VCAM-1/IgG protein, suggesting that VCAM-1 binding may be characteristic of isolated I domain amino acid sequences.

| | |
|---|---|
| 5'-ACGTATGCAGGATCCCATCAAGAGATGGACATCGCT | (SEQ ID NO: 32) |
| 5'-ACTGCATGTCTCGAGGCTGAAGCCTTCTTGGGACAT | (SEQ ID NO: 33) |

The C nucleotide immediately 3' to the BamHI site in SEQ ID NO: 32 corresponds to nucleotide 435 in SEQ ID NO: 1; the G nucleotide 3' to the XhoI site in SEQ ID NO: 33 is complementary to nucleotide 1067 in SEQ ID NO: 1. The Additional $\alpha_d$ I domain constructs Additional $\alpha_d$ I domain constructs are generated in the same fashion as the previous construct, but incorporating more amino acids around the $\alpha_d$ I domain. Specific constructs include: i) sequences from exon 5 (amino acids 127–353 in SEQ ID NO: 2), preceding the current construct, ii) the EF-hand repeats (amino acids 17–603 in SEQ ID NO: 2) following the I domain, and iii) the alpha chain truncated at the transmembrane region (amino acids 17–1029 in SEQ ID NO: 2), with an IgG4 tail for purification and detection purposes. These constructs are ligated into either the mammalian expression vector pDCS1 or the prokaryotic expression vector pGEX-4T-3 (Pharmacia) and the I domain sequenced. The fusion proteins are then be expressed in COS, CHO, or E.coli cells transformed or transfected with an appropriate expression construct. Protein are purified on a ProSepA column (Bioprocessing Limited, Durham, England), tested for reactivity with the anti-IgG4 monoclonal antibody HP6023 and visualized on polyacrylamide gels with Coomassie staining.

In order to construct an expression plasmid for the entire $\alpha_d$ polypeptide, pATM.D12, described supra, is modified to express an $\alpha_d$-IgG4 fusion protein by the following method. IgG4 encoding DNA is isolated from the vector pDCS1 by PCR using primers which individually incorporate a 5' AatII restriction site (SEQ ID NO: 89) and a 3' Xbal restriction site (SEQ ID NO: 90).

| | |
|---|---|
| 5'-CGCTGTGACGTCAGAGTTGAGTCCAAATATGG-3' | (SEQ ID NO: 89) |
| 5'-GGTGACACTATAGAATAGGGC-3' | (SEQ ID NO: 90) |

Plasmid pATM.D12 is digested with AatII and Xbal, and the appropriately digested and purified IgG4 PCR product ligated into the linear vector.

EXAMPLE 15
Production of Human $\alpha_d$-Specific Monoclonal Antibodies

Transiently transfected cells from Example 7 were washed three times in Dulbecco's phosphate buffered saline (D-PBS) and injected at $5 \times 10^6$ cells/mouse into Balb/c mice with 50 µg/mouse muramyl dipeptidase (Sigma) in PBS. Mice were injected two more times in the same fashion at two week intervals. The pre-bleed and immunized serum from the mice were screened by FACS analysis as outlined in Example 9 and the spleen from the mouse with the highest reactivity to cells transfected with $\alpha_d$/CD18 was fused. Hybridoma culture supernatants were then screened separately for lack of reactivity against COS cells transfected with CD11a/CD18 and for reactivity with cells co-transfected with an $\alpha_d$ expression plasmid and CD18.

This method resulted in no monoclonal antibodies.

As an alternative for production of monoclonal antibodies, soluble $\alpha_d$ I domain IgG4 fusion protein was affinity purified from supernatant of stably transfected CHO cells and used to immunize Balb/c mice as described above. Hybridomas were established and supernatants from these hybridomas were screened by ELISA for reactivity against $\alpha_d$ I domain fusion protein. Positive cultures were then analyzed for reactivity with full length $\alpha_d$/CD18 complexes expressed on CHO transfectants.

Mouse 1908 received three initial immunizations of $\alpha_d$/CD18 transfected CHO cells and two subsequent boosts with soluble $\alpha_d$/CD18 heterodimer. Two final immunizations included 50 µg/mouse I$\alpha_d$/IgG$^4$ fusion protein. The fusion produced 270 IgG-producing wells. Supernatant from 45 wells showed at least 7-fold higher binding to I$\alpha_d$/IgG$^4$ fusion protein than to human IgG4 by ELISA. None of the supernatants reacted to $\alpha_d$/CD18 transfected CHO cells as determined by FACS analysis.

To determine whether the supernatants were able to recognize integrin alpha subunit proteins in another context, fresh frozen splenic sections were stained with supernatants from 24 of the 45 wells. Three supernatants were determined to be positive: one stained large cells in the red pulp, while two others stained scattered cells in the red pulp and also trabeculae.

These supernatants were further analyzed by their ability to immunoprecipitate biotinylated CD18 complexes from either $\alpha_d$/CD18 transfected CHO cells or PMA-stimulated HL60 cells. Fusion wells with supernatants that recognized protein in detergent lysates (which should not be as conformationally constrained as protein expressed as heterodimers) were selected for further subcloning. Monoclonal antibodies which recognize protein in detergent may be more useful in immunoprecipitation of heterodimeric complexes from transfectants, tissues, and cell lines.

As another alternative, monoclonal antibodies are generated as follows. Affinity purified $\alpha_d$/CD18 heterodimeric protein from detergent lysates of stably transfected CHO cells is used with 50 µg/ml muramyl dipeptidase to immunize Balb/c mice as described above. Mice receive three immunizations before serum reactivity against $\alpha_d$/CD18 is determined by immunoprecipitation of biotinylated complexes in the CHO transfectants. Hybridomas from positive animals are established according to standard protocols, after which hybridoma cultures are selected by flow cytometry using $\alpha_d$/CD18 transfectants. CD11a/CD18 transfectants are utilized to control for CD18-only reactivity.

As another alternative for monoclonal antibody production, Balb/c mice undergo an immunization/immunosuppression protocol designed to reduce reactivity to CHO cell determinants on transfectants used for immunization. This protocol involves immunization with untransfected CHO cells and subsequent killing of CHO-reactive B-cell blasts with cyclophosphamide treatment. After three rounds of immunization and cyclophosphamide treatment are performed, the mice are immunized with $\alpha_d$/CD18 CHO transfected cells as described above.

As still another alternative, heterodimeric CD18 complexes are immunoprecipitated from detergent lysates of whole spleen using an anti-CD18 monoclonal antibody, following preclearance of CD11a/CD18 and CD11b/CD18. CD11a/CD18 and CD11b/CD18 complexes are precleared by affinity chromatography using monoclonal antibodies TS2/4 and Mo1 respectively, coupled to a chromatographic resin. The remaining CD18 complexes are used as an immunogen in Balb/c mice for the first immunization. Three immunizations are given at three week intervals, the initial immunization administered in conjunction with Freund's Complete Adjuvant and the subsequent immunizations with Freund's Incomplete Adjuvant. Serum is assayed for $\alpha_d$-specific reactivity by immunoprecipitation. Resulting hybridomas are screened by flow cytometry with $\alpha_d$/CD18 CHO transfectants.

As another alternative, CD18 complexes from detergent lysates of PMA stimulated HL60 cells are enriched by preclearance as described above. Other $\beta2$ integrins are cleared on the same columns. Immunization with the resulting complexes, hybridoma production, and screening protocols are performed as described supra.

EXAMPLE 16
Analysis of $\alpha_d$ distribution with polyclonal serum

Tissue distribution of $\alpha_d$/CD18 was determined using polyclonal antiserum. Antiserum used to stain tissue was obtained from a mouse immunized 3 times with $\alpha_d$ transfected CHO cells (D6.CHO, $\alpha_d$/CD18) with adjuvant peptide and once with purified α$_d$/CD18 heterodimer. A final boost included only α$_d$/CD18 heterodimer. Approximately 100 µl immunized serum was precleared by addition of approximately 10$^8$ LFA-1-transfected CHO cells for 2 hours at 4° C. The resulting serum was assayed for α$_d$ reactivity at dilutions of 1/5000, 1/10000, 1/20000 and 1/40000 on normal human spleen. The polyclonal antibody was reactive at a dilution of 1/20000, while a 1/40000 dilution stained very weakly.

Once serum was determined to have specific α$_d$ reactivity, it was used to stain various lymphoid and non-lymphoid tissues. Monoclonal antibodies recognizing CD18, CD11a, CD11b, and CD11c were used in the same experiment as controls. Staining of normal spleen sections with α$_d$ polyclonal sera, and monoclonal antibodies to CD11a, CD11b, CD11c, and CD18 revealed the following results. The pattern observed with α$_d$ polyclonal sera did not display the same pattern of labeling as CD11a, CD11b, CD11c, or CD18. There is a distinct pattern of labeling with some cells located in the marginal zone of the white pulp and a distinct labeling of cells peripheral to the marginal zone. This pattern was not observed with the other antibodies. Individual cells scattered throughout the red pulp were also labeled which may or may not be the same population or subset seen with CD11a and CD18.

Labeling with CD11c did display some cells staining in the marginal zone, but the antibody did not show the distinct ring pattern around the white pulp when compared to α$_d$ polyclonal sera, nor did labeling in the red pulp give the same pattern of staining as α$_d$ polyclonal sera.

Therefore, the labeling pattern seen with α$_d$ polyclonal serum was unique compared to that seen using antibodies to the other β$_2$ integrins (CD11a, CD11b, CD11c, and CD18), and suggests that the in vivo distribution of α$_d$ in man is dinstinct from that of other β$_2$ integrins.

EXAMPLE 17
Isolation of Rat cDNA Clones

In view of the existence of both canine and human α$_d$ subunits, attempts were made to isolate homologous genes in other species, including rat (this example) and mouse (Example 17, infra).

A partial sequence of a rat cDNA showing homology to the human α$_d$ gene was obtained from a rat splenic λgt10 library (Clontech). The library was plated at 2×10$^4$ pfu/plate onto 150 mm LBM/agar plates. The library was lifted onto Hybond membranes (Amersham), denatured 3 minutes, neutralized 3 minutes and washed 5 minutes with buffers as described in standard protocols [Sambrook, et al., *Molecular Cloning: a laboratory manual*, p.2.110]. The membranes were placed immediately into a Stratalinker (Stratagene) and the DNA crosslinked using the autocrosslinking setting. The membranes were prehybridized and hybridized in 30% or 50% formamide, for low and high stringency conditions, respectively. Membranes were initially screened with a $^{32}$P-labeled probe generated from the human α$_d$ cDNA, corresponding to bases 500 to 2100 in clone 19A2 (SEQ ID NO: 1). The probe was labeled using Boehringer Mannheim's Random Prime Kit according to manufacturer's suggested protocol. Filters were washed with 2X SSC at 55° C.

Two clones, designated 684.3 and 705.1, were identified which showed sequence homology to human α$_d$, human CD11b, and human CD11c. Both clones aligned to the human α$_d$ gene in the 3' region of the gene, starting at base 1871 and extending to base 3012 for clone 684.3, and bases 1551 to 3367 for clone 705.1.

In order to isolate a more complete rat sequence which included the 5' region, the same library was rescreened using the same protocol as employed for the initial screening, but using a mouse probe generated from clone A1160 (See Example 17, infra). Single, isolated plaques were selected from the second screening and maintained as single clones on LBM/agar plates. Sequencing primers 434FL and 434FR (SEQ ID NOS: 34 and 35, respectively) were used in a standard PCR protocol to generate DNA for sequencing.

| | |
|---|---|
| 5'-TATAGACTGCTGGGTAGTCCCCAC-3' | (SEQ ID NO: 34) |
| 5'-TGAAGATTGGGGGTAAATAACAGA-3' | (SEQ ID NO: 35) |

DNA from the PCR was purified using a Quick Spin Column (Qiagen) according to manufacturer's suggested protocol.

Two clones, designated 741.4 and 741.11, were identified which overlapped clones 684.3 and 705.1; in the overlapping regions, clones 741.1 and 741.11 were 100% homologous to clones 684.3 and 705.1. A composite rat cDNA having homology to the human α$_d$ gene is set out in SEQ ID NO: 36; the predicted amino acid sequence is set forth in SEQ ID NO: 37.

Cloning of the 5' end of Rat α$_d$

A 5' cDNA fragment for the rat α$_d$ gene was obtained using a Clonetech rat spleen RACE cloning kit according to manufacturer's suggested protocol. The gene specific oligonucleotides used were designated 741.11#2R and 741.2#1R (SEQ ID NOS: 59 and 58, respectively).

| | |
|---|---|
| 5'-CCAAAGCTGGCTGCATCCTCTC-3' | (SEQ ID NO: 59) |
| 5'-GGCCTTGCAGCTGGACAATG-3' | (SEQ ID NO: 58) |

Oligo 741.11#2R encompasses base pairs 131–152 in SEQ ID NO: 36, in the reverse orientation and 741.2#1R encompasses bases pairs 696–715 in SEQ ID NO: 36, also in the reverse orientation. A primary PCR was carried out using the 3'-most oligo, 741.2#1R. A second PCR followed using oligo 741.11#2R and DNA generated from the primary reaction. A band of approximately 300 base pairs was detected on a 1% agarose gel.

The secondary PCR product was ligated into plasmid pCRTAII (Invitrogen) according to manufacturer's suggested protocol. White (positive) colonies were picked and added to 100 µl LBM containing 1 µl of a 50 mg/ml carbenicillin stock solution and 1 µl M13 K07 phage culture in individual wells in a round bottom 96 well tissue culture plate. The mixture was incubated at 37° C. for 30 minutes to one hour. Following the initial incubation period, 100 µl of LBM (containing 1 µl of 50 mg/ml carbenicillin and a 1:250 dilution of a 10 mg/ml kanamycin stock solution) were added and the incubation was continued overnight at 37° C.

Using a sterile 96 well metal transfer prong, supernatant from the 96 well plate was transferred to four Amersham Hybond nylon filters. The filters were denatured, neutralized and cross linked by standard protocols. The filters were prehybridized in 20 mls of prehybridization buffer (5X SSPE; 5X Denhardts; 1% SDS; 50 ugs/ml denatured salmon sperm DNA) at 50° C. for several hours while shaking.

Oligo probes 741.11#1 and 741.11#1R (SEQ ID NOS: 56 and 57, respectively), encompassing base pairs 86–105 (SEQ ID NO: 36) in the forward and reverse orientation respectively, were labeled as follows.

| | |
|---|---|
| 5'-CCTGTCATGGGTCTAACCTG-3' | (SEQ ID NO: 56) |
| 5'-AGGTTAGACCCATGACAGG-3' | (SEQ ID NO: 57) |

Approximately 65 ng oligo DNA in 12 µl dH$_2$O was heated to 65° C. for two minutes. Three µl of 10 mCi/ml λ-$^{32}$P-ATP were added to the tube along with 4 µl 5x Kinase Buffer (Gibco) and 1 µl T4 DNA Kinase (Gibco). The mixture was incubated at 37° C. for 30 minutes. Following incubation, 16 µl of each labeled oligo probe were added to the prehybridization buffer and filters and hybridization was continued overnight at 42° C. The filters were washed three times in 5X SSPE; 0.1% SDS for 5 minutes per wash at room temperature, and autoradiographed for 6 hours. Positive clones were expanded and DNA purified using the Magic Mini Prep Kit (Promega) according to manufacturer's suggested protocol. Clone 2F7 was selected for sequencing and showed 100% homology to clone 741.11 in the overlapping region. The complete rat $\alpha_d$ nucleic acid sequence is set out in SEQ ID NO: 54; the amino acid sequence is set out in SEQ ID NO: 55.

Characteristics of the Rat cDNA and Amino Acid Sequences

Neither nucleic acid nor amino acid sequences have previously been reported for rat a subunits in β$_2$ integrins. However sequence comparisons to reported human β$_2$ integrin a subunits suggests that the isolated rat clone and its predicted amino acid sequence are most closely related to $\alpha_d$ nucleotide and amino acid sequences.

At the nucleic acid level, the isolated rat cDNA clone shows 80% identity in comparison to the human $\alpha_d$ cDNA; 68% identity in comparison to human CD11b; 70% identity in comparison to human CD11c; and 65% identity in comparison to mouse CD11b. No significant identity is found in comparison to human CD11a and to mouse CD11a.

At the amino acid level, the predicted rat polypeptide encoded by the isolated cDNA shows 70% identity in comparison to human $\alpha_d$ polypeptide; 28% identity in comparison to human CD11a; 58% identity in comparison to human CD11b; 61% identity in comparison to human CD11c; 28% identity in comparison to mouse CD11a; and 55% identity in comparison to mouse CD11b.

EXAMPLE 18

Monoclonal Antibodies against Rat $\alpha_d$ I domain/Hu IgG4 Fusion Proteins

In view of the fact that the I domain of human β$_2$ integrins has been demonstrated to participate in ligand binding, it was assumed that the same would be true for rat $\alpha_d$ protein. Monoclonal antibodies immunospecific for the rat $\alpha_d$ I domain may therefore be useful in rat models of human disease states wherein $\alpha_d$ binding is implicated.

Oligos "rat alpha-DI5" (SEQ ID NO: 87) and "rat alpha-DI3" (SEQ ID NO: 88) were generated from the rat $\alpha_d$ sequence corresponding to base pairs 469–493 and base pairs 1101–1125 (in the reverse orientation), respectively, in SEQ ID NO: 54. The oligos were used in a standard PCR reaction to generate a rat $\alpha_d$ DNA fragment containing the I domain spanning base pairs 459–1125 in SEQ ID NO: 54. The PCR product was ligated into vector pCRTAII (Invitrogen) according to manufacturer's suggested protocol. A positive colony was selected and expanded for DNA purification using a Qiagen (Chatswoth, Ga.) Midi Prep kit according to manufacturer's protocol. The DNA was digested with XhoI and BglII in a standard restriction enzyme digest and a 600 base pair band was gel purified which was subsequently ligated into pDCS1/HuIgG4 expression vector. A positive colony was selected, expanded and DNA purified with a Quiagen Maxi Prep Kit.

COS cells were plated at half confluence on 100 mm culture dishes and grown overnight at 37° C. in 7% CO$_2$. Cells were rinsed once with 5 ml DMEM. To 5 ml DMEM, 50 µl DEAE-Dextran, 2 µl chloroquine and 15 µg rat $\alpha_d$ I domain/HuIgG4 DNA described above was added. The mixture was added to the COS cells and incubated at 37°C. for 3 hours. Media was then removed and 5 ml 10% DMSO in CMF-PBS was added for exactly one minute. The cells were gently rinsed once with DMEM. Ten ml DMEM containing 10% FBS was added to the cells and incubation continued overnight at 37°C. in 7% CO$_2$. The next day, media was replaced with fresh media and incubation continued for three additional days. The media was harvested and fresh media was added to the plate. After three days, the media was collected again and the plates discarded. The procedure was repeated until 2 liters of culture supernatant were collected.

Supernatant collected as described above was loaded onto a Prosep-A column (Bioprocessing Limited) and protein purified as described below.

The column was initially washed with 15 column volumes of Wash Buffer containing 35 mM Tris and 150 mM NaCl, pH 7.5. Supernatant was loaded at a slow rate of less than approximately 60 column volumes per hour. After loading, the column was washed with 15 column volumes of Wash Buffer, 15 column volumes of 0.55M diethanolamine, pH 8.5, and 15 column volumes 50 mM citric acid, pH 5.0. Protein was eluted with 50 mM citric acid, pH 3.0. Protein was neutralized with 1.0M Tris, pH 8.0, and dialyzed in sterile PBS.

The rat $\alpha_d$ I domain protein was analyzed as described in Example 14. The detected protein migrated in the same manner as observed with human I domain protein.

Immunization Protocol

Mice were individually immunized with 50 µg purified rat $\alpha_d$ I domain/HuIgG4 fusion protein previously emulsified in an equal volume of Freunds Complete Adjuvant (FCA) (Sigma). Approximately 200 µl of the antigen/adjuvant preparation was injected at 4 sites in the back and flanks of each of the mice. Two weeks later the mice were boosted with an injection of 100 µl rat $\alpha_d$ I domain/HuIgG4 antigen (50 µg/mouse) previously emulsified in an equal volume of Freunds Incomplete Adjuvant (FIA). After two additional weeks, the mice were boosted with 50 µg antigen in 200 µl PBS injected intravenously.

To evaluate serum titers in the immunized mice, retroorbital bleeds were performed on the animals ten days following the third immunization. The blood was allowed to clot and serum isolated by centrifugation. The serum was used in an immunoprecipitation on biotinylated (BIP) rat splenocytes. Serum from each mouse immunoprecipitated protein bands of expected molecular weight for rat $\alpha_d$ and rat CD18. One mouse was selected for the fusion and was boosted a fourth time as described above for the third boost.

The hybridoma supernatants were screened by antibody capture, described as follows. Immulon 4 plates (Dynatech, Cambridge, Mass.) were coated at 4° C. with 50 µl/well goat anti-mouse IgA, IgG or IgM (Organon Teknika) diluted 1:5000 in 50 mM carbonate buffer, pH 9.6. Plates were washed 3x with PBS containing 0.05% Tween 20 (PBST) and 50 µl culture supernatant was added. After incubation at 37° C. for 30 minutes, and washing as described above, 50 µl horseradish peroxidase-conjugated goat anti-mouse IgG9 (Fc) (Jackson ImmunoResearch, West Grove, Pa.) diluted 1:3500 in PBST was added. Plates were incubated as described above and washed 4x with PBST. Immediately thereafter, 100µl substrate, containing 1 mg/ml o-phenylene diamine (Sigma) and 0.1 µl/ml 30% $H_2O_2$ in 100 mM citrate, pH4.5, was added. The color reaction was stopped after 5 minutes with the addition of 50 µl 15% $H_2SO_4$. Absorbance at 490 nm was read on a Dynatech plate reader.

Supernatant from antibody-containing wells was also analyzed by ELISA with immobilized rat $\alpha_d$ I domain/HuIgG4 fusion protein. An ELISA with HuIgG4 antibody coated plates served as a control for reactivity against the IgG fusion partner. Positive wells were selected for further screening by BIP on rat splenocyte lysates using techniques described below.

Biotinylation of Cell Surface Antigens

Rats were sacrificed by asphyxiation with $CO_2$ and spleens were removed using standard surgical techniques. Splenocytes were harvested by gently pushing the spleen through a wire mesh with a 3 cc syringe plunger in 20 mls RPMI. Cells were collected into a 50 ml conical tube and washed in the appropriate buffer.

Cells were washed three times in cold D-PBS and resuspended at a density of $10^8$ to $10^9$ cells in 40 ml PBS. Four mg of NHS-Biotin (Pierce) was added to the cell suspension and the reaction was allowed to continue for exactly 15 minutes at room temperature. The cells were pelleted and washed three times in cold D-PBS.

Cell Lysates

Cells were resuspended at a density of $10^8$ cells/ml in cold lysis Buffer (1% NP40; 50 mM Tris-HCl, pH 8.0; 150 mM NaCl; 2 mM CaCl; 2 mM MgCl; 1:100 solution of pepstain, leupeptine, and aprotinin, added just before adding to cells; and 0.0001 g PMSF crystals, added just before adding to cells). Lysates were vortexed for approximately 30 seconds, incubated for 5 minute at room temperature, and further incubated for 15 minutes on ice. Lysates were centrifuged for 10 minutes at 10,000 xg to pellet the insoluble material. Supernatant was collected into a new tube and stored at between 4° C. and −20 C.

Immunoprecipitation

One ml cell lysate was precleared by incubation with 200 µl of a protein A sepharose slurry (Zymed) overnight at 4° C. Precleared lysate was aliquoted into Eppendorf tubes at 50 µl/tube for each antibody to be tested. Twenty-five µl of polyclonal serum or 100 to 500 µl of monoclonal antibody supernatant were added to the precleared lysates and the resulting mixture incubated for 2 hours at 4° C. with rotation. One hundred µl rabbit anti-mouse IgG (Jackson) bound to protein A sepharose beads in a PBS slurry was then added and incubation continued for 30 minutes at room temperature with rotation. Beads were pelleted with gentle centrifugation, and washed three times with cold Wash Buffer (10 mM HEPES; 0.2M NaCl; 1% Trition X-100). Supernatant was removed by aspiration, and 20 µl 2X SDS sample buffer containing 10% β-mercaptoethanol was added. The sample was boiled for 2 minutes in a water bath, and the sample loaded onto a 5% SDS PAGE gel. Following separation, the proteins were transferred to nitrocellulose at constant current overnight. The nitrocellulose filters were blocked with 3% BSA in TBS-T for 1 hour at room temperature and the blocking buffer was removed. A 1:6000 dilution of Strepavidin-HRP conjugate (Jackson) in 0.1% BSA TBS-T was added and incubation continued for 30 minutes at room temperature. Filters were washed three times for 15 minutes each with TBS-T and autoradiographed using Amersham's ECL kit according to manufacturer's suggested protocol.

EXAMPLE 19
Isolation of Mouse cDNA Clones

Isolation of a mouse $\alpha_d$ homolog was attempted.

Cross-species hybridization was performed using two PCR-generated probes: a 1.5 kb fragment corresponding to bases 522 to 2047 from human clone 19A2 (SEQ ID NO: 1), and a 1.0 kb rat fragment which corresponds to bases 1900 to 2900 in human clone 19A2 (SEQ ID NO: 1). The human probe was generated by PCR using primer pairs designated ATM-2 and 9-10.1 set out in SEQ ID NOS: 38 and 39, respectively; the rat probe was generated using primer pairs 434L and 434R, set out in SEQ ID NOS: 34 and 35, respectively. Samples were incubated at 94° C. for 4 minutes and subjected to 30 cycles of the temperature step sequence: 94° C.; 50° C. 2 minutes; 72° C., 4 minutes.

| | |
|---|---|
| 5'-GTCCAAGCTGTCATGGGCCAG-3' | (SEQ ID NO: 38) |
| 5'-GTCCAGCAGACTGAAGAGCACGG-3' | (SEQ ID NO: 39) |

The PCR products were purified using the Qiagen Quick Spin kit according to manufacturer's suggested protocol, and approximately 180 ng DNA was labeled with 200 µCi [$^{32}$P]-dCTP using a Boehringer Mannheim Random Primer Labeling kit according to manufacturer's suggested protocol. Unincorporated isotope was removed using a Centri-sep Spin Column (Princeton Separations, Adelphia, N.J.) according to manufacturer's suggested protocol. The probes were denatured with 0.2N NaOH and neutralized with 0.4M Tris-HCl, pH 8.0, before use.

A mouse thymic oligo dT-primed cDNA library in lambda ZAP II (Stratagene) was plated at approximately 30,000 plaques per 15 cm plate. Plaque lifts on nitrocellulose filters (Schleicher & Schuell, Keene, N.H.) were incubated at 50° C. with agitation for 1 hour in a prehybridization solution (8 ml/lift) containing 30% formamide. Labeled human and rat probes were added to the prehybridization solution and incubation continued overnight at 50° C. Filters were washed twice in 2X SSC/0.1% at room temperature, once in 2X SSC/0.1% SDS at 37° C., and once in 2X SSC/0.1% SDS at 42° C. Filters were exposed on Kodak X-Omat AR film at −80° C. for 27 hours with an intensifying screen.

Four plaques giving positive signals on duplicate lifts were restreaked on LB medium with magnesium (LBM)/carbenicillin (100 mg/ml) plates and incubated overnight at 37° C. The phage plaques were lifted with Hybond filters (Amersham), probed as in the initial screen, and exposed on Kodak X-Omat AR film for 24 hours at −80° C. with an intensifying screen.

Twelve plaques giving positive signals were transferred into low $Mg^{++}$phage diluent containing 10 mM Tris-HCl and 1 mM $MgCl_2$. Insert size was determined by PCR amplification using T3 and T7 primers (SEQ ID NOS: 13 and 14, respectively) and the following reaction conditions. Samples were incubated at 94° C. for 4 minutes and subjected to 30 cycles of the temperature step sequence: 94° C., for 15 seconds; 50° C., for 30 seconds; and 72° C. for 1 minute.

Six samples produced distinct bands that ranged in size from 300 bases to 1 kb. Phagemids were released via co-infection with helper phage and recircularized to generate Bluescript SK⁻ (Stratagene). The resulting colonies were cultured in LBM/carbenicillin (100 mg/ml) overnight. DNA was isolated with a Promega Wizard miniprep kit (Madison, Wis.) according to manufacturer's suggested protocol. EcoRI restriction analysis of purified DNA confirmed the molecular weights which were detected using PCR. Insert DNA was sequenced with M13 and M13 reverse.1 primers set out in SEQ ID NOS: 40 and 41, respectively.

| | |
|---|---|
| 5'-TGTAAAACGACGGCCAGT-3' | (SEQ ID NO: 40) |
| 5'-GGAAACAGCTATGACCATG-3' | (SEQ ID NO: 41) |

Sequencing was performed as described in Example 4.

Of the six clones, only two, designated 10.3-1 and 10.5-2, provided sequence information and were identical 600 bp fragments. The 600 bp sequence was 68% identical to a corresponding region of human $\alpha_d$, 40% identical to human CD11a, 58% identical to human CD11c, and 54% identical to mouse CD11b. This 600 bp fragment was then utilized to isolate a more complete cDNA encoding a putative mouse $\alpha_d$ homolog.

A mouse splenic cDNA library (oligo dT⁻ and random-primed) in lambda Zap II (Stratagene) was plated at $2.5 \times 10^4$ phage/15 cm LBM plate. Plaques were lifted on Hybond nylon transfer membranes (Amersham), denatured with 0.50M NaOH/1.5M NaCl, neutralized with 0.5M Tris Base/ 1.5M NaCl/11.6 HCl, and washed in 2X SSC. The DNA was cross-linked to filters by ultraviolet irradiation.

Approximately 500,000 plaques were screened using probes 10.3-1 and 10.5-2 previously labeled as described supra. Probes were added to a prehybridization solution and incubated overnight at 50° C. The filters were washed twice in 2X SSC/0.1% SDS at room temperature, once in 2X SSC/0.1% SDS at 37° C., and once in 2X SSC/0.1% SDS at 42° C. Filters were exposed on Kodak X-Omat AR film for 24 hours at −80° C. with an intensifying screen. Fourteen plaques giving positive signals on duplicate lifts were subjected to a secondary screen identical to that for the initial screen except for additional final high stringency washes in 2X SSC/0.1% SDS at 50° C., in 0.5X SSC/0.1% SDS at 50° C., and at 55° C. in 0.2X SSC/0.1% SDS. The filters were exposed on Kodak X-Omat AR film at −80° C. for 13 hours with an intensifying screen.

Eighteen positive plaques were transferred into low Mg⁺⁺ phage diluent and insert size determined by PCR amplification as described above. Seven of the samples gave single bands that ranged in size from 600 bp to 4 kb. EcoRI restriction analysis of purified DNA confirmed the sizes observed from PCR and the DNA was sequenced with primers M13 and M13 reverse.1 (SEQ ID NOS: 40 and 41, respectively).

One clone designated B3800 contained a 4 kb insert which corresponded to a region 200 bases downstream of the 5' end of the human $\alpha_d$ 19A2 clone and includes 553 bases of a 3', untranslated region. Clone B3800 showed 77% identity to a corresponding region of human $\alpha_d$, 44% identity to a corresponding region of human CD11a, 59% identity to a corresponding region of human CD11c, and 51% identity to a corresponding region of mouse CD11b. The second clone A 1160 was a 1.2 kb insert which aligned to the 5' end of the coding region of human $\alpha_d$ approximately 12 nucleic acids downstream of the initiating methionine. Clone A1160 showed 75% identity to a corresponding region of human $\alpha_d$, 46% identity to a corresponding region of human CD11a, 62% identity to a corresponding region of human CD11c, and 66% identity to a corresponding region of mouse CD11b.

Clone A1160, the fragment closer to the 5' end of human clone 19A2, is 1160 bases in length, and shares a region of overlap with clone B3800 starting at base 205 and continuing to base 1134. Clone A1160 has a 110-base insertion (bases 704–814 of clone A1160) not present in the overlapping region of clone B3800. This insertion occurs at a probable exon-intron boundary [Fleming, et al., J.Immunol. 150:480–490 (1993)] and was removed before subsequent ligation of clones A1160 and B3800.

Rapid Amplification of 5' cDNA End of the Putative Mouse $\alpha_d$ Clone

RACE PCR [Frohman, "RACE: Rapid Amplification of cDNA Ends," in PCR Protocols: A Guide to Methods and Applications, Innis, et al. (eds.) pp. 28–38, Academic Press-:New York (1990)] was used to obtain missing 5' sequences of the putative mouse $\alpha_d$ clone, including 5' untranslated sequence and initiating methionine. A mouse splenic RACE-Ready kit (Clontech, Palo Alto, Calif.) was used according to the manufacturer's suggested protocol. Two antisense, gene-specific primers, A1160 RACE1-primary and A1160 RACE2-nested (SEQ ID NOS: 42 and 43), were designed to perform primary and nested PCR.

| | |
|---|---|
| 5'-GGACATGTTCACTGCCTCTAGG-3' | (SEQ ID NO: 42) |
| 5'-GGCGGACAGTCAGACGACTGTCCTG-3' | (SEQ ID NO: 43) |

The primers, SEQ ID NOS: 42 and 43, correspond to regions starting 302 and 247 bases from the 5' end, respectively. PCR was performed as described, supra, using the 5' anchor primer (SEQ ID NO: 44) and mouse spleen cDNA supplied with the kit.

| | |
|---|---|
| 5'-CTGGTTCGGCCCACCTCTGAAGGTTCCAGAATCGAT | (SEQ ID NO: 44) |

Electrophoresis of the PCR product revealed a band approximately 280 bases in size, which was subcloned using a TA cloning kit (Invitrogen) according to manufacturer's suggested protocol. Ten resulting colonies were cultured, and the DNA isolated and sequenced. An additional 60 bases of 5' sequence were identified by this method, which correspond to bases 1 to 60 in SEQ ID NO: 45.

Characteristics of the Mouse cDNA and Predicted Amino Acid Sequence

A composite sequence of the mouse cDNA encoding a putative homolog of human $\alpha_d$ is set out in SEQ ID NO: 45. Although homology between the external domains of the human and mouse clones is high, homology between the cytoplasmic domains is only 30%. The observed variation may indicate Cterminal functional differences between the human and mouse proteins. Alternatively, the variation in the cytoplasmic domains may result from splice variation, or may indicate the existence of an additional $\beta_2$ integrin gene(s).

At the amino acid level, the mouse cDNA predicts a protein (SEQ ID NO: 46) with 28% identity to mouse CD11a, 53% identity to mouse CD11b, 28% identity to human CD11a, 55% identity to human CD11b, 59% identity to human CD11c, and 70% identity to human $\alpha_d$. Comparison of the amino acid sequences of the cytoplasmic domains of human $\alpha_d$ and the putative mouse homolog indicates regions of the same length, but having divergent primary structure. Similar sequence length in these regions suggests species variation rather than splice variant forms. When compared to the predicted rat polypeptide, Example 16, supra, mouse and rat cytoplasmic domains show greater than 60% identity.

EXAMPLE 20
Isolation of additional mouse α d cDNA clones for sequence verification In order to verify the nucleic and amino acids sequences describe in Example 19 for mouse $\alpha_d$, additional mouse sequences were isolated for the purposes of confirmation.

Isolation of mouse cDNA by hybridization with two homologous $\alpha_d$ probes (3' and 5') was performed using both a mouse splenic random primed library and an oligo dT-primed cDNA library in lambda ZAP II (Strategene). The library was plated at 5×10⁵ phage per 15 cm LBM plate. Plaques were lifted on Hybond nylon membranes (Amersham), and the membranes were denatured (0.5M NaOH/1.5M NaCl), neutralized (0.5M Tris Base/1.5M NaCl /11.6M HCl) and washed (2X SSC salt solution). DNA was cross-lined to filters by ultraviolet irradiation.

Probes were generated using primers described below in a PCR reaction under the following conditions. Samples were held at 94° C. for 4 minutes and then run through 30 cycles of the temperature step sequence (94° C. for 15 seconds; 50° C. for 30 seconds; 72° C. for 1 minute in a Perkin-Elmer 9600 thermocycler).

The 3' probe was approximately 900 bases long and spanned a region from nucleotides 2752 to 3651 (in SEQ ID NO: 1) (5'→3') and was produced with primers 11.b-1/2FOR11 and 11.b-1/2REV2 as shown in SEQ ID NOS: 69 and 74, respectively. This probe was used in a first set of lifts.

The 5' probe was approximately 800 bases long and spanned a region from nucleotides 149 to 946 (in SEQ ID NO: 1) (5'→3'1) and was produced with primers 11.b-1/2FOR1 and 11.a-1/1REV1 as shown in SEQ ID NOS: 50 and 85, respectively). This probe was used in a second set of lifts.

In a third set of lifts, both probes described above were used together on the same plates.

Approximately 500,000 plaques were screened using the two probes from above which were labeled in the same way as described in Example 17. Labeled probes were added to a prehybridization solution, containing 45% formamide, and incubated overnight at 50° C. Filters were washed twice in 2X SSC/0.1% SDS at room temperature (22° C.). A final wash was carried out in 2X SSC/0.1% SDS at 50° C. Autoradiography was for 19 hours at −80° C. on Kodak X-Omat AR film with an intensifying screen.

Thirteen plaques giving positive signals on at least duplicate lifts were subjected to a secondary screen performed as described for the initial screen except that both the 3' and 5' labeled probes were used for hybridization and an additional final wash was incorporated using 2X SSC/0.1% SDS at 65' C. Autoradiography was performed as described above for 2.5 hours.

Thirteen plaques (designated MS2P1 through MS2P13) giving positive signals were transferred into low $Mg^{++}$phage diluent. Insert size was determined by PCR amplification (Perkin-Elmer 9600 thermocycler) using T3 and T7 primers which anneal to Bluescript phagemid in ZAP II (sequence previously described) under the same conditions shown above. Band sizes ranged from 500 bases to 4 Kb. Phagemids were isolated, prepared, and sequenced with M13 and M13 reverse. 1 primers (SEQ ID NOS: 40 and 41, respectively). Five of the thirteen clones; MS2P-3, MS2P-6, MS2P-9, MS2P-12, and MS2P-13, were sequenced, and together, represented a region from approximately base 200 at the 5' end to about 300 bases past a first stop codon at the 3' end.

Automated sequencing was performed as described in Example 4 by first using M13 and M13 reverse.1 primers (SEQ ID NOS: 40 and 41, respectively) to sequence the ends of each clone and to determine its position relative to construct #17 (SEQ ID NO: 45). Each clone was then completely sequenced using the appropriate primers (listed below) for that particular region.

| | | |
|---|---|---|
| 11.b-1/2FOR1 | 5'-GCAGCCAGCTTCGGACAGAC-3' | (SEQ ID NO: 50) |
| 11.a-1/1FOR2 | 5'-CCGCCTCCCACTGGCGTGTGC-3' | (SEQ ID NO: 60) |
| 11.a-1/1FOR3 | 5'-CCCAGATGAAGGACTTCGTCAA-3' | (SEQ ID NO: 61) |
| 11.b-1/2FOR4 | 5'-GCTGGGATCATTCGCTATGC-3' | (SEQ ID NO: 62) |
| 11.b-1/2FOR5 | 5'-CAATGGATGGACCAGTTCTGG-3' | (SEQ ID NO: 63) |
| 11.b-1/2FOR6 | 5'-CAGATCGGCTCCTACTTTGG-3' | (SEQ ID NO: 64) |
| 11.b-1/2FOR7 | 5'-CATGGAGCCTCGAGACAGG-3' | (SEQ ID NO: 65) |
| 11.b-1/2FOR8 | 5'-CCACTGTCCTCGAAGCTGGAG-3' | (SEQ ID NO: 66) |
| 11.b-1/2FOR9 | 5'-CTTCGTCCTGTGCTGGCTGTGGGCTC-3 | (SEQ ID NO: 67) |
| 11.b-1/2FOR10 | 5'-CGCCTGGCATGTGAGGCTGAG-3' | (SEQ ID NO: 68) |
| 11.b-1/2FOR11 | 5'-CCGTGATCAGTAGGCAGGAAG-3' | (SEQ ID NO: 69) |
| 11.b-1/2FOR12 | 5'-GTCACAGAGGGAACCTCC-3' | (SEQ ID NO: 70) |
| 11.b-1/2FOR13 | 5'-GCTCCTGAGTGAGGCTGAAATCA-3' | (SEQ ID NO: 71) |
| 11.b-1/2FOR14 | 5'-GAGATGCTGGATCTACCATCTGC-3' | (SEQ ID NO: 72) |
| 11.b-1/2FOR15 | 5'-CTGACCTGGGAGATTTTTATGG-3' | (SEQ ID NO: 73) |
| 11.b-1/2REV2 | 5'-GTGGATCAGCACTGAAATCTG-3' | (SEQ ID NO: 74) |
| 11.b-1/2REV3 | 5'-CGTTTGAAGAAGCCAAGCTTG-3' | (SEQ ID NO: 75) |
| 11.b-1/2REV4 | 5'-CACAGCGGAGGTGCAGGCAG-3' | (SEQ ID NO: 76) |
| 11.b-1/2REV5 | 5'-CTCACTGCTTGCGCTGGC-3' | (SEQ ID NO: 77) |
| 11.b-1/2REV6 | 5'-CGGTAAGATAGCTCTGCTGG-3' | (SEQ ID NO: 78) |
| 11.b-1/2REV7 | 5'-GAGCCCACAGCCAGCACAGG-3' | (SEQ ID NO: 79) |
| 11.b-1/2REV8 | 5'-GATCCAACGCCAGATCATACC-3' | (SEQ ID NO: 80) |
| 11.b-1/2REV9 | 5'-CACGGCCAGGTCCACCAGGC-3' | (SEQ ID NO: 81) |
| 11.b-1/2REV10 | 5'-CACGTCCCCTAGCACTGTCAG-3' | (SEQ ID NO: 82) |
| 11.b-1/2REV11 | 5'-CCATGTCCACAGAACAGAGAG-3' | (SEQ ID NO: 51) |
| 11.b-1/2REV12 | 5'-TTGACGAAGTCCTTCATCTGGG-3' | (SEQ ID NO: 83) |
| 11.b-1/2REV13 | 5'-GAACTGCAAGCTGGAGCCCAG-3' | (SEQ ID NO: 84) |
| 11.a-1/1REV1 | 5'-CTGGATGCTGCGAAGTGCTAC-3' | (SEQ ID NO: 85) |
| 11.a-1/1REV2 | 5'-GCCTTGGAGCTGGACGATGGC-3' | (SEQ ID NO: 86) |

Sequences were edited, aligned, and compared to a previously isolated mouse $\alpha_d$ sequence (construct #17, SEQ ID NO: 45).

Alignment of the new sequences revealed an 18 base deletion in construct #17 beginning at nucleotide 2308; the deletion did not cause a shift in the reading frame. Clone MS2P-9, sequenced as described above, also revealed the same 18 base deletion. The deletion has been observed to occur in 50% of mouse clones that include the region but has not been detected in rat or human $\alpha_d$ clones. The eighteen base deletion is characterized by a 12 base palindromic sequence AAGCAGGAGCTCCTGTGT (SEQ ID NO: 91). This inverted repeat in the nucleic acid sequence is self-complementary and may form a loop out, causing cleavage during reverse transcription. The mouse $\alpha_d$ sequence which includes the additional 18 bases is set forth in SEQ ID NO: 52; the deduced amino acid sequence is set forth in SEQ ID NO: 53.

EXAMPLE 21
In situ hybridizations in Mouse

Tissue distribution was then determined for mouse $\alpha_d$ in order to provide a comparison to that in humans, described in Example 6.

inserts from clones A1160 and B3800 were ligated. Prior to this ligation, however, a 5' leader sequence, including an initiating methionine, was added to clone A1160. A primer designated "5' PCR leader" (SEQ ID NO: 47) was designed to con tain: (1) identical nonspecific bases at positions 1–6 allowing for digestion; (2) a BamHI site (underlined in SEQ ID NO: 47) from positions 7–12 to facilitate subcloning into an expressi on vector; (3) a consensus Koza k sequence from position s 13–18, (4) a signal sequence including a codon for an initiating methionine (bold in SEQ ID NO: 47), and (5) an additional 31 bases of specifically overlapping 5' sequence from clone A1160 to allow primer annealing. A second primer designated "3' end frag" (SEQ ID NO: 48) was used with primer "5' PCR leader" to amplify the insert from clone A1160.

| 5'-AGTTACGGATCCGGCACCATGACCTTCGGCACTGTGATCCTCCTGTGTG-3' | (SEQ ID NO: 47) |
|---|---|
| 5'-GCTGGACGATGGGATCCAC-3' | (SEQ ID NO: 48) |

A single stranded 200 bp mRNA probe was generated from a DNA template, corresponding to nucleotides 3460 to 3707 in the cytoplasmic tail region of the murine cDNA, by in vitro RNA transcription incorporating $^{35}$S-UTP (Amersham).

Whole mouse embryos (harvested at days 11–18 after fertilization) and various mouse tissues, including spleen, kidney, liver, intestine, and thymus, were hybridized in situ with the radiolabeled single-stranded mRNA probe.

Tissues were sectioned at 6 μm thickness, adhered to Vectabond (Vector Laboratories, Inc., Burlingame, Calif.) coated slides, and stored at −70° C. Prior to use, slides were removed from −70° C. and placed at 50° C. for approximately 5 minutes. Sections were fixed in 4% paraformaldehyde for 20 minutes at 4° C., dehydrated with an increasing ethanol gradient (70–95–100%) for 1 minute at 4° C. at each concentration, and air dried for 30 minutes at room temperature. Sections were denatured for 2 minutes at 70° C. in 70% formamide/2X SSC, rinsed twice in 2X SSC, dehydrated with the ethanol gradient described supra and air dried for 30 minutes. Hybridization was carried out overnight (12–16 hours) at 55° C. in a solution containing $^{35}$S-labeled riboprobes at 6×10$^5$ cpm/section and diethylpyrocarbonate (DEPC)-treated water to give a final concentration of 50% formamide, 0.3M NaCl, 20 mM Tris-HCl, pH 7.5, 10% dextran sulfate, 1X Denhardt's solution, 100 mM dithiothreitol (DTT) and 5 mM EDTA. After hybridization, sections were washed for 1 hour at room temperature in 4X SSC/10 mM DTT, 40 minutes at 60° C. in 50% formamide/ 2X SSC/10 mM DTT, 30 minutes at room temperature in 2X SSC, and 30 minutes at room temperature in 0.1X SSC. The sections were dehydrated, air dried for 2 hours, coated with Kodak NTB2 photographic emulsion, air dried for 2 hours, developed (after storage at 4° C. in complete darkness) and counterstained with hematoxylin/eosin.

Spleen tissue showed a strong signal primarily in the red pulp. This pattern is consistent with that of tissue macrophage distribution in the spleen, but does not exclude other cell types.

EXAMPLE 22
Generation of Mouse Expression Constructs

In order to construct an expression plasmid including mouse cDNA sequences exhibiting homology to human $\alpha_d$, The resulting PCR product did not digest with BamHI, suggesting that an insufficient number of bases preceded the restriction site, prohibiting recognition by the enzyme. The length of the "tail" sequence preceding the BamHI site in the 5' primer (SEQ ID NO: 47) was increased and PCR was repeated on the amplification product from the first PCR. A 5' primer, designated mAD.5'.2 (SEQ ID NO: 49), was designed with additional nonspecific bases at positions 1–4 and an additional 20 bases specifically overlapping the previously employed "5' PCR leader" primer sequences.

| 5'-GTAGAGTTACGGATCCGGCACCAT-3' | (SEQ ID NO: 49) |
|---|---|

Primers "mAD.5'.2" and "3' end frag" were used together in PCR with the product from the first amplification as template. A resulting secondary PCR product was subcloned into plasmid pCRtmII (Invitrogen) according to manufacturer's suggested protocol and transformed into competent One shot cells (Invitrogen). One clone containing the PCR product was identified by restriction enzyme analysis using BamHI and EcoRI and sequenced. After the sequence was verified, the insert was isolated by digestion with BamHI and EcoRI and gel purified.

The insert from clone B3800 was isolated by digestion with EcoRI and NotI, gel purified, and added to a ligation reaction which included the augmented A1160 BamHI/ EcoRI fragment. Ligation was allowed to proceed for 14 hours at 14° C. Vector pcDNA.3 (Invitrogen), digested with BamHI and NotI, was added to the ligation reaction with additional ligase and the reaction was continued for another 12 hours. An aliquot of the reaction mixture was transformed into competent E. coli cells, the resulting colonies cultured, and one positive clone identified by PCR analysis with the primers 11.b-1/2FOR1 and 11.b-1/2REV11 (SEQ ID NOS: 50 and 51, respectively). These primers bridge the A1160 and B3800 fragments, therefore detection of an amplification product indicates the two fragments were ligated. The sequence of the positive clone was verified with the primers set out in SEQ ID NOS: 50 and 51, which amplify from base 100 to 1405 after the initiating methionine.

EXAMPLE 23
Construction of a Knock-out Mouse

In order to more accurately assess the immunological role of the protein encoded by the putative mouse $\alpha_d$ cDNA, a "knock-out" mouse is designed wherein the genomic DNA sequence encoding the putative $\alpha_d$ homolog is disrupted by homologous recombination. The significance of the protein encoded by the disrupted gene is thereby assessed by the absence of the encoded protein. Generation of "knock-out" mice is described in Deng, et al., Mol.Cell.Biol. 13:2134–2140 (1993).

Design of such a mouse begins with construction of a plasmid containing sequences to be "knocked out" by homologous recombination events. A 750 base pair fragment of the mouse cDNA (corresponding to nucleotides 1985 to 2733 in SEQ ID NO: 45) was used to identify a mouse genomic sequence encoding the putative mouse $\alpha_d$ homolog from a λFIXII genomic library. Primary screening resulted in 14 positive plaques, seven of which were confirmed by secondary screening. Liquid lysates were obtained from two of the plaques giving the strongest signal and the X DNA was isolated by conventional methods. Restriction mapping and Southern analysis confirmed the authenticity of one clone, designated 14-1, and the insert DNA was isolated by digestion with NotI. This fragment was cloned into Bluescript SKII+.

In order to identify a restriction fragment of approximately 9 to 14 kb, a length reported to optimize the probability of homologous recombination events, Southern hybridization was performed with the 750 bp cDNA probe. Prior to hybridization, a restriction map was constructed for clone 14-1. A 12 kb fragment was identified as a possible candidate and this fragment was subcloned into pBluescript SKII+ in a position wherein the mouse DNA is flanked by thymidine kinase encoding cassettes. Further analysis of this clone with an I domain probe (corresponding to nucleotides 454–1064 in SEQ ID NO: 45) indicated that the clone did not contain I domain encoding sequences.

Using the same I domain probe, the λFIXII genomic library was rescreened. Initially, six positive clones were detected, one of which remained positive upon secondary screening. DNA isolated from this clone reacted strongly in Southern analysis with an I domain probe. No reactivity was detected using the original 750 bp probe, however, indicating that this clone included regions 5 to nucleotides 1985–2773 of SEQ ID NO: 45.

Alternatively, the lack of hybridization to the 750 bp probe may have suggested that the clone was another member of the integrin family of proteins. To determine if this explanation was plausible, the 13 kb insert was subcloned into pBluescript SKII+. Purified DNA was sequenced using primers corresponding to $\alpha_d$ I domain nucleic acid sequences 441–461, 591–612, 717–739, and reverse 898–918 in SEQ ID NO: 52. Sequence information was obtained using only the first 4441–4461 primer, and only the 5' most exon of the I domain was efficiently amplified. The remainder of the I domain was not amplified. The resulting clone therefore comprised exon 6 of the mouse $\alpha_d$ gene, and intronic sequences to the 3' and 5' end of the exon. Exon 7 was not represented in the clone. After sequencing, a construct is generated containing neomycin resistance and thymidine kinase genes.

The neomycin resistance (neo$^r$) gene is inserted into the resulting plasmid in a manner that interrupts the protein coding sequence of the genomic mouse DNA. The resulting plasmid therefore contains a neo$^r$ gene within the mouse genomic DNA sequences, all of which are positioned within a thymidine kinase encoding region. Plasmid construction in this manner is required to favor homologous recombination over random recombination [Chisaka, et al., Nature 355:516–520 (1992)].

EXAMPLE 24
Cloning of Rabbit $\alpha_d$- Construction and Screening of the Rabbit cDNA Library Identification of human $\alpha_d$ homologs in rats and mice led to the investigation of the existence of a rabbit homolog which would be useful in rabbit models of human disease states described infra.

Poly A$^+$ RNA was prepared from a whole rabbit spleen using an Invitrogen FastTrack kit (San Diego, Calif.) according to manufacturer's suggested protocol and reagents supplied with the kit. From 1.65 g tissue, 73 µg poly A$^+$RNA were isolated. The rabbit spleen RNA was used to construct a ZAP Express cDNA library using a kit from Stratagene (La Jolla, Calif.). Resulting cDNA was directionally cloned into EcoRI and XhoI sites in the lambda arms of a pBK-CMV phagemid vector. Gigapack II Gold (Stratagene) was used to package the lambda arms into phage particles. The resulting library titer was estimated to be approximately 8×10$^5$ particles, with an average insert size of 1.2 kb.

The library was amplified once by plating for confluent plaque growth and cell lysate was collected. The amplified library was plated at approximately 30,000 plaque forming units (pfu) per 150 mm plate with E. coli and the resulting mixture incubated for 12–16 hrs at 37° C. to allow plaque formation. Phage DNA was transferred onto Hybond N$^+$nylon membranes (Amersham, Arlington Heights, Ill.). The membranes were hybridized with a mixture of two random primed radiolabeled mouse $\alpha_d$ PCR DNA probes. The first probe was generated from a PCR product spanning nucleotides 149–946 in SEQ ID NO: 52. The second probe was from a PCR product spanning nucleotides 2752–3651 in SEQ ID NO: 52. Probes were labeled by random priming (Boehringer Mannheim Random Primed DNA Labeling Kit) and the reaction mixture was passed over a Sephadex G-50 column to remove unincorporated nucleotides. The hybridization solution was composed of 5X SSPE, 5X Denhardts, 1% SDS, 40% Formamide and the labeled probes at 1×10$^6$ dpm/ml. Hybridization was carried out at 42° C. for 16–18 hours. Filters were washed extensively in 2X SSPE/0.1% SDS at room temperature and exposed to X-ray film to visualize any hybridizing plaques.

Two clones with significant sequence homology to human $\alpha_d$ were identified. Clone #2 was approximately 800 bp in length and mapped to the 5' end of human $\alpha_d$. Clone #2 includes an initiating methionine and complete leader sequence. Clone #7 was approximately 1.5 kb and includes an initiating methionine. The 5' end of clone #7 overlapped that of clone #2, while the 3' sequences terminated at a point beyond the I domain sequences. Internal sequencing of clone #7 is performed using the nested deletions sequencing technique.

The predicted N terminal amino acid sequence for rabbit $\alpha_d$ as determined from clones #2 and #7 indicated a protein with 73% identity with human $\alpha_d$, 65% identity with mouse $\alpha_d$, and 58% identity with mouse CD11b, human CD11b, and human CD11c. The nucleic acid sequence for clone #2 is set out in SEQ ID NO: 92; the predicted amino acid sequence is set out in SEQ ID NO: 93

Isolation of a full length rabbit $\alpha_d$ cDNA is carried out using labeled rabbit fragment, clone #7, and rescreening the cDNA library from which the fragment was derived.

Isolation of a rabbit $\alpha_d$ clone allows expression of the protein, either on the surface of transfectants or as a soluble full length or truncated form. This protein is then used as an immunogen for the production of monoclonal antibodies for use in rabbit models of human disease states.

EXAMPLE 25
Animal Models For Determining $\alpha_d$ Therapeutic Utility

Immunohistologic data in dog and in situ hybridization in rats and mice has determined that in spleen $\alpha_d$ is expressed primarily by macrophages present in red pulp and in lymph nodes. $\alpha_d$ is found in medullary cords and sinuses. The expression pattern is remarkably similar to what has been reported for two murine antigens defined by the monoclonal antibodies F4/80 and SK39. While biochemical characterization of these murine antigens has demonstrated that they are distinct from $\alpha_d$, it is highly probably that $\alpha_d$ defines the same macrophage subset as the murine F4/80 and SK39 antigens.

In mouse, SK39-positive macrophages have been identified in splenic red pulp where they may participate in the clearance of foreign materials from circulation, and in medulla of lymph nodes [Jutila, et al., *J.Leukocyte Biol.* 54:30–39 (1993)]. SK39-positive macrophages have also been reported at sites of both acute and chronic inflammation. Furthermore, monocytes recruited to thioglycolate-inflamed peritoneal cavities also express the SK39 antigen. Collectively, these findings suggest that, if SK39⁺ cells are also $\alpha_d^+$, then these cells are responsible for the clearance of foreign materials in the spleen and participate in inflammation where macrophages play a significant role.

While the function of $\alpha_d$ remains unclear, other more well characterized $\beta_2$ integrins have been shown to participate in a wide variety of adhesion events that facilitate cell migration, enhance phagocytosis, and promote cell—cell interactions, events which all lead to upregulation of inflammatory processes. Therefore, it is highly plausible that interfering with the normal $\alpha_d$ function may also interfere with inflammation where macrophages play a significant role. Such an anti-inflammatory effect could result from: i) blocking macrophage recruitment to sites of inflammation, ii) preventing macrophage activation at the site of inflammation or iii) interfering with macrophage effector functions which damage normal host tissue through either specific autoimmune responses or as a result of bystander cell damage.

Disease states in which there is evidence of macrophages playing a significant role in the disease process include multiple sclerosis, arthritis, graft atherosclerosis, some forms of diabetes and inflammatory bowel disease. Animal models, discussed below, have been shown to reproduce many of the aspects of these human disorders. Inhibitors of $\alpha_d$ function are tested in these model systems to determine if the potential exists for treating the corresponding human diseases.

A. Graft Arteriosclerosis

Cardiac transplantation is now the accepted form of therapeutic intervention for some types of end-state heart disease. As the use of cyclosporin A has increased one year survival rates to 80%, the development of progressive graft arteriosclerosis has emerged as the leading cause of death in cardiac transplants surviving beyond the first year. Recent studies have found that the incidence of significant graft arteriosclerosis 3 years following a cardiac transplant is in the range of 36–44% [Adams, et al., *Transplantation* 53:1115–1119 (1992); Adams, et al., *Transplantation* 56:794–799 (1993)].

Graft arteriosclerosis typically consists of diffuse, occlusive, intimal lesions which affect the entire coronary vessel wall, and are often accompanied by lipid deposition. While the pathogenesis of graft arteriosclerosis remains unknown, it is presumably linked to histocompatibility differences between donor and recipient, and is immunologic in nature. Histologically, the areas of intimal thickening are composed primarily of macrophages, although T cells are occasionally seen. It is therefore possible that macrophages expressing $\alpha_d$ may play a significant role in the induction and/or development of graft arteriosclerosis. In such a case, monoclonal antibodies or small molecule inhibitors (for example, soluble ICAM-R) of $\alpha_d$ function could be given prophylactically to individuals who received heart transplants and are at risk of developing graft arteriosclerosis.

Although atherosclerosis in heart transplants presents the greatest threat to life, graft arteriosclerosis is also seen in other solid organ transplants, including kidneys and livers. Therapeutic use of $\alpha_d$ blocking agents could prevent graft arteriosclerosis in other organ transplants and reduce complications resulting from graft failure.

One model for graft arteriosclerosis in the rat involves heterotopic cardiac allografts transplanted across minor histocompatibility barriers. When Lewis cardiac allografts are transplanted into MHC class I and II compatible F-344 recipients, 80% of the allografts survive at least 3 weeks, while 25% of the grafts survive indefinitely. During this low-grade graft rejection, arteriosclerosis lesions form in the donor heart. Arterial lesions in 120 day old allografts typically have diffuse fibrotic intimal thickening indistinguishable in appearance from graft arteriosclerosis lesions found in rejecting human cardiac allografts.

Rats are transplanted with hearts mismatched at minor histocompatibility antigens, for example Lewis into F-344. Monoclonal antibodies specific for rat $\alpha_d$ or small molecule inhibitors of $\alpha_d$ are given periodically to transplant recipients. Treatment is expected to reduce the incidence of graft arteriosclerosis in non-rejecting donor hearts. Treatment of rats with $\alpha_d$ monoclonal antibodies or small molecule inhibitors may not be limited to prophylactic treatments. Blocking $\alpha_d$ function is also be expected to reduce macrophage mediated inflammation and allow reversal of arterial damage in the graft.

B. Atherosclerosis in Rabbits Fed Cholesterol

Rabbits fed an atherogenic diet containing a cholesterol supplement for approximately 12–16 weeks develop intimal lesions that cover most of the lumenal surface of the ascending aorta [Rosenfeld, et al., *Arteriosclerosis* 7:9–23 (1987); Rosenfeld, et al., *Arteriosclerosis* 7:24–34 (1987)]. The atherosclerotic lesions seen in these rabbits are simmer to those in humans. Lesions contain large numbers of T cells, most of which express CD45RO, a marker associated with memory T cells. Approximately half of the infiltrating T cells also express MHC class II antigen and some express the IL-2 receptor suggesting that many of the cells are in an activated state.

One feature of the atherosclerotic lesions found in cholesterol fed rabbits, but apparently absent in rodent models, is the accumulation of foam cellrich lesions. Foam cell macrophages are believed to result from the uptake of oxidized low-density lipoprotein (LDL) by specific receptors. Oxidized LDL particles have been found to be toxic for some cell types including endothelial cells and smooth muscle cells. The uptake of potentially toxic, oxidized LDL particles by macrophages serves as an irritant and drives macrophage activation, contributing to the inflammation associated with atherosclerotic lesions.

Once monoclonal antibodies have been generated to rabbit $\alpha_d$, cholesterol fed rabbits are treated. Treatments include prophylactic administration of $\alpha_d$ monoclonal antibodies or small molecule inhibitors, to demonstrate that $\alpha_d^+$ macrophages are involved in the disease process. Additional studies would demonstrate that monoclonal antibodies to $\alpha_d$ or small molecule inhibitors are capable of reversing vessel damage detected in rabbits fed an atherogenic diet.

C. Insulin-dependent Diabetes

BB rats spontaneously develop insulin-dependent diabetes at 70–150 days of age. Using immunohistochemistry, MHC class II$^+$, ED1$^+$ macrophages can be detected infiltrating the islets early in the disease. Many of the macrophages appear to be engaged in phagocytosis of cell debris or normal cells. As the disease progresses, larger numbers of macrophages are found infiltrating the islets, although significant numbers of T cells, and later B cells, also appear to be recruited to the site [Hanenberg, et al., *Diabetologia* 32:126–134 (1989)].

Development of diabetes in BB rats appears to depend on both early macrophage infiltration and subsequent T cells recruitment. Treatment of BB rats with silica particles, which are toxic to macrophages, has been effective in blocking the early macrophage infiltration of the islets. In the absence of early macrophage infiltration, subsequent tissue damage by an autoaggressive lymphocyte population fails to occur. Administration of monoclonal antibody OX-19 (specific for rat CD5) or monoclonal antibody OX-8 (specific for rat CD8), which block the T cell-associated phase of the disease, is also effective in suppressing the development of diabetes.

The central role of macrophages in the pathology of this model makes it attractive for testing inhibitors of $\alpha_d$ function. Rats genetically predisposed to the development of insulin-dependent diabetes are treated with monoclonal antibodies to $\alpha_d$ or small molecule inhibitors and evaluated for the development of the disease. Preventing or delaying clinical onset is evidence that $\alpha_d$ plays a pivotal role in macrophage damage to the islet cells.

D. Inflammatory Bowel Disease (Crohn's Disease, Ulcerative Colitis)

Animal models used in the study of inflammatory bowel disease (IBD) are generally elicited by intrarectal administration of noxious irritants (e.g. acetic acid or trinitrobenzene sulfonic acid/ethanol). Colonic inflammation induced by these agents is the result of chemical or metabolic injury and lacks the chronic and spontaneously relapsing inflammation associated with human IBD. However, a recently described model using subserosal injections of purified peptidoglycan-polysaccharide (PG-PS) polymers from either group A or group D streptococci appears to be a more physiologically relevant model for human IBD [Yamada, et al., *Gastroenterolgy* 104:759–771 (1993)].

In this model PG-PS is injected into the subserosal layer of the distal colon. The resulting inflammatory response is biphasic with an initial acute episode three days after injection, which is followed by a spontaneous chronic phase three to four weeks later. The late phase response is granulomatous in nature, and results in colonic thickening, adhesions, colonic nodules and mucosal lesions. In addition to mucosal injury, PG-PS colitis frequently leads to arthritis anemia and granulomatous hepatitis. The extraintestinal manifestations of the disease make the model attractive for studying Crohn's colitis in that a significant number of patients with active Crohn's disease suffer from arthritic joint disease and hepatobillary inflammation.

Granulomatous lesions are the result of chronic inflammation which leads to the recruitment and subsequent activation of cells of the monocyte/macrophage lineage. Presence of granulomatous lesions in Crohn's disease and the above animal model make this an attractive clinical target for $\alpha_d$ monoclonal antibodies or other inhibitors of $\alpha_d$ function. Inhibitors of $\alpha_d$ function are expected to block the formation of lesions associated with IBD or even reverse tissue damage seen in the disease.

E. Arthritis

Arthritis appears to be a multi-factorial disease process involving a variety of inflammatory cell types including neutrophils, T lymphocytes and phagocytic macrophages. Although a variety of arthritis models exist, preparations of streptococcal cell wall proteoglycan produce a disorder most similar to the human disease.

In rats, streptococcal cell wall induces inflammation of peripheral joints characterized by repeated episodes of disease progression followed by remission and eventually resulting in joint destruction over a period of several months [Cromartie, et al., *J.Exp.Med.* 146:1585–1602 (1977); Schwab et al., *Infection and Immunity* 59:4436–4442 (1991)]. During the chronic phase of the disease, mononuclear phagocytes or macrophages are believed to play a major role in destruction of the synovium. Furthermore, agents which suppress the recruitment of macrophages into the synovium effectively reduce the inflammation and pathology characteristic of arthritis.

A central role for the macrophage in synovium destruction that leads to arthritis predicts that monoclonal antibodies to $\alpha_d$ or inhibitors of $\alpha_d$ function may have therapeutic potential in the treatment of this disease. As in other models previously described, $\alpha_d$ monoclonal antibodies or small molecule inhibitors administered prophylactically are expected to block or moderate joint inflammation and prevent destruction of the synovium. Agents that interfere with $\alpha_d$ function may also moderate ongoing inflammation by preventing the recruitment of additional macrophages to the joint or blocking macrophage activation. The net result would be to reverse ongoing destruction of the joint and facilitate tissue repair.

F. Multiple Sclerosis

Although pathogenesis of multiple sclerosis (MS) remains unclear, it is generally accepted that the disease is mediated by CD4$^+$ T cells which recognize autoantigens in the central nervous system and initiate an inflammatory cascade. The resulting immune response results in the recruitment of additional inflammatory cells, including activated macrophages which contribute to the disease. Experimental autoimmune encephalomyelitis (EAE) is an animal model which reproduces some aspects of MS. Recently, monoclonal antibodies reactive with CD11b/CD18 [Huitinga, et al., *Eur.J.Immunol.* 23:709–715 (1993)] present on inflammatory macrophages have been shown to block both clinical and histologic disease. The results suggest that monoclonal antibodies or small molecule inhibitors to $\alpha_d$ are likely to be effective in blocking the inflammatory response in EAE. Such agents also have important therapeutic applications in the treatment of MS.

Numerous modifications and variations in the invention as set forth in the above illustrative examples are expected to occur to those skilled in the art. Consequently only such limitations as appear in the appended claims should be placed on the invention.

What is claimed is:

1. A method for isolating a polynucleotide encoding a protein that binds to $\alpha_d$ comprising the steps of:

a) transforming or transfecting appropriate host cells with a DNA construct comprising a reporter gene under the control of a promoter regulated by a transcription factor having a DNA-binding domain and an activating domain;

b) expressing in said host cells a first hybrid DNA sequence encoding a first fusion of part or all of $\alpha_d$ and either the DNA binding domain or the activating domain of said transcription factor;

c) expressing in said host cells a library of second hybrid DNA sequences encoding second fusions of part or all of putative $\alpha_d$ binding proteins and the DNA binding domain or activating domain of said transcription factor which is not incorporated in said first fusion;

d) detecting binding of an $\alpha_d$ binding protein to $\alpha_d$ in a particular host cell by detecting the production of reporter gene product in said host cell; and e) isolating second hybrid DNA sequences encoding $\alpha_d$ binding protein from said particular host cell.

* * * * *

UNITED STATES PATENT AND TRADEMARK OFFICE
CERTIFICATE OF CORRECTION

PATENT NO. : 5,766,850
DATED : June 16, 1998
INVENTOR(S) : Gallatin et al.

It is certified that error appears in the above-identified patent and that said Letters Patent is hereby corrected as shown below:

Pg. 2, Col. 2, Rojiani et al.: After "...(calreticulin)", delete "3".

Col. 24, line 13: After "...non-reducing", please delete "reducing".

Col. 29, line 24: Please delete "a", and insert - -α- -.

Col. 29, line 26: Please delete "a", and insert - -α- -.

Col. 36, line 37, 11.a-1/1 FOR2: Please delete "5'-CCGCCTCCCACTGGCGTGTGC", and insert - -5'-CCGCCTGCCACTGGCGTGTGC- -.

Col. 38, line 6: Please delete "con tain", and insert - -contain- -.

Col. 38, line 9: Please delete "Koza k", and insert - -Kozak- -.

Col. 38, line 10: Please delete "position s", and insert - -positions- -.

UNITED STATES PATENT AND TRADEMARK OFFICE
CERTIFICATE OF CORRECTION

PATENT NO. : 5,766,850
DATED : June 16, 1998
INVENTOR(S) : Gallatin et al.

It is certified that error appears in the above-identified patent and that said Letters Patent is hereby corrected as shown below:

Col. 38, line 19: Please delete "5'GCTGGACGATGGGATCCAC-3'", and insert

--5'GCTGGACGATGGCATCCAC-3'--.

Col. 39, line 21: Please delete "X", and insert --$\lambda$--.

Col. 39, line 45: Please delete "5", and insert --5'--.

Signed and Sealed this

Twenty-first Day of November, 2000

Attest:

Q. TODD DICKINSON

Attesting Officer

Director of Patents and Trademarks

SEQUENCE LISTING ( 1 ) GENERAL INFORMATION:

( i i i ) NUMBER OF SEQUENCES: 93

( 2 ) INFORMATION FOR SEQ ID NO:1:

( i ) SEQUENCE CHARACTERISTICS:
        ( A ) LENGTH: 3726 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..3485

( x i ) SEQUENCE DESCRIPTION: SEQ ID NO:1:

```
TG ACC TTC GGC ACT GTG CTT CTT CTG AGT GTC CTG GCT TCT TAT CAT        47
   Thr Phe Gly Thr Val Leu Leu Leu Ser Val Leu Ala Ser Tyr His
    1               5                  10                  15

GGA TTC AAC CTG GAT GTG GAG GAG CCT ACG ATC TTC CAG GAG GAT GCA        95
Gly Phe Asn Leu Asp Val Glu Glu Pro Thr Ile Phe Gln Glu Asp Ala
                20                  25                  30

GGC GGC TTT GGG CAG AGC GTG GTG CAG TTC GGT GGA TCT CGA CTC GTG       143
Gly Gly Phe Gly Gln Ser Val Val Gln Phe Gly Gly Ser Arg Leu Val
            35                  40                  45

GTG GGA GCA CCC CTG GAG GTG GTG GCG GCC AAC CAG ACG GGA CGG CTG       191
Val Gly Ala Pro Leu Glu Val Val Ala Ala Asn Gln Thr Gly Arg Leu
        50                  55                  60

TAT GAC TGC GCA GCT GCC ACC GGC ATG TGC CAG CCC ATC CCG CTG CAC       239
Tyr Asp Cys Ala Ala Ala Thr Gly Met Cys Gln Pro Ile Pro Leu His
    65                  70                  75

ATC CGC CCT GAG GCC GTG AAC ATG TCC TTG GGC CTG ACC CTG GCA GCC       287
Ile Arg Pro Glu Ala Val Asn Met Ser Leu Gly Leu Thr Leu Ala Ala
 80                  85                  90                  95

TCC ACC AAC GGC TCC CGG CTC CTG GCC TGT GGC CCG ACC CTG CAC AGA       335
Ser Thr Asn Gly Ser Arg Leu Leu Ala Cys Gly Pro Thr Leu His Arg
                100                 105                 110

GTC TGT GGG GAG AAC TCA TAC TCA AAG GGT TCC TGC CTC CTG CTG GGC       383
Val Cys Gly Glu Asn Ser Tyr Ser Lys Gly Ser Cys Leu Leu Leu Gly
            115                 120                 125

TCG CGC TGG GAG ATC ATC CAG ACA GTC CCC GAC GCC ACG CCA GAG TGT       431
Ser Arg Trp Glu Ile Ile Gln Thr Val Pro Asp Ala Thr Pro Glu Cys
        130                 135                 140

CCA CAT CAA GAG ATG GAC ATC GTC TTC CTG ATT GAC GGC TCT GGA AGC       479
Pro His Gln Glu Met Asp Ile Val Phe Leu Ile Asp Gly Ser Gly Ser
    145                 150                 155

ATT GAC CAA AAT GAC TTT AAC CAG ATG AAG GGC TTT GTC CAA GCT GTC       527
Ile Asp Gln Asn Asp Phe Asn Gln Met Lys Gly Phe Val Gln Ala Val
160                 165                 170                 175

ATG GGC CAG TTT GAG GGC ACT GAC ACC CTG TTT GCA CTG ATG CAG TAC       575
Met Gly Gln Phe Glu Gly Thr Asp Thr Leu Phe Ala Leu Met Gln Tyr
                180                 185                 190

TCA AAC CTC CTG AAG ATC CAC TTC ACC TTC ACC CAA TTC CGG ACC AGC       623
Ser Asn Leu Leu Lys Ile His Phe Thr Phe Thr Gln Phe Arg Thr Ser
            195                 200                 205

CCG AGC CAG CAG AGC CTG GTG GAT CCC ATC GTC CAA CTG AAA GGC CTG       671
Pro Ser Gln Gln Ser Leu Val Asp Pro Ile Val Gln Leu Lys Gly Leu
        210                 215                 220
```

```
ACG TTC ACG GCC ACG GGC ATC CTG ACA GTG GTG ACA CAG CTA TTT CAT    719
Thr Phe Thr Ala Thr Gly Ile Leu Thr Val Val Thr Gln Leu Phe His
    225                 230                 235

CAT AAG AAT GGG GCC CGA AAA AGT GCC AAG AAG ATC CTC ATT GTC ATC    767
His Lys Asn Gly Ala Arg Lys Ser Ala Lys Lys Ile Leu Ile Val Ile
240                 245                 250                 255

ACA GAT GGG CAG AAG TAC AAA GAC CCC CTG GAA TAC AGT GAT GTC ATC    815
Thr Asp Gly Gln Lys Tyr Lys Asp Pro Leu Glu Tyr Ser Asp Val Ile
                    260                 265                 270

CCC CAG GCA GAG AAG GCT GGC ATC ATC CGC TAC GCT ATC GGG GTG GGA    863
Pro Gln Ala Glu Lys Ala Gly Ile Ile Arg Tyr Ala Ile Gly Val Gly
            275                 280                 285

CAC GCT TTC CAG GGA CCC ACT GCC AGG CAG GAG CTG AAT ACC ATC AGC    911
His Ala Phe Gln Gly Pro Thr Ala Arg Gln Glu Leu Asn Thr Ile Ser
        290                 295                 300

TCA GCG CCT CCG CAG GAC CAC GTG TTC AAG GTG GAC AAC TTT GCA GCC    959
Ser Ala Pro Pro Gln Asp His Val Phe Lys Val Asp Asn Phe Ala Ala
    305                 310                 315

CTT GGC AGC ATC CAG AAG CAG CTG CAG GAG AAG ATC TAT GCA GTT GAG   1007
Leu Gly Ser Ile Gln Lys Gln Leu Gln Glu Lys Ile Tyr Ala Val Glu
320                 325                 330                 335

GGA ACC CAG TCC AGG GCA AGC AGC TCC TTC CAG CAC GAG ATG TCC CAA   1055
Gly Thr Gln Ser Arg Ala Ser Ser Ser Phe Gln His Glu Met Ser Gln
                    340                 345                 350

GAA GGC TTC AGC ACA GCC CTC ACA ATG GAT GGC CTC TTC CTG GGG GCT   1103
Glu Gly Phe Ser Thr Ala Leu Thr Met Asp Gly Leu Phe Leu Gly Ala
            355                 360                 365

GTG GGG AGC TTT AGC TGG TCT GGA GGT GCC TTC CTG TAT CCC CCA AAT   1151
Val Gly Ser Phe Ser Trp Ser Gly Gly Ala Phe Leu Tyr Pro Pro Asn
        370                 375                 380

ATG AGC CCC ACC TTC ATC AAC ATG TCT CAG GAG AAT GTG GAC ATG AGG   1199
Met Ser Pro Thr Phe Ile Asn Met Ser Gln Glu Asn Val Asp Met Arg
    385                 390                 395

GAC TCT TAC CTG GGT TAC TCC ACC GAG CTA GCC CTG TGG AAG GGG GTA   1247
Asp Ser Tyr Leu Gly Tyr Ser Thr Glu Leu Ala Leu Trp Lys Gly Val
400                 405                 410                 415

CAG AAC CTG GTC CTG GGG GCC CCC CGC TAC CAG CAT ACC GGG AAG GCT   1295
Gln Asn Leu Val Leu Gly Ala Pro Arg Tyr Gln His Thr Gly Lys Ala
                    420                 425                 430

GTC ATC TTC ACC CAG GTG TCC AGG CAA TGG AGG AAG AAG GCC GAA GTC   1343
Val Ile Phe Thr Gln Val Ser Arg Gln Trp Arg Lys Lys Ala Glu Val
            435                 440                 445

ACA GGG ACG CAG ATC GGC TCC TAC TTC GGG GCC TCC CTC TGC TCC GTG   1391
Thr Gly Thr Gln Ile Gly Ser Tyr Phe Gly Ala Ser Leu Cys Ser Val
        450                 455                 460

GAT GTG GAC AGC GAT GGC AGC ACC GAC CTG ATC CTC ATT GGG GCC CCC   1439
Asp Val Asp Ser Asp Gly Ser Thr Asp Leu Ile Leu Ile Gly Ala Pro
    465                 470                 475

CAT TAC TAT GAG CAG ACC CGA GGG GGC CAG GTG TCC GTG TGT CCC TTG   1487
His Tyr Tyr Glu Gln Thr Arg Gly Gly Gln Val Ser Val Cys Pro Leu
480                 485                 490                 495

CCT AGG GGG CAG AGG GTG CAG TGG CAG TGT GAC GCT GTT CTC CGT GGT   1535
Pro Arg Gly Gln Arg Val Gln Trp Gln Cys Asp Ala Val Leu Arg Gly
                    500                 505                 510

GAG CAG GGC CAC CCC TGG GGC CGC TTT GGG GCA GCC CTG ACA GTG TTG   1583
Glu Gln Gly His Pro Trp Gly Arg Phe Gly Ala Ala Leu Thr Val Leu
            515                 520                 525

GGG GAT GTG AAT GAG GAC AAG CTG ATA GAC GTG GCC ATT GGG GCC CCG   1631
Gly Asp Val Asn Glu Asp Lys Leu Ile Asp Val Ala Ile Gly Ala Pro
        530                 535                 540
```

```
GGA GAG CAG GAG AAC CGG GGT GCT GTC TAC CTG TTT CAC GGA GCC TCA    1679
Gly Glu Gln Glu Asn Arg Gly Ala Val Tyr Leu Phe His Gly Ala Ser
        545                 550                 555

GAA TCC GGC ATC AGC CCC TCC CAC AGC CAG CGG ATT GCC AGC TCC CAG    1727
Glu Ser Gly Ile Ser Pro Ser His Ser Gln Arg Ile Ala Ser Ser Gln
560                 565                 570                 575

CTC TCC CCC AGG CTG CAG TAT TTT GGG CAG GCG CTG AGT GGG GGT CAG    1775
Leu Ser Pro Arg Leu Gln Tyr Phe Gly Gln Ala Leu Ser Gly Gly Gln
                580                 585                 590

GAC CTC ACC CAG GAT GGA CTG ATG GAC CTG GCC GTG GGG GCC CGG GGC    1823
Asp Leu Thr Gln Asp Gly Leu Met Asp Leu Ala Val Gly Ala Arg Gly
            595                 600                 605

CAG GTG CTC CTG CTC AGG AGT CTG CCG GTG CTG AAA GTG GGG GTG GCC    1871
Gln Val Leu Leu Leu Arg Ser Leu Pro Val Leu Lys Val Gly Val Ala
        610                 615                 620

ATG AGA TTC AGC CCT GTG GAG GTG GCC AAG GCT GTG TAC CGG TGC TGG    1919
Met Arg Phe Ser Pro Val Glu Val Ala Lys Ala Val Tyr Arg Cys Trp
625                 630                 635

GAA GAG AAG CCC AGT GCC CTG GAA GCT GGG GAC GCC ACC GTC TGT CTC    1967
Glu Glu Lys Pro Ser Ala Leu Glu Ala Gly Asp Ala Thr Val Cys Leu
640                 645                 650                 655

ACC ATC CAG AAA AGC TCA CTG GAC CAG CTA GGT GAC ATC CAA AGC TCT    2015
Thr Ile Gln Lys Ser Ser Leu Asp Gln Leu Gly Asp Ile Gln Ser Ser
                660                 665                 670

GTC AGG TTT GAT CTG GCA CTG GAC CCA GGT CGT CTG ACT TCT CGT GCC    2063
Val Arg Phe Asp Leu Ala Leu Asp Pro Gly Arg Leu Thr Ser Arg Ala
            675                 680                 685

ATT TTC AAT GAA ACC AAG AAC CCC ACT TTG ACT CGA AGA AAA ACC CTG    2111
Ile Phe Asn Glu Thr Lys Asn Pro Thr Leu Thr Arg Arg Lys Thr Leu
        690                 695                 700

GGA CTG GGG ATT CAC TGT GAA ACC CTG AAG CTG CTT TTG CCA GAT TGT    2159
Gly Leu Gly Ile His Cys Glu Thr Leu Lys Leu Leu Leu Pro Asp Cys
705                 710                 715

GTG GAG GAT GTG GTG AGC CCC ATC ATT CTG CAC CTC AAC TTC TCA CTG    2207
Val Glu Asp Val Val Ser Pro Ile Ile Leu His Leu Asn Phe Ser Leu
720                 725                 730                 735

GTG AGA GAG CCC ATC CCC TCC CCC CAG AAC CTG CGT CCT GTG CTG GCC    2255
Val Arg Glu Pro Ile Pro Ser Pro Gln Asn Leu Arg Pro Val Leu Ala
                740                 745                 750

GTG GGC TCA CAA GAC CTC TTC ACT GCT TCT CTC CCC TTC GAG AAG AAC    2303
Val Gly Ser Gln Asp Leu Phe Thr Ala Ser Leu Pro Phe Glu Lys Asn
            755                 760                 765

TGT GGG CAA GAT GGC CTC TGT GAA GGG GAC CTG GGT GTC ACC CTC AGC    2351
Cys Gly Gln Asp Gly Leu Cys Glu Gly Asp Leu Gly Val Thr Leu Ser
        770                 775                 780

TTC TCA GGC CTG CAG ACC CTG ACC GTG GGG AGC TCC CTG GAG CTC AAC    2399
Phe Ser Gly Leu Gln Thr Leu Thr Val Gly Ser Ser Leu Glu Leu Asn
785                 790                 795

GTG ATT GTG ACT GTG TGG AAC GCA GGT GAG GAT TCC TAC GGA ACC GTG    2447
Val Ile Val Thr Val Trp Asn Ala Gly Glu Asp Ser Tyr Gly Thr Val
800                 805                 810                 815

GTC AGC CTC TAC TAT CCA GCA GGG CTG TCG CAC CGA CGG GTG TCA GGA    2495
Val Ser Leu Tyr Tyr Pro Ala Gly Leu Ser His Arg Arg Val Ser Gly
                820                 825                 830

GCC CAG AAG CAG CCC CAT CAG AGT GCC CTG CGC CTG GCA TGT GAG ACA    2543
Ala Gln Lys Gln Pro His Gln Ser Ala Leu Arg Leu Ala Cys Glu Thr
            835                 840                 845

GTG CCC ACT GAG GAT GAG GGC CTA AGA AGC AGC CGC TGC AGT GTC AAC    2591
Val Pro Thr Glu Asp Glu Gly Leu Arg Ser Ser Arg Cys Ser Val Asn
        850                 855                 860
```

```
CAC  CCC  ATC  TTC  CAT  GAG  GGC  TCT  AAC  GGC  ACC  TTC  ATA  GTC  ACA  TTC      2639
His  Pro  Ile  Phe  His  Glu  Gly  Ser  Asn  Gly  Thr  Phe  Ile  Val  Thr  Phe
     865                      870                      875

GAT  GTC  TCC  TAC  AAG  GCC  ACC  CTG  GGA  GAC  AGG  ATG  CTT  ATG  AGG  GCC      2687
Asp  Val  Ser  Tyr  Lys  Ala  Thr  Leu  Gly  Asp  Arg  Met  Leu  Met  Arg  Ala
880                      885                      890                      895

AGT  GCA  AGC  AGT  GAG  AAC  AAT  AAG  GCT  TCA  AGC  AGC  AAG  GCC  ACC  TTC      2735
Ser  Ala  Ser  Ser  Glu  Asn  Asn  Lys  Ala  Ser  Ser  Ser  Lys  Ala  Thr  Phe
               900                      905                      910

CAG  CTG  GAG  CTC  CCG  GTG  AAG  TAT  GCA  GTC  TAC  ACC  ATG  ATC  AGC  AGG      2783
Gln  Leu  Glu  Leu  Pro  Val  Lys  Tyr  Ala  Val  Tyr  Thr  Met  Ile  Ser  Arg
                    915                      920                      925

CAG  GAA  GAA  TCC  ACC  AAG  TAC  TTC  AAC  TTT  GCA  ACC  TCC  GAT  GAG  AAG      2831
Gln  Glu  Glu  Ser  Thr  Lys  Tyr  Phe  Asn  Phe  Ala  Thr  Ser  Asp  Glu  Lys
               930                      935                      940

AAA  ATG  AAA  GAG  GCT  GAG  CAT  CGA  TAC  CGT  GTG  AAT  AAC  CTC  AGC  CAG      2879
Lys  Met  Lys  Glu  Ala  Glu  His  Arg  Tyr  Arg  Val  Asn  Asn  Leu  Ser  Gln
     945                      950                      955

CGA  GAT  CTG  GCC  ATC  AGC  ATT  AAC  TTC  TGG  GTT  CCT  GTC  CTG  CTG  AAC      2927
Arg  Asp  Leu  Ala  Ile  Ser  Ile  Asn  Phe  Trp  Val  Pro  Val  Leu  Leu  Asn
960                      965                      970                      975

GGG  GTG  GCT  GTG  TGG  GAT  GTG  GTC  ATG  GAG  GCC  CCA  TCT  CAG  AGT  CTC      2975
Gly  Val  Ala  Val  Trp  Asp  Val  Val  Met  Glu  Ala  Pro  Ser  Gln  Ser  Leu
               980                      985                      990

CCC  TGT  GTT  TCA  GAG  AGA  AAA  CCT  CCC  CAG  CAT  TCT  GAC  TTC  CTG  ACC      3023
Pro  Cys  Val  Ser  Glu  Arg  Lys  Pro  Pro  Gln  His  Ser  Asp  Phe  Leu  Thr
               995                      1000                     1005

CAG  ATT  TCA  AGA  AGT  CCC  ATG  CTG  GAC  TGC  TCC  ATT  GCT  GAC  TGC  CTG      3071
Gln  Ile  Ser  Arg  Ser  Pro  Met  Leu  Asp  Cys  Ser  Ile  Ala  Asp  Cys  Leu
          1010                     1015                     1020

CAG  TTC  CGC  TGT  GAC  GTC  CCC  TCC  TTC  AGC  GTC  CAG  GAG  GAG  CTG  GAT      3119
Gln  Phe  Arg  Cys  Asp  Val  Pro  Ser  Phe  Ser  Val  Gln  Glu  Glu  Leu  Asp
     1025                     1030                     1035

TTC  ACC  CTG  AAG  GGC  AAT  CTC  AGT  TTC  GGC  TGG  GTC  CGC  GAG  ACA  TTG      3167
Phe  Thr  Leu  Lys  Gly  Asn  Leu  Ser  Phe  Gly  Trp  Val  Arg  Glu  Thr  Leu
1040                     1045                     1050                     1055

CAG  AAG  AAG  GTG  TTG  GTC  GTG  AGT  GTG  GCT  GAA  ATT  ACG  TTC  GAC  ACA      3215
Gln  Lys  Lys  Val  Leu  Val  Val  Ser  Val  Ala  Glu  Ile  Thr  Phe  Asp  Thr
               1060                     1065                     1070

TCC  GTG  TAC  TCC  CAG  CTT  CCA  GGA  CAG  GAG  GCA  TTT  ATG  AGA  GCT  CAG      3263
Ser  Val  Tyr  Ser  Gln  Leu  Pro  Gly  Gln  Glu  Ala  Phe  Met  Arg  Ala  Gln
               1075                     1080                     1085

ATG  GAG  ATG  GTG  CTA  GAA  GAA  GAC  GAG  GTC  TAC  AAT  GCC  ATT  CCC  ATC      3311
Met  Glu  Met  Val  Leu  Glu  Glu  Asp  Glu  Val  Tyr  Asn  Ala  Ile  Pro  Ile
               1090                     1095                     1100

ATC  ATG  GGC  AGC  TCT  GTG  GGG  GCT  CTG  CTA  CTG  CTG  GCG  CTC  ATC  ACA      3359
Ile  Met  Gly  Ser  Ser  Val  Gly  Ala  Leu  Leu  Leu  Leu  Ala  Leu  Ile  Thr
          1105                     1110                     1115

GCC  ACA  CTG  TAC  AAG  CTT  GGC  TTC  TTC  AAA  CGC  CAC  TAC  AAG  GAA  ATG      3407
Ala  Thr  Leu  Tyr  Lys  Leu  Gly  Phe  Phe  Lys  Arg  His  Tyr  Lys  Glu  Met
1120                     1125                     1130                     1135

CTG  GAG  GAC  AAG  CCT  GAA  GAC  ACT  GCC  ACA  TTC  AGT  GGG  GAC  GAT  TTC      3455
Leu  Glu  Asp  Lys  Pro  Glu  Asp  Thr  Ala  Thr  Phe  Ser  Gly  Asp  Asp  Phe
               1140                     1145                     1150

AGC  TGT  GTG  GCC  CCA  AAT  GTG  CCT  TTG  TCC  TAATAATCCA CTTTCCTGTT              3505
Ser  Cys  Val  Ala  Pro  Asn  Val  Pro  Leu  Ser
               1155                     1160

TATCTCTACC ACTGTGGGCT GGACTTGCTT GCAACCATAA ATCAACTTAC ATGGAAACAA                    3565

CTTCTGCATA GATCTGCACT GGCCTAAGCA AACCTACCAGG TGCTAAGCAC CTTCTCGGAG                   3625
```

```
AGATAGAGAT  TGTAATGTTT  TTACATATCT  GTCCATCTTT  TTCAGCAATG  ACCCACTTTT      3685

TACAGAAGCA  GGCATGGTGC  CAGCATAAAT  TTTCATATGC  T                           3726
```

( 2 ) INFORMATION FOR SEQ ID NO:2:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Thr  Phe  Gly  Thr  Val  Leu  Leu  Leu  Ser  Val  Leu  Ala  Ser  Tyr  His  Gly
 1              5                        10                       15

Phe  Asn  Leu  Asp  Val  Glu  Glu  Pro  Thr  Ile  Phe  Gln  Glu  Asp  Ala  Gly
              20                        25                       30

Gly  Phe  Gly  Gln  Ser  Val  Val  Gln  Phe  Gly  Gly  Ser  Arg  Leu  Val  Val
         35                        40                       45

Gly  Ala  Pro  Leu  Glu  Val  Val  Ala  Ala  Asn  Gln  Thr  Gly  Arg  Leu  Tyr
     50                        55                       60

Asp  Cys  Ala  Ala  Ala  Thr  Gly  Met  Cys  Gln  Pro  Ile  Pro  Leu  His  Ile
 65                       70                       75                       80

Arg  Pro  Glu  Ala  Val  Asn  Met  Ser  Leu  Gly  Leu  Thr  Leu  Ala  Ala  Ser
                   85                        90                       95

Thr  Asn  Gly  Ser  Arg  Leu  Leu  Ala  Cys  Gly  Pro  Thr  Leu  His  Arg  Val
              100                       105                      110

Cys  Gly  Glu  Asn  Ser  Tyr  Ser  Lys  Gly  Ser  Cys  Leu  Leu  Leu  Gly  Ser
              115                       120                      125

Arg  Trp  Glu  Ile  Ile  Gln  Thr  Val  Pro  Asp  Ala  Thr  Pro  Glu  Cys  Pro
     130                       135                      140

His  Gln  Glu  Met  Asp  Ile  Val  Phe  Leu  Ile  Asp  Gly  Ser  Gly  Ser  Ile
145                       150                      155                      160

Asp  Gln  Asn  Asp  Phe  Asn  Gln  Met  Lys  Gly  Phe  Val  Gln  Ala  Val  Met
                   165                       170                      175

Gly  Gln  Phe  Glu  Gly  Thr  Asp  Thr  Leu  Phe  Ala  Leu  Met  Gln  Tyr  Ser
              180                       185                      190

Asn  Leu  Leu  Lys  Ile  His  Phe  Thr  Phe  Thr  Gln  Phe  Arg  Thr  Ser  Pro
              195                       200                      205

Ser  Gln  Gln  Ser  Leu  Val  Asp  Pro  Ile  Val  Gln  Leu  Lys  Gly  Leu  Thr
     210                       215                      220

Phe  Thr  Ala  Thr  Gly  Ile  Leu  Thr  Val  Val  Thr  Gln  Leu  Phe  His  His
225                       230                      235                      240

Lys  Asn  Gly  Ala  Arg  Lys  Ser  Ala  Lys  Lys  Ile  Leu  Ile  Val  Ile  Thr
                   245                       250                      255

Asp  Gly  Gln  Lys  Tyr  Lys  Asp  Pro  Leu  Glu  Tyr  Ser  Asp  Val  Ile  Pro
              260                       265                      270

Gln  Ala  Glu  Lys  Ala  Gly  Ile  Ile  Arg  Tyr  Ala  Ile  Gly  Val  Gly  His
              275                       280                      285

Ala  Phe  Gln  Gly  Pro  Thr  Ala  Arg  Gln  Glu  Leu  Asn  Thr  Ile  Ser  Ser
     290                       295                      300

Ala  Pro  Pro  Gln  Asp  His  Val  Phe  Lys  Val  Asp  Asn  Phe  Ala  Ala  Leu
305                       310                      315                      320

Gly  Ser  Ile  Gln  Lys  Gln  Leu  Gln  Glu  Lys  Ile  Tyr  Ala  Val  Glu  Gly
                   325                       330                      335

Thr  Gln  Ser  Arg  Ala  Ser  Ser  Ser  Phe  Gln  His  Glu  Met  Ser  Gln  Glu
```

-continued

|     |     |     | 340 |     |     |     | 345 |     |     |     | 350 |     |     |     |
|---|---|---|---|---|---|---|---|---|---|---|---|---|---|---|
| Gly | Phe | Ser | Thr | Ala | Leu | Thr | Met | Asp | Gly | Leu | Phe | Leu | Gly | Ala | Val |
|     |     | 355 |     |     |     |     | 360 |     |     |     | 365 |     |     |     |
| Gly | Ser | Phe | Ser | Trp | Ser | Gly | Gly | Ala | Phe | Leu | Tyr | Pro | Pro | Asn | Met |
|     | 370 |     |     |     |     | 375 |     |     |     |     | 380 |     |     |     |     |
| Ser | Pro | Thr | Phe | Ile | Asn | Met | Ser | Gln | Glu | Asn | Val | Asp | Met | Arg | Asp |
| 385 |     |     |     |     | 390 |     |     |     |     | 395 |     |     |     |     | 400 |
| Ser | Tyr | Leu | Gly | Tyr | Ser | Thr | Glu | Leu | Ala | Leu | Trp | Lys | Gly | Val | Gln |
|     |     |     |     | 405 |     |     |     |     | 410 |     |     |     |     | 415 |     |
| Asn | Leu | Val | Leu | Gly | Ala | Pro | Arg | Tyr | Gln | His | Thr | Gly | Lys | Ala | Val |
|     |     |     | 420 |     |     |     |     | 425 |     |     |     |     | 430 |     |     |
| Ile | Phe | Thr | Gln | Val | Ser | Arg | Gln | Trp | Arg | Lys | Lys | Ala | Glu | Val | Thr |
|     |     | 435 |     |     |     |     | 440 |     |     |     |     | 445 |     |     |     |
| Gly | Thr | Gln | Ile | Gly | Ser | Tyr | Phe | Gly | Ala | Ser | Leu | Cys | Ser | Val | Asp |
|     | 450 |     |     |     |     | 455 |     |     |     |     | 460 |     |     |     |     |
| Val | Asp | Ser | Asp | Gly | Ser | Thr | Asp | Leu | Ile | Leu | Ile | Gly | Ala | Pro | His |
| 465 |     |     |     |     | 470 |     |     |     |     | 475 |     |     |     |     | 480 |
| Tyr | Tyr | Glu | Gln | Thr | Arg | Gly | Gly | Gln | Val | Ser | Val | Cys | Pro | Leu | Pro |
|     |     |     |     | 485 |     |     |     |     | 490 |     |     |     |     | 495 |     |
| Arg | Gly | Gln | Arg | Val | Gln | Trp | Gln | Cys | Asp | Ala | Val | Leu | Arg | Gly | Glu |
|     |     |     | 500 |     |     |     |     | 505 |     |     |     |     | 510 |     |     |
| Gln | Gly | His | Pro | Trp | Gly | Arg | Phe | Gly | Ala | Ala | Leu | Thr | Val | Leu | Gly |
|     |     | 515 |     |     |     |     | 520 |     |     |     |     | 525 |     |     |     |
| Asp | Val | Asn | Glu | Asp | Lys | Leu | Ile | Asp | Val | Ala | Ile | Gly | Ala | Pro | Gly |
|     | 530 |     |     |     |     | 535 |     |     |     |     | 540 |     |     |     |     |
| Glu | Gln | Glu | Asn | Arg | Gly | Ala | Val | Tyr | Leu | Phe | His | Gly | Ala | Ser | Glu |
| 545 |     |     |     |     | 550 |     |     |     |     | 555 |     |     |     |     | 560 |
| Ser | Gly | Ile | Ser | Pro | Ser | His | Ser | Gln | Arg | Ile | Ala | Ser | Ser | Gln | Leu |
|     |     |     |     | 565 |     |     |     |     | 570 |     |     |     |     | 575 |     |
| Ser | Pro | Arg | Leu | Gln | Tyr | Phe | Gly | Gln | Ala | Leu | Ser | Gly | Gly | Gln | Asp |
|     |     |     | 580 |     |     |     |     | 585 |     |     |     |     | 590 |     |     |
| Leu | Thr | Gln | Asp | Gly | Leu | Met | Asp | Leu | Ala | Val | Gly | Ala | Arg | Gly | Gln |
|     |     | 595 |     |     |     |     | 600 |     |     |     |     | 605 |     |     |     |
| Val | Leu | Leu | Leu | Arg | Ser | Leu | Pro | Val | Leu | Lys | Val | Gly | Val | Ala | Met |
|     | 610 |     |     |     |     | 615 |     |     |     |     | 620 |     |     |     |     |
| Arg | Phe | Ser | Pro | Val | Glu | Val | Ala | Lys | Ala | Val | Tyr | Arg | Cys | Trp | Glu |
| 625 |     |     |     |     | 630 |     |     |     |     | 635 |     |     |     |     | 640 |
| Glu | Lys | Pro | Ser | Ala | Leu | Glu | Ala | Gly | Asp | Ala | Thr | Val | Cys | Leu | Thr |
|     |     |     |     | 645 |     |     |     |     | 650 |     |     |     |     | 655 |     |
| Ile | Gln | Lys | Ser | Ser | Leu | Asp | Gln | Leu | Gly | Asp | Ile | Gln | Ser | Ser | Val |
|     |     |     | 660 |     |     |     |     | 665 |     |     |     |     | 670 |     |     |
| Arg | Phe | Asp | Leu | Ala | Leu | Asp | Pro | Gly | Arg | Leu | Thr | Ser | Arg | Ala | Ile |
|     |     | 675 |     |     |     |     | 680 |     |     |     |     | 685 |     |     |     |
| Phe | Asn | Glu | Thr | Lys | Asn | Pro | Thr | Leu | Thr | Arg | Arg | Lys | Thr | Leu | Gly |
|     | 690 |     |     |     |     | 695 |     |     |     |     | 700 |     |     |     |     |
| Leu | Gly | Ile | His | Cys | Glu | Thr | Leu | Lys | Leu | Leu | Leu | Pro | Asp | Cys | Val |
| 705 |     |     |     |     | 710 |     |     |     |     | 715 |     |     |     |     | 720 |
| Glu | Asp | Val | Val | Ser | Pro | Ile | Ile | Leu | His | Leu | Asn | Phe | Ser | Leu | Val |
|     |     |     |     | 725 |     |     |     |     | 730 |     |     |     |     | 735 |     |
| Arg | Glu | Pro | Ile | Pro | Ser | Pro | Gln | Asn | Leu | Arg | Pro | Val | Leu | Ala | Val |
|     |     |     | 740 |     |     |     |     | 745 |     |     |     |     | 750 |     |     |
| Gly | Ser | Gln | Asp | Leu | Phe | Thr | Ala | Ser | Leu | Pro | Phe | Glu | Lys | Asn | Cys |
|     |     | 755 |     |     |     |     | 760 |     |     |     |     | 765 |     |     |     |

| | | | | | | | | | | | | | | |
|---|---|---|---|---|---|---|---|---|---|---|---|---|---|---|
|Gly|Gln|Asp|Gly|Leu|Cys|Glu|Gly|Asp|Leu|Gly|Val|Thr|Leu|Ser|Phe|
| |770| | | |775| | | |780| | | | | |
|Ser|Gly|Leu|Gln|Thr|Leu|Thr|Val|Gly|Ser|Ser|Leu|Glu|Leu|Asn|Val|
|785| | | | |790| | | | |795| | | | |800|
|Ile|Val|Thr|Val|Trp|Asn|Ala|Gly|Glu|Asp|Ser|Tyr|Gly|Thr|Val|Val|
| | | | |805| | | | |810| | | | |815| |
|Ser|Leu|Tyr|Tyr|Pro|Ala|Gly|Leu|Ser|His|Arg|Arg|Val|Ser|Gly|Ala|
| | | |820| | | | |825| | | | |830| | |
|Gln|Lys|Gln|Pro|His|Gln|Ser|Ala|Leu|Arg|Leu|Ala|Cys|Glu|Thr|Val|
| | |835| | | | |840| | | | |845| | | |
|Pro|Thr|Glu|Asp|Glu|Gly|Leu|Arg|Ser|Ser|Arg|Cys|Ser|Val|Asn|His|
| |850| | | | |855| | | | |860| | | | |
|Pro|Ile|Phe|His|Glu|Gly|Ser|Asn|Gly|Thr|Phe|Ile|Val|Thr|Phe|Asp|
|865| | | | |870| | | | |875| | | | |880|
|Val|Ser|Tyr|Lys|Ala|Thr|Leu|Gly|Asp|Arg|Met|Leu|Met|Arg|Ala|Ser|
| | | | |885| | | | |890| | | | |895| |
|Ala|Ser|Ser|Glu|Asn|Asn|Lys|Ala|Ser|Ser|Lys|Ala|Thr|Phe|Gln|
| | | |900| | | | |905| | | | |910| | |
|Leu|Glu|Leu|Pro|Val|Lys|Tyr|Ala|Val|Tyr|Thr|Met|Ile|Ser|Arg|Gln|
| | |915| | | | |920| | | | |925| | | |
|Glu|Glu|Ser|Thr|Lys|Tyr|Phe|Asn|Phe|Ala|Thr|Ser|Asp|Glu|Lys|Lys|
| |930| | | | |935| | | | |940| | | | |
|Met|Lys|Glu|Ala|Glu|His|Arg|Tyr|Arg|Val|Asn|Asn|Leu|Ser|Gln|Arg|
|945| | | | |950| | | | |955| | | | |960|
|Asp|Leu|Ala|Ile|Ser|Ile|Asn|Phe|Trp|Val|Pro|Val|Leu|Leu|Asn|Gly|
| | | | |965| | | | |970| | | | |975| |
|Val|Ala|Val|Trp|Asp|Val|Val|Met|Glu|Ala|Pro|Ser|Gln|Ser|Leu|Pro|
| | | |980| | | | |985| | | | |990| | |
|Cys|Val|Ser|Glu|Arg|Lys|Pro|Pro|Gln|His|Ser|Asp|Phe|Leu|Thr|Gln|
| | |995| | | | |1000| | | | |1005| | | |
|Ile|Ser|Arg|Ser|Pro|Met|Leu|Asp|Cys|Ser|Ile|Ala|Asp|Cys|Leu|Gln|
| |1010| | | | |1015| | | | |1020| | | | |
|Phe|Arg|Cys|Asp|Val|Pro|Ser|Phe|Ser|Val|Gln|Glu|Glu|Leu|Asp|Phe|
|1025| | | | |1030| | | | |1035| | | | |1040|
|Thr|Leu|Lys|Gly|Asn|Leu|Ser|Phe|Gly|Trp|Val|Arg|Glu|Thr|Leu|Gln|
| | | | |1045| | | | |1050| | | | |1055| |
|Lys|Lys|Val|Leu|Val|Val|Ser|Val|Ala|Glu|Ile|Thr|Phe|Asp|Thr|Ser|
| | | |1060| | | | |1065| | | | |1070| | |
|Val|Tyr|Ser|Gln|Leu|Pro|Gly|Gln|Glu|Ala|Phe|Met|Arg|Ala|Gln|Met|
| | |1075| | | | |1080| | | | |1085| | | |
|Glu|Met|Val|Leu|Glu|Glu|Asp|Glu|Val|Tyr|Asn|Ala|Ile|Pro|Ile|Ile|
| |1090| | | | |1095| | | | |1100| | | | |
|Met|Gly|Ser|Ser|Val|Gly|Ala|Leu|Leu|Leu|Leu|Ala|Leu|Ile|Thr|Ala|
|1105| | | | |1110| | | | |1115| | | | |1120|
|Thr|Leu|Tyr|Lys|Leu|Gly|Phe|Phe|Lys|Arg|His|Tyr|Lys|Glu|Met|Leu|
| | | | |1125| | | | |1130| | | | |1135| |
|Glu|Asp|Lys|Pro|Glu|Asp|Thr|Ala|Thr|Phe|Ser|Gly|Asp|Asp|Phe|Ser|
| | | |1140| | | | |1145| | | | |1150| | |
|Cys|Val|Ala|Pro|Asn|Val|Pro|Lys|Ser| | | | | | | |
| | | |1155| | | |1160| | | | | | | | |

( 2 ) INFORMATION FOR SEQ ID NO:3:

( i ) SEQUENCE CHARACTERISTICS:
( A ) LENGTH: 1153 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:3:

| Met | Ala | Leu | Arg | Val | Leu | Leu | Leu | Thr | Ala | Leu | Thr | Leu | Cys | His | Gly |
|---|---|---|---|---|---|---|---|---|---|---|---|---|---|---|---|
| 1 | | | | 5 | | | | | 10 | | | | | 15 | |

| Phe | Asn | Leu | Asp | Thr | Glu | Asn | Ala | Met | Thr | Phe | Gln | Glu | Asn | Ala | Arg |
|---|---|---|---|---|---|---|---|---|---|---|---|---|---|---|---|
| | | | 20 | | | | | 25 | | | | | 30 | | |

| Gly | Phe | Gly | Gln | Ser | Val | Val | Gln | Leu | Gln | Gly | Ser | Arg | Val | Val | Val |
|---|---|---|---|---|---|---|---|---|---|---|---|---|---|---|---|
| | | 35 | | | | | 40 | | | | | 45 | | | |

| Gly | Ala | Pro | Gln | Glu | Ile | Val | Ala | Ala | Asn | Gln | Arg | Gly | Ser | Leu | Tyr |
|---|---|---|---|---|---|---|---|---|---|---|---|---|---|---|---|
| | 50 | | | | | 55 | | | | | 60 | | | | |

| Gln | Cys | Asp | Tyr | Ser | Thr | Gly | Ser | Cys | Glu | Pro | Ile | Arg | Leu | Gln | Val |
|---|---|---|---|---|---|---|---|---|---|---|---|---|---|---|---|
| 65 | | | | | 70 | | | | | 75 | | | | | 80 |

| Pro | Val | Glu | Ala | Val | Asn | Met | Ser | Leu | Gly | Leu | Ser | Leu | Ala | Ala | Thr |
|---|---|---|---|---|---|---|---|---|---|---|---|---|---|---|---|
| | | | | 85 | | | | | 90 | | | | | 95 | |

| Thr | Ser | Pro | Pro | Gln | Leu | Leu | Ala | Cys | Gly | Pro | Thr | Val | His | Gln | Thr |
|---|---|---|---|---|---|---|---|---|---|---|---|---|---|---|---|
| | | | 100 | | | | | 105 | | | | | 110 | | |

| Cys | Ser | Glu | Asn | Thr | Tyr | Val | Lys | Gly | Leu | Cys | Phe | Leu | Phe | Gly | Ser |
|---|---|---|---|---|---|---|---|---|---|---|---|---|---|---|---|
| | | 115 | | | | | 120 | | | | | 125 | | | |

| Asn | Leu | Arg | Gln | Gln | Pro | Gln | Lys | Phe | Pro | Glu | Ala | Leu | Arg | Gly | Cys |
|---|---|---|---|---|---|---|---|---|---|---|---|---|---|---|---|
| | 130 | | | | | 135 | | | | | 140 | | | | |

| Pro | Gln | Glu | Asp | Ser | Asp | Ile | Ala | Phe | Leu | Ile | Asp | Gly | Ser | Gly | Ser |
|---|---|---|---|---|---|---|---|---|---|---|---|---|---|---|---|
| 145 | | | | | 150 | | | | | 155 | | | | | 160 |

| Ile | Ile | Pro | His | Asp | Phe | Arg | Arg | Met | Lys | Glu | Phe | Val | Ser | Thr | Val |
|---|---|---|---|---|---|---|---|---|---|---|---|---|---|---|---|
| | | | | 165 | | | | | 170 | | | | | 175 | |

| Met | Glu | Gln | Leu | Lys | Lys | Ser | Lys | Thr | Leu | Phe | Ser | Leu | Met | Gln | Tyr |
|---|---|---|---|---|---|---|---|---|---|---|---|---|---|---|---|
| | | | 180 | | | | | 185 | | | | | 190 | | |

| Ser | Glu | Glu | Phe | Arg | Ile | His | Phe | Thr | Phe | Lys | Glu | Phe | Gln | Asn | Asn |
|---|---|---|---|---|---|---|---|---|---|---|---|---|---|---|---|
| | | 195 | | | | | 200 | | | | | 205 | | | |

| Pro | Asn | Pro | Arg | Ser | Leu | Val | Lys | Pro | Ile | Thr | Gln | Leu | Leu | Gly | Arg |
|---|---|---|---|---|---|---|---|---|---|---|---|---|---|---|---|
| | 210 | | | | | 215 | | | | | 220 | | | | |

| Thr | His | Thr | Ala | Thr | Gly | Ile | Arg | Lys | Val | Val | Arg | Glu | Leu | Phe | Asn |
|---|---|---|---|---|---|---|---|---|---|---|---|---|---|---|---|
| 225 | | | | | 230 | | | | | 235 | | | | | 240 |

| Ile | Thr | Asn | Gly | Ala | Arg | Lys | Asn | Ala | Phe | Lys | Ile | Leu | Val | Val | Ile |
|---|---|---|---|---|---|---|---|---|---|---|---|---|---|---|---|
| | | | | 245 | | | | | 250 | | | | | 255 | |

| Thr | Asp | Gly | Glu | Lys | Phe | Gly | Asp | Pro | Leu | Gly | Tyr | Glu | Asp | Val | Ile |
|---|---|---|---|---|---|---|---|---|---|---|---|---|---|---|---|
| | | | 260 | | | | | 265 | | | | | 270 | | |

| Pro | Glu | Ala | Asp | Arg | Glu | Gly | Val | Ile | Arg | Tyr | Val | Ile | Gly | Val | Gly |
|---|---|---|---|---|---|---|---|---|---|---|---|---|---|---|---|
| | | | 275 | | | | | 280 | | | | | 285 | | |

| Asp | Ala | Phe | Arg | Ser | Glu | Lys | Ser | Arg | Gln | Glu | Leu | Asn | Thr | Ile | Ala |
|---|---|---|---|---|---|---|---|---|---|---|---|---|---|---|---|
| | 290 | | | | | 295 | | | | | 300 | | | | |

| Ser | Lys | Pro | Pro | Arg | Asp | His | Val | Phe | Gln | Val | Asn | Asn | Phe | Glu | Ala |
|---|---|---|---|---|---|---|---|---|---|---|---|---|---|---|---|
| 305 | | | | | 310 | | | | | 315 | | | | | 320 |

| Leu | Lys | Thr | Ile | Gln | Asn | Gln | Leu | Arg | Glu | Lys | Ile | Phe | Ala | Ile | Glu |
|---|---|---|---|---|---|---|---|---|---|---|---|---|---|---|---|
| | | | | 325 | | | | | 330 | | | | | 335 | |

| Gly | Thr | Gln | Thr | Gly | Ser | Ser | Ser | Ser | Phe | Glu | His | Glu | Met | Ser | Gln |
|---|---|---|---|---|---|---|---|---|---|---|---|---|---|---|---|
| | | | 340 | | | | | 345 | | | | | 350 | | |

| Glu | Gly | Phe | Ser | Ala | Ala | Ile | Thr | Ser | Asn | Gly | Pro | Leu | Leu | Ser | Thr |
|---|---|---|---|---|---|---|---|---|---|---|---|---|---|---|---|
| | | | 355 | | | | | 360 | | | | | 365 | | |

| Val | Gly | Ser | Tyr | Asp | Trp | Ala | Gly | Gly | Val | Phe | Leu | Tyr | Thr | Ser | Lys |
|---|---|---|---|---|---|---|---|---|---|---|---|---|---|---|---|
| | 370 | | | | | 375 | | | | | 380 | | | | |

-continued

| | | | | | | | | | | | | | | | |
|---|---|---|---|---|---|---|---|---|---|---|---|---|---|---|---|
| Glu | Lys | Ser | Thr | Phe | Ile | Asn | Met | Thr | Arg | Val | Asp | Ser | Asp | Met | Asn |
| 385 | | | | | 390 | | | | 395 | | | | | | 400 |
| Asp | Ala | Tyr | Leu | Gly | Tyr | Ala | Ala | Ala | Ile | Ile | Leu | Arg | Asn | Arg | Val |
| | | | | 405 | | | | | 410 | | | | | 415 | |
| Gln | Ser | Leu | Val | Leu | Gly | Ala | Pro | Arg | Tyr | Gln | His | Ile | Gly | Leu | Val |
| | | | 420 | | | | | 425 | | | | | 430 | | |
| Ala | Met | Phe | Arg | Gln | Asn | Thr | Gly | Met | Trp | Glu | Ser | Asn | Ala | Asn | Val |
| | | 435 | | | | | 440 | | | | | 445 | | | |
| Lys | Gly | Thr | Gln | Ile | Gly | Ala | Tyr | Phe | Gly | Ala | Ser | Leu | Cys | Ser | Val |
| | 450 | | | | | 455 | | | | | 460 | | | | |
| Asp | Val | Asp | Ser | Asn | Gly | Ser | Thr | Asp | Leu | Val | Leu | Ile | Gly | Ala | Pro |
| 465 | | | | | 470 | | | | | 475 | | | | | 480 |
| His | Tyr | Tyr | Glu | Gln | Thr | Arg | Gly | Gly | Gln | Val | Ser | Val | Cys | Pro | Leu |
| | | | | 485 | | | | | 490 | | | | | 495 | |
| Pro | Arg | Gly | Gln | Arg | Ala | Arg | Trp | Gln | Cys | Asp | Ala | Val | Leu | Tyr | Gly |
| | | | 500 | | | | | 505 | | | | | 510 | | |
| Glu | Gln | Gly | Gln | Pro | Trp | Gly | Arg | Phe | Gly | Ala | Ala | Leu | Thr | Val | Leu |
| | | 515 | | | | | 520 | | | | | 525 | | | |
| Gly | Asp | Val | Asn | Gly | Asp | Lys | Leu | Thr | Asp | Val | Ala | Ile | Gly | Ala | Pro |
| 530 | | | | | 535 | | | | | 540 | | | | | |
| Gly | Glu | Glu | Asp | Asn | Arg | Gly | Ala | Val | Tyr | Leu | Phe | His | Gly | Thr | Ser |
| 545 | | | | | 550 | | | | | 555 | | | | | 560 |
| Gly | Ser | Gly | Ile | Ser | Pro | Ser | His | Ser | Gln | Arg | Ile | Ala | Gly | Ser | Lys |
| | | | | 565 | | | | | 570 | | | | | 575 | |
| Leu | Ser | Pro | Arg | Leu | Gln | Tyr | Phe | Gly | Gln | Ser | Leu | Ser | Gly | Gly | Gln |
| | | | 580 | | | | | 585 | | | | | 590 | | |
| Asp | Leu | Thr | Met | Asp | Gly | Leu | Val | Asp | Leu | Thr | Val | Gly | Ala | Gln | Gly |
| | | 595 | | | | | 600 | | | | | 605 | | | |
| His | Val | Leu | Leu | Leu | Arg | Ser | Gln | Pro | Val | Leu | Arg | Val | Lys | Ala | Ile |
| | 610 | | | | | 615 | | | | | 620 | | | | |
| Met | Glu | Phe | Asn | Pro | Arg | Glu | Val | Ala | Arg | Asn | Val | Phe | Glu | Cys | Asn |
| 625 | | | | | 630 | | | | | 635 | | | | | 640 |
| Asp | Gln | Val | Val | Lys | Gly | Lys | Glu | Ala | Gly | Glu | Val | Arg | Val | Cys | Leu |
| | | | | 645 | | | | | 650 | | | | | 655 | |
| His | Val | Gln | Lys | Ser | Thr | Arg | Asp | Arg | Leu | Arg | Glu | Gly | Gln | Ile | Gln |
| | | | 660 | | | | | 665 | | | | | 670 | | |
| Ser | Val | Val | Thr | Tyr | Asp | Leu | Ala | Leu | Asp | Ser | Gly | Arg | Pro | His | Ser |
| | | | 675 | | | | | 680 | | | | | 685 | | |
| Arg | Ala | Val | Phe | Asn | Glu | Thr | Lys | Asn | Ser | Thr | Arg | Arg | Gln | Thr | Gln |
| | 690 | | | | | 695 | | | | | 700 | | | | |
| Val | Leu | Gly | Leu | Thr | Gln | Thr | Cys | Glu | Thr | Leu | Lys | Leu | Gln | Leu | Pro |
| 705 | | | | | 710 | | | | | 715 | | | | | 720 |
| Asn | Cys | Ile | Glu | Asp | Pro | Val | Ser | Pro | Ile | Val | Leu | Arg | Leu | Asn | Phe |
| | | | | 725 | | | | | 730 | | | | | 735 | |
| Ser | Leu | Val | Gly | Thr | Pro | Leu | Ser | Ala | Phe | Gly | Asn | Leu | Arg | Pro | Val |
| | | | 740 | | | | | 745 | | | | | 750 | | |
| Leu | Ala | Glu | Asp | Ala | Gln | Arg | Leu | Phe | Thr | Ala | Leu | Phe | Pro | Phe | Glu |
| | | | 755 | | | | | 760 | | | | | 765 | | |
| Lys | Asn | Cys | Gly | Asn | Asp | Asn | Ile | Cys | Gln | Asp | Asp | Leu | Ser | Ile | Thr |
| | 770 | | | | | 775 | | | | | 780 | | | | |
| Phe | Ser | Phe | Met | Ser | Leu | Asp | Cys | Leu | Val | Val | Gly | Gly | Pro | Arg | Glu |
| 785 | | | | | 790 | | | | | 795 | | | | | 800 |
| Phe | Asn | Val | Thr | Val | Thr | Val | Arg | Asn | Asp | Gly | Glu | Asp | Ser | Tyr | Arg |
| | | | | 805 | | | | | 810 | | | | | 815 | |

| | | | | | | | | | | | | | | |
|---|---|---|---|---|---|---|---|---|---|---|---|---|---|---|
|Thr|Gln|Val|Thr 820|Phe|Phe|Phe|Pro|Leu 825|Asp|Leu|Ser|Tyr|Arg 830|Lys|Val|
|Ser|Thr|Leu 835|Gln|Asn|Gln|Arg|Ser 840|Gln|Arg|Ser|Trp|Arg 845|Leu|Ala|Cys|
|Glu|Ser 850|Ala|Ser|Ser|Thr|Glu 855|Val|Ser|Gly|Ala|Leu 860|Lys|Ser|Thr|Ser|
|Cys 865|Ser|Ile|Asn|His|Pro 870|Ile|Phe|Pro|Glu|Asn 875|Ser|Glu|Val|Thr|Phe 880|
|Asn|Ile|Thr|Phe|Asp 885|Val|Asp|Ser|Lys|Ala 890|Ser|Leu|Gly|Asn|Lys 895|Leu|
|Leu|Leu|Lys|Ala 900|Asn|Val|Thr|Ser|Glu 905|Asn|Asn|Met|Pro|Arg 910|Thr|Asn|
|Lys|Thr|Glu 915|Phe|Gln|Leu|Glu|Leu 920|Pro|Val|Lys|Tyr|Ala 925|Val|Tyr|Met|
|Val|Val 930|Thr|Ser|His|Gly|Val 935|Ser|Thr|Lys|Tyr|Leu 940|Asn|Phe|Thr|Ala|
|Ser 945|Glu|Asn|Thr|Ser|Arg 950|Val|Met|Gln|His|Gln 955|Tyr|Gln|Val|Ser|Asn 960|
|Leu|Gly|Gln|Arg|Ser 965|Leu|Pro|Ile|Ser|Leu 970|Val|Phe|Leu|Val|Pro 975|Val|
|Arg|Leu|Asn|Gln 980|Thr|Val|Ile|Trp|Asp 985|Arg|Pro|Gln|Val|Thr 990|Phe|Ser|
|Glu|Asn|Leu 995|Ser|Ser|Thr|Cys|His 1000|Thr|Lys|Glu|Arg|Leu 1005|Pro|Ser|His|
|Ser|Asp 1010|Phe|Leu|Ala|Glu|Leu 1015|Arg|Lys|Ala|Pro|Val 1020|Val|Asn|Cys|Ser|
|Ile 1025|Ala|Val|Cys|Gln|Arg 1030|Ile|Gln|Cys|Asp|Ile 1035|Pro|Phe|Phe|Gly|Ile 1040|
|Gln|Glu|Glu|Phe|Asn 1045|Ala|Thr|Leu|Lys|Gly 1050|Asn|Leu|Ser|Phe|Asp 1055|Trp|
|Tyr|Ile|Lys|Thr 1060|Ser|His|Asn|His|Leu 1065|Leu|Ile|Val|Ser|Thr 1070|Ala|Glu|
|Ile|Leu|Phe 1075|Asn|Asp|Ser|Val|Phe 1080|Thr|Leu|Leu|Pro|Gly 1085|Gln|Gly|Ala|
|Phe|Val 1090|Arg|Ser|Gln|Thr|Glu 1095|Thr|Lys|Val|Glu|Pro 1100|Phe|Glu|Val|Pro|
|Asn 1105|Pro|Leu|Pro|Leu|Ile 1110|Val|Gly|Ser|Ser|Val 1115|Gly|Gly|Leu|Leu|Leu 1120|
|Leu|Ala|Leu|Ile|Thr 1125|Ala|Ala|Leu|Tyr|Lys 1130|Leu|Gly|Phe|Phe|Lys 1135|Arg|
|Gln|Tyr|Lys|Asp|Met 1140|Met|Ser|Glu|Gly|Gly 1145|Pro|Pro|Gly|Ala|Glu 1150|Pro|
|Gln| | | | | | | | | | | | | | | |

( 2 ) INFORMATION FOR SEQ ID NO:4:

( i ) SEQUENCE CHARACTERISTICS:
        ( A ) LENGTH: 1163 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
|Met|Thr|Arg|Thr|Arg|Ala|Ala|Leu|Leu|Leu|Phe|Thr|Ala|Leu|Ala|Thr|

|  1  |     |     |     |  5  |     |     |     |     | 10  |     |     |     |     | 15  |
|-----|-----|-----|-----|-----|-----|-----|-----|-----|-----|-----|-----|-----|-----|-----|
| Ser | Leu | Gly | Phe | Asn | Leu | Asp | Thr | Glu | Leu | Thr | Ala | Phe | Arg | Val |
|     |     |     | 20  |     |     |     | 25  |     |     |     | 30  |     |     |     |
| Asp | Ser | Ala | Gly | Phe | Gly | Asp | Ser | Val | Val | Gln | Tyr | Ala | Asn | Ser | Trp |
|     |     | 35  |     |     |     | 40  |     |     |     | 45  |     |     |     |     |
| Val | Val | Val | Gly | Ala | Pro | Gln | Lys | Ile | Ile | Ala | Ala | Asn | Gln | Ile | Gly |
|     | 50  |     |     |     |     | 55  |     |     |     | 60  |     |     |     |     |
| Gly | Leu | Tyr | Gln | Cys | Gly | Tyr | Ser | Thr | Gly | Ala | Cys | Glu | Pro | Ile | Gly |
| 65  |     |     |     |     | 70  |     |     |     |     | 75  |     |     |     |     | 80  |
| Leu | Gln | Val | Pro | Pro | Glu | Ala | Val | Asn | Met | Ser | Leu | Gly | Leu | Ser | Leu |
|     |     |     |     | 85  |     |     |     |     | 90  |     |     |     |     | 95  |     |
| Ala | Ser | Thr | Thr | Ser | Pro | Ser | Gln | Leu | Leu | Ala | Cys | Gly | Pro | Thr | Val |
|     |     |     | 100 |     |     |     |     | 105 |     |     |     |     | 110 |     |     |
| His | His | Glu | Cys | Gly | Arg | Asn | Met | Tyr | Leu | Thr | Gly | Leu | Cys | Phe | Leu |
|     |     | 115 |     |     |     |     | 120 |     |     |     |     | 125 |     |     |     |
| Leu | Gly | Pro | Thr | Gln | Leu | Thr | Gln | Arg | Leu | Pro | Val | Ser | Arg | Gln | Glu |
|     | 130 |     |     |     |     | 135 |     |     |     |     | 140 |     |     |     |     |
| Cys | Pro | Arg | Gln | Glu | Gln | Asp | Ile | Val | Phe | Leu | Ile | Asp | Gly | Ser | Gly |
| 145 |     |     |     |     | 150 |     |     |     |     | 155 |     |     |     |     | 160 |
| Ser | Ile | Ser | Ser | Arg | Asn | Phe | Ala | Thr | Met | Met | Asn | Phe | Val | Arg | Ala |
|     |     |     |     | 165 |     |     |     |     | 170 |     |     |     |     | 175 |     |
| Val | Ile | Ser | Gln | Phe | Gln | Arg | Pro | Ser | Thr | Gln | Phe | Ser | Leu | Met | Gln |
|     |     |     | 180 |     |     |     |     | 185 |     |     |     |     | 190 |     |     |
| Phe | Ser | Asn | Lys | Phe | Gln | Thr | His | Phe | Thr | Phe | Glu | Glu | Phe | Arg | Arg |
|     |     | 195 |     |     |     |     | 200 |     |     |     |     | 205 |     |     |     |
| Thr | Ser | Asn | Pro | Leu | Ser | Leu | Leu | Ala | Ser | Val | His | Gln | Leu | Gln | Gly |
|     | 210 |     |     |     |     | 215 |     |     |     |     | 220 |     |     |     |     |
| Phe | Thr | Tyr | Thr | Ala | Thr | Ala | Ile | Gln | Asn | Val | Val | His | Arg | Leu | Phe |
| 225 |     |     |     |     | 230 |     |     |     |     | 235 |     |     |     |     | 240 |
| His | Ala | Ser | Tyr | Gly | Ala | Arg | Arg | Asp | Ala | Ile | Lys | Ile | Leu | Ile | Val |
|     |     |     |     | 245 |     |     |     |     | 250 |     |     |     |     | 255 |     |
| Ile | Thr | Asp | Gly | Lys | Lys | Glu | Gly | Asp | Ser | Leu | Asp | Tyr | Lys | Asp | Val |
|     |     |     | 260 |     |     |     |     | 265 |     |     |     |     | 270 |     |     |
| Ile | Pro | Met | Ala | Asp | Ala | Ala | Gly | Ile | Ile | Arg | Tyr | Ala | Ile | Gly | Val |
|     |     | 275 |     |     |     |     | 280 |     |     |     |     | 285 |     |     |     |
| Gly | Leu | Ala | Phe | Gln | Asn | Arg | Asn | Ser | Trp | Lys | Glu | Leu | Asn | Asp | Ile |
|     | 290 |     |     |     |     | 295 |     |     |     |     | 300 |     |     |     |     |
| Ala | Ser | Lys | Pro | Ser | Gln | Glu | His | Ile | Phe | Lys | Val | Glu | Asp | Phe | Asp |
| 305 |     |     |     |     | 310 |     |     |     |     | 315 |     |     |     |     | 320 |
| Ala | Leu | Lys | Asp | Ile | Gln | Asn | Gln | Leu | Lys | Glu | Lys | Ile | Phe | Ala | Ile |
|     |     |     |     | 325 |     |     |     |     | 330 |     |     |     |     | 335 |     |
| Glu | Gly | Thr | Glu | Thr | Ile | Ser | Ser | Ser | Phe | Glu | Leu | Glu | Met | Ala |
|     |     |     | 340 |     |     |     |     | 345 |     |     |     |     | 350 |     |
| Gln | Glu | Gly | Phe | Ser | Ala | Val | Phe | Thr | Pro | Asp | Gly | Pro | Val | Leu | Gly |
|     |     | 355 |     |     |     |     | 360 |     |     |     |     | 365 |     |     |     |
| Ala | Val | Gly | Ser | Phe | Thr | Trp | Ser | Gly | Gly | Ala | Phe | Leu | Tyr | Pro | Pro |
|     | 370 |     |     |     |     | 375 |     |     |     |     | 380 |     |     |     |     |
| Asn | Met | Ser | Pro | Thr | Phe | Ile | Asn | Met | Ser | Gln | Glu | Asn | Val | Asp | Met |
| 385 |     |     |     |     | 390 |     |     |     |     | 395 |     |     |     |     | 400 |
| Arg | Asp | Ser | Tyr | Leu | Gly | Tyr | Ser | Thr | Glu | Leu | Ala | Leu | Trp | Lys | Gly |
|     |     |     |     | 405 |     |     |     |     | 410 |     |     |     |     | 415 |     |
| Val | Gln | Ser | Leu | Val | Leu | Gly | Ala | Pro | Arg | Tyr | Gln | His | Ile | Gly | Lys |
|     |     |     | 420 |     |     |     |     | 425 |     |     |     |     | 430 |     |     |

```
Ala  Val  Ile  Phe  Ile  Gln  Val  Ser  Arg  Gln  Trp  Arg  Met  Lys  Ala  Glu
          435                 440                 445
Val  Ile  Gly  Thr  Gln  Ile  Gly  Ser  Tyr  Phe  Gly  Ala  Ser  Leu  Cys  Ser
          450                 455                 460
Val  Asp  Val  Asp  Thr  Asp  Gly  Ser  Thr  Asp  Leu  Val  Leu  Ile  Gly  Ala
465                 470                 475                           480
Pro  His  Tyr  Tyr  Glu  Gln  Thr  Arg  Gly  Gln  Val  Ser  Val  Cys  Pro
               485                 490                      495
Leu  Pro  Arg  Gly  Trp  Arg  Trp  Trp  Cys  Asp  Ala  Val  Leu  Tyr  Gly
          500                 505                      510
Glu  Gln  Gly  His  Pro  Trp  Gly  Arg  Phe  Gly  Ala  Ala  Leu  Thr  Val  Leu
          515                 520                      525
Gly  Asp  Val  Asn  Gly  Asp  Lys  Leu  Thr  Asp  Val  Val  Ile  Gly  Ala  Pro
     530                 535                      540
Gly  Glu  Glu  Glu  Asn  Arg  Gly  Ala  Val  Tyr  Leu  Phe  His  Gly  Val  Leu
545                      550                 555                           560
Gly  Pro  Ser  Ile  Ser  Pro  Ser  His  Ser  Gln  Arg  Ile  Ala  Gly  Ser  Gln
               565                 570                      575
Leu  Ser  Ser  Arg  Leu  Gln  Tyr  Phe  Gly  Gln  Ala  Leu  Ser  Gly  Gly  Gln
          580                 585                      590
Asp  Leu  Thr  Gln  Asp  Gly  Leu  Val  Asp  Leu  Ala  Val  Gly  Ala  Arg  Gly
          595                 600                      605
Gln  Val  Leu  Leu  Leu  Arg  Thr  Arg  Pro  Val  Leu  Trp  Val  Gly  Val  Ser
     610                 615                      620
Met  Gln  Phe  Ile  Pro  Ala  Glu  Ile  Pro  Arg  Ser  Ala  Phe  Glu  Cys  Arg
625                      630                 635                           640
Glu  Gln  Val  Val  Ser  Glu  Gln  Thr  Leu  Val  Gln  Ser  Asn  Ile  Cys  Leu
               645                 650                      655
Tyr  Ile  Asp  Lys  Arg  Ser  Lys  Asn  Leu  Leu  Gly  Ser  Arg  Asp  Leu  Gln
               660                 665                      670
Ser  Ser  Val  Thr  Leu  Asp  Leu  Ala  Leu  Ala  Pro  Gly  Arg  Leu  Ser  Pro
          675                 680                      685
Arg  Ala  Ile  Phe  Gln  Glu  Thr  Lys  Asn  Arg  Ser  Leu  Ser  Arg  Val  Arg
     690                 695                      700
Val  Leu  Gly  Leu  Lys  Ala  His  Cys  Glu  Asn  Phe  Asn  Leu  Leu  Leu  Pro
705                 710                 715                           720
Ser  Cys  Val  Glu  Asp  Ser  Val  Ile  Pro  Ile  Ile  Leu  Arg  Leu  Asn  Phe
               725                 730                      735
Thr  Leu  Val  Gly  Lys  Pro  Leu  Leu  Ala  Phe  Arg  Asn  Leu  Arg  Pro  Met
               740                 745                      750
Leu  Ala  Ala  Leu  Ala  Gln  Arg  Tyr  Phe  Thr  Ala  Ser  Leu  Pro  Phe  Glu
          755                 760                      765
Lys  Asn  Cys  Gly  Ala  Asp  His  Ile  Cys  Gln  Asp  Asn  Leu  Gly  Ile  Ser
770                      775                 780
Phe  Ser  Phe  Pro  Gly  Leu  Lys  Ser  Leu  Leu  Val  Gly  Ser  Asn  Leu  Glu
785                 790                 795                           800
Leu  Asn  Ala  Glu  Val  Met  Val  Trp  Asn  Asp  Gly  Glu  Asp  Ser  Tyr  Gly
               805                 810                      815
Thr  Thr  Ile  Thr  Phe  Ser  His  Pro  Ala  Gly  Leu  Ser  Tyr  Arg  Tyr  Val
               820                 825                      830
Ala  Glu  Gly  Gln  Lys  Gln  Gly  Gln  Leu  Arg  Ser  Leu  His  Leu  Thr  Cys
          835                 840                      845
Cys  Ser  Ala  Pro  Val  Gly  Ser  Gln  Gly  Thr  Trp  Ser  Thr  Ser  Cys  Arg
850                      855                 860
```

```
Ile Asn His Leu Ile Phe Arg Gly Gly Ala Gln Ile Thr Phe Leu Ala
865                 870                 875                 880

Thr Phe Asp Val Ser Pro Lys Ala Val Gly Leu Asp Arg Leu Leu Leu
                885                 890                 895

Ile Ala Asn Val Ser Ser Glu Asn Asn Ile Pro Arg Thr Ser Lys Thr
                900                 905                 910

Ile Phe Gln Leu Glu Leu Pro Val Lys Tyr Ala Val Tyr Ile Val Val
        915                 920                 925

Ser Ser His Glu Gln Phe Thr Lys Tyr Leu Asn Phe Ser Glu Ser Glu
    930                 935                 940

Glu Lys Glu Ser His Val Ala Met His Arg Tyr Gln Val Asn Asn Leu
945                 950                 955                 960

Gly Gln Arg Asp Leu Pro Val Ser Ile Asn Phe Trp Val Pro Val Glu
                965                 970                 975

Leu Asn Gln Glu Ala Val Trp Met Asp Val Glu Val Ser His Pro Gln
            980                 985                 990

Asn Pro Ser Leu Arg Cys Ser Ser Glu Lys Ile Ala Pro Pro Ala Ser
        995                 1000                1005

Asp Phe Leu Ala His Ile Gln Lys Asn Pro Val Leu Asp Cys Ser Ile
    1010                1015                1020

Ala Gly Cys Leu Arg Phe Arg Cys Asp Val Pro Ser Phe Ser Val Gln
1025                1030                1035                1040

Glu Glu Leu Asp Phe Thr Leu Lys Gly Asn Leu Ser Phe Gly Trp Val
                1045                1050                1055

Arg Gln Ile Leu Gln Lys Lys Val Ser Val Val Ser Val Ala Glu Ile
            1060                1065                1070

Ile Phe Asp Thr Ser Val Tyr Ser Gln Leu Pro Gly Gln Glu Ala Phe
        1075                1080                1085

Met Arg Ala Gln Thr Ile Thr Val Leu Glu Lys Tyr Lys Val His Asn
    1090                1095                1100

Pro Ile Pro Leu Ile Val Gly Ser Ser Ile Gly Gly Leu Leu Leu Leu
1105                1110                1115                1120

Ala Leu Ile Thr Ala Val Leu Tyr Lys Val Gly Phe Phe Lys Arg Gln
                1125                1130                1135

Tyr Lys Glu Met Met Glu Glu Ala Asn Gly Gln Ile Ala Pro Glu Asn
            1140                1145                1150

Gly Thr Gln Thr Pro Ser Pro Ser Glu Lys
        1155                1160
```

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Phe Asn Leu Asp Val Glu Glu Pro Met Val Phe Gln
1               5               10
```

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO:6:

TTYAAYYTGG AYGTNGARGA RCCNATGGTN TTYCA                                    35

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

TTCAACCTGG ACGTGGAGGA GCCCATGGTG TTCCAA                                   36

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

TTCAACCTGG ACGTNGAASA NCCCATGGTC TTCCAA                                   36

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

TTYAAYYTNG AYGTNGARGA RCC                                                 23

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TTYAAYYTGG ACGTNGAAGA                                                     20

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

TGRAANACCA TNGGYTC                                                                                          17

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

TTGGAAGACC ATNGGYTC                                                                                         18

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

ATTAACCCTC ACTAAAG                                                                                          17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

AATACGACTC ACTATAG                                                                                          17

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Val  Phe  Gln  Glu  Xaa  Gly  Ala  Gly  Phe  Gly  Gln
    1                   5                        10

( 2 ) INFORMATION FOR SEQ ID NO:16:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Leu  Tyr  Asp  Xaa  Val  Ala  Ala  Thr  Gly  Leu  Xaa  Gln  Pro  Ile
    1                   5                        10

( 2 ) INFORMATION FOR SEQ ID NO:17:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:17:

Pro Leu Glu Tyr Xaa Asp Val Ile Pro Gln Ala Glu
1               5                   10

( 2 ) INFORMATION FOR SEQ ID NO:18:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:18:

Phe Gln Glu Gly Phe Ser Xaa Val Leu Xaa
1               5                   10

( 2 ) INFORMATION FOR SEQ ID NO:19:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:19:

Thr Ser Pro Thr Phe Ile Xaa Met Ser Gln Glu Asn Val Asp
1               5                   10

( 2 ) INFORMATION FOR SEQ ID NO:20:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:20:

Leu Val Val Gly Ala Pro Leu Glu Val Val Ala Val Xaa Gln Thr Gly
1               5                   10                  15
Arg ( 2 ) INFORMATION FOR SEQ ID NO:21:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:21:

Leu Asp Xaa Lys Pro Xaa Asp Thr Ala
1               5

( 2 ) INFORMATION FOR SEQ ID NO:22:

( i ) SEQUENCE CHARACTERISTICS:
    ( A ) LENGTH: 7 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:22:

Phe Gly Glu Gln Phe Ser Glu
1               5

( 2 ) INFORMATION FOR SEQ ID NO:23:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:23:

RAANCCYTCY TGRAAACTYT C                                                      21

( 2 ) INFORMATION FOR SEQ ID NO:24:

( i ) SEQUENCE CHARACTERISTICS:
( A ) LENGTH: 1006 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:24:

| | | | | | | |
|---|---|---|---|---|---|---|
| TTCAACCTGG | ACGTGGAGGA | GCCCATGGTG | TTCAAGAGGA | TGGAGCTGGC | TTTGGACAGA | 60 |
| GCGTGGCCCA | GCTTGGCGGA | TCTAGACTCG | TGGTGGGAGC | CCCCCTGGAG | GTGGTGGCGG | 120 |
| TCAACCAAAC | AGGAAGGTTG | TATGACTGTG | TGGCTGCCAC | TGGCCTTGTC | AACCCATACC | 180 |
| CCTGCACACA | CCCCCAGATG | CTGTGAACAT | GTCCCTGGGT | CTGTCCCTGT | CAGCCGCCGC | 240 |
| CAGTCGCCCC | TGGCTGCTGG | CCTGTGGCCC | AACCATGCAC | AGAGCCTGTG | GGGAGAATAT | 300 |
| GTATGCAGAA | GGCTTTTGCC | TCCTGTTGGA | CTCCCATCTG | CAGACCATTT | GGACAGTACC | 360 |
| TGCTGCCCTA | CCAGAGTGTC | CAAGTCAAGA | GATGGACATT | GTCTTCCTGA | TTGATGGTTC | 420 |
| TGGCAGTATG | AGCAAAGTGA | CTTTAAACAA | ATGAAGGATT | TGTGAGAGCT | GTGATGGGAC | 480 |
| AGTTTGAGGG | CACCCAAACC | CTGTTCTCAC | TGATACAGTA | TCCCACCTCC | CTGAAGATCC | 540 |
| ACTTCACCTT | CACGCAATTC | CAGAGCAGCT | GGAACCCTCT | GAGCCTGGTG | GATCCCATTG | 600 |
| TCCAACTGGA | CGGCCTGACA | TATACAGCCA | CGGGCATCCG | GAAAGTGGTG | GAGGAACTGT | 660 |
| TCATAGTAA | GAATGGGGCC | CGTAAAAGTG | CCAAGAAGAT | CCTCATTGTC | ATCACAGATG | 720 |
| GCAAAAATAC | AAAGACCCCC | TGGAGTACGA | GGACGTATCC | CCAGGCAGAG | AGAGCGGATC | 780 |
| ATCCGCTATG | CCATTGGGGT | GGGAGATGCT | TTCTGGAAAC | CCAGTGCCAA | GCAGGAGCTG | 840 |
| GACAACATTG | GCTCAGAGCC | GGCTCAGGAC | CATGTGTTCA | GGGTGGACAA | CTTTGCAGCA | 900 |
| CTCAGCAGCA | TCCAGGAGCA | GCTGCAGGAG | AAGATCTTTG | CACTCGAAGG | AACCCAGTCG | 960 |
| ACGACAAGTA | GCTCTTTCCA | ACATGAGATG | TTCCAAGAAG | GGTTCA | | 1006 |

( 2 ) INFORMATION FOR SEQ ID NO:25:

( i ) SEQUENCE CHARACTERISTICS:
( A ) LENGTH: 17 base pairs
( B ) TYPE: nucleic acid
( C ) STRANDEDNESS: single (D) TOPOLOGY: linear (ii) MOLECULE TYPE: DNA (xi) SEQUENCE DESCRIPTION: SEQ ID NO:25:

GTNTTYCARG ARGAYGG 17

(2) INFORMATION FOR SEQ ID NO:26:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:26:

CCACTGTCAG GATGCCCGTG 20

(2) INFORMATION FOR SEQ ID NO:27:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:27:

AGTTACGAAT TCGCCACCAT GGCTCTACGG GTGCTTCTTC TG 42

(2) INFORMATION FOR SEQ ID NO:28:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:28:

AGTTACGAAT TCGCCACCAT GACTCGGACT GTGCTTCTTC TG 42

(2) INFORMATION FOR SEQ ID NO:29:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:29:

AGTTACGAAT TCGCCACCAT GACCTTCGGC ACTGTG 36

(2) INFORMATION FOR SEQ ID NO:30:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:30:

TTGCTGACTG CCTGCAGTTC                                                          20

( 2 ) INFORMATION FOR SEQ ID NO:31:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:31:

GTTCTGACGC GTAATGGCAT TGTAGACCTC GTCTTC                                        36

( 2 ) INFORMATION FOR SEQ ID NO:32:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:32:

ACGTATGCAG GATCCCATCA AGAGATGGAC ATCGCT                                        36

( 2 ) INFORMATION FOR SEQ ID NO:33:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:33:

ACTGCATGTC TCGAGGCTGA AGCCTTCTTG GGACATC                                       37

( 2 ) INFORMATION FOR SEQ ID NO:34:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:34:

TATAGACTGC TGGGTAGTCC CCAC                                                     24

( 2 ) INFORMATION FOR SEQ ID NO:35:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:35:

TGAAGATTGG GGGTAAATAA CAGA                                                     24

( 2 ) INFORMATION FOR SEQ ID NO:36:

(i) SEQUENCE CHARACTERISTICS:
   (A) LENGTH: 3528 base pairs
   (B) TYPE: nucleic acid
   (C) STRANDEDNESS: single
   (D) TOPOLOGY: linear (ii) MOLECULE TYPE: cDNA (ix) FEATURE:
   (A) NAME/KEY: CDS
   (B) LOCATION: 1..3456

(xi) SEQUENCE DESCRIPTION: SEQ ID NO:36:

| GGC | TGG | GCC | CTG | GCT | TCC | TGT | CAT | GGG | TCT | AAC | CTG | GAT | GTG | GAG | GAA | 48 |
| Gly | Trp | Ala | Leu | Ala | Ser | Cys | His | Gly | Ser | Asn | Leu | Asp | Val | Glu | Glu | |
| 1 | | | | 5 | | | | | 10 | | | | | 15 | | |

| CCC | ATC | GTG | TTC | AGA | GAG | GAT | GCA | GCC | AGC | TTT | GGA | CAG | ACT | GTG | GTG | 96 |
| Pro | Ile | Val | Phe | Arg | Glu | Asp | Ala | Ala | Ser | Phe | Gly | Gln | Thr | Val | Val | |
| | | | 20 | | | | | 25 | | | | | 30 | | | |

| CAG | TTT | GGT | GGA | TCT | CGA | CTC | GTG | GTG | GGA | GCC | CCT | CTG | GAG | GCG | GTG | 144 |
| Gln | Phe | Gly | Gly | Ser | Arg | Leu | Val | Val | Gly | Ala | Pro | Leu | Glu | Ala | Val | |
| | | 35 | | | | | 40 | | | | | 45 | | | | |

| GCA | GTC | AAC | CAA | ACA | GGA | CGG | TTG | TAT | GAC | TGT | GCA | CCT | GCC | ACT | GGC | 192 |
| Ala | Val | Asn | Gln | Thr | Gly | Arg | Leu | Tyr | Asp | Cys | Ala | Pro | Ala | Thr | Gly | |
| | 50 | | | | | 55 | | | | | 60 | | | | | |

| ATG | TGC | CAG | CCC | ATC | GTA | CTG | CGC | AGT | CCC | CTA | GAG | GCA | GTG | AAC | ATG | 240 |
| Met | Cys | Gln | Pro | Ile | Val | Leu | Arg | Ser | Pro | Leu | Glu | Ala | Val | Asn | Met | |
| 65 | | | | | 70 | | | | | 75 | | | | | 80 | |

| TCC | CTG | GGC | CTG | TCT | CTG | GTG | ACT | GCC | ACC | AAT | AAC | GCC | CAG | TTG | CTG | 288 |
| Ser | Leu | Gly | Leu | Ser | Leu | Val | Thr | Ala | Thr | Asn | Asn | Ala | Gln | Leu | Leu | |
| | | | | 85 | | | | | 90 | | | | | 95 | | |

| GCT | TGT | GGT | CCA | ACT | GCA | CAG | AGA | GCT | TGT | GTG | AAG | AAC | ATG | TAT | GCG | 336 |
| Ala | Cys | Gly | Pro | Thr | Ala | Gln | Arg | Ala | Cys | Val | Lys | Asn | Met | Tyr | Ala | |
| | | | 100 | | | | | 105 | | | | | 110 | | | |

| AAA | GGT | TCC | TGC | CTC | CTT | CTC | GGC | TCC | AGC | TTG | CAG | TTC | ATC | CAG | GCA | 384 |
| Lys | Gly | Ser | Cys | Leu | Leu | Leu | Gly | Ser | Ser | Leu | Gln | Phe | Ile | Gln | Ala | |
| | | 115 | | | | | 120 | | | | | 125 | | | | |

| GTC | CCT | GCC | TCC | ATG | CCA | GAG | TGT | CCA | AGA | CAA | GAG | ATG | GAC | ATT | GCT | 432 |
| Val | Pro | Ala | Ser | Met | Pro | Glu | Cys | Pro | Arg | Gln | Glu | Met | Asp | Ile | Ala | |
| | 130 | | | | | 135 | | | | | 140 | | | | | |

| TTC | CTG | ATT | GAT | GGT | TCT | GGC | AGC | ATT | AAC | CAA | AGG | GAC | TTT | GCC | CAG | 480 |
| Phe | Leu | Ile | Asp | Gly | Ser | Gly | Ser | Ile | Asn | Gln | Arg | Asp | Phe | Ala | Gln | |
| 145 | | | | | 150 | | | | | 155 | | | | | 160 | |

| ATG | AAG | GAC | TTT | GTC | AAA | GCT | TTG | ATG | GGA | GAG | TTT | GCG | AGC | ACC | AGC | 528 |
| Met | Lys | Asp | Phe | Val | Lys | Ala | Leu | Met | Gly | Glu | Phe | Ala | Ser | Thr | Ser | |
| | | | | 165 | | | | | 170 | | | | | 175 | | |

| ACC | TTG | TTC | TCC | CTG | ATG | CAA | TAC | TCG | AAC | ATC | CTG | AAG | ACC | CAT | TTT | 576 |
| Thr | Leu | Phe | Ser | Leu | Met | Gln | Tyr | Ser | Asn | Ile | Leu | Lys | Thr | His | Phe | |
| | | | 180 | | | | | 185 | | | | | 190 | | | |

| ACC | TTC | ACT | GAA | TTC | AAG | AAC | ATC | CTG | GAC | CCT | CAG | AGC | CTG | GTG | GAT | 624 |
| Thr | Phe | Thr | Glu | Phe | Lys | Asn | Ile | Leu | Asp | Pro | Gln | Ser | Leu | Val | Asp | |
| | | 195 | | | | | 200 | | | | | 205 | | | | |

| CCC | ATT | GTC | CAG | CTG | CAA | GGC | CTG | ACC | TAC | ACA | GCC | ACA | GGC | ATC | CGG | 672 |
| Pro | Ile | Val | Gln | Leu | Gln | Gly | Leu | Thr | Tyr | Thr | Ala | Thr | Gly | Ile | Arg | |
| | 210 | | | | | 215 | | | | | 220 | | | | | |

| ACA | GTG | ATG | GAA | GAG | CTA | TTT | CAT | AGC | AAG | AAT | GGG | TCC | CGT | AAA | AGT | 720 |
| Thr | Val | Met | Glu | Glu | Leu | Phe | His | Ser | Lys | Asn | Gly | Ser | Arg | Lys | Ser | |
| 225 | | | | | 230 | | | | | 235 | | | | | 240 | |

| GCC | AAG | AAG | ATC | CTC | CTT | GTC | ATC | ACA | GAT | GGG | CAG | AAA | TAC | AGA | GAC | 768 |
| Ala | Lys | Lys | Ile | Leu | Leu | Val | Ile | Thr | Asp | Gly | Gln | Lys | Tyr | Arg | Asp | |
| | | | | 245 | | | | | 250 | | | | | 255 | | |

| CCC | CTG | GAG | TAT | AGT | GAT | GTC | ATT | CCC | GCC | GCA | GAC | AAA | GCT | GGC | ATC | 816 |

| | | | | | | | | | | | | | | | | |
|---|---|---|---|---|---|---|---|---|---|---|---|---|---|---|---|---|
| Pro | Leu | Glu | Tyr 260 | Ser | Asp | Val | Ile | Pro 265 | Ala | Ala | Asp | Lys | Ala 270 | Gly | Ile | |
| ATT | CGT | TAT | GCT | ATT | GGG | GTG | GGA | GAT | GCC | TTC | CAG | GAG | CCC | ACT | GCC | 864 |
| Ile | Arg | Tyr 275 | Ala | Ile | Gly | Val | Gly 280 | Asp | Ala | Phe | Gln | Glu 285 | Pro | Thr | Ala | |
| CTG | AAG | GAG | CTG | AAC | ACC | ATT | GGC | TCA | GCT | CCC | CCA | CAG | GAC | CAC | GTG | 912 |
| Leu | Lys | Glu | Leu 290 | Asn | Thr | Ile | Gly | Ser 295 | Ala | Pro | Pro | Gln 300 | Asp | His | Val | |
| TTC | AAG | GTA | GGC | AAC | TTT | GCA | GCA | CTT | CGC | AGC | ATC | CAG | AGG | CAA | CTT | 960 |
| Phe 305 | Lys | Val | Gly | Asn | Phe 310 | Ala | Ala | Leu | Arg | Ser 315 | Ile | Gln | Arg | Gln | Leu 320 | |
| CAG | GAG | AAA | ATC | TTC | GCC | ATT | GAG | GGA | ACT | CAA | TCA | AGG | TCA | AGT | AGT | 1008 |
| Gln | Glu | Lys | Ile | Phe 325 | Ala | Ile | Glu | Gly | Thr 330 | Gln | Ser | Arg | Ser | Ser 335 | Ser | |
| TCC | TTT | CAG | CAC | GAG | ATG | TCA | CAA | GAA | GGT | TTC | AGT | TCA | GCT | CTC | ACA | 1056 |
| Ser | Phe | Gln | His 340 | Glu | Met | Ser | Gln | Glu 345 | Gly | Phe | Ser | Ser 350 | Ala | Leu | Thr | |
| TCG | GAT | GGA | CCC | GTT | CTG | GGG | GCC | GYG | GGA | AGC | TTC | AGC | TGG | TCC | GGA | 1104 |
| Ser | Asp | Gly 355 | Pro | Val | Leu | Gly | Ala 360 | Xaa | Gly | Ser | Phe | Ser 365 | Trp | Ser | Gly | |
| GGT | GCC | TTC | TTA | TAT | CCC | CCA | AAT | ACG | AGA | CCC | ACC | TTT | ATC | AAC | ATG | 1152 |
| Gly | Ala | Phe 370 | Leu | Tyr | Pro | Pro 375 | Asn | Thr | Arg | Pro | Thr 380 | Phe | Ile | Asn | Met | |
| TCT | CAG | GAG | AAT | GTG | GAC | ATG | AGA | GAC | TCC | TAC | CTG | GGT | TAC | TCC | ACC | 1200 |
| Ser 385 | Gln | Glu | Asn | Val | Asp 390 | Met | Arg | Asp | Ser | Tyr 395 | Leu | Gly | Tyr | Ser | Thr 400 | |
| GCA | GTG | GCC | TTT | TGG | AAG | GGG | GTT | CAC | AGC | CTG | ATC | CTG | GGG | GCC | CCG | 1248 |
| Ala | Val | Ala | Phe | Trp 405 | Lys | Gly | Val | His | Ser 410 | Leu | Ile | Leu | Gly | Ala 415 | Pro | |
| CGT | CAC | CAG | CAC | ACG | GGG | AAG | GTT | GTC | ATC | TTT | ACC | CAG | GAA | GCC | AGG | 1296 |
| Arg | His | Gln | His 420 | Thr | Gly | Lys | Val | Val 425 | Ile | Phe | Thr | Gln 430 | Glu | Ala | Arg | |
| CAT | TGG | AGG | CCC | AAG | TCT | GAA | GTC | AGA | GGG | ACA | CAG | ATC | GGC | TCC | TAC | 1344 |
| His | Trp | Arg 435 | Pro | Lys | Ser | Glu | Val 440 | Arg | Gly | Thr | Gln | Ile 445 | Gly | Ser | Tyr | |
| TTC | GGG | GCC | TCT | CTC | TGT | TCT | GTG | GAC | GTG | GAT | AGA | GAT | GGC | AGC | ACY | 1392 |
| Phe | Gly | Ala 450 | Ser | Leu | Cys | Ser 455 | Val | Asp | Val | Asp | Arg 460 | Asp | Gly | Ser | Xaa | |
| GAC | CTG | GTC | CTG | ATC | GGA | GCC | CCC | CAT | TAC | TAT | GAG | CAG | ACC | CGA | GGG | 1440 |
| Asp 465 | Leu | Val | Leu | Ile | Gly 470 | Ala | Pro | His | Tyr | Tyr 475 | Glu | Gln | Thr | Arg | Gly 480 | |
| GGG | CAG | GTC | TCA | GTG | TKC | CCC | GTG | CCC | GGT | GTG | AGG | GGC | AGG | TGG | CAG | 1488 |
| Gly | Gln | Val | Ser | Val 485 | Xaa | Pro | Val | Pro | Gly 490 | Val | Arg | Gly | Arg | Trp 495 | Gln | |
| TGT | GAG | GCC | ACC | CTC | CAC | GGG | GAG | CAG | GRC | CAT | CCT | TGG | GGC | CGC | TTT | 1536 |
| Cys | Glu | Ala | Thr 500 | Leu | His | Gly | Glu | Gln 505 | Xaa | His | Pro | Trp | Gly 510 | Arg | Phe | |
| GGG | GTG | GCT | CTG | ACA | GTG | CTG | GGG | GAC | GTA | AAC | GGG | GAC | AAT | CTG | GCA | 1584 |
| Gly | Val | Ala 515 | Leu | Thr | Val | Leu 520 | Gly | Asp | Val | Asn | Gly 525 | Asp | Asn | Leu | Ala | |
| GAC | GTG | GCT | ATT | GGT | GCC | CCT | GGA | GAG | GAG | GAG | AGC | AGA | GGT | GCT | GTC | 1632 |
| Asp | Val 530 | Ala | Ile | Gly | Ala | Pro 535 | Gly | Glu | Glu | Glu | Ser 540 | Arg | Gly | Ala | Val | |
| TAC | ATA | TTT | CAT | GGA | GCC | TCG | AGA | CTG | GAG | ATC | ATG | CCC | TCA | CCC | AGC | 1680 |
| Tyr 545 | Ile | Phe | His | Gly | Ala 550 | Ser | Arg | Leu | Glu | Ile 555 | Met | Pro | Ser | Pro | Ser 560 | |
| CAG | CGG | GTC | ACT | GGC | TCC | CAG | CTC | TCC | CTG | AGA | CTG | CAG | TAT | TTT | GGG | 1728 |
| Gln | Arg | Val | Thr | Gly 565 | Ser | Gln | Leu | Ser | Leu 570 | Arg | Leu | Gln | Tyr | Phe 575 | Gly | |
| CAG | TCA | TTG | AGT | GGG | GGT | CAG | GAC | CTT | ACA | CAG | GAT | GGC | CTG | GTG | GAC | 1776 |

-continued

| | | | | | | | | | | | | | | | |
|---|---|---|---|---|---|---|---|---|---|---|---|---|---|---|---|
| Gln | Ser | Leu | Ser<br>580 | Gly | Gly | Gln | Asp | Leu<br>585 | Thr | Gln | Asp | Gly | Leu<br>590 | Val | Asp |

| CTG | GCC | GTG | GGA | GCC | CAG | GGG | CAC | GTA | CTG | CTG | CTC | AGG | AGT | CTG | CCT | 1824 |
| Leu | Ala | Val<br>595 | Gly | Ala | Gln | Gly | His<br>600 | Val | Leu | Leu | Leu | Arg<br>605 | Ser | Leu | Pro | |

| CTG | CTG | AAA | GTG | GAG | CTC | TCC | ATA | AGA | TTC | GCC | CCC | ATG | GAG | GTG | GCA | 1872 |
| Leu | Leu<br>610 | Lys | Val | Glu | Leu | Ser<br>615 | Ile | Arg | Phe | Ala | Pro<br>620 | Met | Glu | Val | Ala | |

| AAG | GCT | GTG | TAC | CAG | TGC | TGG | GAA | AGG | ACT | CCC | ACT | GTC | CTC | GAA | GCT | 1920 |
| Lys<br>625 | Ala | Val | Tyr | Gln<br>630 | Cys | Trp | Glu | Arg | Thr<br>635 | Pro | Thr | Val | Leu | Glu<br>640 | Ala | |

| GGA | GAG | GCC | ACT | GTC | TGT | CTC | ACT | GTC | CAC | AAA | GGC | TCA | CCT | GAC | CTG | 1968 |
| Gly | Glu | Ala | Thr | Val<br>645 | Cys | Leu | Thr | Val | His<br>650 | Lys | Gly | Ser | Pro | Asp<br>655 | Leu | |

| TTA | GGT | AAT | GTC | CAA | GGC | TCT | GTC | AGG | TAT | GAT | CTG | GCG | TTA | GAT | CCG | 2016 |
| Leu | Gly | Asn | Val<br>660 | Gln | Gly | Ser | Val | Arg<br>665 | Tyr | Asp | Leu | Ala | Leu<br>670 | Asp | Pro | |

| GGC | CGC | CTG | ATT | TCT | CGT | GCC | ATT | TTT | GAT | GAG | ACT | AAG | AAC | TGC | ACT | 2064 |
| Gly | Arg | Leu<br>675 | Ile | Ser | Arg | Ala | Ile<br>680 | Phe | Asp | Glu | Thr | Lys<br>685 | Asn | Cys | Thr | |

| TTG | ACG | GGA | AGG | AAG | ACT | CTG | GGG | CTT | GGT | GAT | CAC | TGC | GAA | ACA | GTG | 2112 |
| Leu | Thr | Gly | Arg | Lys | Thr | Leu | Gly | Leu | Gly | Asp | His | Cys | Glu | Thr | Val | |
| | | 690 | | | | 695 | | | | 700 | | | | | | |

| AAG | CTG | CTT | TTG | CCG | GAC | TGT | GTG | GAA | GAT | GCA | GTG | AGC | CCT | ATC | ATC | 2160 |
| Lys<br>705 | Leu | Leu | Leu | Pro<br>710 | Asp | Cys | Val | Glu | Asp<br>715 | Ala | Val | Ser | Pro | Ile<br>720 | Ile | |

| CTG | CGC | CTC | AAC | TTT | TCC | CTG | GTG | AGA | GAC | TCT | GCT | TCA | CCC | AGG | AAC | 2208 |
| Leu | Arg | Leu | Asn | Phe<br>725 | Ser | Leu | Val | Arg | Asp<br>730 | Ser | Ala | Ser | Pro | Arg<br>735 | Asn | |

| CTG | CAT | CCT | GTG | CTG | GCT | GTG | GGC | TCA | CAA | GAC | CAC | ATA | ACT | GCT | TCT | 2256 |
| Leu | His | Pro | Val<br>740 | Leu | Ala | Val | Gly | Ser<br>745 | Gln | Asp | His | Ile | Thr<br>750 | Ala | Ser | |

| CTG | CCG | TTT | GAG | AAG | AAC | TGT | AAG | CAA | GAA | CTC | CTG | TGT | GAG | GGG | GAC | 2304 |
| Leu | Pro | Phe<br>755 | Glu | Lys | Asn | Cys | Lys<br>760 | Gln | Glu | Leu | Leu | Cys<br>765 | Glu | Gly | Asp | |

| CTG | GGC | ATC | AGC | TTT | AAC | TTC | TCA | GGC | CTG | CAG | GTC | TTG | GTG | GTG | GGA | 2352 |
| Leu | Gly | Ile | Ser | Phe<br>770 | Asn | Phe | Ser | Gly | Leu<br>775 | Gln | Val | Leu | Val | Val<br>780 | Gly | |

| GGC | TCC | CCA | GAG | CTC | ACT | GTG | ACA | GTC | ACT | GTG | TGG | AAT | GAG | GGT | GAG | 2400 |
| Gly<br>785 | Ser | Pro | Glu | Leu | Thr<br>790 | Val | Thr | Val | Thr<br>795 | Val | Trp | Asn | Glu | Gly<br>800 | Glu | |

| GAC | AGC | TAT | GGA | ACT | TTA | GTC | AAG | TTC | TAC | TAC | CCA | GCA | GGG | CTA | TCT | 2448 |
| Asp | Ser | Tyr | Gly | Thr<br>805 | Leu | Val | Lys | Phe | Tyr<br>810 | Tyr | Pro | Ala | Gly | Leu<br>815 | Ser | |

| TAC | CGA | CGG | GTA | ACA | GGG | ACT | CAG | CAA | CCT | CAT | CAG | TAC | CCA | CTA | CGC | 2496 |
| Tyr | Arg | Arg | Val<br>820 | Thr | Gly | Thr | Gln | Gln<br>825 | Pro | His | Gln | Tyr | Pro<br>830 | Leu | Arg | |

| TTG | GCC | TGT | GAG | GCT | GAG | CCC | GCT | GCC | CAG | GAG | GAC | CTG | AGG | AGC | AGC | 2544 |
| Leu | Ala | Cys<br>835 | Glu | Ala | Glu | Pro | Ala<br>840 | Ala | Gln | Glu | Asp | Leu<br>845 | Arg | Ser | Ser | |

| AGC | TGT | AGC | ATT | AAT | CAC | CCC | ATC | TTC | CGA | GAA | GGT | GCA | AAG | ACC | ACC | 2592 |
| Ser | Cys<br>850 | Ser | Ile | Asn | His | Pro<br>855 | Ile | Phe | Arg | Glu | Gly<br>860 | Ala | Lys | Thr | Thr | |

| TTC | ATG | ATC | ACA | TTC | GAT | GTC | TCC | TAC | AAG | GCC | TTC | CTA | GGA | GAC | AGG | 2640 |
| Phe<br>865 | Met | Ile | Thr | Phe<br>870 | Asp | Val | Ser | Tyr | Lys<br>875 | Ala | Phe | Leu | Gly | Asp<br>880 | Arg | |

| TTG | CTT | CTG | AGG | GCC | AAA | GCC | AGC | AGT | GAG | AAT | AAT | AAG | CCT | GAT | ACC | 2688 |
| Leu | Leu | Leu | Arg | Ala<br>885 | Lys | Ala | Ser | Ser | Glu<br>890 | Asn | Asn | Lys | Pro<br>895 | Asp | Thr | |

| AAC | AAG | ACT | GCC | TTC | CAG | CTG | GAG | CTC | CCA | GTG | AAG | TAC | ACC | GTC | TAT | 2736 |

```
Asn Lys Thr Ala Phe Gln Leu Glu Leu Pro Val Lys Tyr Thr Val Tyr
            900                 905                 910

ACC CTG ATC AGT AGG CAA GAA GAT TCC ACC AAC CAT GTC AAC TTT TCA          2784
Thr Leu Ile Ser Arg Gln Glu Asp Ser Thr Asn His Val Asn Phe Ser
            915                 920                 925

TCT TCC CAC GGG GGG AGA AGG CAA GAA GCC GCA CAT CGC TAT CGT GTG          2832
Ser Ser His Gly Gly Arg Arg Gln Glu Ala Ala His Arg Tyr Arg Val
        930                 935                 940

AAT AAC CTG AGT CCA CTG AAG CTG GCC GTC AGA GTT AAC TTC TGG GTC          2880
Asn Asn Leu Ser Pro Leu Lys Leu Ala Val Arg Val Asn Phe Trp Val
945                 950                 955                 960

CCT GTC CTT CTG AAC GGT GTG GCT GTG TGG GAC GTG ACT CTG AGC AGC          2928
Pro Val Leu Leu Asn Gly Val Ala Val Trp Asp Val Thr Leu Ser Ser
                965                 970                 975

CCA GCA CAG GGT GTC TCC TGC GTG TCC CAG ATG AAA CCT CCT CAG AAT          2976
Pro Ala Gln Gly Val Ser Cys Val Ser Gln Met Lys Pro Pro Gln Asn
            980                 985                 990

CCC GAC TTT CTG ACC CAG ATT CAG AGA CGT TCT GTG CTG GAC TGC TCC          3024
Pro Asp Phe Leu Thr Gln Ile Gln Arg Arg Ser Val Leu Asp Cys Ser
            995                 1000                1005

ATT GCT GAC TGC CTG CAC TCC CGC TGT GAC ATC CCC TCC TTG GAC ATC          3072
Ile Ala Asp Cys Leu His Ser Arg Cys Asp Ile Pro Ser Leu Asp Ile
        1010                1015                1020

CAG GAT GAA CTT GAC TTC ATT CTG AGG GGC AAC CTC AGC TTC GGC TGG          3120
Gln Asp Glu Leu Asp Phe Ile Leu Arg Gly Asn Leu Ser Phe Gly Trp
1025                1030                1035                1040

GTC AGT CAG ACA TTG CAG GAA AAG GTG TTG CTT GTG AGT GAG GCT GAA          3168
Val Ser Gln Thr Leu Gln Glu Lys Val Leu Leu Val Ser Glu Ala Glu
                1045                1050                1055

ATC ACT TTC GAC ACA TCT GTG TAC TCC CAG CTG CCA GGA CAG GAG GCA          3216
Ile Thr Phe Asp Thr Ser Val Tyr Ser Gln Leu Pro Gly Gln Glu Ala
            1060                1065                1070

TTT CTG AGA GCC CAG GTG GAG ACA ACG TTA GAA GAA TAC GTG GTC TAT          3264
Phe Leu Arg Ala Gln Val Glu Thr Thr Leu Glu Glu Tyr Val Val Tyr
            1075                1080                1085

GAG CCC ATC TTC CTC GTG GCG GGC AGC TCG GTG GGA GGT CTG CTG TTA          3312
Glu Pro Ile Phe Leu Val Ala Gly Ser Ser Val Gly Gly Leu Leu Leu
        1090                1095                1100

CTG GCT CTC ATC ACA GTG GTA CTG TAC AAG CTT GGC TYC TYC AAA CGT          3360
Leu Ala Leu Ile Thr Val Val Leu Tyr Lys Leu Gly Xaa Xaa Lys Arg
1105                1110                1115                1120

CAG TAC AAA GAA ATG CTG GAC GGC AAG GCT GCA GAT CCT GTC ACA GCC          3408
Gln Tyr Lys Glu Met Leu Asp Gly Lys Ala Ala Asp Pro Val Thr Ala
                1125                1130                1135

GGC CAG GCA GAT TTC GGC TGT GAG ACT CCT CCA TAT CTC GTG                  
Gly Gln Ala Asp Phe Gly Cys Glu Thr Pro Pro Tyr Leu Val
            1140                1145                1150

AGC TAGGAATCCA           3463
                                                Ser

CTCTCCTGCC TATCTCTGNA ATGAAGATTG GTCCTGCCTA TGAGTCTACT GGCATGGGAA        3523

CGAGT                                                                    3528
```

( 2 ) INFORMATION FOR SEQ ID NO:37:

( i ) SEQUENCE CHARACTERISTICS:
        ( A ) LENGTH: 1151 amino acids
        ( B ) TYPE: amino acid
        ( D ) TOPOLOGY: linear ( i i ) MOLECULE TYPE: protein ( x i ) SEQUENCE DESCRIPTION: SEQ ID NO:37:

| Gly | Trp | Ala | Leu | Ala | Ser | Cys | His | Gly | Ser | Asn | Leu | Asp | Val | Glu | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Pro | Ile | Val | Phe | Arg | Glu | Asp | Ala | Ala | Ser | Phe | Gly | Gln | Thr | Val | Val |
|     |     |     | 20  |     |     |     |     | 25  |     |     |     | 30  |     |     |     |
| Gln | Phe | Gly | Gly | Ser | Arg | Leu | Val | Val | Gly | Ala | Pro | Leu | Glu | Ala | Val |
|     |     | 35  |     |     |     |     | 40  |     |     |     |     | 45  |     |     |     |
| Ala | Val | Asn | Gln | Thr | Gly | Arg | Leu | Tyr | Asp | Cys | Ala | Pro | Ala | Thr | Gly |
|     | 50  |     |     |     |     | 55  |     |     |     |     | 60  |     |     |     |     |
| Met | Cys | Gln | Pro | Ile | Val | Leu | Arg | Ser | Pro | Leu | Glu | Ala | Val | Asn | Met |
| 65  |     |     |     |     | 70  |     |     |     |     | 75  |     |     |     |     | 80  |
| Ser | Leu | Gly | Leu | Ser | Leu | Val | Thr | Ala | Thr | Asn | Asn | Ala | Gln | Leu | Leu |
|     |     |     |     | 85  |     |     |     |     | 90  |     |     |     |     | 95  |     |
| Ala | Cys | Gly | Pro | Thr | Ala | Gln | Arg | Ala | Cys | Val | Lys | Asn | Met | Tyr | Ala |
|     |     |     | 100 |     |     |     |     | 105 |     |     |     |     | 110 |     |     |
| Lys | Gly | Ser | Cys | Leu | Leu | Leu | Gly | Ser | Ser | Leu | Gln | Phe | Ile | Gln | Ala |
|     |     | 115 |     |     |     |     | 120 |     |     |     |     | 125 |     |     |     |
| Val | Pro | Ala | Ser | Met | Pro | Glu | Cys | Pro | Arg | Gln | Glu | Met | Asp | Ile | Ala |
|     | 130 |     |     |     |     | 135 |     |     |     |     | 140 |     |     |     |     |
| Phe | Leu | Ile | Asp | Gly | Ser | Gly | Ser | Ile | Asn | Gln | Arg | Asp | Phe | Ala | Gln |
| 145 |     |     |     |     | 150 |     |     |     |     | 155 |     |     |     |     | 160 |
| Met | Lys | Asp | Phe | Val | Lys | Ala | Leu | Met | Gly | Glu | Phe | Ala | Ser | Thr | Ser |
|     |     |     |     | 165 |     |     |     |     | 170 |     |     |     |     | 175 |     |
| Thr | Leu | Phe | Ser | Leu | Met | Gln | Tyr | Ser | Asn | Ile | Leu | Lys | Thr | His | Phe |
|     |     |     | 180 |     |     |     |     | 185 |     |     |     |     | 190 |     |     |
| Thr | Phe | Thr | Glu | Phe | Lys | Asn | Ile | Leu | Asp | Pro | Gln | Ser | Leu | Val | Asp |
|     |     | 195 |     |     |     |     | 200 |     |     |     |     | 205 |     |     |     |
| Pro | Ile | Val | Gln | Leu | Gln | Gly | Leu | Thr | Tyr | Thr | Ala | Thr | Gly | Ile | Arg |
|     | 210 |     |     |     |     | 215 |     |     |     |     | 220 |     |     |     |     |
| Thr | Val | Met | Glu | Glu | Leu | Phe | His | Ser | Lys | Asn | Gly | Ser | Arg | Lys | Ser |
| 225 |     |     |     |     | 230 |     |     |     |     | 235 |     |     |     |     | 240 |
| Ala | Lys | Lys | Ile | Leu | Leu | Val | Ile | Thr | Asp | Gly | Gln | Lys | Tyr | Arg | Asp |
|     |     |     |     | 245 |     |     |     |     | 250 |     |     |     |     | 255 |     |
| Pro | Leu | Glu | Tyr | Ser | Asp | Val | Ile | Pro | Ala | Ala | Asp | Lys | Ala | Gly | Ile |
|     |     |     | 260 |     |     |     |     | 265 |     |     |     |     | 270 |     |     |
| Ile | Arg | Tyr | Ala | Ile | Gly | Val | Gly | Asp | Ala | Phe | Gln | Glu | Pro | Thr | Ala |
|     |     | 275 |     |     |     |     | 280 |     |     |     |     | 285 |     |     |     |
| Leu | Lys | Glu | Leu | Asn | Thr | Ile | Gly | Ser | Ala | Pro | Pro | Gln | Asp | His | Val |
|     | 290 |     |     |     |     | 295 |     |     |     |     | 300 |     |     |     |     |
| Phe | Lys | Val | Gly | Asn | Phe | Ala | Ala | Leu | Arg | Ser | Ile | Gln | Arg | Gln | Leu |
| 305 |     |     |     |     | 310 |     |     |     |     | 315 |     |     |     |     | 320 |
| Gln | Glu | Lys | Ile | Phe | Ala | Ile | Glu | Gly | Thr | Gln | Ser | Arg | Ser | Ser | Ser |
|     |     |     |     | 325 |     |     |     |     | 330 |     |     |     |     | 335 |     |
| Ser | Phe | Gln | His | Glu | Met | Ser | Gln | Glu | Gly | Phe | Ser | Ser | Ala | Leu | Thr |
|     |     |     | 340 |     |     |     |     | 345 |     |     |     |     | 350 |     |     |
| Ser | Asp | Gly | Pro | Val | Leu | Gly | Ala | Xaa | Gly | Ser | Phe | Ser | Trp | Ser | Gly |
|     |     | 355 |     |     |     |     | 360 |     |     |     |     | 365 |     |     |     |
| Gly | Ala | Phe | Leu | Tyr | Pro | Pro | Asn | Thr | Arg | Pro | Thr | Phe | Ile | Asn | Met |
|     | 370 |     |     |     |     | 375 |     |     |     |     | 380 |     |     |     |     |
| Ser | Gln | Glu | Asn | Val | Asp | Met | Arg | Asp | Ser | Tyr | Leu | Gly | Tyr | Ser | Thr |
| 385 |     |     |     |     | 390 |     |     |     |     | 395 |     |     |     |     | 400 |
| Ala | Val | Ala | Phe | Trp | Lys | Gly | Val | His | Ser | Leu | Ile | Leu | Gly | Ala | Pro |
|     |     |     |     | 405 |     |     |     |     | 410 |     |     |     |     | 415 |     |

-continued

| | | | | | | | | | | | | | |
|---|---|---|---|---|---|---|---|---|---|---|---|---|---|
|Arg|His|Gln|His<br>420|Thr|Gly|Lys|Val|Val<br>425|Ile|Phe|Thr|Gln|Glu<br>430|Ala|Arg|
|His|Trp|Arg|Pro<br>435|Lys|Ser|Glu|Val|Arg<br>440|Gly|Thr|Gln|Ile|Gly<br>445|Ser|Tyr|
|Phe|Gly|Ala|Ser<br>450|Leu|Cys|Ser|Val|Asp<br>455|Val|Asp|Arg|Asp<br>460|Gly|Ser|Xaa|
|Asp<br>465|Leu|Val|Leu|Ile|Gly<br>470|Ala|Pro|His|Tyr|Tyr<br>475|Gln|Thr|Arg|Gly<br>480|
|Gly|Gln|Val|Ser|Val<br>485|Xaa|Pro|Val|Pro|Gly<br>490|Val|Arg|Gly|Arg|Trp<br>495|Gln|
|Cys|Glu|Ala|Thr<br>500|Leu|His|Gly|Glu|Gln<br>505|Xaa|His|Pro|Trp|Gly<br>510|Arg|Phe|
|Gly|Val|Ala<br>515|Leu|Thr|Val|Leu|Gly<br>520|Asp|Val|Asn|Gly|Asp<br>525|Asn|Leu|Ala|
|Asp|Val<br>530|Ala|Ile|Gly|Ala|Pro<br>535|Gly|Glu|Glu|Glu|Ser<br>540|Arg|Gly|Ala|Val|
|Tyr<br>545|Ile|Phe|His|Gly|Ala<br>550|Ser|Arg|Leu|Glu|Ile<br>555|Met|Pro|Ser|Pro<br>560|Ser|
|Gln|Arg|Val|Thr|Gly<br>565|Ser|Gln|Leu|Ser|Leu<br>570|Arg|Leu|Gln|Tyr|Phe<br>575|Gly|
|Gln|Ser|Leu|Ser<br>580|Gly|Gly|Gln|Asp|Leu<br>585|Thr|Gln|Asp|Gly|Leu<br>590|Val|Asp|
|Leu|Ala|Val|Gly<br>595|Ala|Gln|Gly|His|Val<br>600|Leu|Leu|Leu|Arg<br>605|Ser|Leu|Pro|
|Leu|Leu|Lys<br>610|Val|Glu|Leu|Ser|Ile<br>615|Arg|Phe|Ala|Pro|Met<br>620|Glu|Val|Ala|
|Lys<br>625|Ala|Val|Tyr|Gln|Cys<br>630|Trp|Glu|Arg|Thr|Pro<br>635|Thr|Val|Leu|Glu|Ala<br>640|
|Gly|Glu|Ala|Thr|Val<br>645|Cys|Leu|Thr|Val|His<br>650|Lys|Gly|Ser|Pro|Asp<br>655|Leu|
|Leu|Gly|Asn|Val<br>660|Gln|Gly|Ser|Val|Arg<br>665|Tyr|Asp|Leu|Ala|Leu<br>670|Asp|Pro|
|Gly|Arg|Leu|Ile<br>675|Ser|Arg|Ala|Ile|Phe<br>680|Asp|Glu|Thr|Lys|Asn<br>685|Cys|Thr|
|Leu|Thr|Gly<br>690|Arg|Lys|Thr|Leu|Gly<br>695|Leu|Gly|Asp|His|Cys<br>700|Glu|Thr|Val|
|Lys<br>705|Leu|Leu|Leu|Pro|Asp<br>710|Cys|Val|Glu|Asp|Ala<br>715|Val|Ser|Pro|Ile|Ile<br>720|
|Leu|Arg|Leu|Asn|Phe<br>725|Ser|Leu|Val|Arg|Asp<br>730|Ser|Ala|Ser|Pro|Arg<br>735|Asn|
|Leu|His|Pro|Val<br>740|Leu|Ala|Val|Gly|Ser<br>745|Gln|Asp|His|Ile|Thr<br>750|Ala|Ser|
|Leu|Pro|Phe<br>755|Glu|Lys|Asn|Cys|Lys<br>760|Gln|Glu|Leu|Leu|Cys<br>765|Glu|Gly|Asp|
|Leu|Gly|Ile<br>770|Ser|Phe|Asn|Phe|Ser<br>775|Gly|Leu|Gln|Val|Leu<br>780|Val|Val|Gly|
|Gly<br>785|Ser|Pro|Glu|Leu|Thr<br>790|Val|Thr|Val|Thr|Val<br>795|Trp|Asn|Glu|Gly<br>800|Glu|
|Asp|Ser|Tyr|Gly|Thr<br>805|Leu|Val|Lys|Phe|Tyr<br>810|Tyr|Pro|Ala|Gly|Leu<br>815|Ser|
|Tyr|Arg|Arg|Val<br>820|Thr|Gly|Thr|Gln|Gln<br>825|Pro|His|Gln|Tyr|Pro<br>830|Leu|Arg|
|Leu|Ala|Cys<br>835|Glu|Ala|Glu|Pro|Ala<br>840|Ala|Gln|Glu|Asp|Leu<br>845|Arg|Ser|Ser|

| | | | | | | | | | | | | | | |
|---|---|---|---|---|---|---|---|---|---|---|---|---|---|---|
|Ser|Cys<br>850|Ser|Ile|Asn|His|Pro<br>855|Ile|Phe|Arg|Glu|Gly<br>860|Ala|Lys|Thr|Thr|
|Phe<br>865|Met|Ile|Thr|Phe|Asp<br>870|Val|Ser|Tyr|Lys|Ala<br>875|Phe|Leu|Gly|Asp|Arg<br>880|
|Leu|Leu|Leu|Arg|Ala<br>885|Lys|Ala|Ser|Ser|Glu<br>890|Asn|Asn|Lys|Pro|Asp<br>895|Thr|
|Asn|Lys|Thr|Ala<br>900|Phe|Gln|Leu|Glu|Leu<br>905|Pro|Val|Lys|Tyr|Thr<br>910|Val|Tyr|
|Thr|Leu|Ile<br>915|Ser|Arg|Gln|Glu|Asp<br>920|Ser|Thr|Asn|His|Val<br>925|Asn|Phe|Ser|
|Ser|Ser<br>930|His|Gly|Gly|Arg|Arg<br>935|Gln|Glu|Ala|Ala|His<br>940|Arg|Tyr|Arg|Val|
|Asn<br>945|Asn|Leu|Ser|Pro|Leu<br>950|Lys|Leu|Ala|Val|Arg<br>955|Val|Asn|Phe|Trp|Val<br>960|
|Pro|Val|Leu|Leu|Asn<br>965|Gly|Val|Ala|Val|Trp<br>970|Asp|Val|Thr|Leu|Ser<br>975|Ser|
|Pro|Ala|Gln|Gly<br>980|Val|Ser|Cys|Val|Ser<br>985|Gln|Met|Lys|Pro|Pro<br>990|Gln|Asn|
|Pro|Asp|Phe<br>995|Leu|Thr|Gln|Ile|Gln<br>1000|Arg|Arg|Ser|Val|Leu<br>1005|Asp|Cys|Ser|
|Ile|Ala|Asp<br>1010|Cys|Leu|His|Ser|Arg<br>1015|Cys|Asp|Ile|Pro|Ser<br>1020|Leu|Asp|Ile|
|Gln|Asp<br>1025|Glu|Leu|Asp|Phe<br>1030|Ile|Leu|Arg|Gly|Asn<br>1035|Leu|Ser|Phe|Gly|Trp<br>1040|
|Val|Ser|Gln|Thr|Leu<br>1045|Gln|Glu|Lys|Val|Leu<br>1050|Leu|Val|Ser|Glu|Ala<br>1055|Glu|
|Ile|Thr|Phe|Asp|Thr<br>1060|Ser|Val|Tyr|Ser|Gln<br>1065|Leu|Pro|Gly|Gln|Glu<br>1070|Ala|
|Phe|Leu|Arg|Ala<br>1075|Gln|Val|Glu|Thr|Thr<br>1080|Leu|Glu|Glu|Tyr|Val<br>1085|Val|Tyr|
|Glu|Pro<br>1090|Ile|Phe|Leu|Val|Ala<br>1095|Gly|Ser|Ser|Val|Gly<br>1100|Gly|Leu|Leu|Leu|
|Leu|Ala<br>1105|Leu|Ile|Thr|Val<br>1110|Val|Leu|Tyr|Lys|Leu<br>1115|Gly|Xaa|Xaa|Lys|Arg<br>1120|
|Gln|Tyr|Lys|Glu|Met<br>1125|Leu|Asp|Gly|Lys|Ala<br>1130|Ala|Asp|Pro|Val|Thr<br>1135|Ala|
|Gly|Gln|Ala|Asp<br>1140|Phe|Gly|Cys|Glu|Thr<br>1145|Pro|Pro|Tyr|Leu|Val<br>1150|Ser|

( 2 ) INFORMATION FOR SEQ ID NO:38:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:38:

GTCCAAGCTG TCATGGGCCA G  21

( 2 ) INFORMATION FOR SEQ ID NO:39:

( i ) SEQUENCE CHARACTERISTICS:
    ( A ) LENGTH: 23 base pairs
    ( B ) TYPE: nucleic acid
    ( C ) STRANDEDNESS: single ( D ) TOPOLOGY: linear ( i i ) MOLECULE TYPE: DNA ( x i ) SEQUENCE DESCRIPTION: SEQ ID NO:39:

GTCCAGCAGA CTGAAGAGCA CGG 23

( 2 ) INFORMATION FOR SEQ ID NO:40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

TGTAAAACGA CGGCCAGT 18

( 2 ) INFORMATION FOR SEQ ID NO:41:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

GGAAACAGCT ATGACCATG 19

( 2 ) INFORMATION FOR SEQ ID NO:42:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

GGACATGTTC ACTGCCTCTA GG 22

( 2 ) INFORMATION FOR SEQ ID NO:43:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GGCGGACAGT CAGACGACTG TCCTG 25

( 2 ) INFORMATION FOR SEQ ID NO:44:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

5,766,850

99                                                                                          100

-continued

CTGGTTCGGC CCACCTCTGA AGGTTCCAGA ATCGATAG                                                                    38

( 2 ) INFORMATION FOR SEQ ID NO:45:

( i ) SEQUENCE CHARACTERISTICS:
        ( A ) LENGTH: 3519 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 52..3519

( x i ) SEQUENCE DESCRIPTION: SEQ ID NO:45:

```
GCTTTCTGAA GGTTCCAGAA TCGATAGTGA ATTCGTGGGC ACTGCTCAGA T ATG GTC          57
                                                         Met Val
                                                           1

CGT GGA GTT GTG ATC CTC CTG TGT GGC TGG GCC CTG GCT TCC TGT CAT         105
Arg Gly Val Val Ile Leu Leu Cys Gly Trp Ala Leu Ala Ser Cys His
          5                  10                  15

GGG TCT AAC CTG GAT GTG GAG AAG CCC GTC GTG TTC AAA GAG GAT GCA         153
Gly Ser Asn Leu Asp Val Glu Lys Pro Val Val Phe Lys Glu Asp Ala
     20                  25                  30

GCC AGC TTC GGA CAG ACT GTG GTG CAG TTT GGT GGA TCT CGA CTC GTG         201
Ala Ser Phe Gly Gln Thr Val Val Gln Phe Gly Gly Ser Arg Leu Val
 35                  40                  45                  50

GTG GGA GCC CCT CTG GAG GCG GTG GCA GTC AAC CAA ACA GGA CAG TCG         249
Val Gly Ala Pro Leu Glu Ala Val Ala Val Asn Gln Thr Gly Gln Ser
                 55                  60                  65

TCT GAC TGT CCG CCT GCC ACT GGC GTG TGC CAG CCC ATC TTA CTG CAC         297
Ser Asp Cys Pro Pro Ala Thr Gly Val Cys Gln Pro Ile Leu Leu His
             70                  75                  80

ATT CCC CTA GAG GCA GTG AAC ATG TCC CTG GGC CTG TCT CTG GTG GCT         345
Ile Pro Leu Glu Ala Val Asn Met Ser Leu Gly Leu Ser Leu Val Ala
         85                  90                  95

GAC ACC AAT AAC TCC CAG TTG CTG GCT TGT GGT CCA ACT GCA CAG AGA         393
Asp Thr Asn Asn Ser Gln Leu Leu Ala Cys Gly Pro Thr Ala Gln Arg
    100                 105                 110

GCT TGT GCA AAG AAC ATG TAT GCA AAA GGT TCC TGC CTC CTT CTG GGC         441
Ala Cys Ala Lys Asn Met Tyr Ala Lys Gly Ser Cys Leu Leu Leu Gly
115                 120                 125                 130

TCC AGC TTG CAG TTC ATC CAG GCA ATC CCT GCT ACC ATG CCA GAG TGT         489
Ser Ser Leu Gln Phe Ile Gln Ala Ile Pro Ala Thr Met Pro Glu Cys
                135                 140                 145

CCA GGA CAA GAG ATG GAC ATT GCT TTC CTG ATT GAT GGC TCC GGC AGC         537
Pro Gly Gln Glu Met Asp Ile Ala Phe Leu Ile Asp Gly Ser Gly Ser
            150                 155                 160

ATT GAT CAA AGT GAC TTT ACC CAG ATG AAG GAC TTC GTC AAA GCT TTG         585
Ile Asp Gln Ser Asp Phe Thr Gln Met Lys Asp Phe Val Lys Ala Leu
        165                 170                 175

ATG GGC CAG TTG GCG AGC ACC AGC ACC TCG TTC TCC CTG ATG CAA TAC         633
Met Gly Gln Leu Ala Ser Thr Ser Thr Ser Phe Ser Leu Met Gln Tyr
    180                 185                 190

TCA AAC ATC CTG AAG ACT CAT TTT ACC TTC ACG GAA TTC AAG AGC AGC         681
Ser Asn Ile Leu Lys Thr His Phe Thr Phe Thr Glu Phe Lys Ser Ser
195                 200                 205                 210

CTG AGC CCT CAG AGC CTG GTG GAT GCC ATC GTC CAG CTC CAA GGC CTG         729
Leu Ser Pro Gln Ser Leu Val Asp Ala Ile Val Gln Leu Gln Gly Leu
                215                 220                 225
```

| | | | | | | | | | | | | | | | | |
|---|---|---|---|---|---|---|---|---|---|---|---|---|---|---|---|---|
| ACG | TAC | ACA | GCC | TCG | GGC | ATC | CAG | AAA | GTG | GTG | AAA | GAG | CTA | TTT | CAT | 777 |
| Thr | Tyr | Thr | Ala | Ser | Gly | Ile | Gln | Lys | Val | Val | Lys | Glu | Leu | Phe | His | |
| | | | 230 | | | | | 235 | | | | | 240 | | | |
| AGC | AAG | AAT | GGG | GCC | CGA | AAA | AGT | GCC | AAG | AAG | ATA | CTA | ATT | GTC | ATC | 825 |
| Ser | Lys | Asn | Gly | Ala | Arg | Lys | Ser | Ala | Lys | Lys | Ile | Leu | Ile | Val | Ile | |
| | | | 245 | | | | | 250 | | | | | 255 | | | |
| ACA | GAT | GGG | CAG | AAA | TTC | AGA | GAC | CCC | CTG | GAG | TAT | AGA | CAT | GTC | ATC | 873 |
| Thr | Asp | Gly | Gln | Lys | Phe | Arg | Asp | Pro | Leu | Glu | Tyr | Arg | His | Val | Ile | |
| | 260 | | | | | 265 | | | | | 270 | | | | | |
| CCT | GAA | GCA | GAG | AAA | GCT | GGG | ATC | ATT | CGC | TAT | GCT | ATA | GGG | GTG | GGA | 921 |
| Pro | Glu | Ala | Glu | Lys | Ala | Gly | Ile | Ile | Arg | Tyr | Ala | Ile | Gly | Val | Gly | |
| 275 | | | | | 280 | | | | | 285 | | | | | 290 | |
| GAT | GCC | TTC | CGG | GAA | CCC | ACT | GCC | CTA | CAG | GAG | CTG | AAC | ACC | ATT | GGC | 969 |
| Asp | Ala | Phe | Arg | Glu | Pro | Thr | Ala | Leu | Gln | Glu | Leu | Asn | Thr | Ile | Gly | |
| | | | | 295 | | | | | 300 | | | | | 305 | | |
| TCA | GCT | CCC | TCG | CAG | GAC | CAC | GTG | TTC | AAG | GTG | GGC | AAT | TTT | GTA | GCA | 1017 |
| Ser | Ala | Pro | Ser | Gln | Asp | His | Val | Phe | Lys | Val | Gly | Asn | Phe | Val | Ala | |
| | | | 310 | | | | | 315 | | | | | 320 | | | |
| CTT | CGC | AGC | ATC | CAG | CGG | CAA | ATT | CAG | GAG | AAA | ATC | TTT | GCC | ATT | GAA | 1065 |
| Leu | Arg | Ser | Ile | Gln | Arg | Gln | Ile | Gln | Glu | Lys | Ile | Phe | Ala | Ile | Glu | |
| | | 325 | | | | | 330 | | | | | 335 | | | | |
| GGA | ACC | GAA | TCA | AGG | TCA | AGT | AGT | TCC | TTT | CAG | CAC | GAG | ATG | TCA | CAA | 1113 |
| Gly | Thr | Glu | Ser | Arg | Ser | Ser | Ser | Ser | Phe | Gln | His | Glu | Met | Ser | Gln | |
| | 340 | | | | | 345 | | | | | 350 | | | | | |
| GAA | GGT | TTC | AGC | TCA | GCT | CTC | TCA | ATG | GAT | GGA | CCA | GTT | CTG | GGG | GCT | 1161 |
| Glu | Gly | Phe | Ser | Ser | Ala | Leu | Ser | Met | Asp | Gly | Pro | Val | Leu | Gly | Ala | |
| 355 | | | | | 360 | | | | | 365 | | | | | 370 | |
| GTG | GGA | GGC | TTC | AGC | TGG | TCT | GGA | GGT | GCC | TTC | TTG | TAC | CCC | TCA | AAT | 1209 |
| Val | Gly | Gly | Phe | Ser | Trp | Ser | Gly | Gly | Ala | Phe | Leu | Tyr | Pro | Ser | Asn | |
| | | | | 375 | | | | | 380 | | | | | 385 | | |
| ATG | AGA | TCC | ACC | TTC | ATC | AAC | ATG | TCT | CAG | GAG | AAC | GAG | GAT | ATG | AGG | 1257 |
| Met | Arg | Ser | Thr | Phe | Ile | Asn | Met | Ser | Gln | Glu | Asn | Glu | Asp | Met | Arg | |
| | | | 390 | | | | | 395 | | | | | 400 | | | |
| GAC | GCT | TAC | CTG | GGT | TAC | TCC | ACC | GCA | CTG | GCC | TTT | TGG | AAG | GGG | GTC | 1305 |
| Asp | Ala | Tyr | Leu | Gly | Tyr | Ser | Thr | Ala | Leu | Ala | Phe | Trp | Lys | Gly | Val | |
| | | 405 | | | | | 410 | | | | | 415 | | | | |
| CAC | AGC | CTG | ATC | CTG | GGG | GCC | CCT | CGC | CAC | CAG | CAC | ACG | GGG | AAG | GTT | 1353 |
| His | Ser | Leu | Ile | Leu | Gly | Ala | Pro | Arg | His | Gln | His | Thr | Gly | Lys | Val | |
| | 420 | | | | | 425 | | | | | 430 | | | | | |
| GTC | ATC | TTT | ACC | CAG | GAA | TCC | AGG | CAC | TGG | AGG | CCC | AAG | TCT | GAA | GTC | 1401 |
| Val | Ile | Phe | Thr | Gln | Glu | Ser | Arg | His | Trp | Arg | Pro | Lys | Ser | Glu | Val | |
| 435 | | | | | 440 | | | | | 445 | | | | | 450 | |
| AGA | GGG | ACA | CAG | ATC | GGC | TCC | TAC | TTT | GGG | GCA | TCT | CTC | TGT | TCT | GTG | 1449 |
| Arg | Gly | Thr | Gln | Ile | Gly | Ser | Tyr | Phe | Gly | Ala | Ser | Leu | Cys | Ser | Val | |
| | | | 455 | | | | | 460 | | | | | 465 | | | |
| GAC | ATG | GAT | AGA | GAT | GGC | AGC | ACT | GAC | CTG | GTC | CTG | ATT | GGA | GTC | CCC | 1497 |
| Asp | Met | Asp | Arg | Asp | Gly | Ser | Thr | Asp | Leu | Val | Leu | Ile | Gly | Val | Pro | |
| | | | 470 | | | | | 475 | | | | | 480 | | | |
| CAT | TAC | TAT | GAG | CAC | ACC | CGA | GGG | GGG | CAG | GTG | TCG | GTG | TGC | CCC | ATG | 1545 |
| His | Tyr | Tyr | Glu | His | Thr | Arg | Gly | Gly | Gln | Val | Ser | Val | Cys | Pro | Met | |
| | | 485 | | | | | 490 | | | | | 495 | | | | |
| CCT | GGT | GTG | AGG | AGC | AGG | TGG | CAT | TGT | GGG | ACC | ACC | CTC | CAT | GGG | GAG | 1593 |
| Pro | Gly | Val | Arg | Ser | Arg | Trp | His | Cys | Gly | Thr | Thr | Leu | His | Gly | Glu | |
| | 500 | | | | | 505 | | | | | 510 | | | | | |
| CAG | GGC | CAT | CCT | TGG | GGC | CGC | TTT | GGG | GCG | GCT | CTG | ACA | GTG | CTA | GGG | 1641 |
| Gln | Gly | His | Pro | Trp | Gly | Arg | Phe | Gly | Ala | Ala | Leu | Thr | Val | Leu | Gly | |
| 515 | | | | | 520 | | | | | 525 | | | | | 530 | |
| GAC | GTG | AAT | GGG | GAC | AGT | CTG | GCG | GAT | GTG | GCT | ATT | GGT | GCA | CCC | GGA | 1689 |
| Asp | Val | Asn | Gly | Asp | Ser | Leu | Ala | Asp | Val | Ala | Ile | Gly | Ala | Pro | Gly | |
| | | | 535 | | | | | 540 | | | | | 545 | | | |

| | | | | | | | | | | | | | | | | |
|---|---|---|---|---|---|---|---|---|---|---|---|---|---|---|---|---|
| GAG | GAG | GAG | AAC | AGA | GGT | GCT | GTC | TAC | ATA | TTT | CAT | GGA | GCC | TCG | AGA | 1737 |
| Glu | Glu | Glu | Asn | Arg | Gly | Ala | Val | Tyr | Ile | Phe | His | Gly | Ala | Ser | Arg | |
| | | | 550 | | | | 555 | | | | | 560 | | | | |
| CAG | GAC | ATC | GCT | CCC | TCG | CCT | AGC | CAG | CGG | GTC | ACT | GGC | TCC | CAG | CTC | 1785 |
| Gln | Asp | Ile | Ala | Pro | Ser | Pro | Ser | Gln | Arg | Val | Thr | Gly | Ser | Gln | Leu | |
| | | 565 | | | | | 570 | | | | | 575 | | | | |
| TTC | CTG | AGG | CTC | CAA | TAT | TTT | GGG | CAG | TCA | TTA | AGT | GGG | GGT | CAG | GAC | 1833 |
| Phe | Leu | Arg | Leu | Gln | Tyr | Phe | Gly | Gln | Ser | Leu | Ser | Gly | Gly | Gln | Asp | |
| | | | 580 | | | | 585 | | | | | 590 | | | | |
| CTT | ACA | CAG | GAT | GGC | CTG | GTG | GAC | CTG | GCC | GTG | GGA | GCC | CAG | GGG | CAC | 1881 |
| Leu | Thr | Gln | Asp | Gly | Leu | Val | Asp | Leu | Ala | Val | Gly | Ala | Gln | Gly | His | |
| 595 | | | | | 600 | | | | 605 | | | | | | 610 | |
| GTG | CTG | CTG | CTT | AGG | AGT | CTG | CCT | TTG | CTG | AAA | GTG | GGG | ATC | TCC | ATT | 1929 |
| Val | Leu | Leu | Leu | Arg | Ser | Leu | Pro | Leu | Leu | Lys | Val | Gly | Ile | Ser | Ile | |
| | | | | 615 | | | | | 620 | | | | | 625 | | |
| AGA | TTT | GCC | CCC | TCA | GAG | GTG | GCA | AAG | ACT | GTG | TAC | CAG | TGC | TGG | GGA | 1977 |
| Arg | Phe | Ala | Pro | Ser | Glu | Val | Ala | Lys | Thr | Val | Tyr | Gln | Cys | Trp | Gly | |
| | | | 630 | | | | | 635 | | | | | 640 | | | |
| AGG | ACT | CCC | ACT | GTC | CTC | GAA | GCT | GGA | GAG | GCC | ACC | GTC | TGT | CTC | ACT | 2025 |
| Arg | Thr | Pro | Thr | Val | Leu | Glu | Ala | Gly | Glu | Ala | Thr | Val | Cys | Leu | Thr | |
| | | 645 | | | | | 650 | | | | | 655 | | | | |
| GTC | CGC | AAA | GGT | TCA | CCT | GAC | CTG | TTA | GGT | GAT | GTC | CAA | AGC | TCT | GTC | 2073 |
| Val | Arg | Lys | Gly | Ser | Pro | Asp | Leu | Leu | Gly | Asp | Val | Gln | Ser | Ser | Val | |
| | 660 | | | | | 665 | | | | | 670 | | | | | |
| AGG | TAT | GAT | CTG | GCG | TTG | GAT | CCG | GGC | CGT | CTG | ATT | TCT | CGT | GCC | ATT | 2121 |
| Arg | Tyr | Asp | Leu | Ala | Leu | Asp | Pro | Gly | Arg | Leu | Ile | Ser | Arg | Ala | Ile | |
| 675 | | | | | 680 | | | | | 685 | | | | | 690 | |
| TTT | GAT | GAG | ACG | AAG | AAC | TGC | ACT | TTG | ACC | CGA | AGG | AAG | ACT | CTG | GGG | 2169 |
| Phe | Asp | Glu | Thr | Lys | Asn | Cys | Thr | Leu | Thr | Arg | Arg | Lys | Thr | Leu | Gly | |
| | | | | | 695 | | | | | 700 | | | | | 705 | |
| CTT | GGT | GAT | CAC | TGC | GAA | ACA | ATG | AAG | CTG | CTT | TTG | CCA | GAC | TGT | GTG | 2217 |
| Leu | Gly | Asp | His | Cys | Glu | Thr | Met | Lys | Leu | Leu | Leu | Pro | Asp | Cys | Val | |
| | | | 710 | | | | | 715 | | | | | 720 | | | |
| GAG | GAT | GCA | GTG | ACC | CCT | ATC | ATC | CTG | CGC | CTT | AAC | TTA | TCC | CTG | GCA | 2265 |
| Glu | Asp | Ala | Val | Thr | Pro | Ile | Ile | Leu | Arg | Leu | Asn | Leu | Ser | Leu | Ala | |
| | | 725 | | | | | 730 | | | | | 735 | | | | |
| GGG | GAC | TCT | GCT | CCA | TCC | AGG | AAC | CTT | CGT | CCT | GTG | CTG | GCT | GTG | GGC | 2313 |
| Gly | Asp | Ser | Ala | Pro | Ser | Arg | Asn | Leu | Arg | Pro | Val | Leu | Ala | Val | Gly | |
| | 740 | | | | | 745 | | | | | 750 | | | | | |
| TCA | CAA | GAC | CAT | GTA | ACA | GCT | TCT | TTC | CCG | TTT | GAG | AAG | AAC | TGT | GAG | 2361 |
| Ser | Gln | Asp | His | Val | Thr | Ala | Ser | Phe | Pro | Phe | Glu | Lys | Asn | Cys | Glu | |
| 755 | | | | | 760 | | | | | 765 | | | | | 770 | |
| GGG | AAC | CTG | GGC | GTC | AGC | TTC | AAC | TTC | TCA | GGC | CTG | CAG | GTC | TTG | GAG | 2409 |
| Gly | Asn | Leu | Gly | Val | Ser | Phe | Asn | Phe | Ser | Gly | Leu | Gln | Val | Leu | Glu | |
| | | | | 775 | | | | | 780 | | | | | 785 | | |
| GTA | GGA | AGC | TCC | CCA | GAG | CTC | ACT | GTG | ACA | GTA | ACA | GTT | TGG | AAT | GAG | 2457 |
| Val | Gly | Ser | Ser | Pro | Glu | Leu | Thr | Val | Thr | Val | Thr | Val | Trp | Asn | Glu | |
| | | | 790 | | | | | 795 | | | | | 800 | | | |
| GGT | GAG | GAC | AGC | TAT | GGA | ACC | TTA | ATC | AAG | TTC | TAC | TAC | CCA | GCA | GAG | 2505 |
| Gly | Glu | Asp | Ser | Tyr | Gly | Thr | Leu | Ile | Lys | Phe | Tyr | Tyr | Pro | Ala | Glu | |
| | | 805 | | | | | 810 | | | | | 815 | | | | |
| CTA | TCT | TAC | CGA | CGG | GTG | ACA | AGA | GCC | CAG | CAA | CCT | CAT | CCG | TAC | CCA | 2553 |
| Leu | Ser | Tyr | Arg | Arg | Val | Thr | Arg | Ala | Gln | Gln | Pro | His | Pro | Tyr | Pro | |
| | 820 | | | | | 825 | | | | | 830 | | | | | |
| CTA | CGC | CTG | GCA | TGT | GAG | GCT | GAG | CCC | ACG | GGC | CAG | GAG | AGC | CTG | AGG | 2601 |
| Leu | Arg | Leu | Ala | Cys | Glu | Ala | Glu | Pro | Thr | Gly | Gln | Glu | Ser | Leu | Arg | |
| 835 | | | | | 840 | | | | | 845 | | | | | 850 | |
| AGC | AGC | AGC | TGT | AGC | ATC | AAT | CAC | CCC | ATC | TTC | CGA | GAA | GGT | GCC | AAG | 2649 |
| Ser | Ser | Ser | Cys | Ser | Ile | Asn | His | Pro | Ile | Phe | Arg | Glu | Gly | Ala | Lys | |
| | | | | 855 | | | | | 860 | | | | | 865 | | |

```
GCC ACC TTC ATG ATC ACA TTT GAT GTC TCC TAC AAG GCC TTC CTG GGA         2697
Ala Thr Phe Met Ile Thr Phe Asp Val Ser Tyr Lys Ala Phe Leu Gly
            870             875             880

GAC AGG TTG CTT CTG AGG GCC AGC GCA AGC AGT GAG AAT AAT AAG CCT         2745
Asp Arg Leu Leu Leu Arg Ala Ser Ala Ser Ser Glu Asn Asn Lys Pro
        885             890             895

GAA ACC AGC AAG ACT GCC TTC CAG CTG GAG CTT CCG GTG AAG TAC ACG         2793
Glu Thr Ser Lys Thr Ala Phe Gln Leu Glu Leu Pro Val Lys Tyr Thr
900             905             910

GTC TAT ACC GTG ATC AGT AGG CAG GAA GAT TCT ACC AAG CAT TTC AAC         2841
Val Tyr Thr Val Ile Ser Arg Gln Glu Asp Ser Thr Lys His Phe Asn
915             920             925             930

TTC TCA TCT TCC CAC GGG GAG AGA CAG AAA GAG GCC GAA CAT CGA TAT         2889
Phe Ser Ser Ser His Gly Glu Arg Gln Lys Glu Ala Glu His Arg Tyr
            935             940             945

CGT GTG AAT AAC CTG AGT CCA TTG ACG CTG GCC ATC AGC GTT AAC TTC         2937
Arg Val Asn Asn Leu Ser Pro Leu Thr Leu Ala Ile Ser Val Asn Phe
        950             955             960

TGG GTC CCC ATC CTT CTG AAT GGT GTG GCC GTG TGG GAT GTG ACT CTG         2985
Trp Val Pro Ile Leu Leu Asn Gly Val Ala Val Trp Asp Val Thr Leu
        965             970             975

AGG AGC CCA GCA CAG GGT GTC TCC TGT GTG TCA CAG AGG GAA CCT CCT         3033
Arg Ser Pro Ala Gln Gly Val Ser Cys Val Ser Gln Arg Glu Pro Pro
        980             985             990

CAA CAT TCC GAC CTT CTG ACC CAG ATC CAA GGA CGC TCT GTG CTG GAC         3081
Gln His Ser Asp Leu Leu Thr Gln Ile Gln Gly Arg Ser Val Leu Asp
995             1000            1005            1010

TGC GCC ATC GCC GAC TGC CTG CAC CTC CGC TGT GAC ATC CCC TCC TTG         3129
Cys Ala Ile Ala Asp Cys Leu His Leu Arg Cys Asp Ile Pro Ser Leu
            1015            1020            1025

GGC ACC CTG GAT GAG CTT GAC TTC ATT CTG AAG GGC AAC CTC AGC TTC         3177
Gly Thr Leu Asp Glu Leu Asp Phe Ile Leu Lys Gly Asn Leu Ser Phe
        1030            1035            1040

GGC TGG ATC AGT CAG ACA TTG CAG AAA AAG GTG TTG CTC CTG AGT GAG         3225
Gly Trp Ile Ser Gln Thr Leu Gln Lys Lys Val Leu Leu Leu Ser Glu
        1045            1050            1055

GCT GAA ATC ACA TTC AAC ACA TCT GTG TAT TCC CAG CTG CCG GGA CAG         3273
Ala Glu Ile Thr Phe Asn Thr Ser Val Tyr Ser Gln Leu Pro Gly Gln
1060            1065            1070

GAG GCA TTT CTG AGA GCC CAG GTG TCA ACG ATG CTA GAA GAA TAC GTG         3321
Glu Ala Phe Leu Arg Ala Gln Val Ser Thr Met Leu Glu Glu Tyr Val
1075            1080            1085            1090

GTC TAT GAG CCC GTC TTC CTC ATG GTG TTC AGC TCA GTG GGA GGT CTG         3369
Val Tyr Glu Pro Val Phe Leu Met Val Phe Ser Ser Val Gly Gly Leu
            1095            1100            1105

CTG TTA CTG GCT CTC ATC ACT GTG GCG CTG TAC AAG CTT GGC TTC TTC         3417
Leu Leu Leu Ala Leu Ile Thr Val Ala Leu Tyr Lys Leu Gly Phe Phe
            1110            1115            1120

AAA CGT CAG TAT AAA GAG ATG CTG GAT CTA CCA TCT GCA GAT CCT GAC         3465
Lys Arg Gln Tyr Lys Glu Met Leu Asp Leu Pro Ser Ala Asp Pro Asp
        1125            1130            1135

CCA GCC GGC CAG GCA GAT TCC AAC CAT GAG ACT CCT CCA CAT CTC ACG         3513
Pro Ala Gly Gln Ala Asp Ser Asn His Glu Thr Pro Pro His Leu Thr
1140            1145            1150

TCC TAG                                                                 3519
Ser
1155
```

( 2 ) INFORMATION FOR SEQ ID NO:46:

( i ) SEQUENCE CHARACTERISTICS:

( A ) LENGTH: 1155 amino acids
( B ) TYPE: amino acid
( D ) TOPOLOGY: linear ( i i ) MOLECULE TYPE: protein ( x i ) SEQUENCE DESCRIPTION: SEQ ID NO:46:

| Met | Val | Arg | Gly | Val | Val | Ile | Leu | Leu | Cys | Gly | Trp | Ala | Leu | Ala | Ser |
|---|---|---|---|---|---|---|---|---|---|---|---|---|---|---|---|
| 1 | | | | 5 | | | | | 10 | | | | | 15 | |
| Cys | His | Gly | Ser | Asn | Leu | Asp | Val | Glu | Lys | Pro | Val | Val | Phe | Lys | Glu |
| | | | 20 | | | | 25 | | | | | 30 | | | |
| Asp | Ala | Ala | Ser | Phe | Gly | Gln | Thr | Val | Val | Gln | Phe | Gly | Gly | Ser | Arg |
| | | 35 | | | | 40 | | | | | 45 | | | | |
| Leu | Val | Val | Gly | Ala | Pro | Leu | Glu | Ala | Val | Ala | Val | Asn | Gln | Thr | Gly |
| | 50 | | | | | 55 | | | | | 60 | | | | |
| Gln | Ser | Ser | Asp | Cys | Pro | Pro | Ala | Thr | Gly | Val | Cys | Gln | Pro | Ile | Leu |
| 65 | | | | 70 | | | | | 75 | | | | | | 80 |
| Leu | His | Ile | Pro | Leu | Glu | Ala | Val | Asn | Met | Ser | Leu | Gly | Leu | Ser | Leu |
| | | | | 85 | | | | | 90 | | | | | 95 | |
| Val | Ala | Asp | Thr | Asn | Asn | Ser | Gln | Leu | Leu | Ala | Cys | Gly | Pro | Thr | Ala |
| | | | 100 | | | | | 105 | | | | | 110 | | |
| Gln | Arg | Ala | Cys | Ala | Lys | Asn | Met | Tyr | Ala | Lys | Gly | Ser | Cys | Leu | Leu |
| | | 115 | | | | | 120 | | | | | 125 | | | |
| Leu | Gly | Ser | Ser | Leu | Gln | Phe | Ile | Gln | Ala | Ile | Pro | Ala | Thr | Met | Pro |
| | 130 | | | | | 135 | | | | | 140 | | | | |
| Glu | Cys | Pro | Gly | Gln | Glu | Met | Asp | Ile | Ala | Phe | Leu | Ile | Asp | Gly | Ser |
| 145 | | | | | 150 | | | | | 155 | | | | | 160 |
| Gly | Ser | Ile | Asp | Gln | Ser | Asp | Phe | Thr | Gln | Met | Lys | Asp | Phe | Val | Lys |
| | | | | 165 | | | | | 170 | | | | | 175 | |
| Ala | Leu | Met | Gly | Gln | Leu | Ala | Ser | Thr | Ser | Thr | Ser | Phe | Ser | Leu | Met |
| | | | 180 | | | | | 185 | | | | | 190 | | |
| Gln | Tyr | Ser | Asn | Ile | Leu | Lys | Thr | His | Phe | Thr | Phe | Thr | Glu | Phe | Lys |
| | | 195 | | | | | 200 | | | | | 205 | | | |
| Ser | Ser | Leu | Ser | Pro | Gln | Ser | Leu | Val | Asp | Ala | Ile | Val | Gln | Leu | Gln |
| | 210 | | | | | 215 | | | | | 220 | | | | |
| Gly | Leu | Thr | Tyr | Thr | Ala | Ser | Gly | Ile | Gln | Lys | Val | Val | Lys | Glu | Leu |
| 225 | | | | | 230 | | | | | 235 | | | | | 240 |
| Phe | His | Ser | Lys | Asn | Gly | Ala | Arg | Lys | Ser | Ala | Lys | Lys | Ile | Leu | Ile |
| | | | | 245 | | | | | 250 | | | | | 255 | |
| Val | Ile | Thr | Asp | Gly | Gln | Lys | Phe | Arg | Asp | Pro | Leu | Glu | Tyr | Arg | His |
| | | | 260 | | | | | 265 | | | | | 270 | | |
| Val | Ile | Pro | Glu | Ala | Glu | Lys | Ala | Gly | Ile | Ile | Arg | Tyr | Ala | Ile | Gly |
| | | 275 | | | | | 280 | | | | | 285 | | | |
| Val | Gly | Asp | Ala | Phe | Arg | Glu | Pro | Thr | Ala | Leu | Gln | Glu | Leu | Asn | Thr |
| | 290 | | | | | 295 | | | | | 300 | | | | |
| Ile | Gly | Ser | Ala | Pro | Ser | Gln | Asp | His | Val | Phe | Lys | Val | Gly | Asn | Phe |
| 305 | | | | | 310 | | | | | 315 | | | | | 320 |
| Val | Ala | Leu | Arg | Ser | Ile | Gln | Arg | Gln | Ile | Gln | Glu | Lys | Ile | Phe | Ala |
| | | | | 325 | | | | | 330 | | | | | 335 | |
| Ile | Glu | Gly | Thr | Glu | Ser | Arg | Ser | Ser | Ser | Ser | Phe | Gln | His | Glu | Met |
| | | | 340 | | | | | 345 | | | | | 350 | | |
| Ser | Gln | Glu | Gly | Phe | Ser | Ser | Ala | Leu | Ser | Met | Asp | Gly | Pro | Val | Leu |
| | | 355 | | | | | 360 | | | | | 365 | | | |
| Gly | Ala | Val | Gly | Gly | Phe | Ser | Trp | Ser | Gly | Gly | Ala | Phe | Leu | Tyr | Pro |
| | 370 | | | | | 375 | | | | | 380 | | | | |

| | | | | | | | | | | | | | | |
|---|---|---|---|---|---|---|---|---|---|---|---|---|---|---|
| Ser 385 | Asn | Met | Arg | Ser | Thr 390 | Phe | Ile | Asn | Met | Ser 395 | Gln | Glu | Asn | Glu Asp 400 |
| Met | Arg | Asp | Ala | Tyr 405 | Leu | Gly | Tyr | Ser | Thr 410 | Ala | Leu | Ala | Phe | Trp Lys 415 |
| Gly | Val | His | Ser 420 | Leu | Ile | Leu | Gly | Ala 425 | Pro | Arg | His | Gln | His 430 | Thr Gly |
| Lys | Val | Val 435 | Ile | Phe | Thr | Gln | Glu 440 | Ser | Arg | His | Trp | Arg 445 | Pro | Lys Ser |
| Glu | Val 450 | Arg | Gly | Thr | Gln | Ile 455 | Gly | Ser | Tyr | Phe | Gly 460 | Ala | Ser | Leu Cys |
| Ser 465 | Val | Asp | Met | Asp | Arg 470 | Asp | Gly | Ser | Thr | Asp 475 | Leu | Val | Leu | Ile Gly 480 |
| Val | Pro | His | Tyr | Tyr 485 | Glu | His | Thr | Arg | Gly 490 | Gly | Gln | Val | Ser | Val Cys 495 |
| Pro | Met | Pro | Gly 500 | Val | Arg | Ser | Arg | Trp 505 | His | Cys | Gly | Thr | Thr 510 | Leu His |
| Gly | Glu | Gln 515 | Gly | His | Pro | Trp | Gly 520 | Arg | Phe | Gly | Ala | Ala 525 | Leu | Thr Val |
| Leu | Gly 530 | Asp | Val | Asn | Gly | Asp 535 | Ser | Leu | Ala | Asp | Val 540 | Ala | Ile | Gly Ala |
| Pro 545 | Gly | Glu | Glu | Glu | Asn 550 | Arg | Gly | Ala | Val | Tyr 555 | Ile | Phe | His | Gly Ala 560 |
| Ser | Arg | Gln | Asp | Ile 565 | Ala | Pro | Ser | Pro | Ser 570 | Gln | Arg | Val | Thr | Gly Ser 575 |
| Gln | Leu | Phe | Leu 580 | Arg | Leu | Gln | Tyr | Phe 585 | Gly | Gln | Ser | Leu | Ser 590 | Gly Gly |
| Gln | Asp | Leu 595 | Thr | Gln | Asp | Gly | Leu 600 | Val | Asp | Leu | Ala | Val 605 | Gly | Ala Gln |
| Gly | His 610 | Val | Leu | Leu | Leu | Arg 615 | Ser | Leu | Pro | Leu | Leu 620 | Lys | Val | Gly Ile |
| Ser 625 | Ile | Arg | Phe | Ala | Pro 630 | Ser | Glu | Val | Ala | Lys 635 | Thr | Val | Tyr | Gln Cys 640 |
| Trp | Gly | Arg | Thr | Pro 645 | Thr | Val | Leu | Glu | Ala 650 | Gly | Glu | Ala | Thr | Val Cys 655 |
| Leu | Thr | Val | Arg 660 | Lys | Gly | Ser | Pro | Asp 665 | Leu | Leu | Gly | Asp | Val 670 | Gln Ser |
| Ser | Val | Arg 675 | Tyr | Asp | Leu | Ala | Leu 680 | Asp | Pro | Gly | Arg | Leu 685 | Ile | Ser Arg |
| Ala | Ile | Phe 690 | Asp | Glu | Thr | Lys | Asn 695 | Cys | Thr | Leu | Thr | Arg 700 | Arg | Lys Thr |
| Leu 705 | Gly | Leu | Gly | Asp | His 710 | Cys | Glu | Thr | Met | Lys 715 | Leu | Leu | Leu | Pro Asp 720 |
| Cys | Val | Glu | Asp | Ala 725 | Val | Thr | Pro | Ile | Ile 730 | Leu | Arg | Leu | Asn | Leu Ser 735 |
| Leu | Ala | Gly | Asp 740 | Ser | Ala | Pro | Ser | Arg 745 | Asn | Leu | Arg | Pro | Val 750 | Leu Ala |
| Val | Gly | Ser 755 | Gln | Asp | His | Val | Thr 760 | Ala | Ser | Phe | Pro | Phe 765 | Glu | Lys Asn |
| Cys | Glu 770 | Gly | Asn | Leu | Gly | Val 775 | Ser | Phe | Asn | Phe | Ser 780 | Gly | Leu | Gln Val |
| Leu 785 | Glu | Val | Gly | Ser | Ser 790 | Pro | Glu | Leu | Thr | Val 795 | Thr | Val | Thr | Val Trp 800 |
| Asn | Glu | Gly | Glu | Asp 805 | Ser | Tyr | Gly | Thr | Leu 810 | Ile | Lys | Phe | Tyr | Tyr Pro 815 |

| | | | | | | | | | | | | | | |
|---|---|---|---|---|---|---|---|---|---|---|---|---|---|---|
| Ala | Glu | Leu | Ser 820 | Tyr | Arg | Arg | Val | Thr 825 | Arg | Ala | Gln | Gln | Pro 830 | His | Pro |
| Tyr | Pro | Leu 835 | Arg | Leu | Ala | Cys | Glu 840 | Ala | Glu | Pro | Thr | Gly 845 | Gln | Glu | Ser |
| Leu | Arg 850 | Ser | Ser | Ser | Cys | Ser 855 | Ile | Asn | His | Pro | Ile 860 | Phe | Arg | Glu | Gly |
| Ala 865 | Lys | Ala | Thr | Phe | Met 870 | Ile | Thr | Phe | Asp | Val 875 | Ser | Tyr | Lys | Ala | Phe 880 |
| Leu | Gly | Asp | Arg | Leu 885 | Leu | Leu | Arg | Ala | Ser 890 | Ala | Ser | Ser | Glu | Asn 895 | Asn |
| Lys | Pro | Glu | Thr 900 | Ser | Lys | Thr | Ala | Phe 905 | Gln | Leu | Glu | Leu | Pro 910 | Val | Lys |
| Tyr | Thr | Val 915 | Tyr | Thr | Val | Ile | Ser 920 | Arg | Gln | Glu | Asp | Ser 925 | Thr | Lys | His |
| Phe | Asn 930 | Phe | Ser | Ser | Ser | His 935 | Gly | Glu | Arg | Gln | Lys 940 | Glu | Ala | Glu | His |
| Arg 945 | Tyr | Arg | Val | Asn | Asn 950 | Leu | Ser | Pro | Leu | Thr 955 | Leu | Ala | Ile | Ser | Val 960 |
| Asn | Phe | Trp | Val | Pro 965 | Ile | Leu | Leu | Asn | Gly 970 | Val | Ala | Val | Trp | Asp 975 | Val |
| Thr | Leu | Arg | Ser 980 | Pro | Ala | Gln | Gly | Val 985 | Ser | Cys | Val | Ser | Gln 990 | Arg | Glu |
| Pro | Pro | Gln 995 | His | Ser | Asp | Leu | Leu 1000 | Thr | Gln | Ile | Gln | Gly 1005 | Arg | Ser | Val |
| Leu | Asp 1010 | Cys | Ala | Ile | Ala | Asp 1015 | Cys | Leu | His | Leu | Arg 1020 | Cys | Asp | Ile | Pro |
| Ser 1025 | Leu | Gly | Thr | Leu | Asp 1030 | Glu | Leu | Asp | Phe | Ile 1035 | Leu | Lys | Gly | Asn | Leu 1040 |
| Ser | Phe | Gly | Trp | Ile 1045 | Ser | Gln | Thr | Leu | Gln 1050 | Lys | Lys | Val | Leu | Leu 1055 | Leu |
| Ser | Glu | Ala | Glu | Ile 1060 | Thr | Phe | Asn | Thr | Ser 1065 | Val | Tyr | Ser | Gln | Leu 1070 | Pro |
| Gly | Gln | Glu | Ala 1075 | Phe | Leu | Arg | Ala | Gln 1080 | Val | Ser | Thr | Met | Leu 1085 | Glu | Glu |
| Tyr | Val | Val 1090 | Tyr | Glu | Pro | Val 1095 | Phe | Leu | Met | Val | Phe 1100 | Ser | Ser | Val | Gly |
| Gly 1105 | Leu | Leu | Leu | Leu | Ala 1110 | Leu | Ile | Thr | Val | Ala 1115 | Leu | Tyr | Lys | Leu | Gly 1120 |
| Phe | Phe | Lys | Arg | Gln 1125 | Tyr | Lys | Glu | Met | Leu 1130 | Asp | Leu | Pro | Ser | Ala 1135 | Asp |
| Pro | Asp | Pro | Ala 1140 | Gly | Gln | Ala | Asp | Ser 1145 | Asn | His | Glu | Thr | Pro 1150 | Pro | His |
| Leu | Thr | Ser 1155 | | | | | | | | | | | | | |

( 2 ) INFORMATION FOR SEQ ID NO:47:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

```
AGTTACGGAT CCGGCACCAT GACCTTCGGC ACTGTGATCC TCCTGTGTG                        49
```

(2) INFORMATION FOR SEQ ID NO:48:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

```
GCTGGACGAT GGCATCCAC                                                         19
```

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

```
GTAGAGTTAC GGATCCGGCA CCAT                                                   24
```

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

```
GCAGCCAGCT TCGGACAGAC                                                        20
```

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:51:

```
CCATGTCCAC AGAACAGAGA G                                                      21
```

(2) INFORMATION FOR SEQ ID NO:52:

(i) SEQUENCE CHARACTERISTICS:
        (A) LENGTH: 3803 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..3486

(xi) SEQUENCE DESCRIPTION: SEQ ID NO:52:

```
ATG GTC CGT GGA GTT GTG ATC CTC CTG TGT GGC TGG GCC CTG GCT TCC              48
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Met | Val | Arg | Gly | Val | Val | Ile | Leu | Leu | Cys | Gly | Trp | Ala | Leu | Ala | Ser | |
| 1   |     |     |     | 5   |     |     |     |     | 10  |     |     |     |     | 15  | | |
| TGT | CAT | GGG | TCT | AAC | CTG | GAT | GTG | GAG | AAG | CCC | GTC | GTG | TTC | AAA | GAG | 96 |
| Cys | His | Gly | Ser | Asn | Leu | Asp | Val | Glu | Lys | Pro | Val | Val | Phe | Lys | Glu | |
|     |     |     | 20  |     |     |     | 25  |     |     |     |     | 30  |     |     | | |
| GAT | GCA | GCC | AGC | TTC | GGA | CAG | ACT | GTG | GTG | CAG | TTT | GGT | GGA | TCT | CGA | 144 |
| Asp | Ala | Ala | Ser | Phe | Gly | Gln | Thr | Val | Val | Gln | Phe | Gly | Gly | Ser | Arg | |
|     |     | 35  |     |     |     | 40  |     |     |     |     | 45  |     |     | | | |
| CTC | GTG | GTG | GGA | GCC | CCT | CTG | GAG | GCG | GTG | GCA | GTC | AAC | CAA | ACA | GGA | 192 |
| Leu | Val | Val | Gly | Ala | Pro | Leu | Glu | Ala | Val | Ala | Val | Asn | Gln | Thr | Gly | |
|     | 50  |     |     |     | 55  |     |     |     |     | 60  |     |     |     | | | |
| CAG | TCG | TCT | GAC | TGT | CCG | CCT | GCC | ACT | GGC | GTG | TGC | CAG | CCC | ATC | TTA | 240 |
| Gln | Ser | Ser | Asp | Cys | Pro | Pro | Ala | Thr | Gly | Val | Cys | Gln | Pro | Ile | Leu | |
| 65  |     |     |     | 70  |     |     |     |     | 75  |     |     |     |     | 80  | | |
| CTG | CAC | ATT | CCC | CTA | GAG | GCA | GTG | AAC | ATG | TCC | CTG | GGC | CTG | TCT | CTG | 288 |
| Leu | His | Ile | Pro | Leu | Glu | Ala | Val | Asn | Met | Ser | Leu | Gly | Leu | Ser | Leu | |
|     |     |     |     | 85  |     |     |     |     | 90  |     |     |     |     | 95  | | |
| GTG | GCT | GAC | ACC | AAT | AAC | TCC | CAG | TTG | CTG | GCT | TGT | GGT | CCA | ACT | GCA | 336 |
| Val | Ala | Asp | Thr | Asn | Asn | Ser | Gln | Leu | Leu | Ala | Cys | Gly | Pro | Thr | Ala | |
|     |     |     | 100 |     |     |     |     | 105 |     |     |     |     | 110 | | | |
| CAG | AGA | GCT | TGT | GCA | AAG | AAC | ATG | TAT | GCA | AAA | GGT | TCC | TGC | CTC | CTT | 384 |
| Gln | Arg | Ala | Cys | Ala | Lys | Asn | Met | Tyr | Ala | Lys | Gly | Ser | Cys | Leu | Leu | |
|     |     | 115 |     |     |     |     | 120 |     |     |     |     | 125 |     | | | |
| CTG | GGC | TCC | AGC | TTG | CAG | TTC | ATC | CAG | GCA | ATC | CCT | GCT | ACC | ATG | CCA | 432 |
| Leu | Gly | Ser | Ser | Leu | Gln | Phe | Ile | Gln | Ala | Ile | Pro | Ala | Thr | Met | Pro | |
|     | 130 |     |     |     |     | 135 |     |     |     |     | 140 |     |     | | | |
| GAG | TGT | CCA | GGA | CAA | GAG | ATG | GAC | ATT | GCT | TTC | CTG | ATT | GAT | GGC | TCC | 480 |
| Glu | Cys | Pro | Gly | Gln | Glu | Met | Asp | Ile | Ala | Phe | Leu | Ile | Asp | Gly | Ser | |
| 145 |     |     |     |     | 150 |     |     |     |     | 155 |     |     |     |     | 160 | |
| GGC | AGC | ATT | GAT | CAA | AGT | GAC | TTT | ACC | CAG | ATG | AAG | GAC | TTC | GTC | AAA | 528 |
| Gly | Ser | Ile | Asp | Gln | Ser | Asp | Phe | Thr | Gln | Met | Lys | Asp | Phe | Val | Lys | |
|     |     |     |     | 165 |     |     |     |     | 170 |     |     |     |     | 175 | | |
| GCT | TTG | ATG | GGC | CAG | TTG | GCG | AGC | ACC | AGC | ACC | TCG | TTC | TCC | CTG | ATG | 576 |
| Ala | Leu | Met | Gly | Gln | Leu | Ala | Ser | Thr | Ser | Thr | Ser | Phe | Ser | Leu | Met | |
|     |     |     | 180 |     |     |     |     | 185 |     |     |     |     | 190 | | | |
| CAA | TAC | TCA | AAC | ATC | CTG | AAG | ACT | CAT | TTT | ACC | TTC | ACG | GAA | TTC | AAG | 624 |
| Gln | Tyr | Ser | Asn | Ile | Leu | Lys | Thr | His | Phe | Thr | Phe | Thr | Glu | Phe | Lys | |
|     |     | 195 |     |     |     |     | 200 |     |     |     |     | 205 |     | | | |
| AGC | AGC | CTG | AGC | CCT | CAG | AGC | CTG | GTG | GAT | GCC | ATC | GTC | CAG | CTC | CAA | 672 |
| Ser | Ser | Leu | Ser | Pro | Gln | Ser | Leu | Val | Asp | Ala | Ile | Val | Gln | Leu | Gln | |
|     | 210 |     |     |     |     | 215 |     |     |     |     | 220 |     |     | | | |
| GGC | CTG | ACG | TAC | ACA | GCC | TCG | GGC | ATC | CAG | AAA | GTG | GTG | AAA | GAG | CTA | 720 |
| Gly | Leu | Thr | Tyr | Thr | Ala | Ser | Gly | Ile | Gln | Lys | Val | Val | Lys | Glu | Leu | |
| 225 |     |     |     | 230 |     |     |     |     | 235 |     |     |     |     | 240 | | |
| TTT | CAT | AGC | AAG | AAT | GGG | GCC | CGA | AAA | AGT | GCC | AAG | AAG | ATA | CTA | ATT | 768 |
| Phe | His | Ser | Lys | Asn | Gly | Ala | Arg | Lys | Ser | Ala | Lys | Lys | Ile | Leu | Ile | |
|     |     |     | 245 |     |     |     |     | 250 |     |     |     |     | 255 | | | |
| GTC | ATC | ACA | GAT | GGG | CAG | AAA | TTC | AGA | GAC | CCC | CTG | GAG | TAT | AGA | CAT | 816 |
| Val | Ile | Thr | Asp | Gly | Gln | Lys | Phe | Arg | Asp | Pro | Leu | Glu | Tyr | Arg | His | |
|     |     | 260 |     |     |     |     | 265 |     |     |     |     | 270 |     | | | |
| GTC | ATC | CCT | GAA | GCA | GAG | AAA | GCT | GGG | ATC | ATT | CGC | TAT | GCT | ATA | GGG | 864 |
| Val | Ile | Pro | Glu | Ala | Glu | Lys | Ala | Gly | Ile | Ile | Arg | Tyr | Ala | Ile | Gly | |
|     |     | 275 |     |     |     |     | 280 |     |     |     |     | 285 |     | | | |
| GTG | GGA | GAT | GCC | TTC | CGG | GAA | CCC | ACT | GCC | CTA | CAG | GAG | CTG | AAC | ACC | 912 |
| Val | Gly | Asp | Ala | Phe | Arg | Glu | Pro | Thr | Ala | Leu | Gln | Glu | Leu | Asn | Thr | |
|     | 290 |     |     |     |     | 295 |     |     |     |     | 300 |     |     | | | |
| ATT | GGC | TCA | GCT | CCC | TCG | CAG | GAC | CAC | GTG | TTC | AAG | GTG | GGC | AAT | TTT | 960 |
| Ile | Gly | Ser | Ala | Pro | Ser | Gln | Asp | His | Val | Phe | Lys | Val | Gly | Asn | Phe | |
| 305 |     |     |     |     | 310 |     |     |     |     | 315 |     |     |     |     | 320 | |
| GTA | GCA | CTT | CGC | AGC | ATC | CAG | CGG | CAA | ATT | CAG | GAG | AAA | ATC | TTT | GCC | 1008 |

```
         Val Ala Leu Arg Ser Ile Gln Arg Gln Ile Gln Glu Lys Ile Phe Ala
                         325                 330                 335

ATT GAA GGA ACC GAA TCA AGG TCA AGT AGT TCC TTT CAG CAC GAG ATG             1056
Ile Glu Gly Thr Glu Ser Arg Ser Ser Ser Ser Phe Gln His Glu Met
                340                 345                 350

TCA CAA GAA GGT TTC AGC TCA GCT CTC TCA ATG GAT GGA CCA GTT CTG             1104
Ser Gln Glu Gly Phe Ser Ser Ala Leu Ser Met Asp Gly Pro Val Leu
                355                 360                 365

GGG GCT GTG GGA GGC TTC AGC TGG TCT GGA GGT GCC TTC TTG TAC CCC             1152
Gly Ala Val Gly Gly Phe Ser Trp Ser Gly Gly Ala Phe Leu Tyr Pro
        370                 375                 380

TCA AAT ATG AGA TCC ACC TTC ATC AAC ATG TCT CAG GAG AAC GAG GAT             1200
Ser Asn Met Arg Ser Thr Phe Ile Asn Met Ser Gln Glu Asn Glu Asp
385                 390                 395                 400

ATG AGG GAC GCT TAC CTG GGT TAC TCC ACC GCA CTG GCC TTT TGG AAG             1248
Met Arg Asp Ala Tyr Leu Gly Tyr Ser Thr Ala Leu Ala Phe Trp Lys
                405                 410                 415

GGG GTC CAC AGC CTG ATC CTG GGG GCC CCT CGC CAC CAG CAC ACG GGG             1296
Gly Val His Ser Leu Ile Leu Gly Ala Pro Arg His Gln His Thr Gly
                420                 425                 430

AAG GTT GTC ATC TTT ACC CAG GAA TCC AGG CAC TGG AGG CCC AAG TCT             1344
Lys Val Val Ile Phe Thr Gln Glu Ser Arg His Trp Arg Pro Lys Ser
                435                 440                 445

GAA GTC AGA GGG ACA CAG ATC GGC TCC TAC TTT GGG GCA TCT CTC TGT             1392
Glu Val Arg Gly Thr Gln Ile Gly Ser Tyr Phe Gly Ala Ser Leu Cys
        450                 455                 460

TCT GTG GAC ATG GAT AGA GAT GGC AGC ACT GAC CTG GTC CTG ATT GGA             1440
Ser Val Asp Met Asp Arg Asp Gly Ser Thr Asp Leu Val Leu Ile Gly
465                 470                 475                 480

GTC CCC CAT TAC TAT GAG CAC ACC CGA GGG GGG CAG GTG TCG GTG TGC             1488
Val Pro His Tyr Tyr Glu His Thr Arg Gly Gly Gln Val Ser Val Cys
                485                 490                 495

CCC ATG CCT GGT GTG AGG AGC AGG TGG CAT TGT GGG ACC ACC CTC CAT             1536
Pro Met Pro Gly Val Arg Ser Arg Trp His Cys Gly Thr Thr Leu His
                500                 505                 510

GGG GAG CAG GGC CAT CCT TGG GGC CGC TTT GGG GCG GCT CTG ACA GTG             1584
Gly Glu Gln Gly His Pro Trp Gly Arg Phe Gly Ala Ala Leu Thr Val
                515                 520                 525

CTA GGG GAC GTG AAT GGG GAC AGT CTG GCG GAT GTG GCT ATT GGT GCA             1632
Leu Gly Asp Val Asn Gly Asp Ser Leu Ala Asp Val Ala Ile Gly Ala
        530                 535                 540

CCC GGA GAG GAG GAG AAC AGA GGT GCT GTC TAC ATA TTT CAT GGA GCC             1680
Pro Gly Glu Glu Glu Asn Arg Gly Ala Val Tyr Ile Phe His Gly Ala
545                 550                 555                 560

TCG AGA CAG GAC ATC GCT CCC TCG CCT AGC CAG CGG GTC ACT GGC TCC             1728
Ser Arg Gln Asp Ile Ala Pro Ser Pro Ser Gln Arg Val Thr Gly Ser
                565                 570                 575

CAG CTC TTC CTG AGG CTC CAA TAT TTT GGG CAG TCA TTA AGT GGG GGT             1776
Gln Leu Phe Leu Arg Leu Gln Tyr Phe Gly Gln Ser Leu Ser Gly Gly
                580                 585                 590

CAG GAC CTT ACA CAG GAT GGC CTG GTG GAC CTG GCC GTG GGA GCC CAG             1824
Gln Asp Leu Thr Gln Asp Gly Leu Val Asp Leu Ala Val Gly Ala Gln
                595                 600                 605

GGG CAC GTG CTG CTG CTT AGG AGT CTG CCT TTG CTG AAA GTG GGG ATC             1872
Gly His Val Leu Leu Leu Arg Ser Leu Pro Leu Leu Lys Val Gly Ile
        610                 615                 620

TCC ATT AGA TTT GCC CCC TCA GAG GTG GCA AAG ACT GTG TAC CAG TGC             1920
Ser Ile Arg Phe Ala Pro Ser Glu Val Ala Lys Thr Val Tyr Gln Cys
625                 630                 635                 640

TGG GGA AGG ACT CCC ACT GTC CTC GAA GCT GGA GAG GCC ACC GTC TGT             1968
```

| | | | | | | | | | | | | | | | |
|---|---|---|---|---|---|---|---|---|---|---|---|---|---|---|---|
| Trp | Gly | Arg | Thr | Pro | Thr | Val | Leu | Glu | Ala | Gly | Glu | Ala | Thr | Val | Cys |
| | | | | 645 | | | | 650 | | | | | | 655 | |

```
CTC  ACT  GTC  CGC  AAA  GGT  TCA  CCT  GAC  CTG  TTA  GGT  GAT  GTC  CAA  AGC    2016
Leu  Thr  Val  Arg  Lys  Gly  Ser  Pro  Asp  Leu  Leu  Gly  Asp  Val  Gln  Ser
          660                 665                      670

TCT  GTC  AGG  TAT  GAT  CTG  GCG  TTG  GAT  CCG  GGC  CGT  CTG  ATT  TCT  CGT    2064
Ser  Val  Arg  Tyr  Asp  Leu  Ala  Leu  Asp  Pro  Gly  Arg  Leu  Ile  Ser  Arg
          675                 680                      685

GCC  ATT  TTT  GAT  GAG  ACG  AAG  AAC  TGC  ACT  TTG  ACC  CGA  AGG  AAG  ACT    2112
Ala  Ile  Phe  Asp  Glu  Thr  Lys  Asn  Cys  Thr  Leu  Thr  Arg  Arg  Lys  Thr
     690                      695                     700

CTG  GGG  CTT  GGT  GAT  CAC  TGC  GAA  ACA  ATG  AAG  CTG  CTT  TTG  CCA  GAC    2160
Leu  Gly  Leu  Gly  Asp  His  Cys  Glu  Thr  Met  Lys  Leu  Leu  Leu  Pro  Asp
705                      710                     715                      720

TGT  GTG  GAG  GAT  GCA  GTG  ACC  CCT  ATC  ATC  CTG  CGC  CTT  AAC  TTA  TCC    2208
Cys  Val  Glu  Asp  Ala  Val  Thr  Pro  Ile  Ile  Leu  Arg  Leu  Asn  Leu  Ser
               725                           730                     735

CTG  GCA  GGG  GAC  TCT  GCT  CCA  TCC  AGG  AAC  CTT  CGT  CCT  GTG  CTG  GCT    2256
Leu  Ala  Gly  Asp  Ser  Ala  Pro  Ser  Arg  Asn  Leu  Arg  Pro  Val  Leu  Ala
               740                      745                     750

GTG  GGC  TCA  CAA  GAC  CAT  GTA  ACA  GCT  TCT  TTC  CCG  TTT  GAG  AAG  AAC    2304
Val  Gly  Ser  Gln  Asp  His  Val  Thr  Ala  Ser  Phe  Pro  Phe  Glu  Lys  Asn
          755                      760                     765

TGT  AAG  CAG  GAG  CTC  CTG  TGT  GAG  GGG  AAC  CTG  GGC  GTC  AGC  TTC  AAC    2352
Cys  Lys  Gln  Glu  Leu  Leu  Cys  Glu  Gly  Asn  Leu  Gly  Val  Ser  Phe  Asn
     770                      775                      780

TTC  TCA  GGC  CTG  CAG  GTC  TTG  GAG  GTA  GGA  AGC  TCC  CCA  GAG  CTC  ACT    2400
Phe  Ser  Gly  Leu  Gln  Val  Leu  Glu  Val  Gly  Ser  Ser  Pro  Glu  Leu  Thr
785                      790                      795                      800

GTG  ACA  GTA  ACA  GTT  TGG  AAT  GAG  GGT  GAG  GAC  AGC  TAT  GGA  ACC  TTA    2448
Val  Thr  Val  Thr  Val  Trp  Asn  Glu  Gly  Glu  Asp  Ser  Tyr  Gly  Thr  Leu
                    805                      810                     815

ATC  AAG  TTC  TAC  TAC  CCA  GCA  GAG  CTA  TCT  TAC  CGA  CGG  GTG  ACA  AGA    2496
Ile  Lys  Phe  Tyr  Tyr  Pro  Ala  Glu  Leu  Ser  Tyr  Arg  Arg  Val  Thr  Arg
               820                      825                     830

GCC  CAG  CAA  CCT  CAT  CCG  TAC  CCA  CTA  CGC  CTG  GCA  TGT  GAG  GCT  GAG    2544
Ala  Gln  Gln  Pro  His  Pro  Tyr  Pro  Leu  Arg  Leu  Ala  Cys  Glu  Ala  Glu
          835                      840                     845

CCC  ACG  GGC  CAG  GAG  AGC  CTG  AGG  AGC  AGC  AGC  TGT  AGC  ATC  AAT  CAC    2592
Pro  Thr  Gly  Gln  Glu  Ser  Leu  Arg  Ser  Ser  Ser  Cys  Ser  Ile  Asn  His
     850                      855                      860

CCC  ATC  TTC  CGA  GAA  GGT  GCC  AAG  GCC  ACC  TTC  ATG  ATC  ACA  TTT  GAT    2640
Pro  Ile  Phe  Arg  Glu  Gly  Ala  Lys  Ala  Thr  Phe  Met  Ile  Thr  Phe  Asp
865                      870                      875                      880

GTC  TCC  TAC  AAG  GCC  TTC  CTG  GGA  GAC  AGG  TTG  CTT  CTG  AGG  GCC  AGC    2688
Val  Ser  Tyr  Lys  Ala  Phe  Leu  Gly  Asp  Arg  Leu  Leu  Leu  Arg  Ala  Ser
               885                      890                     895

GCA  AGC  AGT  GAG  AAT  AAT  AAG  CCT  GAA  ACC  AGC  AAG  ACT  GCC  TTC  CAG    2736
Ala  Ser  Ser  Glu  Asn  Asn  Lys  Pro  Glu  Thr  Ser  Lys  Thr  Ala  Phe  Gln
               900                      905                     910

CTG  GAG  CTT  CCG  GTG  AAG  TAC  ACG  GTC  TAT  ACC  GTG  ATC  AGT  AGG  CAG    2784
Leu  Glu  Leu  Pro  Val  Lys  Tyr  Thr  Val  Tyr  Thr  Val  Ile  Ser  Arg  Gln
          915                      920                     925

GAA  GAT  TCT  ACC  AAG  CAT  TTC  AAC  TTC  TCA  TCT  TCC  CAC  GGG  GAG  AGA    2832
Glu  Asp  Ser  Thr  Lys  His  Phe  Asn  Phe  Ser  Ser  Ser  His  Gly  Glu  Arg
     930                      935                      940

CAG  AAA  GAG  GCC  GAA  CAT  CGA  TAT  CGT  GTG  AAT  AAC  CTG  AGT  CCA  TTG    2880
Gln  Lys  Glu  Ala  Glu  His  Arg  Tyr  Arg  Val  Asn  Asn  Leu  Ser  Pro  Leu
945                      950                      955                      960

ACG  CTG  GCC  ATC  AGC  GTT  AAC  TTC  TGG  GTC  CCC  ATC  CTT  CTG  AAT  GGT    2928
```

|                                                                                           |      |
|-------------------------------------------------------------------------------------------|------|
| Thr Leu Ala Ile Ser Val Asn Phe Trp Val Pro Ile Leu Leu Asn Gly<br>            965              970            975 |      |
| GTG GCC GTG TGG GAT GTG ACT CTG AGG AGC CCA GCA CAG GGT GTC TCC<br>Val Ala Val Trp Asp Val Thr Leu Arg Ser Pro Ala Gln Gly Val Ser<br>            980             985              990 | 2976 |
| TGT GTG TCA CAG AGG GAA CCT CCT CAA CAT TCC GAC CTT CTG ACC CAG<br>Cys Val Ser Gln Arg Glu Pro Pro Gln His Ser Asp Leu Leu Thr Gln<br>            995            1000            1005 | 3024 |
| ATC CAA GGA CGC TCT GTG CTG GAC TGC GCC ATC GCC GAC TGC CTG CAC<br>Ile Gln Gly Arg Ser Val Leu Asp Cys Ala Ile Ala Asp Cys Leu His<br>           1010            1015            1020 | 3072 |
| CTC CGC TGT GAC ATC CCC TCC TTG GGC ACC CTG GAT GAG CTT GAC TTC<br>Leu Arg Cys Asp Ile Pro Ser Leu Gly Thr Leu Asp Glu Leu Asp Phe<br>1025           1030            1035           1040 | 3120 |
| ATT CTG AAG GGC AAC CTC AGC TTC GGC TGG ATC AGT CAG ACA TTG CAG<br>Ile Leu Lys Gly Asn Leu Ser Phe Gly Trp Ile Ser Gln Thr Leu Gln<br>           1045            1050            1055 | 3168 |
| AAA AAG GTG TTG CTC CTG AGT GAG GCT GAA ATC ACA TTC AAC ACA TCT<br>Lys Lys Val Leu Leu Leu Ser Glu Ala Glu Ile Thr Phe Asn Thr Ser<br>           1060            1065            1070 | 3216 |
| GTG TAT TCC CAG CTG CCG GGA CAG GAG GCA TTT CTG AGA GCC CAG GTG<br>Val Tyr Ser Gln Leu Pro Gly Gln Glu Ala Phe Leu Arg Ala Gln Val<br>           1075            1080            1085 | 3264 |
| TCA ACG ATG CTA GAA GAA TAC GTG GTC TAT GAG CCC GTC TTC CTC ATG<br>Ser Thr Met Leu Glu Glu Tyr Val Val Tyr Glu Pro Val Phe Leu Met<br>           1090            1095            1100 | 3312 |
| GTG TTC AGC TCA GTG GGA GGT CTG CTG TTA CTG GCT CTC ATC ACT GTG<br>Val Phe Ser Ser Val Gly Gly Leu Leu Leu Leu Ala Leu Ile Thr Val<br>1105            1110           1115           1120 | 3360 |
| GCG CTG TAC AAG CTT GGC TTC TTC AAA CGT CAG TAT AAA GAG ATG CTG<br>Ala Leu Tyr Lys Leu Gly Phe Phe Lys Arg Gln Tyr Lys Glu Met Leu<br>           1125            1130            1135 | 3408 |
| GAT CTA CCA TCT GCA GAT CCT GAC CCA GCC GGC CAG GCA GAT TCC AAC<br>Asp Leu Pro Ser Ala Asp Pro Asp Pro Ala Gly Gln Ala Asp Ser Asn<br>           1140            1145            1150 | 3456 |
| CAT GAG ACT CCT CCA CAT CTC ACG TCC TAGGAATCTA CTTTCCTGTA<br>His Glu Thr Pro Pro His Leu Thr Ser<br>           1155            1160 | 3503 |
| TATCTCCACA ATTACGAGAT TGGTTTTGCT TTTGCCTATG AATCTACTGG CATGGGAACA | 3563 |
| AGTTCTCTTC AGCTCTGGGC TAGCCTGGGA AACTTCCCAG AAATGATGCC CTACCTCCTG | 3623 |
| AGCTGGGAGA TTTTTATGGT TTGCCCATGT GTCAGATTTC AGTGCTGATC CACTTTTTTT | 3683 |
| GCAAGAGCAG GAATGGGGTC AGCATAAATT TACATATGGA TAAGAACTAA CACAAGACTG | 3743 |
| AGTAATATGC TCAATATTCA ATGTATTGCT TGTATAAATT TTTAAAAAAT AAAATGAAAN | 3803 |

( 2 ) INFORMATION FOR SEQ ID NO:53:

( i ) SEQUENCE CHARACTERISTICS:
    ( A ) LENGTH: 1161 amino acids
    ( B ) TYPE: amino acid
    ( D ) TOPOLOGY: linear ( i i ) MOLECULE TYPE: protein ( x i ) SEQUENCE DESCRIPTION: SEQ ID NO:53:

Met Val Arg Gly Val Val Ile Leu Leu Cys Gly Trp Ala Leu Ala Ser
 1               5              10                  15

Cys His Gly Ser Asn Leu Asp Val Glu Lys Pro Val Val Phe Lys Glu
            20              25                  30

Asp Ala Ala Ser Phe Gly Gln Thr Val Val Gln Phe Gly Gly Ser Arg

|  |  |  | 35 |  |  |  | 40 |  |  |  | 45 |  |  |
|---|---|---|---|---|---|---|---|---|---|---|---|---|---|
| Leu | Val | Val | Gly | Ala | Pro | Leu | Glu | Ala | Val | Ala | Val | Asn | Gln | Thr | Gly |
|  | 50 |  |  |  |  | 55 |  |  |  |  | 60 |  |  |  |  |
| Gln | Ser | Ser | Asp | Cys | Pro | Pro | Ala | Thr | Gly | Val | Cys | Gln | Pro | Ile | Leu |
| 65 |  |  |  |  | 70 |  |  |  |  | 75 |  |  |  |  | 80 |
| Leu | His | Ile | Pro | Leu | Glu | Ala | Val | Asn | Met | Ser | Leu | Gly | Leu | Ser | Leu |
|  |  |  |  | 85 |  |  |  |  | 90 |  |  |  |  | 95 |  |
| Val | Ala | Asp | Thr | Asn | Asn | Ser | Gln | Leu | Leu | Ala | Cys | Gly | Pro | Thr | Ala |
|  |  |  | 100 |  |  |  | 105 |  |  |  | 110 |  |  |  |  |
| Gln | Arg | Ala | Cys | Ala | Lys | Asn | Met | Tyr | Ala | Lys | Gly | Ser | Cys | Leu | Leu |
|  | 115 |  |  |  |  | 120 |  |  |  |  | 125 |  |  |  |  |
| Leu | Gly | Ser | Ser | Leu | Gln | Phe | Ile | Gln | Ala | Ile | Pro | Ala | Thr | Met | Pro |
|  | 130 |  |  |  |  | 135 |  |  |  |  | 140 |  |  |  |  |
| Glu | Cys | Pro | Gly | Gln | Glu | Met | Asp | Ile | Ala | Phe | Leu | Ile | Asp | Gly | Ser |
| 145 |  |  |  |  | 150 |  |  |  |  | 155 |  |  |  |  | 160 |
| Gly | Ser | Ile | Asp | Gln | Ser | Asp | Phe | Thr | Gln | Met | Lys | Asp | Phe | Val | Lys |
|  |  |  |  | 165 |  |  |  |  | 170 |  |  |  |  | 175 |  |
| Ala | Leu | Met | Gly | Gln | Leu | Ala | Ser | Thr | Ser | Thr | Ser | Phe | Ser | Leu | Met |
|  |  |  | 180 |  |  |  |  | 185 |  |  |  |  | 190 |  |  |
| Gln | Tyr | Ser | Asn | Ile | Leu | Lys | Thr | His | Phe | Thr | Phe | Thr | Glu | Phe | Lys |
|  | 195 |  |  |  |  | 200 |  |  |  |  | 205 |  |  |  |  |
| Ser | Ser | Leu | Ser | Pro | Gln | Ser | Leu | Val | Asp | Ala | Ile | Val | Gln | Leu | Gln |
|  | 210 |  |  |  |  | 215 |  |  |  |  | 220 |  |  |  |  |
| Gly | Leu | Thr | Tyr | Thr | Ala | Ser | Gly | Ile | Gln | Lys | Val | Val | Lys | Glu | Leu |
| 225 |  |  |  |  | 230 |  |  |  |  | 235 |  |  |  |  | 240 |
| Phe | His | Ser | Lys | Asn | Gly | Ala | Arg | Lys | Ser | Ala | Lys | Lys | Ile | Leu | Ile |
|  |  |  |  | 245 |  |  |  |  | 250 |  |  |  |  | 255 |  |
| Val | Ile | Thr | Asp | Gly | Gln | Lys | Phe | Arg | Asp | Pro | Leu | Glu | Tyr | Arg | His |
|  |  |  | 260 |  |  |  |  | 265 |  |  |  |  | 270 |  |  |
| Val | Ile | Pro | Glu | Ala | Glu | Lys | Ala | Gly | Ile | Ile | Arg | Tyr | Ala | Ile | Gly |
|  |  |  | 275 |  |  |  |  | 280 |  |  |  |  | 285 |  |  |
| Val | Gly | Asp | Ala | Phe | Arg | Glu | Pro | Thr | Ala | Leu | Gln | Glu | Leu | Asn | Thr |
|  |  |  | 290 |  |  |  |  | 295 |  |  |  |  | 300 |  |  |
| Ile | Gly | Ser | Ala | Pro | Ser | Gln | Asp | His | Val | Phe | Lys | Val | Gly | Asn | Phe |
| 305 |  |  |  |  | 310 |  |  |  |  | 315 |  |  |  |  | 320 |
| Val | Ala | Leu | Arg | Ser | Ile | Gln | Arg | Gln | Ile | Gln | Glu | Lys | Ile | Phe | Ala |
|  |  |  |  | 325 |  |  |  |  | 330 |  |  |  |  | 335 |  |
| Ile | Glu | Gly | Thr | Glu | Ser | Arg | Ser | Ser | Ser | Phe | Gln | His | Glu | Met |  |
|  |  |  | 340 |  |  |  |  | 345 |  |  |  |  | 350 |  |  |
| Ser | Gln | Glu | Gly | Phe | Ser | Ser | Ala | Leu | Ser | Met | Asp | Gly | Pro | Val | Leu |
|  |  |  | 355 |  |  |  |  | 360 |  |  |  |  | 365 |  |  |
| Gly | Ala | Val | Gly | Gly | Phe | Ser | Trp | Ser | Gly | Gly | Ala | Phe | Leu | Tyr | Pro |
|  |  |  | 370 |  |  |  |  | 375 |  |  |  |  | 380 |  |  |
| Ser | Asn | Met | Arg | Ser | Thr | Phe | Ile | Asn | Met | Ser | Gln | Glu | Asn | Glu | Asp |
| 385 |  |  |  |  | 390 |  |  |  |  | 395 |  |  |  |  | 400 |
| Met | Arg | Asp | Ala | Tyr | Leu | Gly | Tyr | Ser | Thr | Ala | Leu | Ala | Phe | Trp | Lys |
|  |  |  |  | 405 |  |  |  |  | 410 |  |  |  |  | 415 |  |
| Gly | Val | His | Ser | Leu | Ile | Leu | Gly | Ala | Pro | Arg | His | Gln | His | Thr | Gly |
|  |  |  | 420 |  |  |  |  | 425 |  |  |  |  | 430 |  |  |
| Lys | Val | Val | Ile | Phe | Thr | Gln | Glu | Ser | Arg | His | Trp | Arg | Pro | Lys | Ser |
|  |  |  | 435 |  |  |  |  | 440 |  |  |  |  | 445 |  |  |
| Glu | Val | Arg | Gly | Thr | Gln | Ile | Gly | Ser | Tyr | Phe | Gly | Ala | Ser | Leu | Cys |
|  | 450 |  |  |  |  | 455 |  |  |  |  | 460 |  |  |  |  |

| | | | | | | | | | | | | | | | |
|---|---|---|---|---|---|---|---|---|---|---|---|---|---|---|---|
| Ser | Val | Asp | Met | Asp | Arg | Asp | Gly | Ser | Thr | Asp | Leu | Val | Leu | Ile | Gly |
| 465 | | | | 470 | | | | 475 | | | | | | | 480 |
| Val | Pro | His | Tyr | Tyr | Glu | His | Thr | Arg | Gly | Gln | Val | Ser | Val | Cys | |
| | | | | 485 | | | | | 490 | | | | 495 | | |
| Pro | Met | Pro | Gly | Val | Arg | Ser | Arg | Trp | His | Cys | Gly | Thr | Thr | Leu | His |
| | | | 500 | | | | | 505 | | | | | 510 | | |
| Gly | Glu | Gln | Gly | His | Pro | Trp | Gly | Arg | Phe | Gly | Ala | Ala | Leu | Thr | Val |
| | | | 515 | | | | 520 | | | | | 525 | | | |
| Leu | Gly | Asp | Val | Asn | Gly | Asp | Ser | Leu | Ala | Asp | Val | Ala | Ile | Gly | Ala |
| | | 530 | | | | 535 | | | | | 540 | | | | |
| Pro | Gly | Glu | Glu | Glu | Asn | Arg | Gly | Ala | Val | Tyr | Ile | Phe | His | Gly | Ala |
| 545 | | | | | 550 | | | | | 555 | | | | | 560 |
| Ser | Arg | Gln | Asp | Ile | Ala | Pro | Ser | Pro | Gln | Arg | Val | Thr | Gly | Ser | |
| | | | | 565 | | | | | 570 | | | | | 575 | |
| Gln | Leu | Phe | Leu | Arg | Leu | Gln | Tyr | Phe | Gly | Gln | Ser | Leu | Ser | Gly | Gly |
| | | | 580 | | | | | 585 | | | | | 590 | | |
| Gln | Asp | Leu | Thr | Gln | Asp | Gly | Leu | Val | Asp | Leu | Ala | Val | Gly | Ala | Gln |
| | | | 595 | | | | 600 | | | | | 605 | | | |
| Gly | His | Val | Leu | Leu | Leu | Arg | Ser | Leu | Pro | Leu | Leu | Lys | Val | Gly | Ile |
| | 610 | | | | | 615 | | | | | 620 | | | | |
| Ser | Ile | Arg | Phe | Ala | Pro | Ser | Glu | Val | Ala | Lys | Thr | Val | Tyr | Gln | Cys |
| 625 | | | | | 630 | | | | | 635 | | | | | 640 |
| Trp | Gly | Arg | Thr | Pro | Thr | Val | Leu | Glu | Ala | Gly | Glu | Ala | Thr | Val | Cys |
| | | | | 645 | | | | | 650 | | | | | 655 | |
| Leu | Thr | Val | Arg | Lys | Gly | Ser | Pro | Asp | Leu | Leu | Gly | Asp | Val | Gln | Ser |
| | | | 660 | | | | | 665 | | | | | 670 | | |
| Ser | Val | Arg | Tyr | Asp | Leu | Ala | Leu | Asp | Pro | Gly | Arg | Leu | Ile | Ser | Arg |
| | | 675 | | | | | 680 | | | | | 685 | | | |
| Ala | Ile | Phe | Asp | Glu | Thr | Lys | Asn | Cys | Thr | Leu | Thr | Arg | Arg | Lys | Thr |
| | | | 690 | | | | 695 | | | | | 700 | | | |
| Leu | Gly | Leu | Gly | Asp | His | Cys | Glu | Thr | Met | Lys | Leu | Leu | Leu | Pro | Asp |
| 705 | | | | | 710 | | | | | 715 | | | | | 720 |
| Cys | Val | Glu | Asp | Ala | Val | Thr | Pro | Ile | Ile | Leu | Arg | Leu | Asn | Leu | Ser |
| | | | | 725 | | | | | 730 | | | | | 735 | |
| Leu | Ala | Gly | Asp | Ser | Ala | Pro | Ser | Arg | Asn | Leu | Arg | Pro | Val | Leu | Ala |
| | | | 740 | | | | | 745 | | | | | 750 | | |
| Val | Gly | Ser | Gln | Asp | His | Val | Thr | Ala | Ser | Phe | Pro | Phe | Glu | Lys | Asn |
| | | 755 | | | | | 760 | | | | | 765 | | | |
| Cys | Lys | Gln | Glu | Leu | Leu | Cys | Glu | Gly | Asn | Leu | Gly | Val | Ser | Phe | Asn |
| | 770 | | | | | 775 | | | | | 780 | | | | |
| Phe | Ser | Gly | Leu | Gln | Val | Leu | Glu | Val | Gly | Ser | Ser | Pro | Glu | Leu | Thr |
| 785 | | | | | 790 | | | | | 795 | | | | | 800 |
| Val | Thr | Val | Thr | Val | Trp | Asn | Glu | Gly | Glu | Asp | Ser | Tyr | Gly | Thr | Leu |
| | | | | 805 | | | | | 810 | | | | | 815 | |
| Ile | Lys | Phe | Tyr | Tyr | Pro | Ala | Glu | Leu | Ser | Tyr | Arg | Arg | Val | Thr | Arg |
| | | | | 820 | | | | | 825 | | | | | 830 | |
| Ala | Gln | Gln | Pro | His | Pro | Tyr | Pro | Leu | Arg | Leu | Ala | Cys | Glu | Ala | Glu |
| | | | 835 | | | | | 840 | | | | | 845 | | |
| Pro | Thr | Gly | Gln | Glu | Ser | Leu | Arg | Ser | Ser | Ser | Cys | Ser | Ile | Asn | His |
| | 850 | | | | | 855 | | | | | 860 | | | | |
| Pro | Ile | Phe | Arg | Glu | Gly | Ala | Lys | Ala | Thr | Phe | Met | Ile | Thr | Phe | Asp |
| 865 | | | | | 870 | | | | | 875 | | | | | 880 |
| Val | Ser | Tyr | Lys | Ala | Phe | Leu | Gly | Asp | Arg | Leu | Leu | Leu | Arg | Ala | Ser |
| | | | | 885 | | | | | 890 | | | | | 895 | |

| | | | | | | | | | | | | | |
|---|---|---|---|---|---|---|---|---|---|---|---|---|---|
| Ala | Ser | Ser | Glu<br>900 | Asn | Asn | Lys | Pro | Glu<br>905 | Thr | Ser | Lys | Thr | Ala<br>910 | Phe | Gln |
| Leu | Glu | Leu<br>915 | Pro | Val | Lys | Tyr | Thr<br>920 | Val | Tyr | Thr | Val<br>925 | Ile | Ser | Arg | Gln |
| Glu | Asp<br>930 | Ser | Thr | Lys | His<br>935 | Phe | Asn | Phe | Ser | Ser<br>940 | Ser | His | Gly | Glu | Arg |
| Gln<br>945 | Lys | Glu | Ala | Glu | His<br>950 | Arg | Tyr | Arg | Val | Asn<br>955 | Asn | Leu | Ser | Pro | Leu<br>960 |
| Thr | Leu | Ala | Ile | Ser<br>965 | Val | Asn | Phe | Trp | Val<br>970 | Pro | Ile | Leu | Leu | Asn<br>975 | Gly |
| Val | Ala | Val | Trp<br>980 | Asp | Val | Thr | Leu | Arg<br>985 | Ser | Pro | Ala | Gln | Gly<br>990 | Val | Ser |
| Cys | Val | Ser<br>995 | Gln | Arg | Glu | Pro | Pro<br>1000 | Gln | His | Ser | Asp | Leu<br>1005 | Leu | Thr | Gln |
| Ile | Gln | Gly<br>1010 | Arg | Ser | Val | Leu<br>1015 | Asp | Cys | Ala | Ile | Ala<br>1020 | Asp | Cys | Leu | His |
| Leu<br>1025 | Arg | Cys | Asp | Ile | Pro<br>1030 | Ser | Leu | Gly | Thr | Leu<br>1035 | Asp | Glu | Leu | Asp | Phe<br>1040 |
| Ile | Leu | Lys | Gly | Asn<br>1045 | Leu | Ser | Phe | Gly | Trp<br>1050 | Ile | Ser | Gln | Thr | Leu<br>1055 | Gln |
| Lys | Lys | Val | Leu<br>1060 | Leu | Leu | Ser | Glu | Ala<br>1065 | Glu | Ile | Thr | Phe | Asn<br>1070 | Thr | Ser |
| Val | Tyr | Ser<br>1075 | Gln | Leu | Pro | Gly | Gln<br>1080 | Glu | Ala | Phe | Leu | Arg<br>1085 | Ala | Gln | Val |
| Ser | Thr<br>1090 | Met | Leu | Glu | Glu | Tyr<br>1095 | Val | Val | Tyr | Glu | Pro<br>1100 | Val | Phe | Leu | Met |
| Val<br>1105 | Phe | Ser | Ser | Val | Gly<br>1110 | Gly | Leu | Leu | Leu | Leu<br>1115 | Ala | Leu | Ile | Thr | Val<br>1120 |
| Ala | Leu | Tyr | Lys | Leu<br>1125 | Gly | Phe | Phe | Lys | Arg<br>1130 | Gln | Tyr | Lys | Glu | Met<br>1135 | Leu |
| Asp | Leu | Pro<br>1140 | Ser | Ala | Asp | Pro | Asp<br>1145 | Pro | Ala | Gly | Gln | Ala<br>1150 | Asp | Ser | Asn |
| His | Glu | Thr<br>1155 | Pro | Pro | His | Leu | Thr<br>1160 | Ser |

( 2 ) INFORMATION FOR SEQ ID NO:54:

( i ) SEQUENCE CHARACTERISTICS:
        ( A ) LENGTH: 3597 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 40..3525

( x i ) SEQUENCE DESCRIPTION: SEQ ID NO:54:

```
AGCTTTACAG CTCTCTACTT CTCAGTGCAC TGCTCAGTG ATG GCC GGT GGA GTT            54
                                            Met Ala Gly Gly Val
                                              1               5

GTG ATC CTC CTG TGT GGC TGG GTC CTG GCT TCC TGT CAT GGG TCT AAC          102
Val Ile Leu Leu Cys Gly Trp Val Leu Ala Ser Cys His Gly Ser Asn
             10                  15                  20

CTG GAT GTG GAG GAA CCC ATC GTG TTC AGA GAG GAT GCA GCC AGC TTT          150
Leu Asp Val Glu Glu Pro Ile Val Phe Arg Glu Asp Ala Ala Ser Phe
         25                  30                  35
```

```
GGA CAG ACT GTG GTG CAG TTT GGT GGA TCT CGA CTC GTG GTG GGA GCC        198
Gly Gln Thr Val Val Gln Phe Gly Gly Ser Arg Leu Val Val Gly Ala
        40                      45                      50

CCT CTG GAG GCG GTG GCA GTC AAC CAA ACA GGA CGG TTG TAT GAC TGT        246
Pro Leu Glu Ala Val Ala Val Asn Gln Thr Gly Arg Leu Tyr Asp Cys
    55                      60                      65

GCA CCT GCC ACT GGC ATG TGC CAG CCC ATC GTA CTG CGC AGT CCC CTA        294
Ala Pro Ala Thr Gly Met Cys Gln Pro Ile Val Leu Arg Ser Pro Leu
70                      75                      80                 85

GAG GCA GTG AAC ATG TCC CTG GGC CTG TCT CTG GTG ACT GCC ACC AAT        342
Glu Ala Val Asn Met Ser Leu Gly Leu Ser Leu Val Thr Ala Thr Asn
            90                      95                     100

AAC GCC CAG TTG CTG GCT TGT GGT CCA ACT GCA CAG AGA GCT TGT GTG        390
Asn Ala Gln Leu Leu Ala Cys Gly Pro Thr Ala Gln Arg Ala Cys Val
            105                     110                     115

AAG AAC ATG TAT GCG AAA GGT TCC TGC CTC CTT CTC GGC TCC AGC TTG        438
Lys Asn Met Tyr Ala Lys Gly Ser Cys Leu Leu Leu Gly Ser Ser Leu
            120                     125                     130

CAG TTC ATC CAG GCA GTC CCT GCC TCC ATG CCA GAG TGT CCA AGA CAA        486
Gln Phe Ile Gln Ala Val Pro Ala Ser Met Pro Glu Cys Pro Arg Gln
        135                     140                     145

GAG ATG GAC ATT GCT TTC CTG ATT GAT GGT TCT GGC AGC ATT AAC CAA        534
Glu Met Asp Ile Ala Phe Leu Ile Asp Gly Ser Gly Ser Ile Asn Gln
150                     155                     160                165

AGG GAC TTT GCC CAG ATG AAG GAC TTT GTC AAA GCT TTG ATG GGA GAG        582
Arg Asp Phe Ala Gln Met Lys Asp Phe Val Lys Ala Leu Met Gly Glu
                170                     175                     180

TTT GCG AGC ACC AGC ACC TTG TTC TCC CTG ATG CAA TAC TCG AAC ATC        630
Phe Ala Ser Thr Ser Thr Leu Phe Ser Leu Met Gln Tyr Ser Asn Ile
            185                     190                     195

CTG AAG ACC CAT TTT ACC TTC ACT GAA TTC AAG AAC ATC CTG GAC CCT        678
Leu Lys Thr His Phe Thr Phe Thr Glu Phe Lys Asn Ile Leu Asp Pro
            200                     205                     210

CAG AGC CTG GTG GAT CCC ATT GTC CAG CTG CAA GGC CTG ACC TAC ACA        726
Gln Ser Leu Val Asp Pro Ile Val Gln Leu Gln Gly Leu Thr Tyr Thr
        215                     220                     225

GCC ACA GGC ATC CGG ACA GTG ATG GAA GAG CTA TTT CAT AGC AAG AAT        774
Ala Thr Gly Ile Arg Thr Val Met Glu Glu Leu Phe His Ser Lys Asn
230                     235                     240                245

GGG TCC CGT AAA AGT GCC AAG AAG ATC CTC CTT GTC ATC ACA GAT GGG        822
Gly Ser Arg Lys Ser Ala Lys Lys Ile Leu Leu Val Ile Thr Asp Gly
                250                     255                     260

CAG AAA TAC AGA GAC CCC CTG GAG TAT AGT GAT GTC ATT CCC GCC GCA        870
Gln Lys Tyr Arg Asp Pro Leu Glu Tyr Ser Asp Val Ile Pro Ala Ala
            265                     270                     275

GAC AAA GCT GGC ATC ATT CGT TAT GCT ATT GGG GTG GGA GAT GCC TTC        918
Asp Lys Ala Gly Ile Ile Arg Tyr Ala Ile Gly Val Gly Asp Ala Phe
            280                     285                     290

CAG GAG CCC ACT GCC CTG AAG GAG CTG AAC ACC ATT GGC TCA GCT CCC        966
Gln Glu Pro Thr Ala Leu Lys Glu Leu Asn Thr Ile Gly Ser Ala Pro
        295                     300                     305

CCA CAG GAC CAC GTG TTC AAG GTA GGC AAC TTT GCA GCA CTT CGC AGC       1014
Pro Gln Asp His Val Phe Lys Val Gly Asn Phe Ala Ala Leu Arg Ser
310                     315                     320                325

ATC CAG AGG CAA CTT CAG GAG AAA ATC TTC GCC ATT GAG GGA ACT CAA       1062
Ile Gln Arg Gln Leu Gln Glu Lys Ile Phe Ala Ile Glu Gly Thr Gln
                330                     335                     340

TCA AGG TCA AGT AGT TCC TTT CAG CAC GAG ATG TCA CAA GAA GGT TTC       1110
Ser Arg Ser Ser Ser Ser Phe Gln His Glu Met Ser Gln Glu Gly Phe
        345                     350                     355
```

| | | | | | | | | | | | | | | | | |
|---|---|---|---|---|---|---|---|---|---|---|---|---|---|---|---|---|
| AGT | TCA | GCT | CTC | ACA | TCG | GAT | GGA | CCC | GTT | CTG | GGG | GCC | GTG | GGA | AGC | 1158 |
| Ser | Ser | Ala | Leu | Thr | Ser | Asp | Gly | Pro | Val | Leu | Gly | Ala | Val | Gly | Ser | |
| | | 360 | | | | | 365 | | | | | 370 | | | | |
| TTC | AGC | TGG | TCC | GGA | GGT | GCC | TTC | TTA | TAT | CCC | CCA | AAT | ACG | AGA | CCC | 1206 |
| Phe | Ser | Trp | Ser | Gly | Gly | Ala | Phe | Leu | Tyr | Pro | Pro | Asn | Thr | Arg | Pro | |
| | 375 | | | | | 380 | | | | | 385 | | | | | |
| ACC | TTT | ATC | AAC | ATG | TCT | CAG | GAG | AAT | GTG | GAC | ATG | AGA | GAC | TCC | TAC | 1254 |
| Thr | Phe | Ile | Asn | Met | Ser | Gln | Glu | Asn | Val | Asp | Met | Arg | Asp | Ser | Tyr | |
| 390 | | | | | 395 | | | | | 400 | | | | | 405 | |
| CTG | GGT | TAC | TCC | ACC | GCA | GTG | GCC | TTT | TGG | AAG | GGG | GTT | CAC | AGC | CTG | 1302 |
| Leu | Gly | Tyr | Ser | Thr | Ala | Val | Ala | Phe | Trp | Lys | Gly | Val | His | Ser | Leu | |
| | | | | 410 | | | | | 415 | | | | | 420 | | |
| ATC | CTG | GGG | GCC | CCG | CGT | CAC | CAG | CAC | ACG | GGG | AAG | GTT | GTC | ATC | TTT | 1350 |
| Ile | Leu | Gly | Ala | Pro | Arg | His | Gln | His | Thr | Gly | Lys | Val | Val | Ile | Phe | |
| | | | 425 | | | | | 430 | | | | | 435 | | | |
| ACC | CAG | GAA | GCC | AGG | CAT | TGG | AGG | CCC | AAG | TCT | GAA | GTC | AGA | GGG | ACA | 1398 |
| Thr | Gln | Glu | Ala | Arg | His | Trp | Arg | Pro | Lys | Ser | Glu | Val | Arg | Gly | Thr | |
| | | 440 | | | | | 445 | | | | | 450 | | | | |
| CAG | ATC | GGC | TCC | TAC | TTC | GGG | GCC | TCT | CTC | TGT | TCT | GTG | GAC | GTG | GAT | 1446 |
| Gln | Ile | Gly | Ser | Tyr | Phe | Gly | Ala | Ser | Leu | Cys | Ser | Val | Asp | Val | Asp | |
| | 455 | | | | | 460 | | | | | 465 | | | | | |
| AGA | GAT | GGC | AGC | ACY | GAC | CTG | GTC | CTG | ATC | GGA | GCC | CCC | CAT | TAC | TAT | 1494 |
| Arg | Asp | Gly | Ser | Xaa | Asp | Leu | Val | Leu | Ile | Gly | Ala | Pro | His | Tyr | Tyr | |
| 470 | | | | | 475 | | | | | 480 | | | | | 485 | |
| GAG | CAG | ACC | CGA | GGG | GGG | CAG | GTC | TCA | GTG | TTC | CCC | GTG | CCC | GGT | GTG | 1542 |
| Glu | Gln | Thr | Arg | Gly | Gly | Gln | Val | Ser | Val | Phe | Pro | Val | Pro | Gly | Val | |
| | | | | 490 | | | | | 495 | | | | | 500 | | |
| AGG | GGC | AGG | TGG | CAG | TGT | GAG | GCC | ACC | CTC | CAC | GGG | GAG | CAG | GGC | CAT | 1590 |
| Arg | Gly | Arg | Trp | Gln | Cys | Glu | Ala | Thr | Leu | His | Gly | Glu | Gln | Gly | His | |
| | | | 505 | | | | | 510 | | | | | 515 | | | |
| CCT | TGG | GGC | CGC | TTT | GGG | GTG | GCT | CTG | ACA | GTG | CTG | GGG | GAC | GTA | AAC | 1638 |
| Pro | Trp | Gly | Arg | Phe | Gly | Val | Ala | Leu | Thr | Val | Leu | Gly | Asp | Val | Asn | |
| | | 520 | | | | | 525 | | | | | 530 | | | | |
| GGG | GAC | AAT | CTG | GCA | GAC | GTG | GCT | ATT | GGT | GCC | CCT | GGA | GAG | GAG | GAG | 1686 |
| Gly | Asp | Asn | Leu | Ala | Asp | Val | Ala | Ile | Gly | Ala | Pro | Gly | Glu | Glu | Glu | |
| | 535 | | | | | 540 | | | | | 545 | | | | | |
| AGC | AGA | GGT | GCT | GTC | TAC | ATA | TTT | CAT | GGA | GCC | TCG | AGA | CTG | GAG | ATC | 1734 |
| Ser | Arg | Gly | Ala | Val | Tyr | Ile | Phe | His | Gly | Ala | Ser | Arg | Leu | Glu | Ile | |
| 550 | | | | | 555 | | | | | 560 | | | | | 565 | |
| ATG | CCC | TCA | CCC | AGC | CAG | CGG | GTC | ACT | GGC | TCC | CAG | CTC | TCC | CTG | AGA | 1782 |
| Met | Pro | Ser | Pro | Ser | Gln | Arg | Val | Thr | Gly | Ser | Gln | Leu | Ser | Leu | Arg | |
| | | | | 570 | | | | | 575 | | | | | 580 | | |
| CTG | CAG | TAT | TTT | GGG | CAG | TCA | TTG | AGT | GGG | GGT | CAG | GAC | CTT | ACA | CAG | 1830 |
| Leu | Gln | Tyr | Phe | Gly | Gln | Ser | Leu | Ser | Gly | Gly | Gln | Asp | Leu | Thr | Gln | |
| | | | 585 | | | | | 590 | | | | | 595 | | | |
| GAT | GGC | CTG | GTG | GAC | CTG | GCC | GTG | GGA | GCC | CAG | GGG | CAC | GTA | CTG | CTG | 1878 |
| Asp | Gly | Leu | Val | Asp | Leu | Ala | Val | Gly | Ala | Gln | Gly | His | Val | Leu | Leu | |
| | | 600 | | | | | 605 | | | | | 610 | | | | |
| CTC | AGG | AGT | CTG | CCT | CTG | CTG | AAA | GTG | GAG | CTC | TCC | ATA | AGA | TTC | GCC | 1926 |
| Leu | Arg | Ser | Leu | Pro | Leu | Leu | Lys | Val | Glu | Leu | Ser | Ile | Arg | Phe | Ala | |
| | 615 | | | | | 620 | | | | | 625 | | | | | |
| CCC | ATG | GAG | GTG | GCA | AAG | GCT | GTG | TAC | CAG | TGC | TGG | GAA | AGG | ACT | CCC | 1974 |
| Pro | Met | Glu | Val | Ala | Lys | Ala | Val | Tyr | Gln | Cys | Trp | Glu | Arg | Thr | Pro | |
| 630 | | | | | 635 | | | | | 640 | | | | | 645 | |
| ACT | GTC | CTC | GAA | GCT | GGA | GAG | GCC | ACT | GTC | TGT | CTC | ACT | GTC | CAC | AAA | 2022 |
| Thr | Val | Leu | Glu | Ala | Gly | Glu | Ala | Thr | Val | Cys | Leu | Thr | Val | His | Lys | |
| | | | | 650 | | | | | 655 | | | | | 660 | | |
| GGC | TCA | CCT | GAC | CTG | TTA | GGT | AAT | GTC | CAA | GGC | TCT | GTC | AGG | TAT | GAT | 2070 |
| Gly | Ser | Pro | Asp | Leu | Leu | Gly | Asn | Val | Gln | Gly | Ser | Val | Arg | Tyr | Asp | |
| | | | 665 | | | | | 670 | | | | | 675 | | | |

```
CTG GCG TTA GAT CCG GGC CGC CTG ATT TCT CGT GCC ATT TTT GAT GAG          2118
Leu Ala Leu Asp Pro Gly Arg Leu Ile Ser Arg Ala Ile Phe Asp Glu
        680                 685                 690

ACT AAG AAC TGC ACT TTG ACG GGA AGG AAG ACT CTG GGG CTT GGT GAT          2166
Thr Lys Asn Cys Thr Leu Thr Gly Arg Lys Thr Leu Gly Leu Gly Asp
    695                 700                 705

CAC TGC GAA ACA GTG AAG CTG CTT TTG CCG GAC TGT GTG GAA GAT GCA          2214
His Cys Glu Thr Val Lys Leu Leu Leu Pro Asp Cys Val Glu Asp Ala
710                 715                 720                 725

GTG AGC CCT ATC ATC CTG CGC CTC AAC TTT TCC CTG GTG AGA GAC TCT          2262
Val Ser Pro Ile Ile Leu Arg Leu Asn Phe Ser Leu Val Arg Asp Ser
                730                 735                 740

GCT TCA CCC AGG AAC CTG CAT CCT GTG CTG GCT GTG GGC TCA CAA GAC          2310
Ala Ser Pro Arg Asn Leu His Pro Val Leu Ala Val Gly Ser Gln Asp
            745                 750                 755

CAC ATA ACT GCT TCT CTG CCG TTT GAG AAG AAC TGT AAG CAA GAA CTC          2358
His Ile Thr Ala Ser Leu Pro Phe Glu Lys Asn Cys Lys Gln Glu Leu
        760                 765                 770

CTG TGT GAG GGG GAC CTG GGC ATC AGC TTT AAC TTC TCA GGC CTG CAG          2406
Leu Cys Glu Gly Asp Leu Gly Ile Ser Phe Asn Phe Ser Gly Leu Gln
    775                 780                 785

GTC TTG GTG GTG GGA GGC TCC CCA GAG CTC ACT GTG ACA GTC ACT GTG          2454
Val Leu Val Val Gly Gly Ser Pro Glu Leu Thr Val Thr Val Thr Val
790                 795                 800                 805

TGG AAT GAG GGT GAG GAC AGC TAT GGA ACT TTA GTC AAG TTC TAC TAC          2502
Trp Asn Glu Gly Glu Asp Ser Tyr Gly Thr Leu Val Lys Phe Tyr Tyr
                810                 815                 820

CCA GCA GGG CTA TCT TAC CGA CGG GTA ACA GGG ACT CAG CAA CCT CAT          2550
Pro Ala Gly Leu Ser Tyr Arg Arg Val Thr Gly Thr Gln Gln Pro His
            825                 830                 835

CAG TAC CCA CTA CGC TTG GCC TGT GAG GCT GAG CCC GCT GCC CAG GAG          2598
Gln Tyr Pro Leu Arg Leu Ala Cys Glu Ala Glu Pro Ala Ala Gln Glu
        840                 845                 850

GAC CTG AGG AGC AGC AGC TGT AGC ATT AAT CAC CCC ATC TTC CGA GAA          2646
Asp Leu Arg Ser Ser Ser Cys Ser Ile Asn His Pro Ile Phe Arg Glu
    855                 860                 865

GGT GCA AAG ACC ACC TTC ATG ATC ACA TTC GAT GTC TCC TAC AAG GCC          2694
Gly Ala Lys Thr Thr Phe Met Ile Thr Phe Asp Val Ser Tyr Lys Ala
870                 875                 880                 885

TTC CTA GGA GAC AGG TTG CTT CTG AGG GCC AAA GCC AGC AGT GAG AAT          2742
Phe Leu Gly Asp Arg Leu Leu Leu Arg Ala Lys Ala Ser Ser Glu Asn
                890                 895                 900

AAT AAG CCT GAT ACC AAC AAG ACT GCC TTC CAG CTG GAG CTC CCA GTG          2790
Asn Lys Pro Asp Thr Asn Lys Thr Ala Phe Gln Leu Glu Leu Pro Val
            905                 910                 915

AAG TAC ACC GTC TAT ACC CTG ATC AGT AGG CAA GAA GAT TCC ACC AAC          2838
Lys Tyr Thr Val Tyr Thr Leu Ile Ser Arg Gln Glu Asp Ser Thr Asn
        920                 925                 930

CAT GTC AAC TTT TCA TCT TCC CAC GGG GGG AGA AGG CAA GAA GCC GCA          2886
His Val Asn Phe Ser Ser Ser His Gly Gly Arg Arg Gln Glu Ala Ala
    935                 940                 945

CAT CGC TAT CGT GTG AAT AAC CTG AGT CCA CTG AAG CTG GCC GTC AGA          2934
His Arg Tyr Arg Val Asn Asn Leu Ser Pro Leu Lys Leu Ala Val Arg
950                 955                 960                 965

GTT AAC TTC TGG GTC CCT GTC CTT CTG AAC GGT GTG GCT GTG TGG GAC          2982
Val Asn Phe Trp Val Pro Val Leu Leu Asn Gly Val Ala Val Trp Asp
                970                 975                 980

GTG ACT CTG AGC AGC CCA GCA CAG GGT GTC TCC TGC GTG TCC CAG ATG          3030
Val Thr Leu Ser Ser Pro Ala Gln Gly Val Ser Cys Val Ser Gln Met
            985                 990                 995
```

| | | | | | | | | | | | | | | | | |
|---|---|---|---|---|---|---|---|---|---|---|---|---|---|---|---|---|
| AAA | CCT | CCT | CAG | AAT | CCC | GAC | TTT | CTG | ACC | CAG | ATT | CAG | AGA | CGT | TCT | 3078 |
| Lys | Pro 1000 | Pro | Gln | Asn | Pro 1005 | Asp | Phe | Leu | Thr | Gln | Ile | Gln 1010 | Arg | Arg | Ser | |
| GTG | CTG | GAC | TGC | TCC | ATT | GCT | GAC | TGC | CTG | CAC | TTC | CGC | TGT | GAC | ATC | 3126 |
| Val | Leu 1015 | Asp | Cys | Ser | Ile 1020 | Ala | Asp | Cys | Leu | His | Phe 1025 | Arg | Cys | Asp | Ile | |
| CCC | TCC | TTG | GAC | ATC | CAG | GAT | GAA | CTT | GAC | TTC | ATT | CTG | AGG | GGC | AAC | 3174 |
| Pro 1030 | Ser | Leu | Asp | Ile | Gln 1035 | Asp | Glu | Leu | Asp | Phe 1040 | Ile | Leu | Arg | Gly | Asn 1045 | |
| CTC | AGC | TTC | GGC | TGG | GTC | AGT | CAG | ACA | TTG | CAG | GAA | AAG | GTG | TTG | CTT | 3222 |
| Leu | Ser | Phe | Gly | Trp 1050 | Val | Ser | Gln | Thr | Leu 1055 | Gln | Glu | Lys | Val | Leu 1060 | Leu | |
| GTG | AGT | GAG | GCT | GAA | ATC | ACT | TTC | GAC | ACA | TCT | GTG | TAC | TCC | CAG | CTG | 3270 |
| Val | Ser | Glu | Ala 1065 | Glu | Ile | Thr | Phe | Asp 1070 | Thr | Ser | Val | Tyr | Ser 1075 | Gln | Leu | |
| CCA | GGA | CAG | GAG | GCA | TTT | CTG | AGA | GCC | CAG | GTG | GAG | ACA | ACG | TTA | GAA | 3318 |
| Pro | Gly | Gln | Glu 1080 | Ala | Phe | Leu | Arg | Ala 1085 | Gln | Val | Glu | Thr | Thr 1090 | Leu | Glu | |
| GAA | TAC | GTG | GTC | TAT | GAG | CCC | ATC | TTC | CTC | GTG | GCG | GGC | AGC | TCG | GTG | 3366 |
| Glu | Tyr | Val 1095 | Val | Tyr | Glu | Pro | Ile 1100 | Phe | Leu | Val | Ala | Gly 1105 | Ser | Ser | Val | |
| GGA | GGT | CTG | CTG | TTA | CTG | GCT | CTC | ATC | ACA | GTG | GTA | CTG | TAC | AAG | CTT | 3414 |
| Gly 1110 | Gly | Leu | Leu | Leu | Leu 1115 | Ala | Leu | Ile | Thr | Val 1120 | Val | Leu | Tyr | Lys | Leu 1125 | |
| GGC | TTC | TYC | AAA | CGT | CAG | TAC | AAA | GAA | ATG | CTG | GAC | GGC | AAG | GCT | GCA | 3462 |
| Gly | Phe | Xaa | Lys | Arg 1130 | Gln | Tyr | Lys | Glu | Met 1135 | Leu | Asp | Gly | Lys | Ala 1140 | Ala | |
| GAT | CCT | GTC | ACA | GCC | GGC | CAG | GCA | GAT | TTC | GGC | TGT | GAG | ACT | CCT | CCA | 3510 |
| Asp | Pro | Val | Thr | Ala 1145 | Gly | Gln | Ala | Asp | Phe 1150 | Gly | Cys | Glu | Thr | Pro 1155 | Pro | |
| TAT | CTC | GTG | AGC | TAGGAATCCA | CTCTCCTGCC | TATCTCTGCA | ATGAAGATTG | | | | | | | | | 3562 |
| Tyr | Leu | Val | Ser 1160 | | | | | | | | | | | | | |
| GTCCTGCCTA | TGAGTCTACT | GGCATGGGAA | CGAGT | | | | | | | | | | | | | 3597 |

( 2 ) INFORMATION FOR SEQ ID NO:55:

( i ) SEQUENCE CHARACTERISTICS:
    ( A ) LENGTH: 1161 amino acids
    ( B ) TYPE: amino acid
    ( D ) TOPOLOGY: linear ( i i ) MOLECULE TYPE: protein ( x i ) SEQUENCE DESCRIPTION: SEQ ID NO:55:

| | | | | | | | | | | | | | | |
|---|---|---|---|---|---|---|---|---|---|---|---|---|---|---|
| Met 1 | Ala | Gly | Gly | Val 5 | Val | Ile | Leu | Leu | Cys 10 | Gly | Trp | Val | Leu | Ala 15 | Ser |
| Cys | His | Gly | Ser 20 | Asn | Leu | Asp | Val | Glu 25 | Glu | Pro | Ile | Val | Phe 30 | Arg | Glu |
| Asp | Ala | Ala 35 | Ser | Phe | Gly | Gln | Thr 40 | Val | Val | Gln | Phe | Gly 45 | Gly | Ser | Arg |
| Leu | Val 50 | Val | Gly | Ala | Pro | Leu 55 | Glu | Ala | Val | Ala | Val 60 | Asn | Gln | Thr | Gly |
| Arg 65 | Leu | Tyr | Asp | Cys | Ala 70 | Pro | Ala | Thr | Gly | Met 75 | Cys | Gln | Pro | Ile | Val 80 |
| Leu | Arg | Ser | Pro | Leu 85 | Glu | Ala | Val | Asn | Met 90 | Ser | Leu | Gly | Leu | Ser 95 | Leu |
| Val | Thr | Ala | Thr 100 | Asn | Asn | Ala | Gln | Leu 105 | Leu | Ala | Cys | Gly | Pro 110 | Thr | Ala |

```
Gln Arg Ala Cys Val Lys Asn Met Tyr Ala Lys Gly Ser Cys Leu Leu
        115                 120                 125

Leu Gly Ser Ser Leu Gln Phe Ile Gln Ala Val Pro Ala Ser Met Pro
        130                 135                 140

Glu Cys Pro Arg Gln Glu Met Asp Ile Ala Phe Leu Ile Asp Gly Ser
145                     150                 155                 160

Gly Ser Ile Asn Gln Arg Asp Phe Ala Gln Met Lys Asp Phe Val Lys
                    165                 170                 175

Ala Leu Met Gly Glu Phe Ala Ser Thr Ser Thr Leu Phe Ser Leu Met
            180                 185                 190

Gln Tyr Ser Asn Ile Leu Lys Thr His Phe Thr Phe Thr Glu Phe Lys
        195                 200                 205

Asn Ile Leu Asp Pro Gln Ser Leu Val Asp Pro Ile Val Gln Leu Gln
        210                 215                 220

Gly Leu Thr Tyr Thr Ala Thr Gly Ile Arg Thr Val Met Glu Glu Leu
225                     230                 235                 240

Phe His Ser Lys Asn Gly Ser Arg Lys Ser Ala Lys Lys Ile Leu Leu
                    245                 250                 255

Val Ile Thr Asp Gly Gln Lys Tyr Arg Asp Pro Leu Glu Tyr Ser Asp
            260                 265                 270

Val Ile Pro Ala Ala Asp Lys Ala Gly Ile Ile Arg Tyr Ala Ile Gly
        275                 280                 285

Val Gly Asp Ala Phe Gln Glu Pro Thr Ala Leu Lys Glu Leu Asn Thr
        290                 295                 300

Ile Gly Ser Ala Pro Pro Gln Asp His Val Phe Lys Val Gly Asn Phe
305                     310                 315                 320

Ala Ala Leu Arg Ser Ile Gln Arg Gln Leu Gln Glu Lys Ile Phe Ala
                    325                 330                 335

Ile Glu Gly Thr Gln Ser Arg Ser Ser Ser Phe Gln His Glu Met
            340                 345                 350

Ser Gln Glu Gly Phe Ser Ser Ala Leu Thr Ser Asp Gly Pro Val Leu
        355                 360                 365

Gly Ala Val Gly Ser Phe Ser Trp Ser Gly Gly Ala Phe Leu Tyr Pro
        370                 375                 380

Pro Asn Thr Arg Pro Thr Phe Ile Asn Met Ser Gln Glu Asn Val Asp
385                     390                 395                 400

Met Arg Asp Ser Tyr Leu Gly Tyr Ser Thr Ala Val Ala Phe Trp Lys
                    405                 410                 415

Gly Val His Ser Leu Ile Leu Gly Ala Pro Arg His Gln His Thr Gly
            420                 425                 430

Lys Val Val Ile Phe Thr Gln Glu Ala Arg His Trp Arg Pro Lys Ser
        435                 440                 445

Glu Val Arg Gly Thr Gln Ile Gly Ser Tyr Phe Gly Ala Ser Leu Cys
        450                 455                 460

Ser Val Asp Val Asp Arg Asp Gly Ser Xaa Asp Leu Val Leu Ile Gly
465                     470                 475                 480

Ala Pro His Tyr Tyr Glu Gln Thr Arg Gly Gly Gln Val Ser Val Phe
                    485                 490                 495

Pro Val Pro Gly Val Arg Gly Arg Trp Gln Cys Glu Ala Thr Leu His
            500                 505                 510

Gly Glu Gln Gly His Pro Trp Gly Arg Phe Gly Val Ala Leu Thr Val
        515                 520                 525

Leu Gly Asp Val Asn Gly Asp Asn Leu Ala Asp Val Ala Ile Gly Ala
530                     535                 540
```

```
Pro  Gly  Glu  Glu  Glu  Ser  Arg  Gly  Ala  Val  Tyr  Ile  Phe  His  Gly  Ala
545                 550                      555                           560

Ser  Arg  Leu  Glu  Ile  Met  Pro  Ser  Pro  Ser  Gln  Arg  Val  Thr  Gly  Ser
                    565                      570                           575

Gln  Leu  Ser  Leu  Arg  Leu  Gln  Tyr  Phe  Gly  Gln  Ser  Leu  Ser  Gly  Gly
               580                      585                      590

Gln  Asp  Leu  Thr  Gln  Asp  Gly  Leu  Val  Asp  Leu  Ala  Val  Gly  Ala  Gln
          595                      600                      605

Gly  His  Val  Leu  Leu  Leu  Arg  Ser  Leu  Pro  Leu  Leu  Lys  Val  Glu  Leu
     610                      615                      620

Ser  Ile  Arg  Phe  Ala  Pro  Met  Glu  Val  Ala  Lys  Ala  Val  Tyr  Gln  Cys
625                      630                      635                           640

Trp  Glu  Arg  Thr  Pro  Thr  Val  Leu  Glu  Ala  Gly  Glu  Ala  Thr  Val  Cys
                    645                      650                           655

Leu  Thr  Val  His  Lys  Gly  Ser  Pro  Asp  Leu  Leu  Gly  Asn  Val  Gln  Gly
               660                      665                      670

Ser  Val  Arg  Tyr  Asp  Leu  Ala  Leu  Asp  Pro  Gly  Arg  Leu  Ile  Ser  Arg
          675                      680                      685

Ala  Ile  Phe  Asp  Glu  Thr  Lys  Asn  Cys  Thr  Leu  Thr  Gly  Arg  Lys  Thr
     690                      695                      700

Leu  Gly  Leu  Gly  Asp  His  Cys  Glu  Thr  Val  Lys  Leu  Leu  Leu  Pro  Asp
705                      710                      715                           720

Cys  Val  Glu  Asp  Ala  Val  Ser  Pro  Ile  Ile  Leu  Arg  Leu  Asn  Phe  Ser
                    725                      730                           735

Leu  Val  Arg  Asp  Ser  Ala  Ser  Pro  Arg  Asn  Leu  His  Pro  Val  Leu  Ala
               740                      745                      750

Val  Gly  Ser  Gln  Asp  His  Ile  Thr  Ala  Ser  Leu  Pro  Phe  Glu  Lys  Asn
          755                      760                      765

Cys  Lys  Gln  Glu  Leu  Leu  Cys  Glu  Gly  Asp  Leu  Gly  Ile  Ser  Phe  Asn
     770                      775                      780

Phe  Ser  Gly  Leu  Gln  Val  Leu  Val  Val  Gly  Gly  Ser  Pro  Glu  Leu  Thr
785                      790                      795                           800

Val  Thr  Val  Thr  Val  Trp  Asn  Glu  Gly  Glu  Asp  Ser  Tyr  Gly  Thr  Leu
                    805                      810                           815

Val  Lys  Phe  Tyr  Tyr  Pro  Ala  Gly  Leu  Ser  Tyr  Arg  Arg  Val  Thr  Gly
               820                      825                      830

Thr  Gln  Gln  Pro  His  Gln  Tyr  Pro  Leu  Arg  Leu  Ala  Cys  Glu  Ala  Glu
          835                      840                      845

Pro  Ala  Ala  Gln  Glu  Asp  Leu  Arg  Ser  Ser  Ser  Cys  Ser  Ile  Asn  His
850                      855                      860

Pro  Ile  Phe  Arg  Glu  Gly  Ala  Lys  Thr  Thr  Phe  Met  Ile  Thr  Phe  Asp
865                      870                      875                           880

Val  Ser  Tyr  Lys  Ala  Phe  Leu  Gly  Asp  Arg  Leu  Leu  Leu  Arg  Ala  Lys
               885                      890                      895

Ala  Ser  Ser  Glu  Asn  Asn  Lys  Pro  Asp  Thr  Asn  Lys  Thr  Ala  Phe  Gln
          900                      905                      910

Leu  Glu  Leu  Pro  Val  Lys  Tyr  Thr  Val  Tyr  Thr  Leu  Ile  Ser  Arg  Gln
     915                      920                      925

Glu  Asp  Ser  Thr  Asn  His  Val  Asn  Phe  Ser  Ser  Ser  His  Gly  Gly  Arg
930                      935                      940

Arg  Gln  Glu  Ala  Ala  His  Arg  Tyr  Arg  Val  Asn  Asn  Leu  Ser  Pro  Leu
945                      950                      955                           960

Lys  Leu  Ala  Val  Arg  Val  Asn  Phe  Trp  Val  Pro  Val  Leu  Leu  Asn  Gly
```

```
                            965                     970                      975
Val  Ala  Val  Trp  Asp  Val  Thr  Leu  Ser  Ser  Pro  Ala  Gln  Gly  Val  Ser
               980                     985                    990

Cys  Val  Ser  Gln  Met  Lys  Pro  Pro  Gln  Asn  Pro  Asp  Phe  Leu  Thr  Gln
          995                     1000                   1005

Ile  Gln  Arg  Arg  Ser  Val  Leu  Asp  Cys  Ser  Ile  Ala  Asp  Cys  Leu  His
          1010                    1015                   1020

Phe  Arg  Cys  Asp  Ile  Pro  Ser  Leu  Asp  Ile  Gln  Asp  Glu  Leu  Asp  Phe
1025                    1030                   1035                        1040

Ile  Leu  Arg  Gly  Asn  Leu  Ser  Phe  Gly  Trp  Val  Ser  Gln  Thr  Leu  Gln
                    1045                   1050                   1055

Glu  Lys  Val  Leu  Leu  Val  Ser  Glu  Ala  Glu  Ile  Thr  Phe  Asp  Thr  Ser
               1060                    1065                   1070

Val  Tyr  Ser  Gln  Leu  Pro  Gly  Gln  Glu  Ala  Phe  Leu  Arg  Ala  Gln  Val
          1075                    1080                   1085

Glu  Thr  Thr  Leu  Glu  Glu  Tyr  Val  Val  Tyr  Glu  Pro  Ile  Phe  Leu  Val
          1090                    1095                   1100

Ala  Gly  Ser  Ser  Val  Gly  Gly  Leu  Leu  Leu  Leu  Ala  Leu  Ile  Thr  Val
1105                    1110                   1115                        1120

Val  Leu  Tyr  Lys  Leu  Gly  Xaa  Xaa  Lys  Arg  Gln  Tyr  Lys  Glu  Met  Leu
                    1125                   1130                   1135

Asp  Gly  Lys  Ala  Ala  Asp  Pro  Val  Thr  Xaa  Gly  Gln  Ala  Asp  Phe  Gly
               1140                    1145                   1150

Cys  Glu  Thr  Pro  Pro  Tyr  Leu  Val  Ser
          1155                    1160
```

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

CCTGTCATGG GTCTAACCTG                                                       20

( 2 ) INFORMATION FOR SEQ ID NO:57:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

AGGTTAGACC CATGACAGG                                                        19

( 2 ) INFORMATION FOR SEQ ID NO:58:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

GGCCTTGCAG CTGGACAATG                                                          20

(2) INFORMATION FOR SEQ ID NO:59:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:59:

CCAAAGCTGG CTGCATCCTC TC                                                       22

(2) INFORMATION FOR SEQ ID NO:60:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:60:

CCGCCTGCCA CTGGCGTGTG C                                                        21

(2) INFORMATION FOR SEQ ID NO:61:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:61:

CCCAGATGAA GGACTTCGTC AA                                                       22

(2) INFORMATION FOR SEQ ID NO:62:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:62:

GCTGGGATCA TTCGCTATGC                                                          20

(2) INFORMATION FOR SEQ ID NO:63:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:63:

CAATGGATGG ACCAGTTCTG G                                                        21

(2) INFORMATION FOR SEQ ID NO:64:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:64:

CAGATCGGCT CCTACTTTGG                                           20

( 2 ) INFORMATION FOR SEQ ID NO:65:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:65:

CATGGAGCCT CGAGACAGG                                            19

( 2 ) INFORMATION FOR SEQ ID NO:66:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:66:

CCACTGTCCT CGAAGCTGGA G                                         21

( 2 ) INFORMATION FOR SEQ ID NO:67:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:67:

CTTCGTCCTG TGCTGGCTGT GGGCTC                                    26

( 2 ) INFORMATION FOR SEQ ID NO:68:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:68:

CGCCTGGCAT GTGAGGCTGA G                                         21

( 2 ) INFORMATION FOR SEQ ID NO:69:

( i ) SEQUENCE CHARACTERISTICS:
    ( A ) LENGTH: 21 base pairs
    ( B ) TYPE: nucleic acid
    ( C ) STRANDEDNESS: single (D) TOPOLOGY: linear (ii) MOLECULE TYPE: DNA (xi) SEQUENCE DESCRIPTION: SEQ ID NO:69:

CCGTGATCAG TAGGCAGGAA G　　　　　　　　　　　　　　　　　　　　　　　　21

(2) INFORMATION FOR SEQ ID NO:70:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:70:

GTCACAGAGG GAACCTCC　　　　　　　　　　　　　　　　　　　　　　　　　　18

(2) INFORMATION FOR SEQ ID NO:71:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:71:

GCTCCTGAGT GAGGCTGAAA TCA　　　　　　　　　　　　　　　　　　　　　　23

(2) INFORMATION FOR SEQ ID NO:72:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:72:

GAGATGCTGG ATCTACCATC TGC　　　　　　　　　　　　　　　　　　　　　　23

(2) INFORMATION FOR SEQ ID NO:73:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:73:

CTGAGCTGGG AGATTTTTAT GG　　　　　　　　　　　　　　　　　　　　　　　22

(2) INFORMATION FOR SEQ ID NO:74:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:74:

GTGGATCAGC ACTGAAATCT G    21

( 2 ) INFORMATION FOR SEQ ID NO:75:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:75:

CGTTTGAAGA AGCCAAGCTT G    21

( 2 ) INFORMATION FOR SEQ ID NO:76:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:76:

CACAGCGGAG GTGCAGGCAG    20

( 2 ) INFORMATION FOR SEQ ID NO:77:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:77:

CTCACTGCTT GCGCTGGC    18

( 2 ) INFORMATION FOR SEQ ID NO:78:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:78:

CGGTAAGATA GCTCTGCTGG    20

( 2 ) INFORMATION FOR SEQ ID NO:79:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:79:

GAGCCCACAG CCAGCACAGG    20

( 2 ) INFORMATION FOR SEQ ID NO:80:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:80:

GATCCAACGC CAGATCATAC C     21

( 2 ) INFORMATION FOR SEQ ID NO:81:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:81:

CACGGCCAGG TCCACCAGGC     20

( 2 ) INFORMATION FOR SEQ ID NO:82:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:82:

CACGTCCCCT AGCACTGTCA G     21

( 2 ) INFORMATION FOR SEQ ID NO:83:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:83:

TTGACGAAGT CCTTCATCTG GG     22

( 2 ) INFORMATION FOR SEQ ID NO:84:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:84:

GAACTGCAAG CTGGAGCCCA G     21

( 2 ) INFORMATION FOR SEQ ID NO:85:

( i ) SEQUENCE CHARACTERISTICS:
  ( A ) LENGTH: 21 base pairs
  ( B ) TYPE: nucleic acid
  ( C ) STRANDEDNESS: single ( D ) TOPOLOGY: linear ( i i ) MOLECULE TYPE: DNA ( x i ) SEQUENCE DESCRIPTION: SEQ ID NO:85:

CTGGATGCTG CGAAGTGCTA C                    21

( 2 ) INFORMATION FOR SEQ ID NO:86:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:86:

GCCTTGGAGC TGGACGATGG C                    21

( 2 ) INFORMATION FOR SEQ ID NO:87:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:87:

GTAAGATCTC CAGAGTGTCC AAGACAAGAG ATG        33

( 2 ) INFORMATION FOR SEQ ID NO:88:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:88:

CTTCTCGAGT GTGAGAGCTG AACTGAAACC TTC        33

( 2 ) INFORMATION FOR SEQ ID NO:89:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:89:

CGCTGTGACG TCAGAGTTGA GTCCAAATAT GG         32

( 2 ) INFORMATION FOR SEQ ID NO:90:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:90:

```
GGTGACACTA TAGAATAGGG C                                                                             21

( 2 ) INFORMATION FOR SEQ ID NO:91:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:91:

AAGCAGGAGCTCCTGTGT                                                                                  18

( 2 ) INFORMATION FOR SEQ ID NO:92:

( i ) SEQUENCE CHARACTERISTICS:
                ( A ) LENGTH: 852 base pairs
                ( B ) TYPE: nucleic acid
                ( C ) STRANDEDNESS: single
                ( D ) TOPOLOGY: linear ( i i ) MOLECULE TYPE: cDNA ( i x ) FEATURE:
                ( A ) NAME/KEY: CDS
                ( B ) LOCATION: 61..852

( x i ) SEQUENCE DESCRIPTION: SEQ ID NO:92:

TGATCTCCCT  CCAGGCCACT  GTTCCCTCTC  CACTTCCCCT  CACCGCTGCA  CTGCTCAGAG       60

ATG  GCC  CTT  GGG  GCT  GTG  GTC  CTC  CTT  GGG  GTC  CTG  GCT  TCT  TAC  CAC      108
Met  Ala  Leu  Gly  Ala  Val  Val  Leu  Leu  Gly  Val  Leu  Ala  Ser  Tyr  His
 1                  5                        10                       15

GGA  TTC  AAC  TTG  GAC  GTG  ATG  AGC  GGT  GAT  CTT  CCA  GGA  AGA  CGC  AGC      156
Gly  Phe  Asn  Leu  Asp  Val  Met  Ser  Gly  Asp  Leu  Pro  Gly  Arg  Arg  Ser
                20                       25                       30

GGG  CTT  CGG  GCA  GAG  CGT  GAT  GCA  GTT  TGG  GGA  TCT  CGA  CTC  GTG  GTG      204
Gly  Leu  Arg  Ala  Glu  Arg  Asp  Ala  Val  Trp  Gly  Ser  Arg  Leu  Val  Val
          35                       40                       45

GGA  GCC  CCC  CTG  GCG  GTG  GTG  TCG  GCC  AAC  CAC  ACA  GGA  CGG  CTG  TAC      252
Gly  Ala  Pro  Leu  Ala  Val  Val  Ser  Ala  Asn  His  Thr  Gly  Arg  Leu  Tyr
     50                       55                       60

GAG  TGT  GCG  CCT  GCC  TCC  GGC  ACC  TGC  ACG  CCC  ATT  TTC  CCA  TTC  ATG      300
Glu  Cys  Ala  Pro  Ala  Ser  Gly  Thr  Cys  Thr  Pro  Ile  Phe  Pro  Phe  Met
 65                      70                       75                       80

CCC  CCC  GAA  GCC  GTG  AAC  ATG  TCC  CTG  GGC  CTG  TCC  CTG  GCA  GCC  TCC      348
Pro  Pro  Glu  Ala  Val  Asn  Met  Ser  Leu  Gly  Leu  Ser  Leu  Ala  Ala  Ser
                     85                       90                       95

CCC  AAC  CAT  TCC  CAG  CTG  CTG  GCT  TGT  GGC  CCG  ACC  GTG  CAT  AGA  GCC      396
Pro  Asn  His  Ser  Gln  Leu  Leu  Ala  Cys  Gly  Pro  Thr  Val  His  Arg  Ala
               100                      105                      110

TGC  GGG  GAG  GAC  GTG  TAC  GCC  CAG  GGT  TTC  TGT  GTG  CTG  CTG  GAT  GCC      444
Cys  Gly  Glu  Asp  Val  Tyr  Ala  Gln  Gly  Phe  Cys  Val  Leu  Leu  Asp  Ala
          115                      120                      125

CAC  GCA  CAG  CCC  ATC  GGG  ACT  GTG  CCA  GCT  GCC  CTG  CCC  GAG  TGC  CCA      492
His  Ala  Gln  Pro  Ile  Gly  Thr  Val  Pro  Ala  Ala  Leu  Pro  Glu  Cys  Pro
     130                      135                      140

GAT  CAA  GAG  ATG  GAC  ATT  GTC  TTC  CTG  ATT  GAC  GGC  TCT  GGC  AGC  ATT      540
Asp  Gln  Glu  Met  Asp  Ile  Val  Phe  Leu  Ile  Asp  Gly  Ser  Gly  Ser  Ile
145                      150                      155                      160

AGC  TCA  AAT  GAC  TTC  CGC  AAG  ATG  AAG  GAC  TTT  GTC  AGA  GCT  GTG  ATG      588
Ser  Ser  Asn  Asp  Phe  Arg  Lys  Met  Lys  Asp  Phe  Val  Arg  Ala  Val  Met
                    165                      170                      175
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| GAC | CAG | TTC | AAG | GAC | ACC | AAC | ACC | CAG | TTC | TCG | CTG | ATG | CAG | TAC | TCC | 636 |
| Asp | Gln | Phe | Lys | Asp | Thr | Asn | Thr | Gln | Phe | Ser | Leu | Met | Gln | Tyr | Ser |     |
|     |     |     | 180 |     |     |     |     | 185 |     |     |     |     | 190 |     |     |     |
| AAT | GTG | CTG | GTG | ACA | CAT | TTC | ACC | TTC | AGC | AGC | TTC | CGG | AAC | AGC | TCC | 684 |
| Asn | Val | Leu | Val | Thr | His | Phe | Thr | Phe | Ser | Ser | Phe | Arg | Asn | Ser | Ser |     |
|     |     | 195 |     |     |     |     | 200 |     |     |     |     | 205 |     |     |     |     |
| AAT | CCT | CAG | GGC | CTA | GTG | GAG | CCC | ATT | GTG | CAG | CTG | ACA | GGC | CTC | ACG | 732 |
| Asn | Pro | Gln | Gly | Leu | Val | Glu | Pro | Ile | Val | Gln | Leu | Thr | Gly | Leu | Thr |     |
|     | 210 |     |     |     |     | 215 |     |     |     |     | 220 |     |     |     |     |     |
| TTC | ACG | GCC | ACA | GGG | ATC | CTG | AAA | GTG | GTG | ACA | GAG | CTG | TTT | CAA | ACC | 780 |
| Phe | Thr | Ala | Thr | Gly | Ile | Leu | Lys | Val | Val | Thr | Glu | Leu | Phe | Gln | Thr |     |
| 225 |     |     |     |     | 230 |     |     |     |     | 235 |     |     |     |     | 240 |     |
| AAG | AAC | GGG | GCC | CGC | GAA | AGT | GCC | AAG | AAG | ATC | CTC | ATC | GTC | ATC | ACA | 828 |
| Lys | Asn | Gly | Ala | Arg | Glu | Ser | Ala | Lys | Lys | Ile | Leu | Ile | Val | Ile | Thr |     |
|     |     |     |     | 245 |     |     |     |     | 250 |     |     |     |     | 255 |     |     |
| GAT | GGG | CAG | AAG | TAC | AAA | GCG | GCA |     |     |     |     |     |     |     |     | 852 |
| Asp | Gly | Gln | Lys | Tyr | Lys | Ala | Ala |     |     |     |     |     |     |     |     |     |
|     |     |     | 260 |     |     |     |     |     |     |     |     |     |     |     |     |     |

( 2 ) INFORMATION FOR SEQ ID NO:93:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:93:

|     |     |     |     |     |     |     |     |     |     |     |     |     |     |     |
|-----|-----|-----|-----|-----|-----|-----|-----|-----|-----|-----|-----|-----|-----|-----|
| Met | Ala | Leu | Gly | Ala | Val | Val | Leu | Leu | Gly | Val | Leu | Ala | Ser | Tyr | His |
| 1   |     |     |     | 5   |     |     |     |     | 10  |     |     |     |     | 15  |
| Gly | Phe | Asn | Leu | Asp | Val | Met | Ser | Gly | Asp | Leu | Pro | Gly | Arg | Arg | Ser |
|     |     |     | 20  |     |     |     |     | 25  |     |     |     | 30  |     |     |
| Gly | Leu | Arg | Ala | Glu | Arg | Asp | Ala | Val | Trp | Gly | Ser | Arg | Leu | Val | Val |
|     |     | 35  |     |     |     |     | 40  |     |     |     | 45  |     |     |     |
| Gly | Ala | Pro | Leu | Ala | Val | Val | Ser | Ala | Asn | His | Thr | Gly | Arg | Leu | Tyr |
|     | 50  |     |     |     |     | 55  |     |     |     |     | 60  |     |     |     |
| Glu | Cys | Ala | Pro | Ala | Ser | Gly | Thr | Cys | Thr | Pro | Ile | Phe | Pro | Phe | Met |
| 65  |     |     |     |     | 70  |     |     |     |     | 75  |     |     |     |     | 80  |
| Pro | Pro | Glu | Ala | Val | Asn | Met | Ser | Leu | Gly | Leu | Ser | Leu | Ala | Ala | Ser |
|     |     |     |     | 85  |     |     |     |     | 90  |     |     |     |     | 95  |
| Pro | Asn | His | Ser | Gln | Leu | Leu | Ala | Cys | Gly | Pro | Thr | Val | His | Arg | Ala |
|     |     |     | 100 |     |     |     |     | 105 |     |     |     | 110 |     |     |
| Cys | Gly | Glu | Asp | Val | Tyr | Ala | Gln | Gly | Phe | Cys | Val | Leu | Leu | Asp | Ala |
|     |     | 115 |     |     |     |     | 120 |     |     |     | 125 |     |     |     |
| His | Ala | Gln | Pro | Ile | Gly | Thr | Val | Pro | Ala | Ala | Leu | Pro | Glu | Cys | Pro |
|     | 130 |     |     |     |     | 135 |     |     |     |     | 140 |     |     |     |
| Asp | Gln | Glu | Met | Asp | Ile | Val | Phe | Leu | Ile | Asp | Gly | Ser | Gly | Ser | Ile |
| 145 |     |     |     |     | 150 |     |     |     |     | 155 |     |     |     |     | 160 |
| Ser | Ser | Asn | Asp | Phe | Arg | Lys | Met | Lys | Asp | Phe | Val | Arg | Ala | Val | Met |
|     |     |     |     | 165 |     |     |     |     | 170 |     |     |     |     | 175 |
| Asp | Gln | Phe | Lys | Asp | Thr | Asn | Thr | Gln | Phe | Ser | Leu | Met | Gln | Tyr | Ser |
|     |     |     | 180 |     |     |     |     | 185 |     |     |     | 190 |     |     |
| Asn | Val | Leu | Val | Thr | His | Phe | Thr | Phe | Ser | Ser | Phe | Arg | Asn | Ser | Ser |
|     |     | 195 |     |     |     |     | 200 |     |     |     | 205 |     |     |     |
| Asn | Pro | Gln | Gly | Leu | Val | Glu | Pro | Ile | Val | Gln | Leu | Thr | Gly | Leu | Thr |
|     | 210 |     |     |     |     | 215 |     |     |     |     | 220 |     |     |     |
| Phe | Thr | Ala | Thr | Gly | Ile | Leu | Lys | Val | Val | Thr | Glu | Leu | Phe | Gln | Thr |

-continued

```
225                 230                     235                     240
Lys Asn Gly Ala Arg Glu Ser Ala Lys Lys Ile Leu Ile Val Ile Thr
                245                 250                 255
Asp Gly Gln Lys Tyr Lys Ala Ala
            260
```